(12) United States Patent
Thanos et al.

(10) Patent No.: US 11,951,206 B2
(45) Date of Patent: Apr. 9, 2024

(54) CELL HOUSING DEVICE

(71) Applicant: Vertex Pharmaceuticals Incorporated, Boston, MA (US)

(72) Inventors: Christopher Thanos, Cumberland, RI (US); Danya M. Lavin, Mansfield, MA (US); Briannan E. Bintz, Lincoln, RI (US); Divya Bhatnagar, Highland Park, NJ (US); John Mills, Warwick, RI (US); Megan Billings, Warwick, RI (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 326 days.

(21) Appl. No.: 16/650,933

(22) PCT Filed: Sep. 29, 2018

(86) PCT No.: PCT/US2018/053665
§ 371 (c)(1),
(2) Date: Mar. 26, 2020

(87) PCT Pub. No.: WO2019/068059
PCT Pub. Date: Apr. 4, 2019

(65) Prior Publication Data
US 2020/0289407 A1    Sep. 17, 2020

Related U.S. Application Data

(60) Provisional application No. 62/671,297, filed on May 14, 2018, provisional application No. 62/565,962, filed on Sep. 29, 2017.

(51) Int. Cl.
*A61K 9/00* (2006.01)
*A61K 35/39* (2015.01)
*A61K 47/32* (2006.01)
*A61K 47/34* (2017.01)

(52) U.S. Cl.
CPC ............ *A61K 9/0024* (2013.01); *A61K 35/39* (2013.01); *A61K 47/32* (2013.01); *A61K 47/34* (2013.01)

(58) Field of Classification Search
None
See application file for complete search history.

(56) References Cited

U.S. PATENT DOCUMENTS

| 2,984,599 | A | 5/1961 | Edwards et al. |
| 4,892,538 | A | 1/1990 | Aebischer et al. |
| 5,066,397 | A | 11/1991 | Muto et al. |
| 5,320,512 | A | 6/1994 | Moore, Sr. |
| 7,407,703 | B2 | 8/2008 | DeYoung et al. |
| 8,425,928 | B2 | 4/2013 | Martinson et al. |
| 8,784,710 | B2 * | 7/2014 | Hansen ............ B01D 53/228 264/211.13 |
| 9,132,226 | B2 | 9/2015 | Martinson et al. |
| 10,272,179 | B2 | 4/2019 | Martinson et al. |
| 2004/0022691 | A1 | 2/2004 | Allen et al. |
| 2010/0196439 | A1 | 8/2010 | Beck et al. |
| 2013/0131828 | A1 | 5/2013 | Legeay et al. |
| 2015/0283514 | A1 | 10/2015 | Aguilar et al. |
| 2015/0298388 | A1 | 10/2015 | Wong et al. |
| 2016/0184569 | A1 | 6/2016 | Lathuiliere et al. |
| 2016/0310541 | A1 | 10/2016 | Bou Aoun et al. |
| 2017/0092986 | A1 | 3/2017 | Ogawa et al. |
| 2017/0113028 | A1 | 4/2017 | So et al. |
| 2017/0203255 | A1 | 7/2017 | Mundrigi et al. |

FOREIGN PATENT DOCUMENTS

| DE | 10 2007 006634 A1 | 8/2008 | |
| EP | 2 056 759 B1 | 1/2015 | |
| JP | 2701977 B2 * | 1/1998 | ........... A61K 9/0004 |
| WO | WO 96/32076 A1 | 10/1996 | |
| WO | WO-9632076 A1 * | 10/1996 | ............ A61F 2/022 |
| WO | WO 2015/025686 A1 | 2/2015 | |
| WO | WO 2015/048184 A1 | 4/2015 | |
| WO | WO 2017/078177 A1 | 5/2017 | |
| WO | WO 2018/232180 A1 | 12/2018 | |

OTHER PUBLICATIONS

Skrzypek et al. (Pancreatic islet macroencapsulation using microwell porous membranes, Scientific Reports, vol. 7. No. 1, Aug. 23, 2017). (Year: 2017).*
International Search Report and Written Opinion for International Application No. PCT/US2018/053665 dated Jan. 24, 2019.
Chang et al., Nanoporous Immunoprotective Device for Stem-Cell-Derived β-Cell Replacement Therapy. ACS Nano. Aug. 2017;11(8):7747-57.
Skrzypek et al., Pancreatic islet macroencapsulation using microwell porous membranes. Scientific Reports. Aug. 2017;7(1):1-12. Epub Aug. 23, 2017.
[No Author Listed]. Vertex to Acquire ViaCyte. With the Goal of Accelerating its Potentially Curative VX-880 Programs in Type 1 Diabetes. Business Wire. Jul. 11, 2022. Accessible from < https://www.businesswire.com/news/home/20220711005280/en/> 2 pages.

* cited by examiner

*Primary Examiner* — Melissa S Mercier

(74) *Attorney, Agent, or Firm* — Wolf, Greenfield & Sacks, P.C.

(57) ABSTRACT

The present disclosure provides a cell housing device and a method of manufacturing such a device that has an array of channels to increase the ratio of surface area to volume.

30 Claims, 99 Drawing Sheets

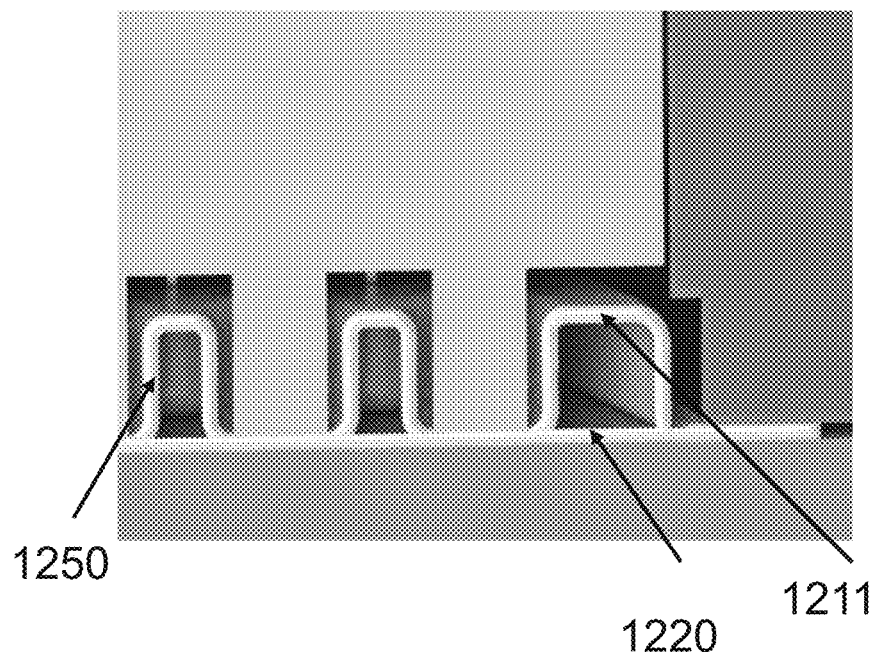
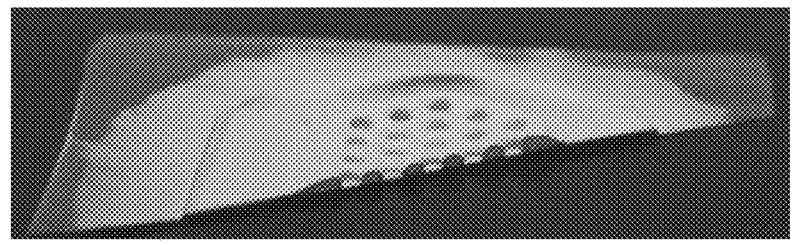
FIG. 9

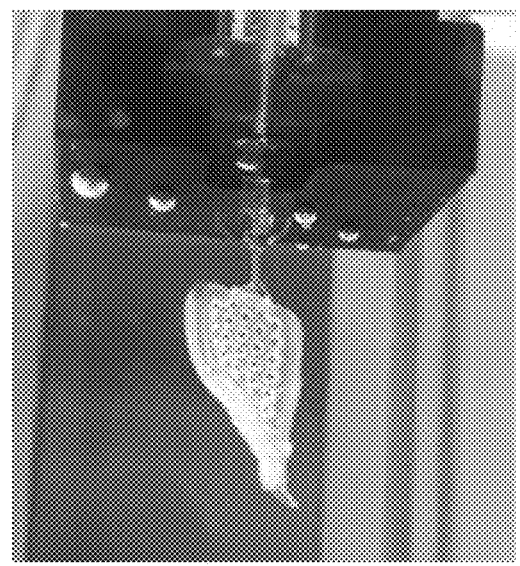
Device Burst Pressure
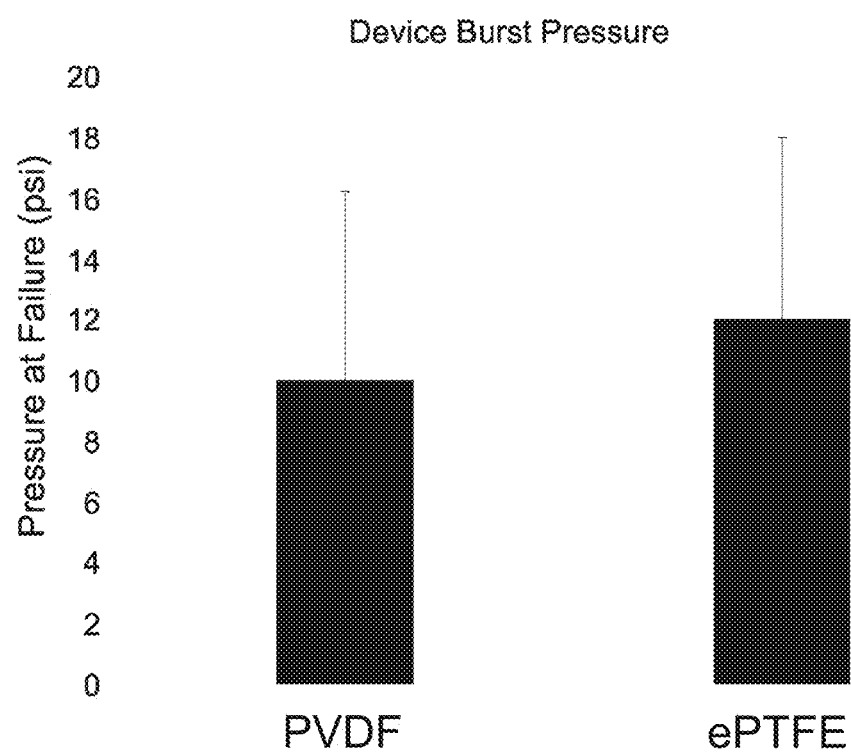
FIG. 39

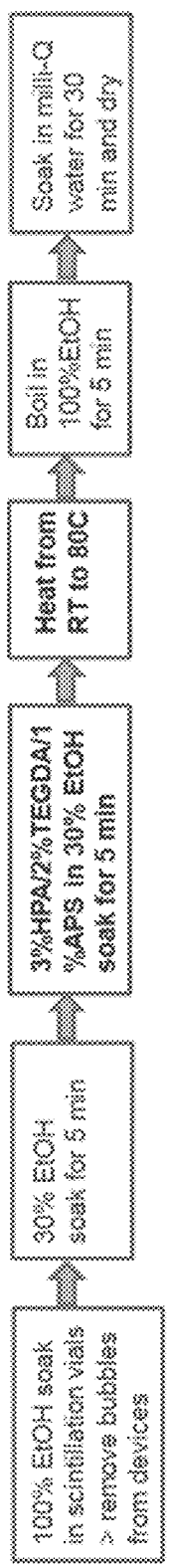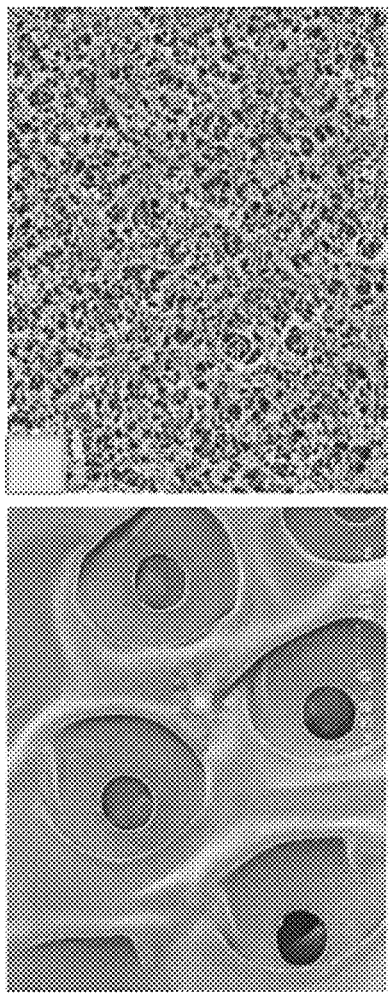
FIG. 41

Coated Membranes
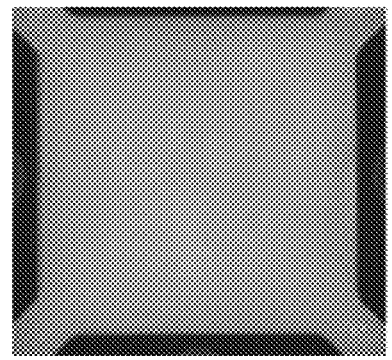
Dry
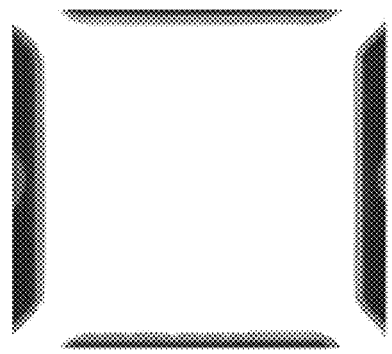
Wet
*Transilluminated membranes show post-coating wettability*
FIG. 55

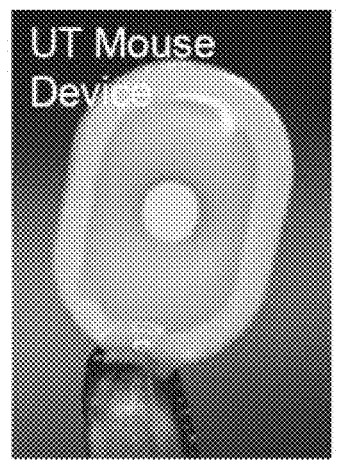 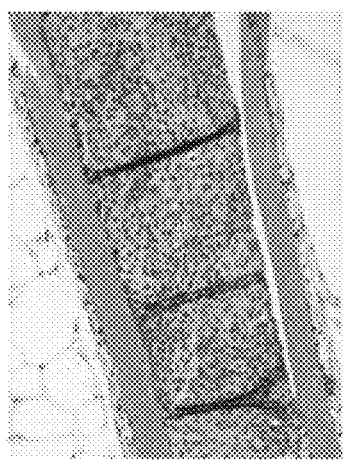
FIG. 61A  FIG. 61B
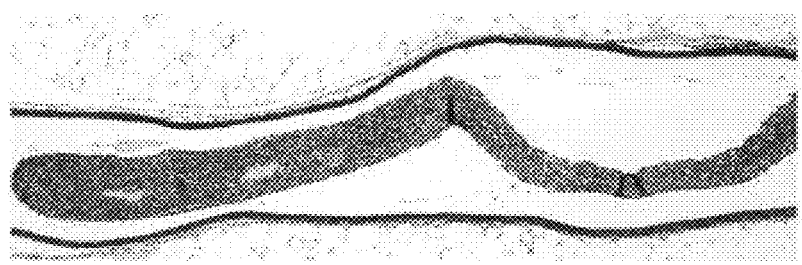
FIG. 61C

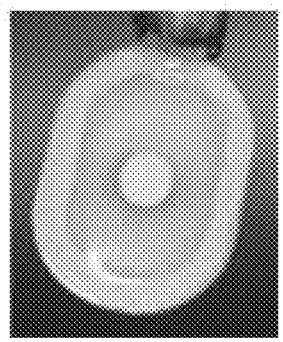
Rodent Device Module
FIG. 73
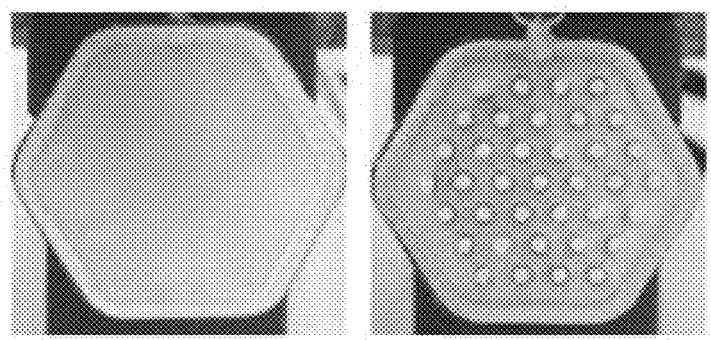
Human Device Modules:
FIG. 74A          FIG. 74B
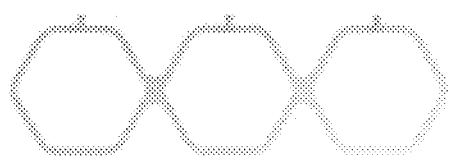    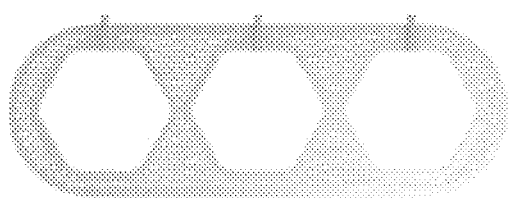
FIG. 75A          FIG. 75B

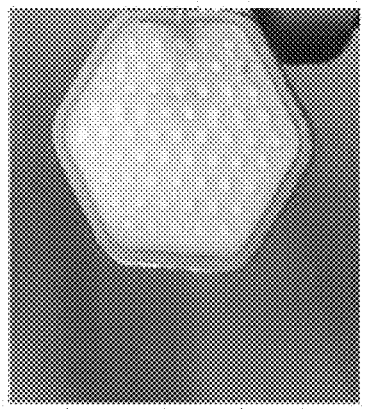
FIG. 76A Adhesive Restraint
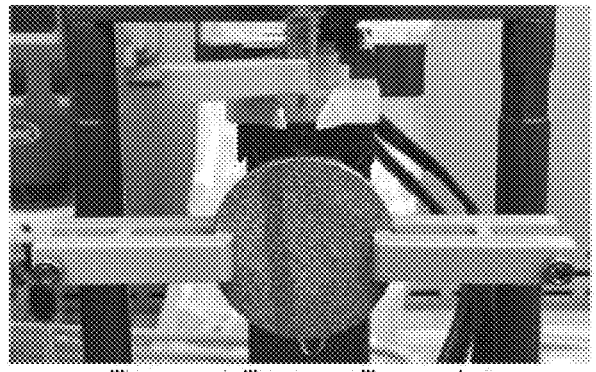
FIG. 76B External Porous Restraint
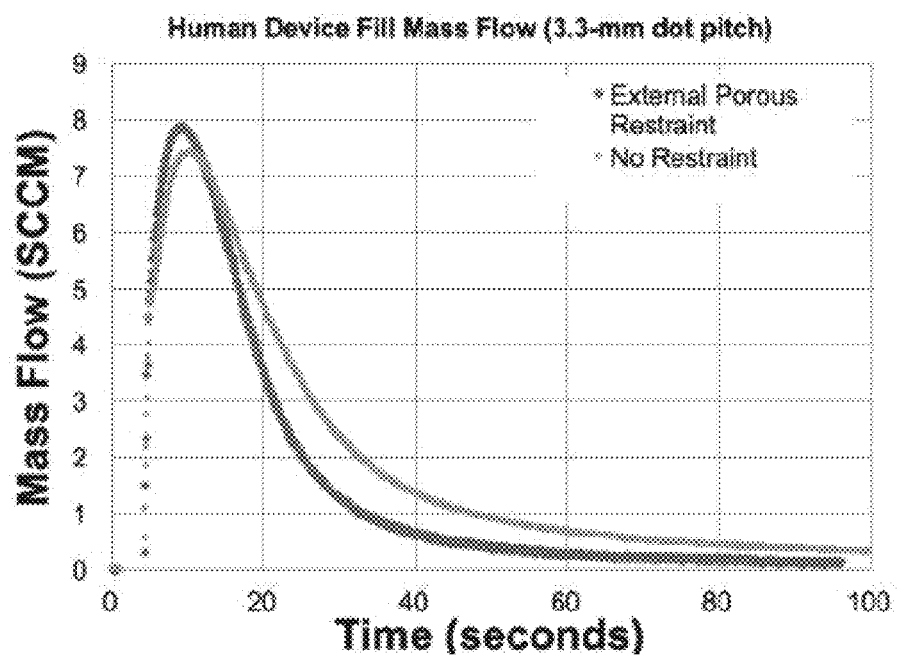
FIG. 77
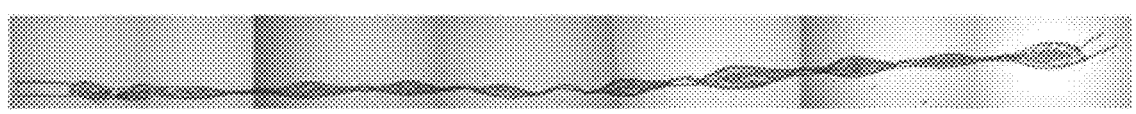
FIG. 78 Adhesive Restraint Device

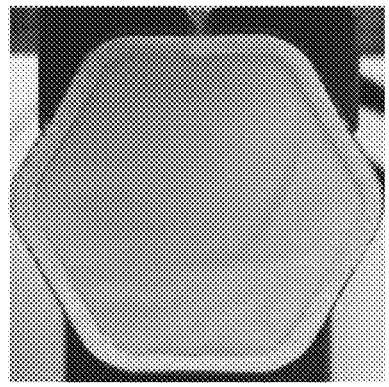
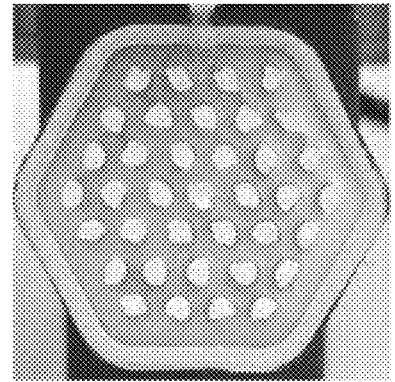
No Dot
FIG. 79A
3.3 mm Dot
FIG. 79B
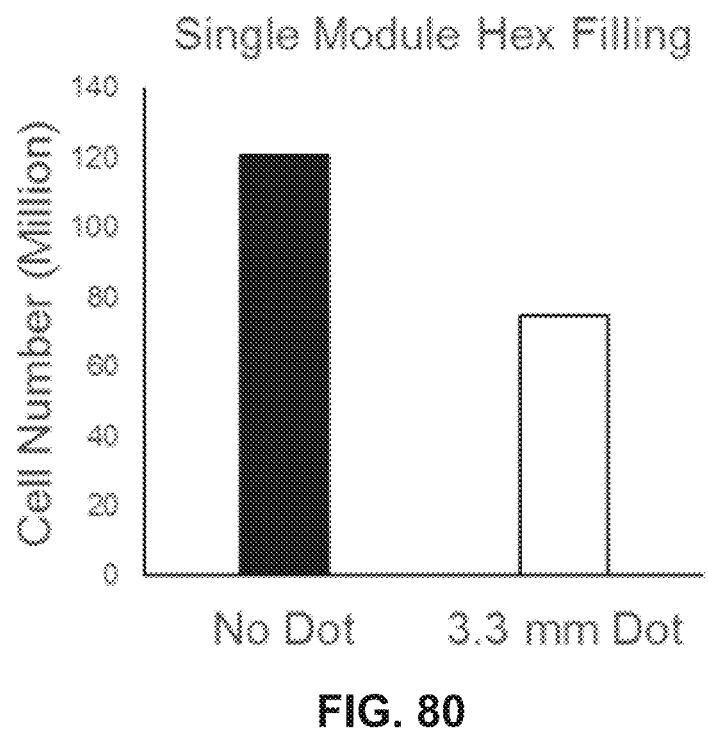
FIG. 80

No Restraint

Frit Restraint
400 um Spacer

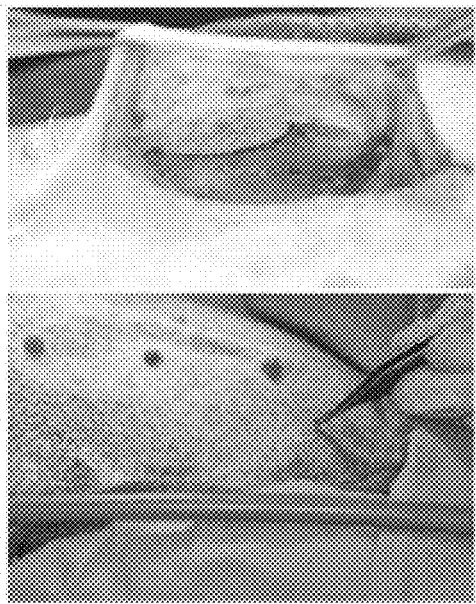
FIG. 84A
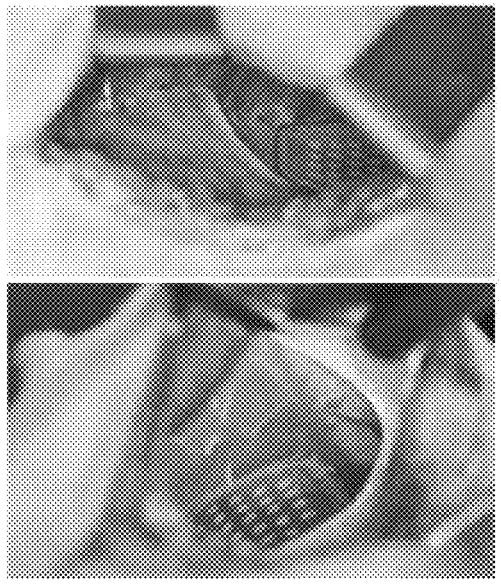
FIG. 84B
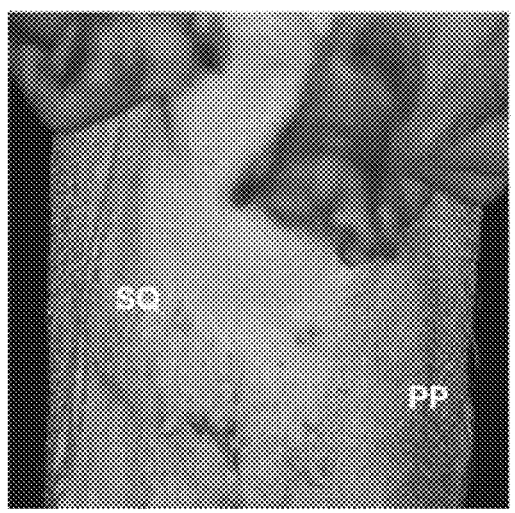 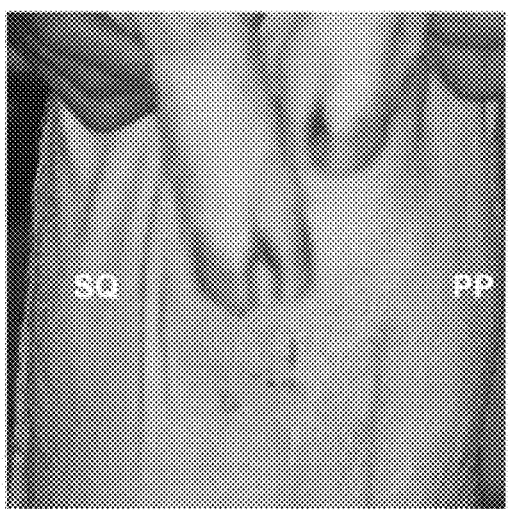
FIG. 85

CELL HOUSING DEVICE

CROSS-REFERENCE

This application is a national stage filing under 35 U.S.C. § 371 of International Patent Application Serial No. PCT/US2018/053665, filed Sep. 29, 2018, which claims the benefit of U.S. Provisional Application Ser. No. 62/565,962, filed Sep. 29, 2017, and U.S. Provisional Application Ser. No. 62/671,297, filed May 14, 2018, the disclosures of each of which are hereby incorporated herein by reference in their entirety.

BACKGROUND OF THE DISCLOSURE

Therapeutic devices that deliver biological products can be used to treat metabolic disorders, such as diabetes. The therapeutic devices may be implantable to provide a biological product, such as insulin, for an extended period of time. These devices may comprise a cell housing device and a matrix housed within the cell housing device. The matrix may comprise cells to produce the biological products. As the dimensions of the matrix increase, the availability of oxygen and other nutrients may decrease further away from the edge surfaces of the matrix, and there may be regions of low or no oxygen and nutrient concentrations within the matrix. These regions of low or no oxygen and nutrient concentrations may not be able to support cell viability and synthesis of biological products in the matrix. Spatial limitations in transport of oxygen, nutrients, and other agents can limit the size of the device to a dimension where the oxygen, nutrients, and other agents can reach the cells. Thus, it may be beneficial to improve the mass transport to interior regions of such devices and of the matrix housed within the cell housing device.

SUMMARY OF THE DISCLOSURE

The present disclosure generally relates to medical devices and methods. In various aspects, the present disclosure provides medical devices including cell housing devices, devices related thereto, and methods of manufacturing and utilizing such devices.

In a certain aspect, described herein, is a cell housing device, comprising: a first membrane having a first surface comprising a plurality of channels, and a plurality of second surfaces opposing the first surface; and a second membrane opposite and attached to the plurality of second surfaces of the first membrane; wherein the first membrane and the second membrane form an enclosed compartment having a surface area to the volume ratio of at least about 40 cm−1, and wherein the enclosed compartment provides a volume for housing a cell within the device.

In some embodiments, the compartment comprises a single continuous open space. In some embodiments, the volume is about 8 uL to about 1,000 uL. In some embodiments, the device has at least one of a length and a width of about 0.25 cm to about 3 cm. In some embodiments, the device has a thickness of at least about 300 μm. In some embodiments, the plurality of channels are generally perpendicular with respect to the first membrane. In some embodiments, the plurality of channels are arranged in a rectilinear array. In some embodiments, the plurality of channels are arranged in a polar array. In some embodiments, the channel has an average diameter of about 400 μm to about 3,000 μm. In some embodiments, the diameter is measured at a narrowest point in the channel. In some embodiments, a center of each channel is separated from the center of another channel by a distance of about 75 μm to about 500 μm. In some embodiments, the channel has a height to diameter ratio of at least about 0.2. In some embodiments, the device has a number of channels per area along a transverse plane is greater than about 50/cm2. In some embodiments, at least one of the first membrane and the second membrane comprise a plurality of nodes interconnected by a plurality of fibrils. In some embodiments, at least one of the first membrane and the second membrane comprise polyvinylidene fluoride (PVDF), polytetrafluoroethylene (PTFE), expanded polytetrafluoroethylene (ePTFE), polycaprolactone (PCL), polyethylene (PE)/polyethersulfone (PES), polypropylene (PP), polystyrene (PSI, poly(methyl methacrylate) (PMMA), poly(lactic-co-glycolic acid) (PLGA), poly(l-lactic acid) (PLLA), or any combination thereof. In some embodiments, the device further comprises an opening through the first membrane and the second membrane within the channel. In some embodiments, the opening has a concentricity with respect to the channel of at most 25% the diameter of the channel. In some embodiments, the device further comprises a frame configured to receive the device. In some embodiments, the frame is configured to receive a plurality of cell housing devices. In some embodiments, the frame comprises a flexing mechanism configured to prevent buckling of the cell housing device. In some embodiments, the device further comprises a cell population. In some embodiments, the cell population is an insulin secreting population. In some embodiments, the cell population is a stem cell derived cell that are capable of glucose-stimulated insulin secretion (GSIS). In some embodiments, the device further comprises a coating comprising a hydrophilic polymer. In some embodiments, the device has an insulin diffusion coefficient of about $2 \times 10^{-6}$ cm$^2$/s to about $1 \times 10^{5}$ cm$^2$/s. In some embodiments, the device has a maximum insulin diffusion distance of less than about 150 μm. In some embodiments, the first membrane and the second membrane are fused with a fusion peel force of at least about 0.4 N. In some embodiments, at least one of the first membrane and the second membrane are semi-permeable. In some embodiments, the semi-permeability of the first membrane, the second membrane, or both is configured to protect the cell from an immune attack. In some embodiments, the semi-permeability of the first membrane, the second membrane, or both is configured to protect the cell from an immune attack in the absence of an immune suppression therapy. In some embodiments, at least one of the first membrane and the second membrane are configured to enable vascularization of the cell within the device. In some embodiments, at least one of the first membrane and the second membrane are configured to enable vascularization of the cell within the device in absence of an immune suppression therapy.

Another aspect provided herein is a cell housing device, comprising: a first membrane having a first surface comprising a plurality of channels, and a plurality of second surfaces opposing the first surface; and a second membrane opposite and attached to the plurality of second surfaces of the first membrane; wherein the first membrane and the second membrane form an enclosed compartment wherein the enclosed compartment provides a volume for housing 1 million to 1 billion insulin producing cells within the device and wherein said membrane allows for diffusion of insulin from the device while retaining the insulin producing cells within the device.

Another aspect provided herein is a composition comprising insulin producing cells and a device housing said insulin producing cells, wherein said device upon implantation in an individual releases insulin while retaining the insulin producing cells in the device, and facilitates tissue vascularization in and around the device. In some embodiments, individual is not administered an immune suppression agent during the implantation or vascularization of the device. In some embodiments, the device comprises 1 million to 1 billion insulin producing cells. In some embodiments, the device has a thickness of at least about 300 µm. In some embodiments, the device comprises a membrane comprising a plurality of nodes interconnected by a plurality of fibrils.

In another aspect, described herein, is a method of manufacturing a cell housing device, comprising: providing a first membrane having a first face and an opposing second face; forming a plurality of channels within the first face of the first membrane; and fusing a second membrane to the second face of the first membrane to form a compartment for housing a cell between the second face of the first membrane and the second membrane.

In some embodiments, forming a plurality of channels within the first membrane comprises: heating the first membrane for a predetermined time at a predetermined pressure and a predetermined temperature; and molding the plurality of channels with a mold. In some embodiments, the fusing of the second membrane to the first membrane is performed in the mold. In some embodiments, the mold comprises a positive mold. In some embodiments, the mold comprises a negative mold. In some embodiments, the predetermined temperature is about 100° Celsius (C) to about 600° C. In some embodiments, the predetermined pressure is about 2 pounds per square inch (psi) to about 140 psi. In some embodiments, the predetermined time is about 3 minutes to about 30 minutes. In some embodiments, the predetermined pressure is about 3.5 psi, and wherein the predetermined temperature is about 370° C. In some embodiments, forming a plurality of channels within the first membrane and fusing the second membrane to the first membrane comprises: placing the first membrane and the second membrane in a frame, wherein the first membrane and the second membrane are generally parallel, generally aligned, and separated by a gap distance; and striking one or more points on the first membrane with a fusion tool, wherein the fusion tool is heated to a set fusion temperature, and wherein the fusion tool contacts the membrane for a set fusion time during each strike. In some embodiments, striking the first membrane pierces the first membrane, the second membrane, or both and fuses a portion of the first membrane to the second membrane. In some embodiments, the frame encompasses at least a portion of the outer edges of the first membrane and the second membrane. In some embodiments, the gap distance is about 300 µm to about 1,200 µm. In some embodiments, the fusion tool has a striking contact area of at least about 0.07 mm2. In some embodiments, the striking one or more points on the first membrane by a fusion tool comprises striking each of the one or more points for at most about 16 times. In some embodiments, the striking one or more points on the first membrane by a fusion tool comprises striking each of the one or more points for 1 to 6 times. In some embodiments, the set fusion temperature is about 250° C. to about 600° C. In some embodiments, the set fusion time is less than about 1 second. In some embodiments, at least one of the first membrane and the second membrane is substantially flat. In some embodiments, the method further comprises embossing the first membrane before the forming of the plurality of channels within the first membrane. In some embodiments, the method further comprises laser ablating a portion of the first membrane and the second membrane within the plurality of channels. In some embodiments, the laser ablation removes the fused portions of the first membrane and the second membrane to form an opening. In some embodiments, the opening has a concentricity with respect to the channel of at most 25% of the diameter of the channel. In some embodiments, at least one of the first membrane and the second membrane comprises PVDF, PTFE, ePTFE, PCL, PE/PES, PP, PS, PMMA, PLGA, PLLA, or any combination thereof. In some embodiments, the method further comprises coating the device with a hydrophilic polymer. In some embodiments, the first membrane is sintered. In some embodiments, the second membrane is not sintered. In some embodiments, the second membrane and the first membrane are fused with a fusion peel force of at least about 0.2 N.

Another aspect provided herein is a method, comprising: contacting a tissue of a diabetic or prediabetic subject with a device comprising an insulin secreting cell population, wherein the device comprises: a first membrane having a first surface comprising a plurality of channels, and a plurality of second surfaces opposing the first surface; and a second membrane opposite and attached to the plurality of the second surfaces of the first membrane; wherein the first membrane and the second membrane form an enclosed compartment having a surface area to the volume ratio of at least about 40 cm−1, and wherein the enclosed compartment provides a volume for housing a cell within the device; and releasing insulin from the insulin secreting cell population in response to an elevated blood glucose level in the diabetic subject, wherein the elevated glucose level is higher than a blood glucose level in a non-diabetic subject.

In some embodiments, the insulin secreting cell population releases an amount of insulin sufficient for a reduction of blood glucose level in the diabetic or prediabetic subject. In some embodiments, the releasing insulin stops when the blood glucose level in the diabetic subject is reduced to a normal level. In some embodiments, the releasing insulin re-starts when the insulin secreting cell population is re-exposed to an elevated blood glucose level in the diabetic subject. In some embodiments, the insulin secreting cell population is a stem cell derived cell population. In some embodiments, the insulin secreting cell population is capable of glucose-stimulated insulin secretion (GSIS). In some embodiments, at least one of the first membrane and the second membrane are semi-permeable. In some embodiments, the semi-permeability of the first membrane, the second membrane, or both is configured to protect the cell from an immune attack. In some embodiments, the semi-permeability of the first membrane, the second membrane, or both is configured to protect the cell from an immune attack in the absence of an immune suppression therapy. In some embodiments, at least one of the first membrane and the second membrane are configured to enable vascularization of the cell within the device. In some embodiments, at least one of the first membrane and the second membrane are configured to enable vascularization of the cell within the device in absence of an immune suppression therapy.

In a certain aspect, described herein, is a cell housing device comprising a first surface defining an exterior surface of the device and having a surface area; a second surface opposite the first surface, wherein the second surface defines an interior surface of the device; and a compartment enclosed within the second surface, wherein the compartment provides a volume for housing a cell within the device; wherein a ratio of the surface area to the volume is equal to or greater than 50 cm$^{-1}$. In some aspects, the device comprises a plurality of channels going through a transverse plane of the device. In some aspects, each channel of the plurality of channels comprises a diameter equal to or greater than 400 µm. In some aspects, the diameter is measured at a narrowest point in the channel. In some aspects, each channel of the plurality of channels is separated from one another by a distance of no more than 450 µm. In some aspects, each channel of the plurality of channels comprises a height to diameter ratio equal to or greater than 0.2. In some aspects, a number of channels per area measured along a transverse plane of the device is greater than 50/cm$^2$. In some aspects, a number of channels per area measured along a transverse plane of the device is greater than 100/cm$^2$. In some aspects, the ratio of the surface area to the volume is greater than 80 cm$^{-1}$. In some aspects, the ratio of the surface area to the volume is greater than 100 cm$^{-1}$. In some aspects, the ratio of the surface area to the volume is greater than 120 cm$^{-1}$. In some aspects, the device comprises a single continuous open space having the volume. In some aspects, the first surface or the second surface comprises a plurality of nodes interconnected by a plurality of fibrils. In some aspects, the device comprises a thickness greater than 300 µm measured along a transverse plane of the device. In some aspects, the first surface or the second surface comprises PVDF, PTFE, ePTFE, PCL, PE/PES, PP, PS, PMMA, PLGA, or PLLA. In some aspects, the device further comprises a frame, wherein the frame is configured to receive the device. In some aspects, the frame is configured to receive a plurality of cell housing devices. In some aspects, the frame comprises a flexing mechanism to prevent buckling of the cell housing device. In some aspects, the device further comprises a cell population. In some aspects, the cell population is an insulin secreting population. In some aspects, the cell population is a stem cell derived cell that is capable of glucose-stimulated insulin secretion (GSIS).

In some aspects, the device further comprises a coating with hydrophilic polymers. In some aspects, the volume for housing the cell is inversely proportional to at least one of the diameter of the plurality of channels and a number of channels per area of the device. In some aspects, the ratio of the surface area to the volume of the device is directly proportional to at least one of the diameter of the plurality of channels and a number of channels per area of the device. In some aspects, the ratio of the surface area to the volume of the device enables a greater mass transport into and/or out of the device. In other aspects, described herein, is a cell housing device, comprising a base; a top surface opposite the base; a height extending from the base to the top surface along a transverse plane of the device, wherein the height is greater than 300 µm; a compartment for housing a cell, wherein the compartment is enclosed between the base and the top surface; and a plurality of channels extending along the transverse plane of the device, wherein a maximum oxygen diffusion distance of the device is less than 150 µm. In some aspects, the device comprises a height greater than 600 µm. In some aspects, the base is substantially flat. In some aspects, each channel of the plurality of channels comprises a diameter equal to or greater than 400 µm. In some aspects, each channel of the plurality of channels is separated from one another by a distance of no more than 450 µm. In some aspects, each channel of the plurality of channels comprises a diameter equal to or greater than 400 µm. In some aspects, the diameter is measured at a narrowest point in the channel. In some aspects, each channel of the plurality is separated from one another by a distance of no more than 450 µm. In some aspects, each channel of the plurality comprises a height to diameter ratio equal to or greater than 0.2. In some aspects, a number of channels per area measured along the transverse plane of the device is greater than 50/cm$^2$. In some aspects, a number of channels per area measured along a transverse plane of the device is greater than 100/cm$^2$. In some aspects, the device comprises a single continuous compartment for housing the cell. In some aspects, the first surface or the second surface comprises a plurality of nodes interconnected by a plurality of fibrils. In some aspects, the first surface or the second surface comprises PVDF, PTFE, ePTFE, PCL, PE/PES, PP, PS, PMMA, PLGA, or PLLA. In some aspects, the device further comprises a frame, wherein the frame is configured to receive the device. In some aspects, the frame is configured to receive a plurality of cell housing devices. In some aspects, the frame comprises a flexing mechanism to prevent buckling of the cell housing device. In some aspects, the device further comprises a cell population. In some aspects, the cell population is an insulin secreting population. In some aspects, the cell population is a stem cell derived cell that is capable of glucose-stimulated insulin secretion (GSIS). In some aspects, the device further comprises a coating with hydrophilic polymers. In some aspects, the volume for housing the cell is inversely proportional to at least one of the diameter of the plurality of channels and a number of channels per area of the device. In some aspects, the ratio of the surface area to the volume of the device is directly proportional to at least one of the diameter of the plurality of channels and a number of channels per area of the device. In some aspects, the ratio of the surface area to the volume of the device is directly proportional to at least one of the diameter of the plurality of channels and a number of channels per area of the device. In some aspects, a greater ratio of the surface area to the volume of the device enables a greater mass transport into and/or out of the device.

In other aspects, described herein, is a method of manufacturing a cell housing device, comprising providing a first membrane; adjusting a temperature and/or pressure surrounding the first membrane to a predetermined value; deforming the first membrane; and fusing a second membrane to the first membrane, wherein a compartment between the first membrane and the second membrane defines a compartment for housing a cell. In some aspects, the predetermined value is less than 170° Celsius (C). In some aspects, the predetermined value is less than 140 pounds per square inch (psi). In some aspects, the predetermined value is less than 370° C. In some aspects, the predetermined value is less than 5 psi. In some aspects, deforming the first membrane comprises depressing portions of the first membrane with a tool. In some aspects, the tool comprises a substantially flat surface configured to be parallel to the first membrane and a plurality of protrusions on the surface configured to depress portions of the first membrane. In some aspects, each of the plurality of protrusions comprises a cylinder. In some aspects, the tool comprises a tip, wherein the tip has a contact area at a free end. In some aspects, the contact area is equal to or greater than 0.07 mm$^2$. In some aspects, fusing is performed with the tip, wherein the tip presses the first and second membrane in contact with each other for a predetermined time. In some aspects, deforming and fusing is performed with the tip in one step, wherein the tip contacts a first membrane, moves vertically toward a second membrane offset from the first membrane, and presses first and second membrane in contact with each other for a predetermined time. In some aspects, the tip is adjusted to a predetermined value of temperature. In some aspects, the tip presses at a predetermined value of pressure.

In some aspects, the predetermined time is equal or more than 1 second. In some aspects, the cylinder comprises a diameter equal to or greater than 300 µm. In some aspects, the cylinder comprises a height equal to or greater than 300 µm. In some aspects, deforming the first membrane is done without causing breach of the membrane. In some aspects, deforming the first membrane comprises forming a plurality of features on the membrane. In some aspects, each of the plurality of features comprises a diameter equal to or greater than 300 µm. In some aspects, each of the plurality of features comprises a depth equal to or greater than 300 µm. In some aspects, the method further comprises adjusting the temperature and/or pressure surrounding the first membrane to control characteristics of the feature. In some aspects, increasing the temperature and/or pressure surrounding the first membrane increases a depth of the feature. In some aspects, fusing the second membrane to the first membrane comprises fusing the second membrane and the first membrane into one continuous layer. In some aspects, fusing the second membrane to the first membrane is undertaken at a temperature and/or pressure having a second predetermined value. In some aspects, the second predetermined value is less than 230° Celsius (C). In some aspects, the second membrane is substantially flat. In some aspects, subsequent to deforming, the first membrane is embossed. In some aspects, subsequent to fusing, the device has a substantially flat surface and an embossed surface opposite the substantially flat surface. In some aspects, the method further comprises removing fused portions of the first membrane and the second membrane via laser ablation, thereby forming channels traversing through the device. In some aspects, the method further comprises mounting the device on a frame. In some aspects, the method further comprises implanting the device on the frame into a subject. In some aspects, the method further comprises encapsulating the cell within the compartment. In some aspects, the method further comprises implanting the device into a subject. In some aspects, the first membrane or the second membrane comprises PVDF, PTFE, ePTFE, PCL, PE/PES, PP, PS, PMMA, PLGA, or PLLA. In some aspects, the method further comprises coating the device with hydrophilic polymers. In some aspects, the first membrane is sintered. In some aspects, the second membrane is not sintered.

In other aspects, described herein, is a cell housing device, comprising a base, a top surface opposite the base, a height extending from the base to the top surface along a transverse plane of the device, wherein the height is equal to or less than 300 µm, and a compartment for housing cells, wherein the compartment is enclosed between the base and the top surface. In some aspects, the height is less than 250 µm. In some aspects, the base comprises a sintered membrane. In some aspects, the top surface comprises a sintered membrane. In some aspects, the base comprises a coated membrane, wherein the coating increases the hydrophilicity of the membrane. In some aspects, the device comprises at least one fused dot, wherein the dot comprises fusing a portion of the base and a portion of the top surface corresponding to the portion of the base and wherein the dot is configured to limit a change to the height. In some aspects, the dot has a diameter of about 0.5 mm to about 3 mm. In some aspects, the dot has a diameter of at least about 0.5 mm. In some aspects, the dot has a diameter of at most about 3 mm. In some aspects, the dot has a diameter of about 0.5 mm to about 0.75 mm, about 0.5 mm to about 1 mm, about 0.5 mm to about 1.25 mm, about 0.5 mm to about 1.5 mm, about 0.5 mm to about 1.75 mm, about 0.5 mm to about 2 mm, about 0.5 mm to about 2.25 mm, about 0.5 mm to about 2.5 mm, about 0.5 mm to about 2.75 mm, about 0.5 mm to about 3 mm, about 0.75 mm to about 1 mm, about 0.75 mm to about 1.25 mm, about 0.75 mm to about 1.5 mm, about 0.75 mm to about 1.75 mm, about 0.75 mm to about 2 mm, about 0.75 mm to about 2.25 mm, about 0.75 mm to about 2.5 mm, about 0.75 mm to about 2.75 mm, about 0.75 mm to about 3 mm, about 1 mm to about 1.25 mm, about 1 mm to about 1.5 mm, about 1 mm to about 1.75 mm, about 1 mm to about 2 mm, about 1 mm to about 2.25 mm, about 1 mm to about 2.5 mm, about 1 mm to about 2.75 mm, about 1 mm to about 3 mm, about 1.25 mm to about 1.5 mm, about 1.25 mm to about 1.75 mm, about 1.25 mm to about 2 mm, about 1.25 mm to about 2.25 mm, about 1.25 mm to about 2.5 mm, about 1.25 mm to about 2.75 mm, about 1.25 mm to about 3 mm, about 1.5 mm to about 1.75 mm, about 1.5 mm to about 2 mm, about 1.5 mm to about 2.25 mm, about 1.5 mm to about 2.5 mm, about 1.5 mm to about 2.75 mm, about 1.5 mm to about 3 mm, about 1.75 mm to about 2 mm, about 1.75 mm to about 2.25 mm, about 1.75 mm to about 2.5 mm, about 1.75 mm to about 2.75 mm, about 1.75 mm to about 3 mm, about 2 mm to about 2.25 mm, about 2 mm to about 2.5 mm, about 2 mm to about 2.75 mm, about 2 mm to about 3 mm, about 2.25 mm to about 2.5 mm, about 2.25 mm to about 2.75 mm, about 2.25 mm to about 3 mm, about 2.5 mm to about 2.75 mm, about 2.5 mm to about 3 mm, or about 2.75 mm to about 3 mm. In some aspects, the dot has a diameter of about 0.5 mm, about 0.75 mm, about 1 mm, about 1.25 mm, about 1.5 mm, about 1.75 mm, about 2 mm, about 2.25 mm, about 2.5 mm, about 2.75 mm, or about 3 mm. In some aspects, the dot is spaced at least 3 mm from another fused dot. In some aspects, the dot is formed with an adhesive placed in between the portion of the base and the portion of the top surface. In some aspects, a volume of the compartment is inversely proportional to at least one of the diameter of the dots and a number of dots per area of the device. In some aspects, a ratio of a surface area of the device to a volume of the device is directly proportional to at least one of the diameter of the dots and a number of dots per area of the device. In some aspects, a greater ratio of the surface area to the volume of the device enables a greater mass transport into and/or out of the device.

In other aspects, described herein, is a method, comprising: a) contacting a tissue of a diabetic subject with a device comprising an insulin secreting cell population, wherein the device comprises: a first surface defining an exterior surface of the device and having a surface area; a second surface opposite the first surface, wherein the second surface defines an interior surface of the device; and a compartment enclosed within the second surface, wherein the compartment provides a volume for housing a cell within the device; wherein a ratio of the surface area to the volume is equal to or greater than 50 $cm^{-1}$; and b) releasing insulin from the insulin secreting cell population in response to an elevated blood glucose level in the diabetic subject, wherein the elevated glucose level is higher than a blood glucose level in a non-diabetic subject. In some aspects, the insulin secreting cell population releases an amount of insulin sufficient for a reduction of blood glucose level in the diabetic subject. In some aspects, the releasing insulin stops when the blood glucose level in the diabetic subject is reduced to a normal level. In some aspects, the releasing insulin re-starts when the insulin secreting cell population is re-exposed to an elevated blood glucose level in the diabetic subject. In some aspects, the insulin secreting cell population is a stem cell derived cell population. In some aspects, the insulin secreting cell population is capable of glucose-stimulated insulin secretion (GSIS).

In other aspects, described herein, is a method, comprising: a) contacting a tissue of a diabetic subject with a device comprising an insulin secreting cell population, wherein the wherein the device comprises: a base; a top surface opposite the base; a height extending from the base to the top surface along a transverse plane of the device, wherein the height is greater than 300 µm; a compartment for housing a cell, wherein the compartment is enclosed between the base and the top surface; and a plurality of channels extending along the transverse plane of the device, wherein a maximum oxygen diffusion distance of the device is less than 150 µm; and b) releasing insulin from the insulin secreting cell population in response to an elevated blood glucose level in the diabetic subject, wherein the elevated glucose level is higher than a blood glucose level in a non-diabetic subject. In some aspects, the insulin secreting cell population releases an amount of insulin sufficient for a reduction of blood glucose level in the diabetic subject. In some aspects, the releasing insulin stops when the blood glucose level in the diabetic subject is reduced to a normal level. In some aspects, the releasing insulin re-starts when the insulin secreting cell population is re-exposed to an elevated blood glucose level in the diabetic subject. In some aspects, the insulin secreting cell population is a stem cell derived cell population. In some aspects, the insulin secreting cell population is capable of glucose-stimulated insulin secretion (GSIS).

In other aspects, described herein, is a method, comprising: a) contacting a tissue of a diabetic subject with a device comprising an insulin secreting cell population, wherein the wherein the device comprises: a base; a top surface opposite the base; a height extending from the base to the top surface along a transverse plane of the device, wherein the height is equal to or less than 300 µm; and a compartment for housing cells, wherein the compartment is enclosed between the base and the top surface; and b) releasing insulin from the insulin secreting cell population in response to an elevated blood glucose level in the diabetic subject, wherein the elevated glucose level is higher than a blood glucose level in a non-diabetic subject. In some aspects, the insulin secreting cell population releases an amount of insulin sufficient for a reduction of blood glucose level in the diabetic subject. In some aspects, the releasing insulin stops when the blood glucose level in the diabetic subject is reduced to a normal level. In some aspects, the releasing insulin re-starts when the insulin secreting cell population is re-exposed to an elevated blood glucose level in the diabetic subject. In some aspects, the insulin secreting cell population is a stem cell derived cell population. In some aspects, the insulin secreting cell population is capable of glucose-stimulated insulin secretion (GSIS).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 9 illustrates the fusing of first membrane after deformation step with a flat second membrane and an image of a fused first and second membrane, in accordance with some embodiments.

FIG. 39 shows an ePTFE cell housing device without a frame that is filled until bursting and a graph of filling pressure (psi) at failure for a PVDF and an ePTFE cell housing device prototype, in accordance with some embodiments;

FIG. 41 shows an example of a protocol for forming a hydrophilic coating on the surface of the membranes, in accordance with some embodiments;

FIG. 55 shows a set up to scale up the coating process along with a dry and a wet coated membrane, in accordance with some embodiments;

FIG. 61A shows an image of an ultrathin device with high flux ePTFE membranes with a hydrophilic coating and filled with 8 million SC islet cells, in accordance with some embodiments;

FIG. 61B shows an H&E stained image of high density of cells throughout the device, including the core of the device after 90 days of implantation in a NSG mouse model, in accordance with some embodiments;

FIG. 61C shows an H&E stained image of high density of cells throughout the device, including the core of the device after 90 days of implantation in a NSG mouse model, in accordance with some embodiments;

FIG. 73 shows an ultrathin device with a fused dot in the center of the device designed for implantation in a mouse, in accordance with some embodiments;

FIG. 74A and FIG. 74B show various configurations of the macrodevice frame for holding multiple cell housing devices, in accordance with some embodiments;

FIG. 75A shows an ultrathin device for human implantation with an array of fused spots that provide an adhesive restraint, in accordance with some embodiments;

FIG. 75B shows a set up with porous metal platens to provide external restraint for the ultrathin devices, in accordance with some embodiments;

FIG. 76A shows a configuration of an ultrathin device with an adhesive restraint.

FIG. 76B shows a configuration of an ultrathin device with an external porous restraint.

FIG. 77 shows the mass flow rate measured from filling of ultrathin devices for human implantation with 3.3 mm dot pitch with or without external porous restraint, in accordance with some embodiments;

FIG. 78 shows an H&E stained image of the cells distribution throughout the entire ultrathin device with adhesive restraint, similar to the device shown in FIG. 75A, in accordance with some embodiments;

FIG. 79A shows exemplary configurations of hexagonal ultrathin devices with no dots, in accordance with some embodiments;

FIG. 79B shows a detailed view of exemplary configurations of hexagonal ultrathin devices with no dots, in accordance with some embodiments;

FIG. 80 shows the amount of cells that can fill a single ultrathin device with no dots, as in FIG. 79A, and with 3.3 mm dot array matrix, as in FIG. 79B, in accordance with some embodiments;

FIG. 84A shows examples of subcutaneous placement of the ultrathin devices, in accordance with some embodiments;

FIG. 84B shows examples of pre-peritoneal placement of the ultrathin devices, in accordance with some embodiments;

FIG. 85 shows images of mini-pigs 2 weeks after the subcutaneous (SQ) and pre-peritoneal (PP) implantation of ultrathin devices, in accordance with some embodiments;

FIG. 99B shows an image of a thermoformed membrane, in accordance with some embodiments;

FIG. 100 shows a bar graph showing the feature height of an exemplary membrane, in accordance with some embodiments;

FIG. 101 shows a bar graph showing the fusion peel force of exemplary membranes formed using a fusion tool, in accordance with some embodiments;

FIG. 102A shows a line graph of a differential scanning calorimetry analysis of exemplary membranes formed using a fusion tool, in accordance with some embodiment;

FIG. 102B shows an electron micrograph of exemplary sintered and non-sintered membranes, in accordance with some embodiments;

FIG. 103 shows an illustration of a non-load cell enabled tool for the thermal fusion of the membranes, by spot welding, in accordance with some embodiments;

FIG. 104 shows an image of an exemplary channel array device with inconsistent fusion using a non-load cell enabled positional based fusion tool, in accordance with some embodiments;

FIG. 105A shows a stress-strain curve of a channel array curve made using a non-load cell enabled positional based fusion tool with inconsistent fusion, wherein the fusion strength decreases across the channel array device, in accordance with some embodiments;

FIG. 105B shows an image of an exemplary channel array device in a peel test, in accordance with some embodiments;

FIG. 106A shows an image of an exemplary channel array device made using a non-load cell enabled positional based fusion tool, wherein the fused area does not align with the laser drilled area, in accordance with some embodiments;

FIG. 106B shows an image of an exemplary channel array device made using a non-load cell enabled positional based fusion tool, wherein a leak was detected in a leak test post fusion and repaired using an adhesive, in accordance with some embodiments;

FIG. 107 shows an image of an exemplary channel array device with a single row made using the load cell enabled load/force based fusion tool, in accordance with some embodiments;

Figure 108:
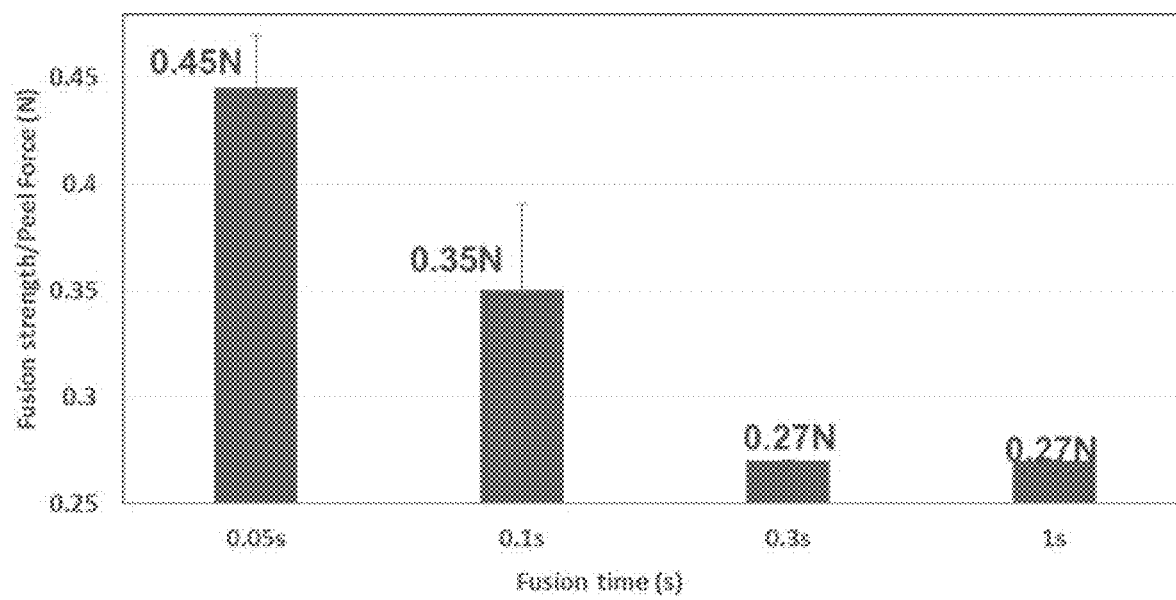
Figure 109:
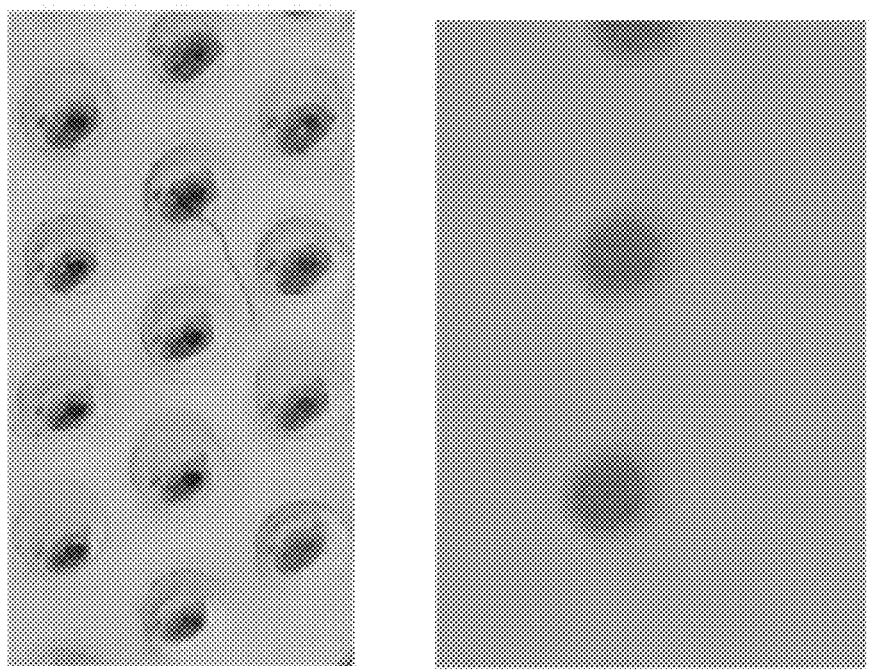
Figure 110:
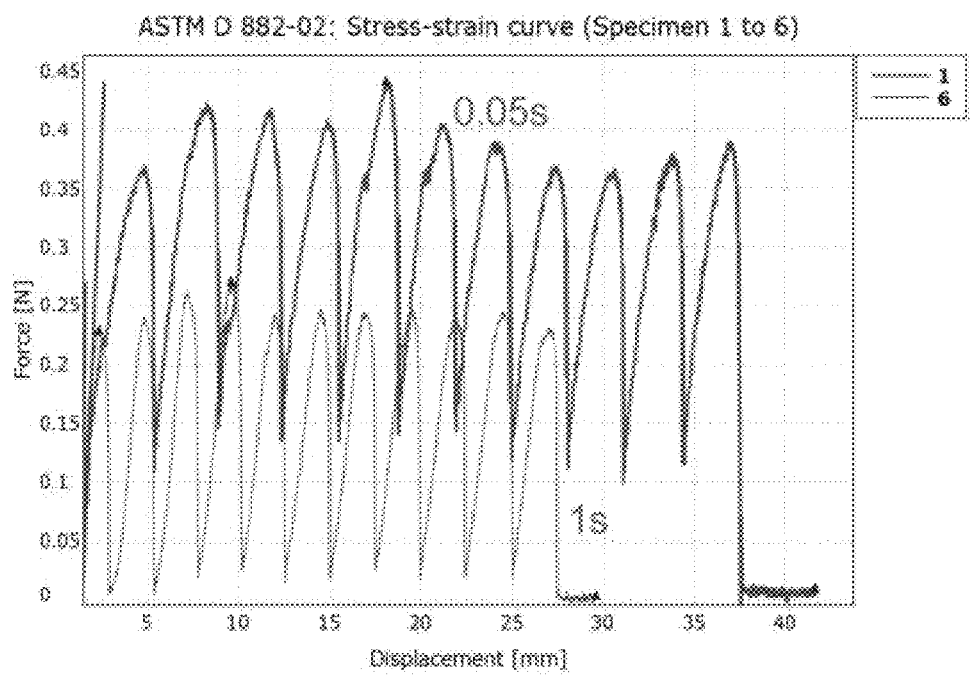
Figure 111:
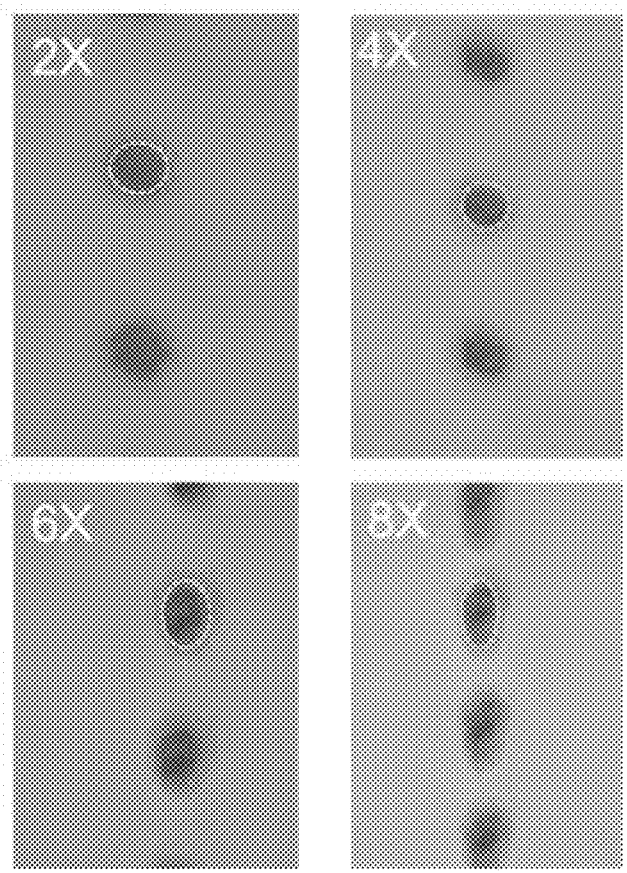
Figure 112:
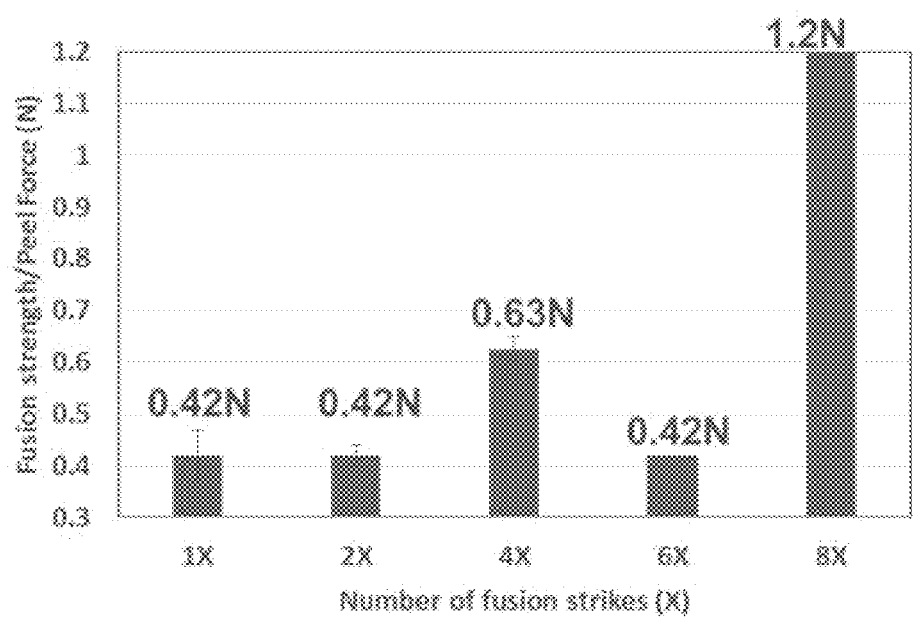
Figure 113:
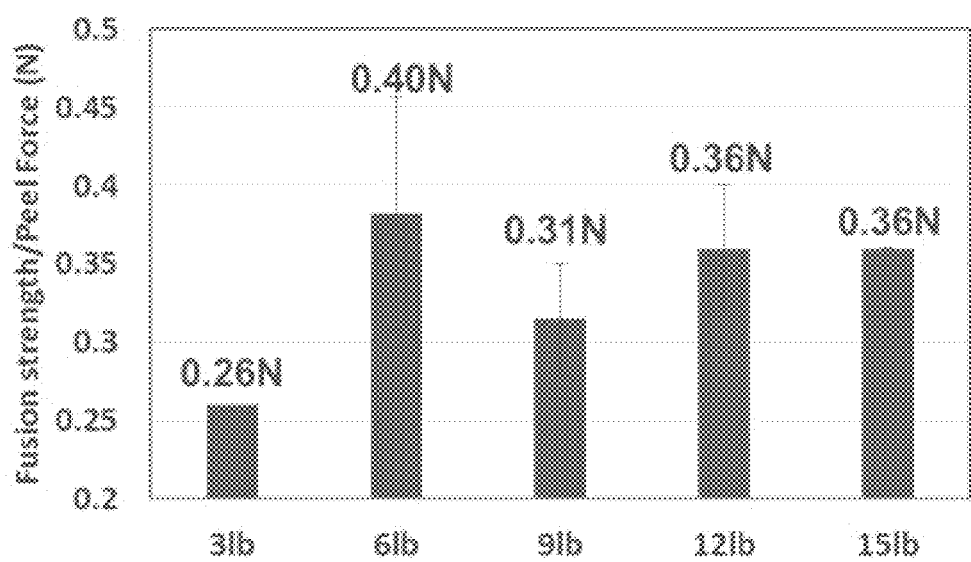
Figure 114:
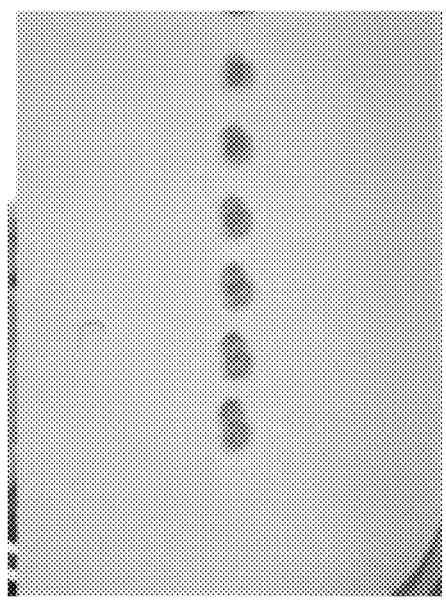
Figure 115:
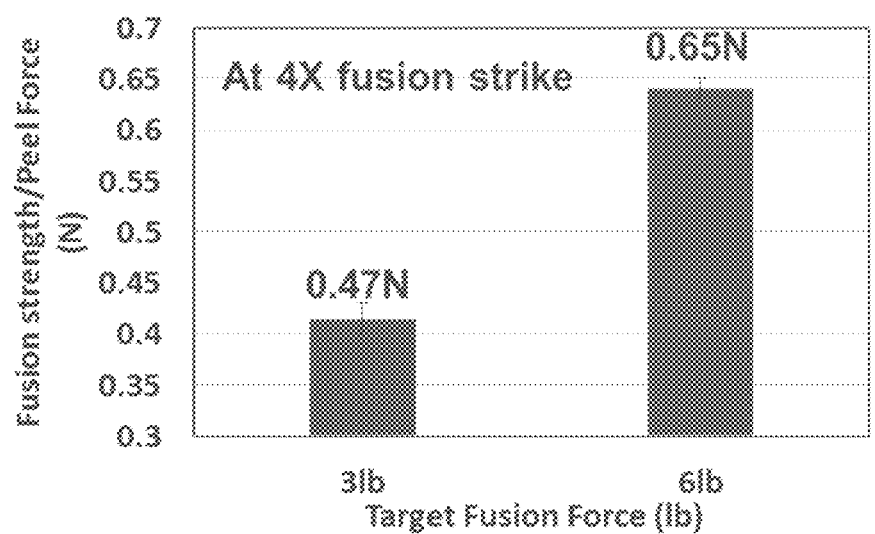
Figure 116:
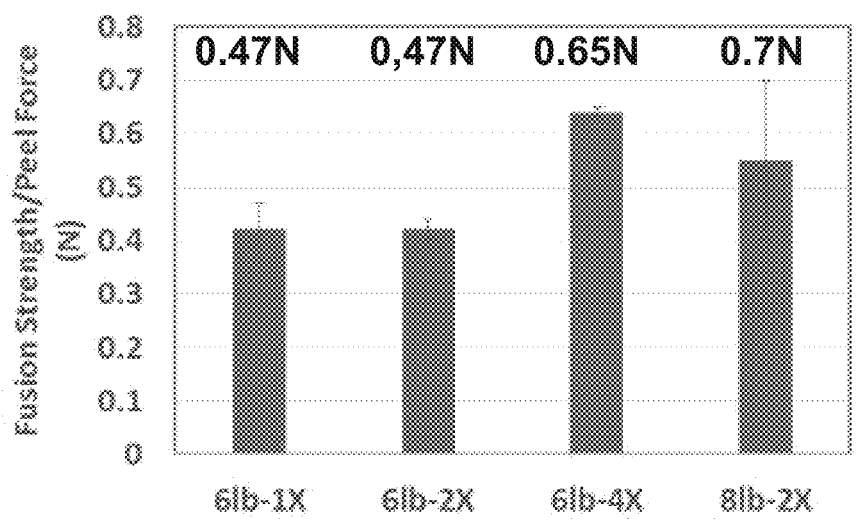
Figure 117A:
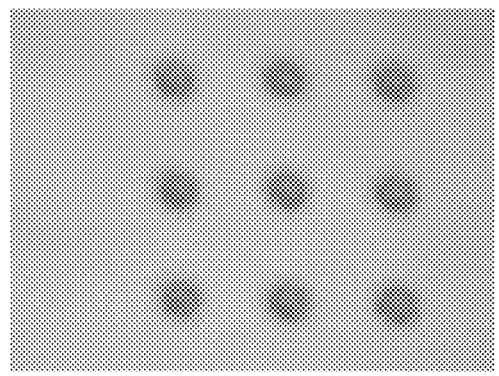
Figure 117B:
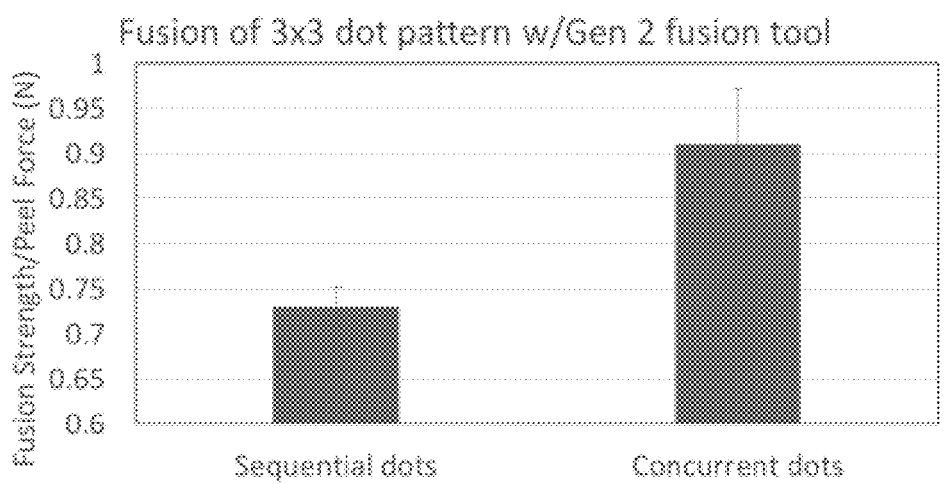
Figure 118:
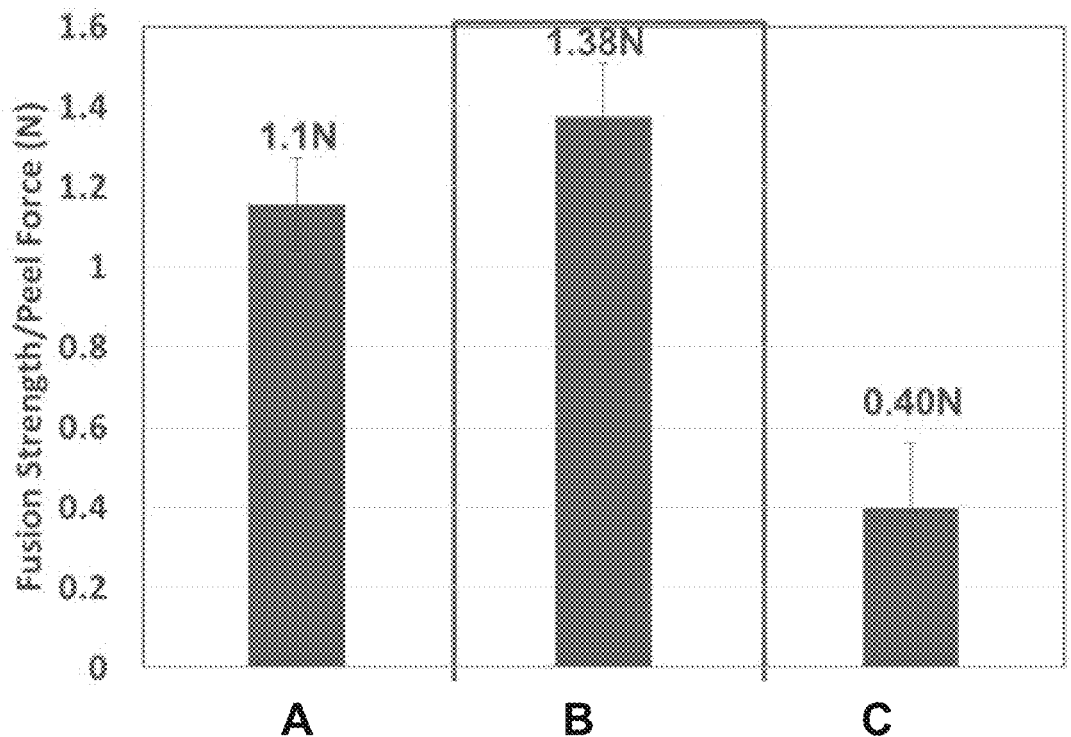
Figure 119:
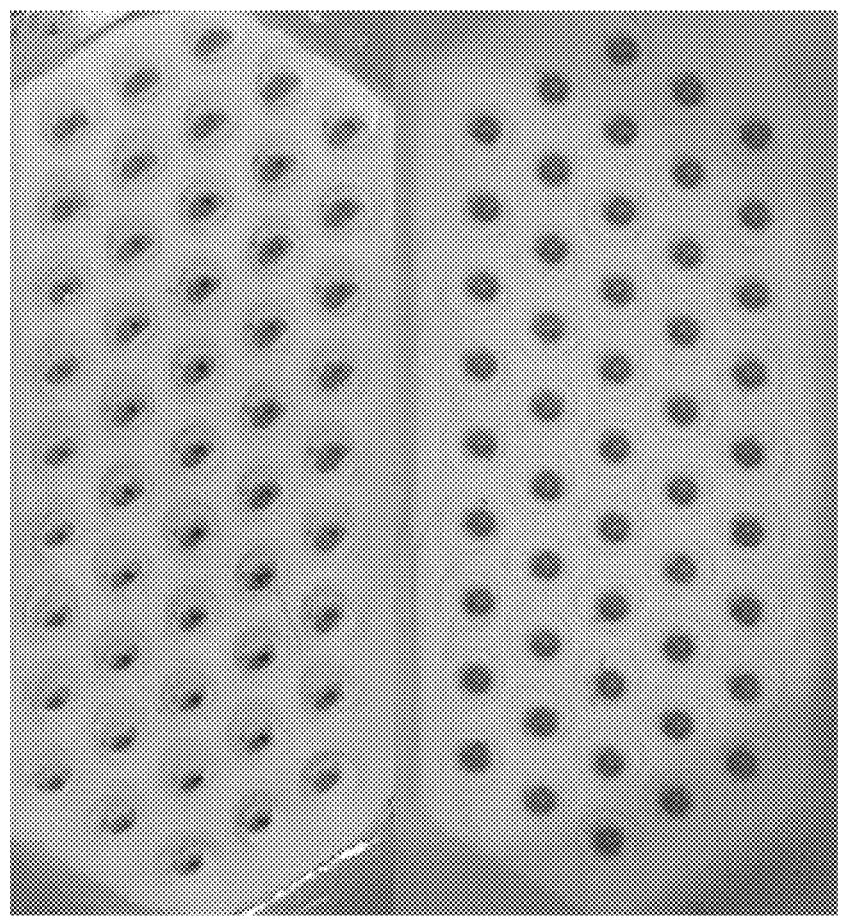
Figure 120:
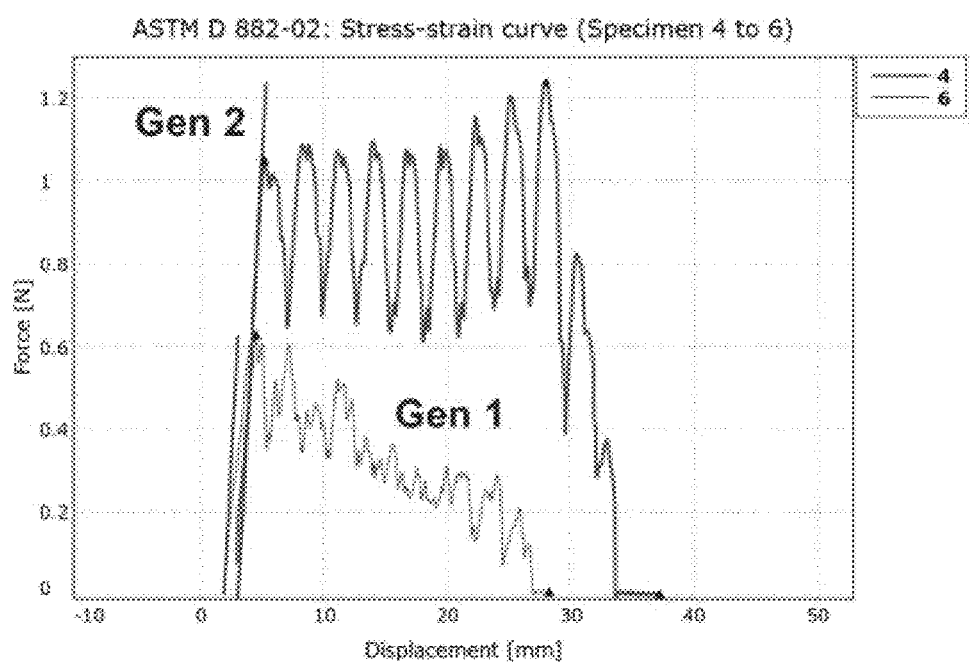
Figure 121:
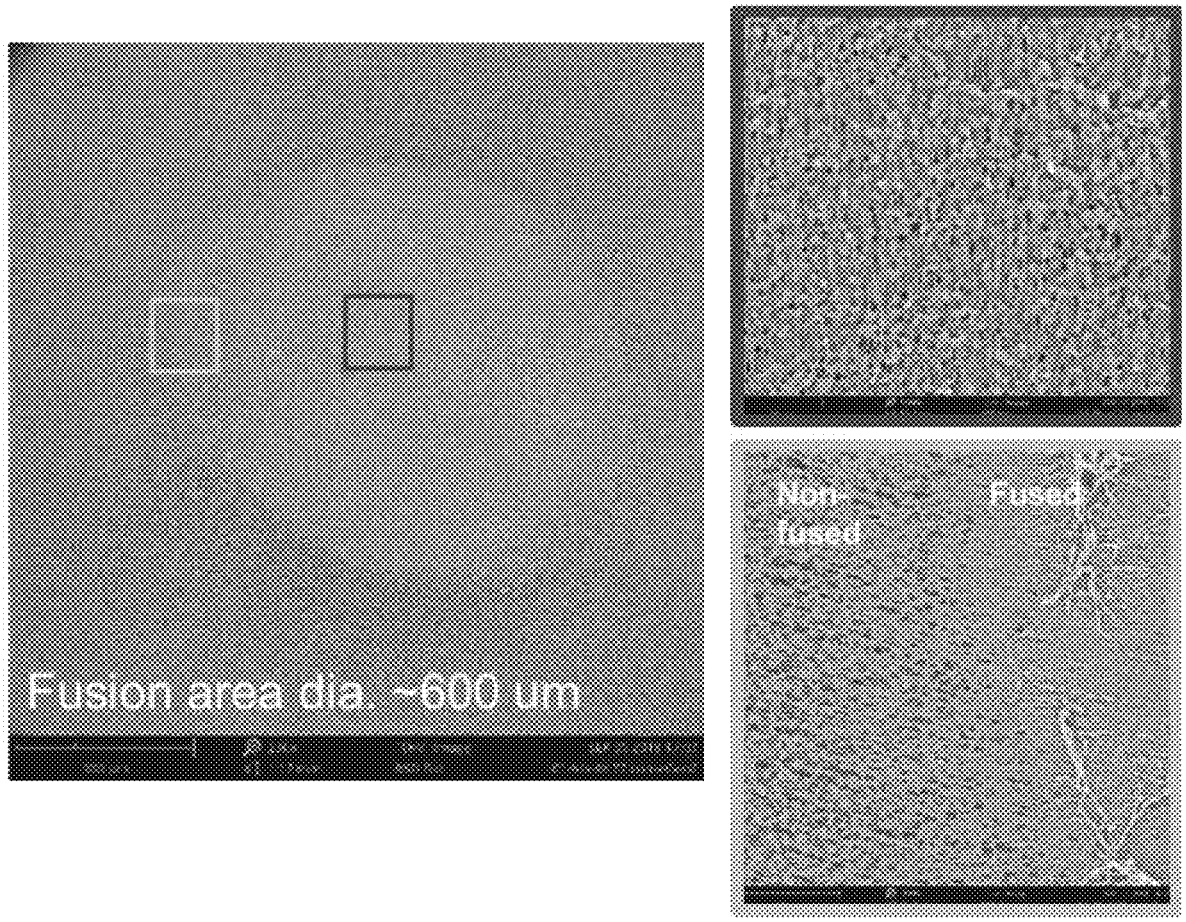
Figure 122A:
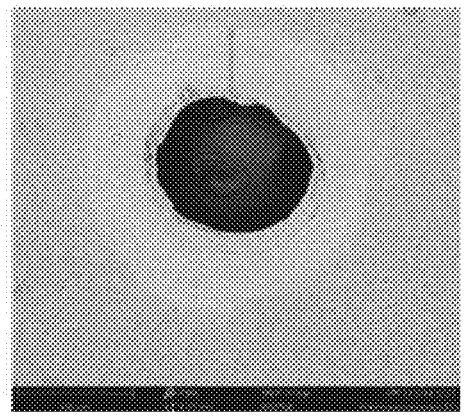
Figure 122B:
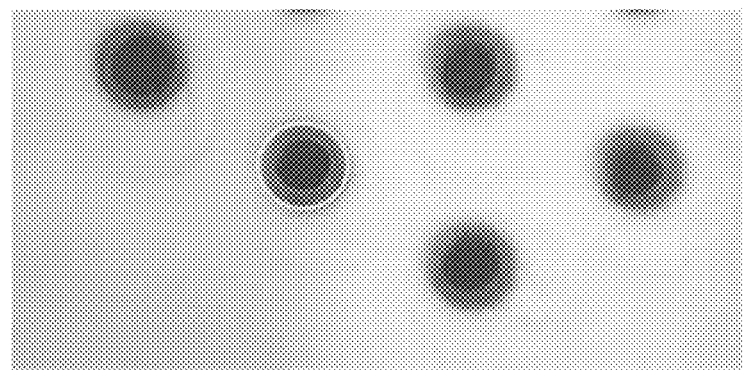
Figure 123:
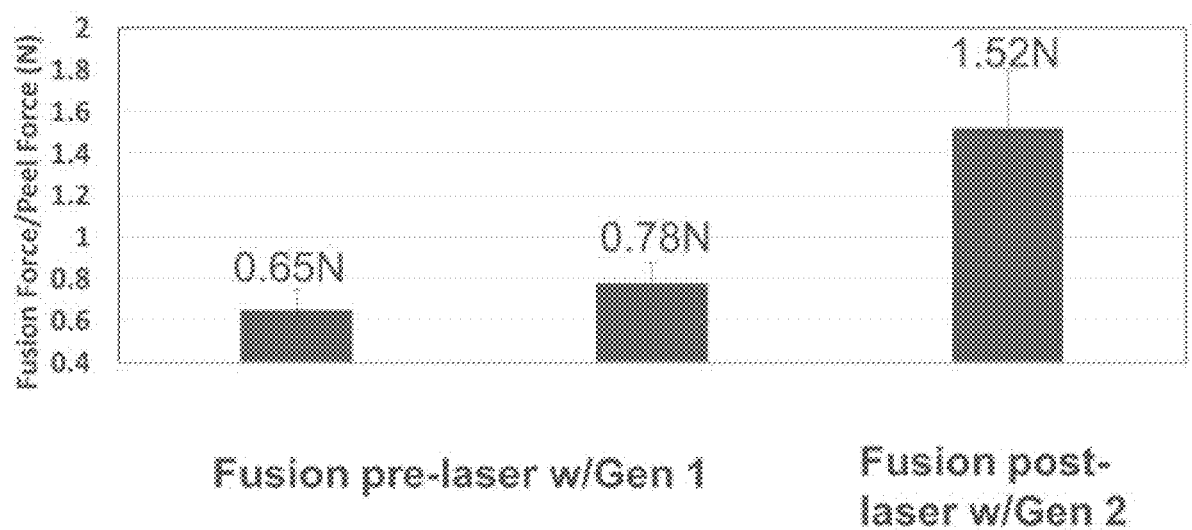

FIG. 108 shows a bar graph measuring the fusion strength/peel force (N) against fusion time of channel array devices made using the load cell enabled load/force based fusion tool, in accordance with some embodiments;

FIG. 109 shows an image of an exemplary channel array device with an array design and a fusion strength of about 0.4-0.6N (left), and an image of an exemplary channel array device with a single row design and a fusion strength of about 0.45N (right), in accordance with some embodiments;

FIG. 110 shows a stress-strain curve of an exemplary channel array device with a first deformed membrane and a second flat membrane, in accordance with some embodiments;

FIG. 111 shows images of exemplary the channel array devices made using 2×, 4×, 6×, or 8× fusion strikes, in accordance with some embodiments;

FIG. 112 shows a bar graph measuring the fusion strength/peel force (N) versus the number of fusion strikes used to fuse a first deformed membrane and a second flat membrane using the load cell enabled load/force based fusion tool at a fusion temperature of 800° F., a fusion time of 0.05 seconds, and a fusion force was 6 lb, in accordance with some embodiments;

FIG. 113 shows a bar graph measuring the fusion strength/peel force (N) versus the fusion force of exemplary channel array devices with a first deformed membrane and a second flat membrane at a fusion temperature of 800° F., a fusion time was 0.05 seconds, and a fusion strike number was 1×, in accordance with some embodiments;

FIG. 114 shows an image of an exemplary channel array device with a first deformed membrane and a second flat membrane made using the load cell enabled fusion tool in a pull test, wherein there is membrane drag resulting in double fusion dots, in accordance with some embodiments;

FIG. 115 shows a bar graph showing the fusion strength/peel force (N) versus the target fusion force using a 4× fusion strike of exemplary channel array devices, in accordance with some embodiments;

FIG. 116 shows a bar graph showing the fusion strength/peel force (N) of exemplary channel array devices, in accordance with some embodiments;

FIG. 117A shows an image of an exemplary channel array device with a 3×3 array of current dots, in accordance with some embodiment herein, in accordance with some embodiments;

FIG. 117B shows a bar graph showing the fusion strength/peel force (N) of exemplary channel array devices, in accordance with some embodiments;

FIG. 118 shows a bar graph showing the fusion strength/peel force (N) of exemplary channel array devices, in accordance with some embodiments;

FIG. 119 shows an image of an exemplary channel array device in a peel test, wherein the fusion points remaining intact while the membrane tears, in accordance with some embodiments;

FIG. 120 shows a stress-strain curve for exemplary channel array devices made using the non-load cell enabled or load cell enabled fusion tools, in accordance with some embodiments;

FIG. 121 shows an image of the fused and non-fused areas of a membrane using the load cell enabled fusion tool, in accordance with some embodiments;

FIG. 122A shows an image of a channel of an exemplary channel array device, made using the load cell enabled fusion tool, showing the average seal/shelf size of a fusion point, in accordance with some embodiments;

FIG. 122B shows an image of an exemplary channel array device, made using the load cell enabled fusion tool, showing concentricity between the laser drill hole and the fusion area in a fusion point, in accordance with some embodiments; and FIG. 123 shows a bar graph showing the fusion force/peel force (N) of pre-laser channel array devices made using generation 1 and generation 2 fusion tools, in accordance with some embodiments.

DETAILED DESCRIPTION OF THE DISCLOSURE

The present disclosure generally relates to medical devices and methods. The medical devices may include cell housing devices, devices related thereto, and methods of manufacturing and utilizing such devices. The devices may help provide improved mass transport between the environment outside and inside the device.

In some instances, the cell housing devices may comprise a high surface area to volume ratio. The high surface area to volume ratio may enable the device to provide improved mass transport into and/or out of the device such that nutrients can be delivered to cells within the device with greater effectiveness. In some instances, a cell housing device may comprise a first surface. The first surface may define an exterior surface of the device and having a surface area. The cell housing device may also comprise a second surface opposite the first surface, wherein the second surface defines an interior surface of the device. The cell housing device may also comprise a compartment enclosed within the second surface, wherein the compartment provides a volume for housing the cell within the device. The device may comprise a single continuous open space having the volume. The first surface or the second surface of the device may comprise a plurality of nodes interconnected by a plurality of fibrils. The device may also comprise a plurality of channels going through a transverse plane of the device. The channels may provide a high surface area to volume ratio for the cell housing device. Each channel may comprise a diameter equal to or greater than 400 µm, where the diameter may be measured at a narrowest point in the channel. Each channel of the plurality may be separated from one another by a distance of no more than 450 µm. The device may comprise a thickness greater than 250 µm measured along a transverse plane of the device. In some instances, the channels may be such that a thickness of the cell housing device is not an issue for mass transport (e.g., of nutrients) into and/or out of the device. The first surface or the second surface of the device may comprise PVDF, PTFE, ePTFE, PCL, PE/PES, PP, PS, PMMA, PLGA, or PLLA. The device may further comprise a frame, wherein the frame is configured to receive one or a plurality of cell housing devices. The frame may comprise a flexing mechanism to prevent buckling of the cell housing device. The device may comprise a coating with hydrophilic polymers. The volume for housing the cell may be inversely proportional to at least one of the diameter of the plurality of channels and a number of channels per area of the device. The ratio of the surface area to the volume of the device may be directly proportional to at least one of the diameter of the plurality of channels and a number of channels per area of the device. The ratio of the surface area to the volume of the device may enable a greater mass transport into and/or out of the device.

In some instances, the cell housing devices may comprise a short oxygen diffusion distance. This low oxygen diffusion distance may be independent of a dimension of the cell housing device, such as its thickness. For example, the cell housing device may comprise a base and a top surface opposite the base. A compartment for housing cells may be enclosed between the base and the top surfaces, and in some instances may rely on mass transport from outside the cell to access nutrients for sustenance. A height extending from the base to the top surface along a transverse plane of the device may be of a high value, for example, greater than 300 µm. Regardless, the oxygen diffusion distance for the device may be less than 150 µm. In some instances, this may be enabled by various channels or lumens of the device. The channels may in some instances extend across the transverse plane of the device and may enable the device to have a low oxygen diffusion distance regardless of a thickness of the device. The base may be substantially flat.

Figure 1:
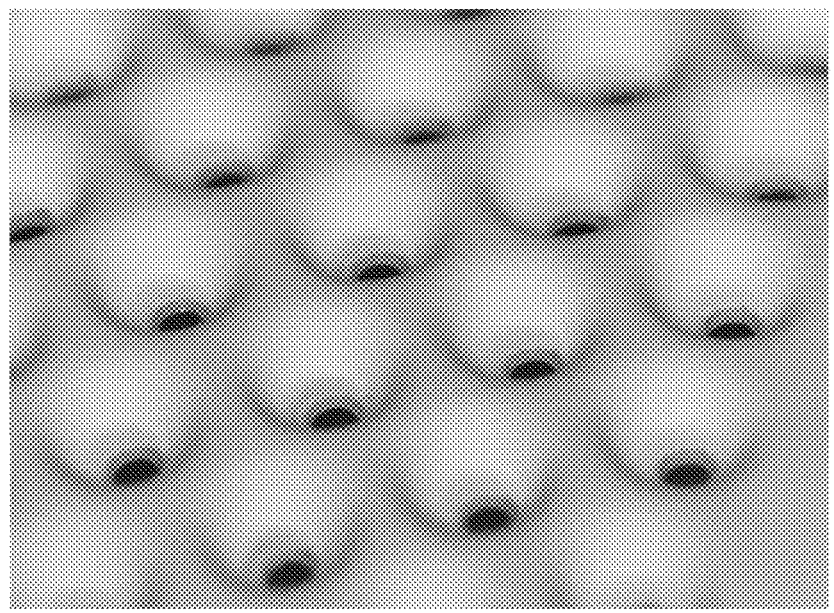
FIG. 1 shows a high magnification image of a polyvinylidene fluoride (PVDF) cell housing device, in accordance with some embodiments.

The cell housing devices described herein may be manufactured utilizing two membranes. In one step, a first membrane may be provided using various materials described herein. In some instances, the first membrane may be provided within a chamber in which a temperature and/or pressure may be set and/or adjusted to a predetermined value. The first membrane may be deformed (e.g., to form a compartment or volume for housing the cells). Afterwards, a second membrane may be fused to the first membrane to form the compartment. Optionally, an aperture may be created within the channels of the device to allow a continuous passage through the cell housing device using various means such as lasers. In some instances, the temperature and/or pressure may be adjusted for deforming the first membrane or for fusing the first membrane to the second membrane. The temperature and/or pressure utilized in each of these processes may be an integral part of manufacturing the cell housing device. Adjusting the temperature and/or pressure of the deformation or fusion area may control characteristics of the feature. In some instances, increasing the temperature and/or pressure of the deformation or fusion area may increase a depth of the feature. In some instances, subsequent to deforming, the first membrane may be embossed. In some instances, subsequent to fusing, the device may have a substantially flat surface and an embossed surface opposite the substantially flat surface. FIG. 1 show a high magnification image of a cell housing device made with PVDF membranes and with a regularly-spaced array of apertures within the channels of the device. Deforming the membrane may further, or alternatively comprise defibrillation, wherein nodes from one membrane unwind and interact with fibrils from another, creating entanglement and a seal.

As described above, devices encapsulating cells that produce various biological products may be of great utility, e.g., for delivering therapeutics. The devices may be referred to herein as cell housing devices and may comprise a matrix housed therein. The matrix can be a biomaterial in the interior space of the cell housing device. The matrix may comprise a hydrogel, a porous sponge, electrospun fibers, a polymeric material, or other porous biocompatible material. The matrix may further comprise growth factors, nutrients, or other agents to enhance the activity of cells and synthesis of biological products. The matrix may be laden with cells or other protein expression systems, such as a cell-free expression system, to enable production of biological products. As the thickness of the matrix increases, the availability of oxygen and other nutrients may decrease further away from the edge surfaces of the matrix. For example, this may happen when the transport of oxygen or nutrients relies mainly on passive transport or diffusion. This may result in very low or no nutrients delivered to regions in the matrix far away from the surface. The availability of nutrients can be further depleted by consumption by cells as the nutrient passes through the matrix. The decrease in nutrients within the matrix may be problematic for cells or systems with a high demand for oxygen or other nutrients. Oxygen consumption by the cells can increase over the basal state with a stimulus as the cells become very active after the stimulus. The decreased availability of nutrients important for cell viability and activity may limit the increase in dimension of the matrix and the cell housing device that encase the matrix. The mass transport limitation within the matrix may restrict the scaling up of device size to increase the output of the biological products. Decreasing a density of cells within the matrix to reduce consumption generally may not desirable as the increase in matrix dimension to offset the lower cell density would be impractical.

The design of the cell housing device may be adjusted to control the surface area to volume (SA:V) ratios of the devices. In some instances, designs may be provided to increase the SA:V ratios of the present devices. The increase in the SA:V ratio may help improve the transport (e.g., of nutrients) into interior regions of the device. One such design to increase SA:V ration may incorporate channels and/or other geometries through the matrix and the cell housing device. In some instances, the channels may help increase the SA:V ratio of the device and of the matrix housed within the device. The channel can comprise a through hole or a lumen that runs completely from one side to the opposing side of the cell housing device. The channels can be arranged in a pattern, or may be provided without a distinct pattern. As one example, the channels may be provided in an array pattern with a predetermined spacing between the channels. Alternatively, the channels may be provided in a random pattern.

Figure 3:
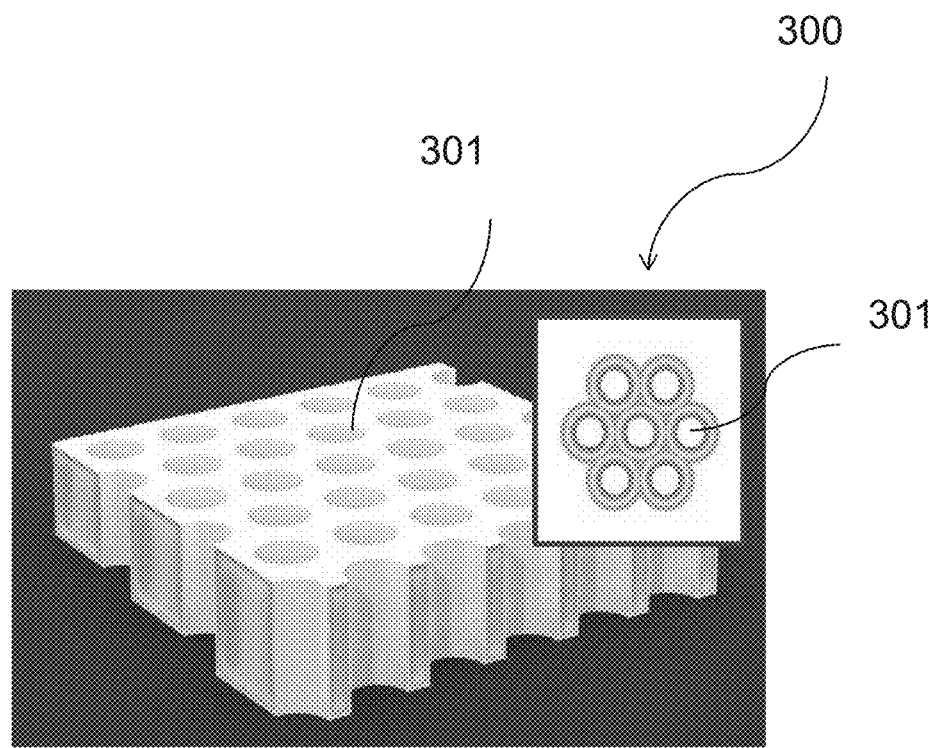
FIG. 3 illustrates zones of varying oxygen pressures within bilayer flat sheet and channel array device, in accordance with some embodiments.

Inclusion of channels to the cell housing device may allow for the device to be scaled up in size more easily than devices without channels. FIG. 3 illustrates zones of varying oxygen pressures within bilayer flat sheet and channel array device. As shown in FIG. 3, a device 300 with an array of channels 301 (also referred to herein as a channel array device) can have channels that run through the matrix and the cell housing device. The cell housing device with channels 300 may be of any thickness but may still avoid having a zone of low oxygen or nutrients. A traditional bilayer flat sheet may be limited in their thickness to 300 µm or less to avoid a zone of low oxygen or nutrients. A cell housing device with channels may have enhanced mass transport and enhanced vascularization potential as compared to the bilayer flat sheet designs or other designs without channels. These features may allow a channel array device to be scaled up in size more easily than devices without channels.

Figure 4:
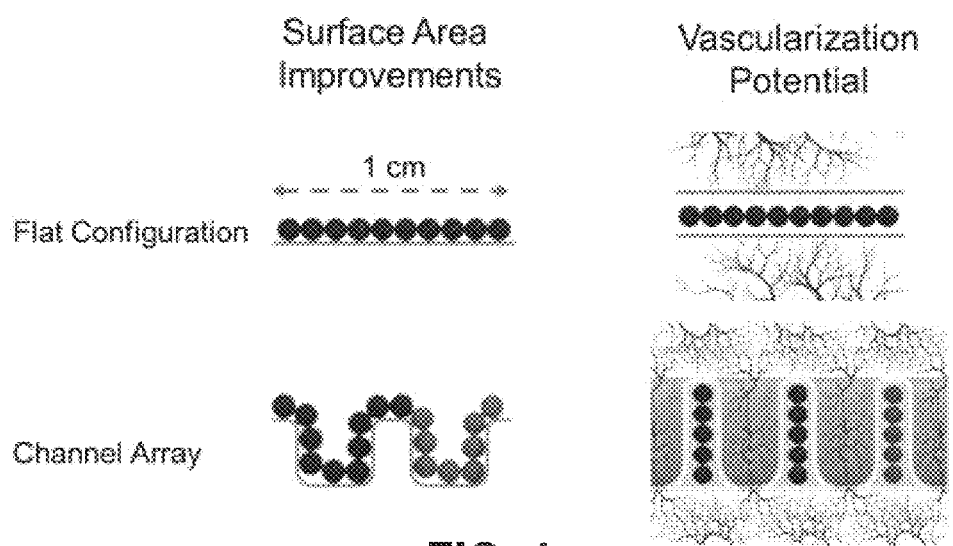
FIG. 4 illustrates surface area and vascularization potential of a device with a flat configuration and a device with a channel array, in accordance with some embodiments.
Figure 5:
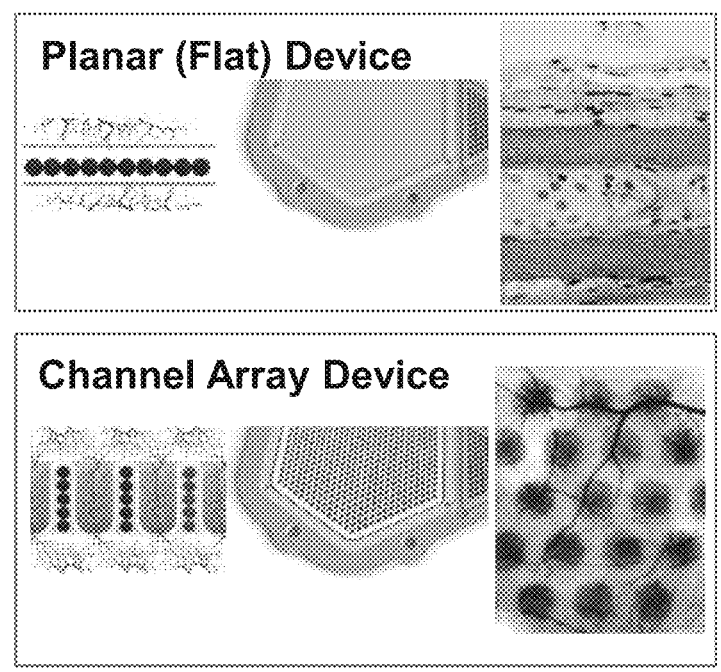
FIG. 5 illustrates devices with a flat configuration or with a channel array device along with increased vascularization, in accordance with some embodiments.
Figure 6:
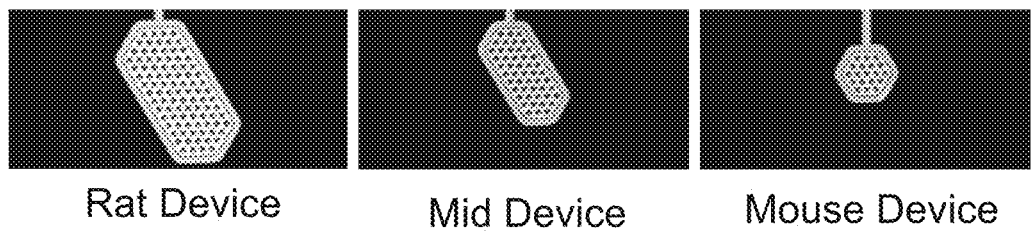
FIG. 6 shows computer aided design (CAD) renderings of hexagonal channel array devices of varying sizes, in accordance with some embodiments.

The cell housing device with channels, also referred to as a channel array device, can provide an increase in surface area for mass transport to occur. The increase in mass transport can provide an increase in overall diffusive flux throughout the matrix and the device. This increase can allow for matrix and devices with larger dimensions having less regions of very low or no nutrients. As a result, the device may have a maximum oxygen diffusion distance that is less than 150 µm. Optionally, the cell housing device with channels may allow for an increased vascularization potential. FIG. 4 illustrates surface area and vascularization potential of a device with a flat configuration and a device with channels. FIG. 5 illustrates devices with a flat configuration for with a device with channels along with increased vascularization. FIG. 6 shows computer aided design (CAD) renderings of hexagonal devices with channels increasing in size but with similar SA:V ratios. As shown in FIG. 4, devices with channels may allow for more cells per area as compared to a device with a flat configuration since the cells can be provided with sufficient nutrients throughout the matrix to support its viability and activity. When implanted in vivo, the channels may allow for vasculature to grow around and through the channel as compared to a device with a flat configuration, where vascularization is limited to top and bottom surfaces of the device, as shown in FIG. 4 and FIG. 5. In some instances, characteristics of the channels and/or a number or density of the channels may allow for increased vascularization. For example, the diameter of the channels may be a cross-section distance of the channel. The diameter of the channels may be measured at its narrowest point in one transverse plane parallel to the plane of the second membrane. The channel density of the device may be a number of channels per area of the device, where the channels may be arranged so that there are a number of channels per area along a transverse plane of the device. The size, number, and/or density of the channels as described herein may provide increased vascularization and enable increased mass transport of nutrients to cells. The cell housing device may protect the matrix and the cells or other contents of the matrix from direct contact with the vasculature in the channels. The design of the array, including its channel size and spacing, can be altered to change surface area and vasculature growth pattern and potential.

The dimensions of the channels may be adjusted to control the volume within the cell housing device and the SA:V ratio. In some embodiments, the diameter of the channels may be increased to decrease the volume within the cell housing device. In turn, the increased diameter of the channels may provide a higher SA:V ratio for the cell housing device. In some embodiments, the diameter of the channels may be decreased to increase the volume within the cell housing device. The decrease in the diameter of the channels may provide a lower SA:V ratio for the cell housing device.

Figure 7:
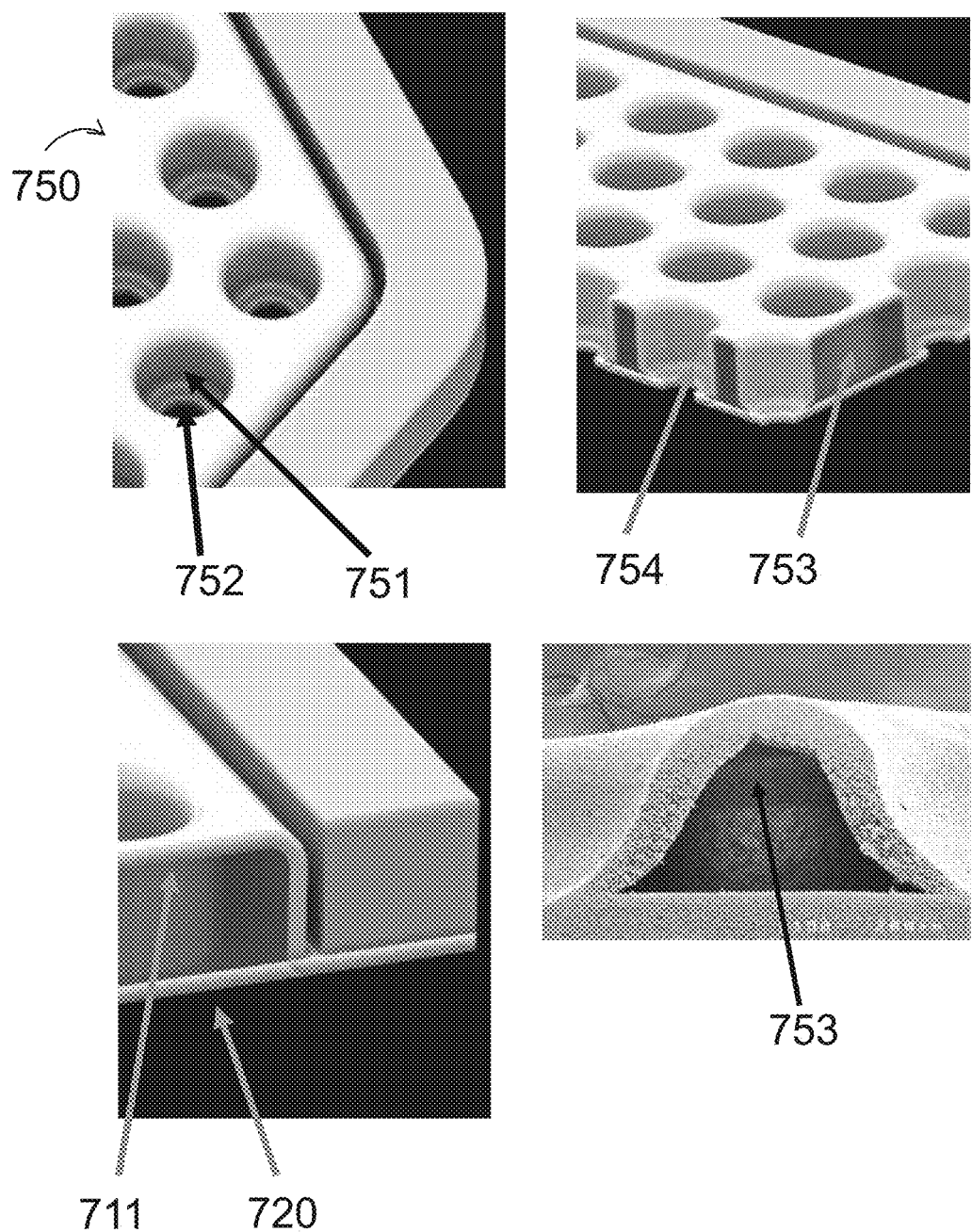
FIG. 7 shows CAD renderings of cell housing devices and a scanning electron micrograph of the cross-section of a cell housing device, in accordance with some embodiments.

The matrix can be connected as one or more pieces housed within the cell housing device. The matrix may comprise a single continuous piece within the cell housing device. The matrix may also have channels running through its thickness at locations where the channels run through the cell housing device. The matrix can be a biomaterial in the interior space of the cell housing device. The matrix may comprise a hydrogel, a porous sponge, electrospun fibers, a polymeric material, or other porous biocompatible material. The matrix may further comprise growth factors, nutrients, or other agents to enhance the activity of cells and synthesis of biological products. The matrix may be laden with cells or other protein expression systems to enable production of biological products. FIG. 7 shows renderings of cell housing devices and a scanning electron micrograph of the cross-section of a cell housing device with connected interior within which the matrix may be housed.

The cell housing device may have various lengths, width, and height appropriate for its application. Length may be the longest dimension on top surface of the device. Width may be the dimension perpendicular to the length on the top surface. The height of the device may also be referred to as thickness of the device and may extend from the base to the top surface along a transverse plane of the device. In some instances, the cell housing device may have a length equal to, or greater than about 0.2 cm, 0.5 cm, 1.0 cm, 1.5 cm, 2.0 cm, 2.5 cm, 3.0 cm, 4.0 cm, 5.0 cm, 6.0 cm, 7.0 cm, 8.0 cm, 9.0 cm, 10 cm, 20 cm, 30 cm, 40 cm, 60 cm, 100 cm, 120 cm, 150 cm, 180 cm, or 200 cm. In some instances, the cell housing device may have a width equal to, or greater than about 0.2 cm, 0.5 cm, 1.0 cm, 1.5 cm, 2.0 cm, 3.0 cm, 4.0 cm, or 5.0 cm, 6.0 cm, 7.0 cm, 8.0 cm, 9.0 cm, or 10 cm. In some instances, the cell housing device may have a height equal to, or greater than about 100 µm, 200 µm, 300 µm, 400 µm, 500 µm, 600 µm, 700 µm, 800 µm, 900 µm, 1000 µm, 0.2 cm, 0.3 cm, 0.4 cm, 0.5 cm, 0.6 cm, 0.7 cm, 0.8 cm, 0.9 cm, 1.0 cm. 2 cm, 3 cm, 4 cm, or 5 cm measured along the transverse plane of the device.

The cell housing device may be designed to have a SA:V ratio appropriate for the transport of nutrients and desired products through the device. In some instances, the SA:V ratio may be equal to or greater than 50 $cm^{-1}$. In other instances, the SA:V ratio may be equal to, or greater than about 20 $cm^{-1}$, 40 $cm^{-1}$, 60 $cm^{-1}$, 80 $cm^{-1}$, 100 $cm^{-1}$, 120 $cm^{-1}$, 150 $cm^{-1}$, 200 $cm^{-1}$, 250 $cm^{-1}$, 300 $cm^{-1}$, or any value therebetween. The maximum oxygen diffusion distance of the device may be less than 50 µm, 100 µm, 150 µm, 200 µm, 250 µm, 300 µm, 350 µm, 400 µm, 450 µm, or 500 µm.

In some instances, the channels 751 of the cell housing device 750 may be generally cylindrical in shape. FIGS. 3, 6, and 7 illustrate cylindrical channels within the cell housing devices. Although channels having a cylindrical shape are primarily described herein for illustrative purposes, it is to be understood that the channels may be of any shape, for example, walls of the channel may be generally straight, curved, barrel-shaped, or other shapes. In some instances, the cross-sectional area of the channel may vary from top surface of the first membrane 711 to the base of the second membrane 720 of the cell housing device. In some instances, the device may comprise fused portions 754. For example, the device may comprise a first membrane 711 fused to a second membrane 720, providing a compartment 753 within the cell housing device. The compartment 753 may be filled with cells. In some instances, the fused portion (e.g., portions where the first membrane meet the second membrane) of the channel may be generally circular or other shapes. As described elsewhere herein, in some instances, an opening 752 may be created in fused portions of the membranes to provide a channel going through the cell housing device. The channels as described herein may comprise a cross-section distance, or diameter. Alternatively, the cross-sectional distance of the channels may refer to the diameter when the cross-section of the channel is generally circular. The diameter of the channels may be measured at its narrowest point in one transverse plane parallel to the plane of the second membrane. Alternatively, the diameter may be measured as an average of the channel width along the height of the channel or device. Alternatively, the diameter may be measured at its widest point in one transverse plane parallel to the plane of the second membrane. In some instances, the diameter of the channels can be equal to or greater than 100 µm, 200 µm, 300 µm, 400 µm, 500 µm, 600 µm, 700 µm, 800 µm, 900 µm, or 1000 µm. Optionally, the channels may have a height which is proportional to diameter. In some instances, the height to diameter ratio of a channel may be equal to or greater than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, or 10.

A plurality of channels may go through the transverse plane of the device. The channels may be arranged so that there are a number of channels per area along a transverse plane. The number of channels per area may also be referred to herein as a channel density of the device. In some instances, the number of channels per area along a traverse plane may be equal to or greater than about 10 channels/$cm^2$, 15 channels/$cm^2$, 20 channels/$cm^2$, 25 channels/$cm^2$, 30 channels/$cm^2$, 35 channels/$cm^2$, 40 channels/$cm^2$, 45 channels/$cm^2$, 50 channels/$cm^2$, 60 channels/$cm^2$, 70 channels/ cm², 80 channels/cm², 90 channels/cm², 100 channels/cm², 110 channels/cm², 120 channels/cm², 130 channels/cm², 140 channels/cm², 150 channels/cm², 175 channels/cm², or 200 channels/cm².

The channels can be spaced apart such as to eliminate regions receiving low or no oxygen or other nutrients important for cell viability and activity. In some instances, the channels can be spaced apart or separated from one another by a distance equal to or no more than about 100 µm, 200 µm, 300 µm, 400 µm, 500 µm, 600 µm, 700 µm, 800 µm, 900 µm, or 1000 µm. Optionally, the distance may be measured from the center of one channel to a center to the adjacent channel. In some instances, the cell housing device can have one distance of channel spacing throughout the device. Alternatively, the cell housing device can have a plurality of different distances of channel spacings across the cell housing device. In some instances, the channels can be arranged into a regular array with a regular channel spacing distance across the device. For example, as illustrated on FIG. 6, the channels may be arranged in a hexagonal array. Alternatively, other arrangements of the channels, such as circular, square, etc may be provided.

In some instances, area of the lumen of the channels can be proportional to the cross-sectional area of the channel. The lumens may be cut from a portion of the fused region of the device. In some instances, the area of the lumen may be equal to or greater than about 0, 10, 20, 30, 40, 50, 60, 70, 80, 90, or 99% of the cross-sectional area of the channel.

A plurality of lumens may go through the transverse plane of the device. The lumens may be arranged so that there are a number of lumens per area along a transverse plane. The number of lumens per area may also be referred to herein as a lumen density of the device. In some instances, the number of lumens per area along a traverse plane may be equal to or greater than about 10 lumens/cm², 15 lumens/cm², 20 lumens/cm², 25 lumens/cm², 30 lumens/cm², 35 lumens/cm², 40 lumens/cm², 45 lumens/cm², 50 lumens/cm², 60 lumens/cm², 70 lumens/cm², 80 lumens/cm², 90 lumens/cm², 100 lumens/cm², 110 lumens/cm², 120 lumens/cm², 130 lumens/cm², 140 lumens/cm², 150 lumens/cm², 175 lumens/cm², or 200 lumens/cm².

The channel array device can be applied for various in vivo and in vitro applications. In one example, the device can house cells or expression systems with islet cell-like functions in its matrix. The matrix may comprise isolated islet cells, isolated cells from pancreas, isolated cells from a tissue, stem cells, stem cell-derived cells, induced pluripotent cells, differentiated cells, transformed cells, or expression systems, which can synthesize one or more biological products. Optionally, the matrix may comprise a second type of cells that support the first type of cells that synthesize one or more biological products. The cells can be encapsulated before being placed within the matrix. The cells may be encapsulated in a microcapsule or conformally coated. This device can be used to supplement the islet cell function.

The design of the channel array in the device can affect the vascularization potential or the amount of vasculature that can grow through and around the device. The channels in the device can be designed to increase the vascularization potential. Such devices can have improved transport of nutrients and lower risk for hypoxia for cells housed therein. Such devices can have larger device dimensions, and house larger matrices with cells or other expression systems. Such devices with increased transport can increase cell viability to more than a year after initial production. In some instances, cell viability can be more than 1 month, 2 months, 4 months, 6 months, 8 months, 10 months, 12 months, 14 months, 16 months, 18 months, 20 months, 22 months, 24 months, 36 months, 48 months, or more.

Figure 18:
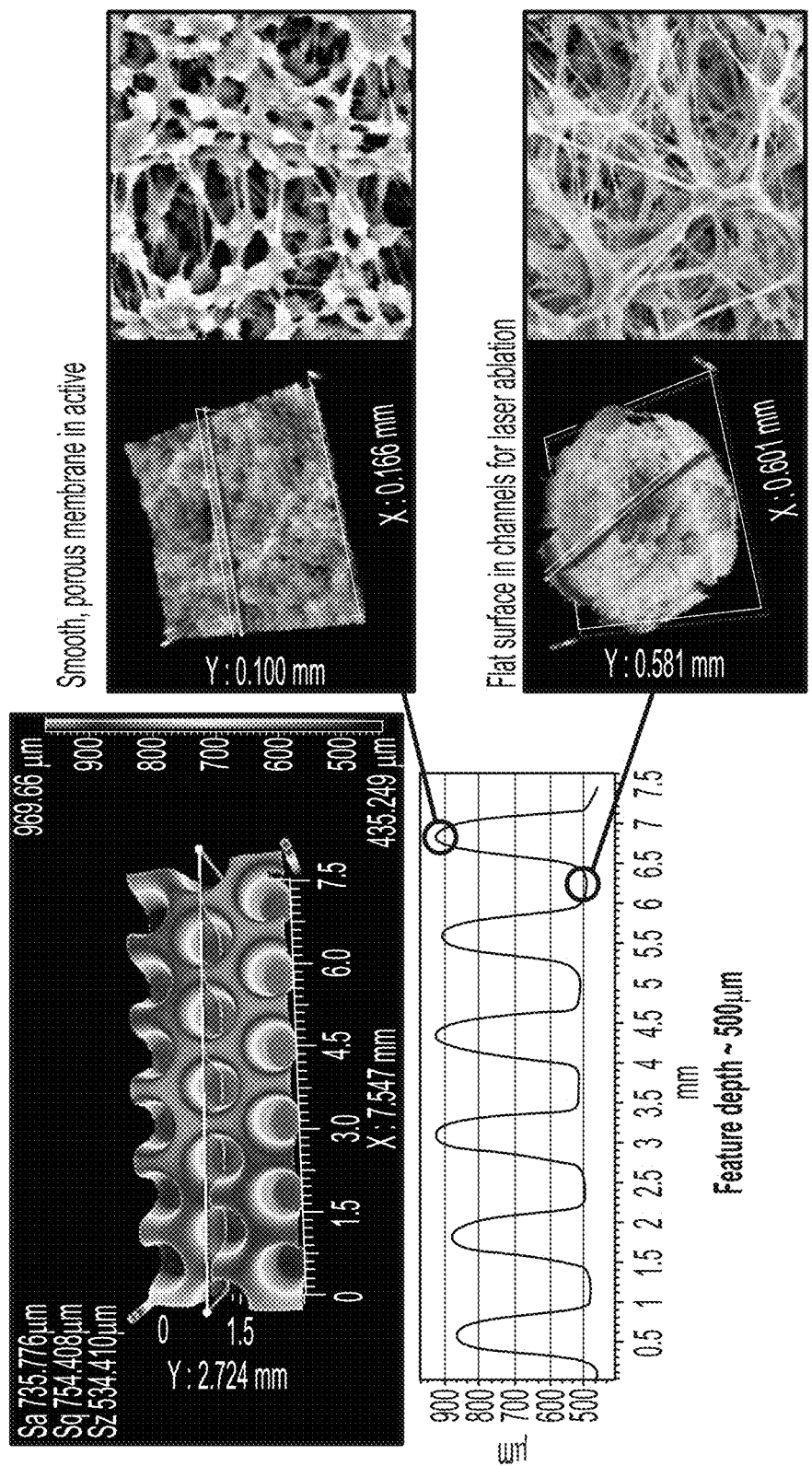
FIG. 18 shows the surface interferometry profile of a cell housing device, in accordance with some embodiments.
Figure 32:
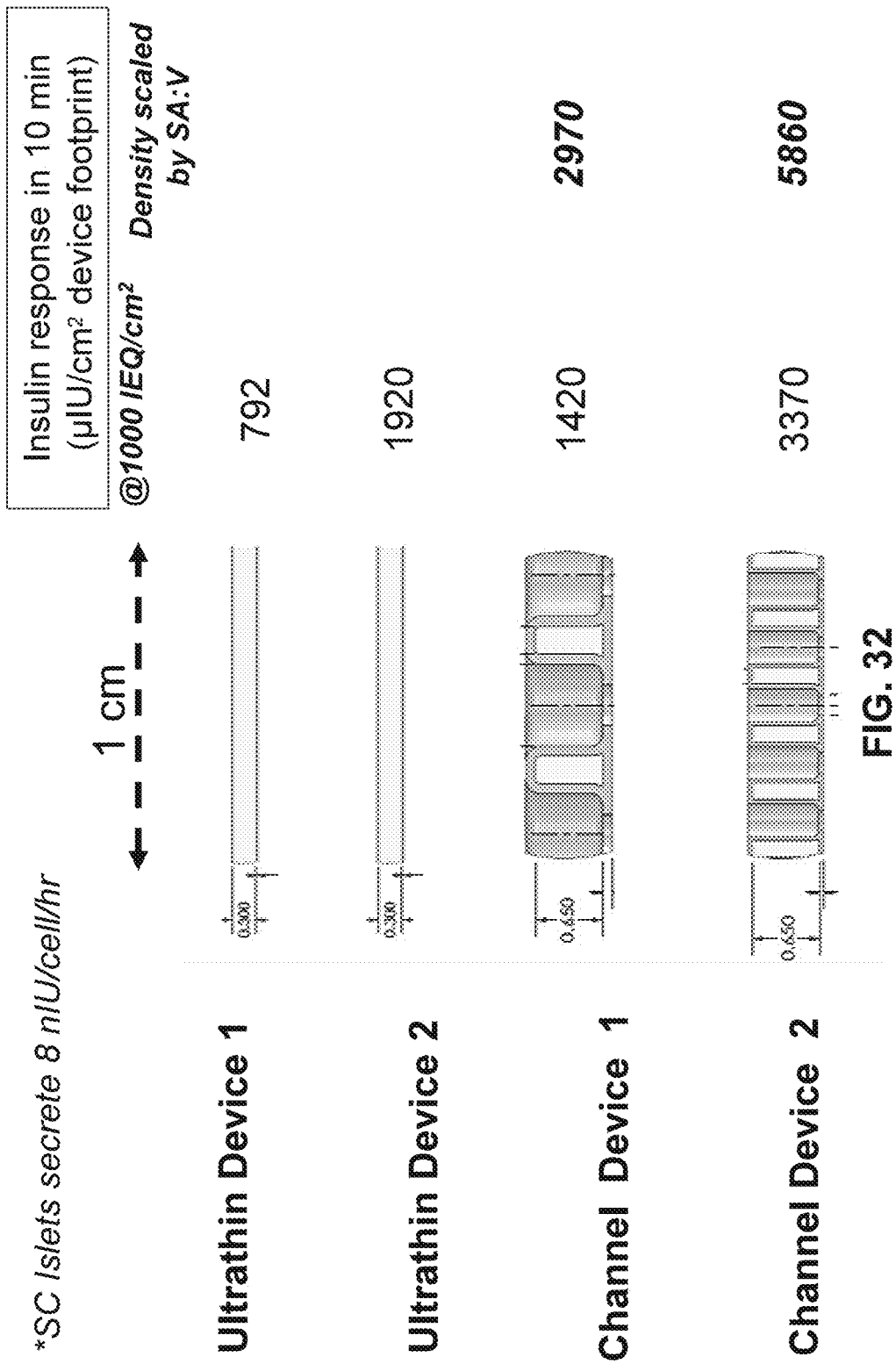
FIG. 32 illustrates the effect of device design on insulin response and surface area to volume ratio, in accordance with some embodiments.
Figure 33:
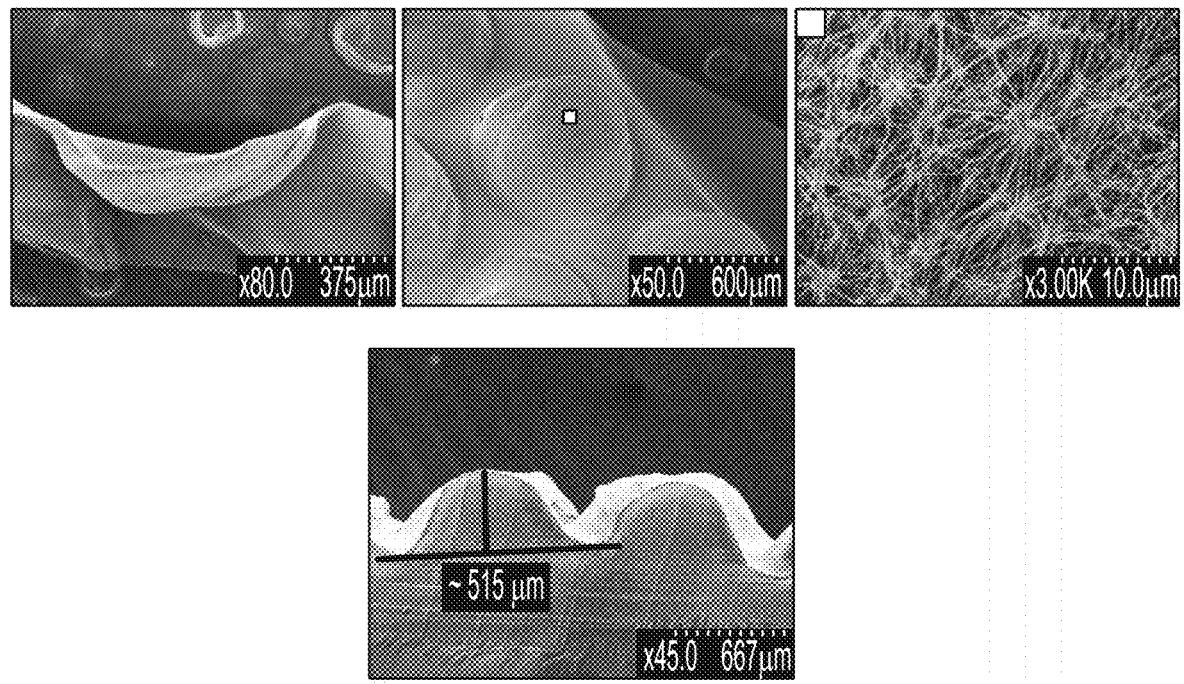
FIG. 33 illustrates the surface area to volume ratio and estimated allowable cluster diameter achievable with the variation in channel density for a channel with a diameter of 500 μm, in accordance with some embodiments.
Figure 34:
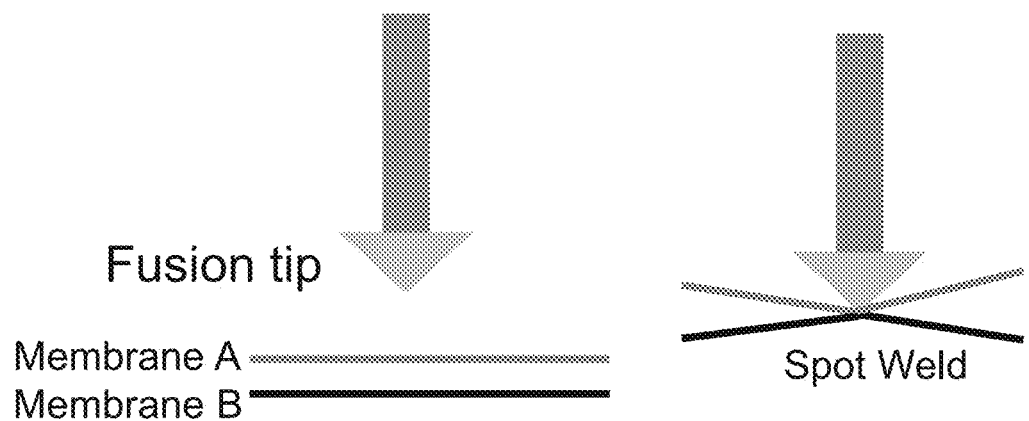
FIG. 34 shows a schematic of fusion process by spot welding of two membranes with a tip, in accordance with some embodiments.
Figure 35:
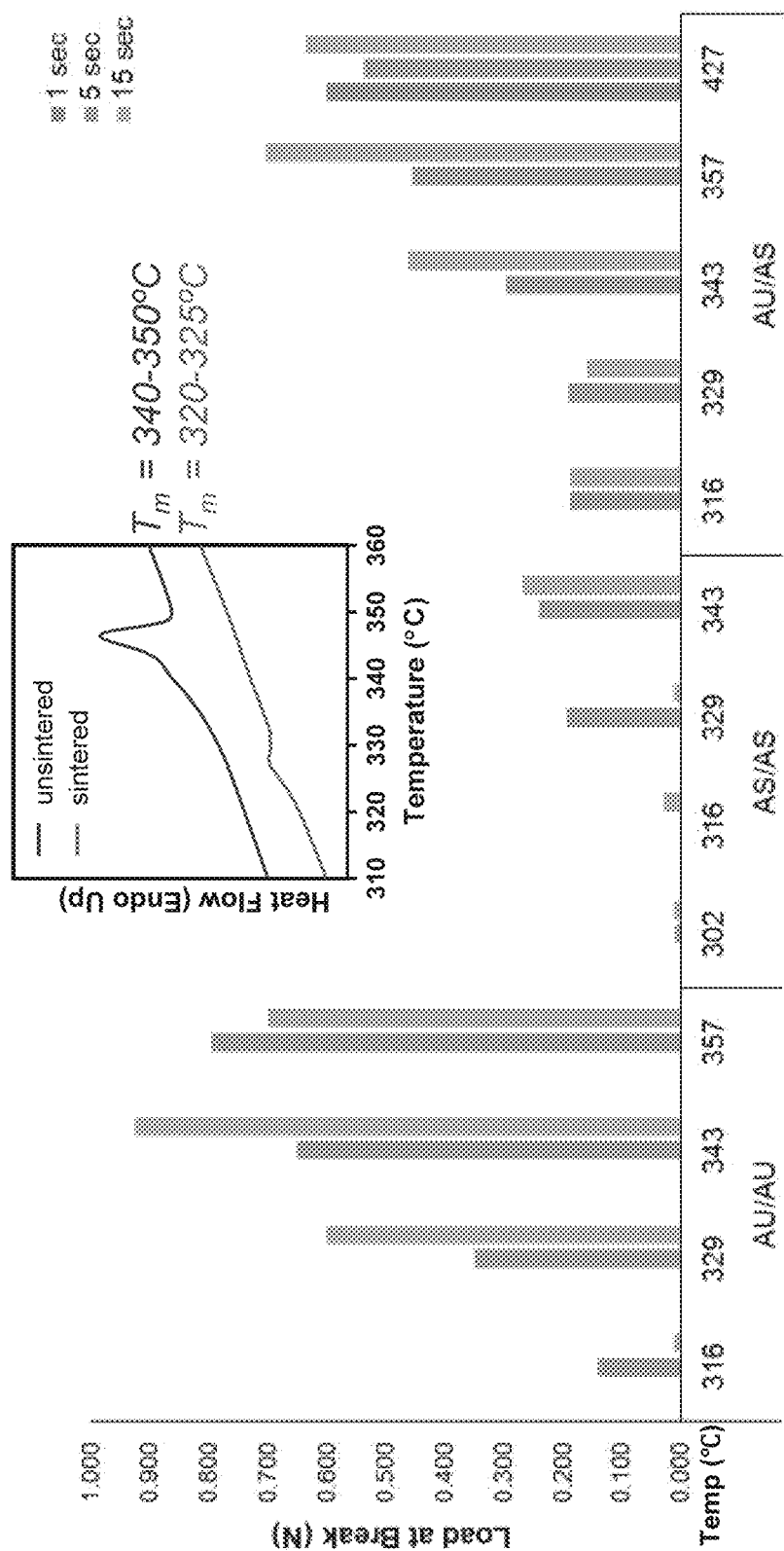
FIG. 35 shows the load at break of two flat ePTFE membranes fused at different temperatures for different lengths of time, in accordance with some embodiments.
Figure 36:
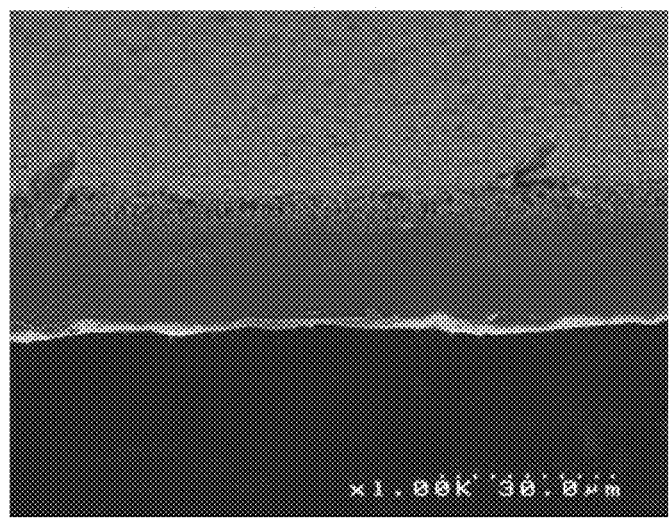
FIG. 36 shows a scanning electron micrograph of the edge of a device that was sealed at 345° C. for 0.5 seconds, in accordance with some embodiments.

The change in the surface area of the channel array device can affect the kinetics of the biological product. The biological product may comprise a human cell, an animal cell, or a genetically modified Due to an increase in surface area, a channel array device can increase the production and release of the biological product. FIG. 32 illustrates the effect of device design on insulin response and surface area to volume ratio. As shown in FIG. 32, a channel array device may increase the production and release of a biological product as compared to a similarly sized device without a channel array. The channel array device may have a higher SA:V ratio than a similarly sized device without a channel array. The increase in SA:V ratio in channel array device may allow for higher biological product flux than in a similarly sized device without a channel array. For matrix with cells with islet cell-like function, the increase in SA:V ratio may allow for higher islet equivalent (IEQ) per area. In some instances, this allows for increased insulin production and increased insulin flux. FIG. 6 shows renderings of hexagonal channel array devices increasing in size with similar SA:V ratios. FIG. 18 shows a rendering of cell housing devices similar overall dimension and variations of channel dimensions to achieve different SA:V ratios.

Figure 50:
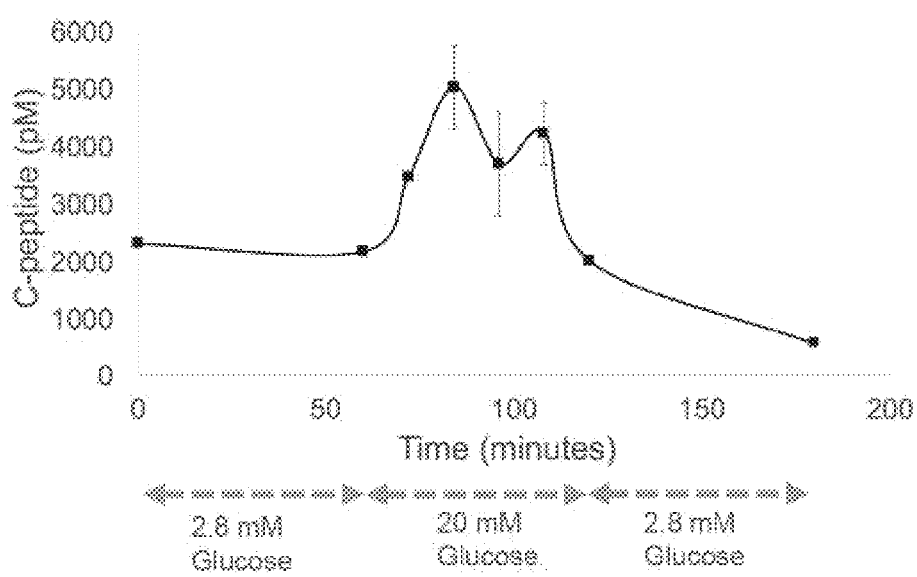
FIG. 50 shows the dynamic GSIS (glucose stimulated insulin secretion) of ultrathin devices with AS-1 membranes, in accordance with some embodiments.

In some instances, the devices described herein can be assembled and/or mounted onto a frame as further described below. The frame may be configured to receive one cell housing device or a plurality of cell housing devices. Optionally, a device can be mounted to a subframe in addition to a frame. The frame may provide a flexible support for the devices of the present disclosure, e.g., the channel array devices. The frame may prevent unwanted folding of the devices. The frame can have one or more flexing mechanisms that prevent buckling of the cell housing device. The flexing mechanisms may prevent buckling of sensitive device regions in the device. The flexing mechanism can have notches that allow for bending of the frame. The flexing mechanism allows the assembly to flex along the tissue at the location of its implantation. Alternatively, the devices described herein may be utilized without a frame. For example, the devices may be implanted in an individual by itself without use of any structural supports or frames. FIG. 50 shows a prototype of three cell housing devices assembled onto a frame for human use. The devices and the frame that hold the devices can be made with materials that elicit low foreign body response. The materials for the devices and the frame can be chosen to reduce inflammation or fibrosis. The devices and the frame can be used with an anti-inflammatory or anti-macrophage therapy to further reduce foreign body response.

The cell housing device can be manufactured using a simple process. In some instances, the cell housing device may be manufactured by deforming a first membrane to the shape of the channel array and fusing a second membrane to the deformed first membrane. In some instances, a tool may be used as a guide to deform the first membrane. In some instances, a tip in the shape of the channel may be used to deform the membrane at a location the tip contacts the membrane.

The membranes may comprise biocompatible porous material. The material for the membranes can allow diffusion of biological product of about 6 kDa or smaller after the manufacturing steps. Alternatively, the material for the membranes may allow diffusion of biological products equal to or smaller than about 2, 4, 6, 8, 10, 12, 14, 16, 18, 20, 25, 30, 35, 40, 45, 50, 60, 70, 80, 90, 100, 200, 300, 400, or 500 kDa after the manufacturing steps. The material for the membranes may have an average pore size equal to or smaller than about 1 nm, 2 nm, 3 nm, 4 nm, 5 nm, 6 nm, 7 nm, 8 nm, 9 nm, 10 nm, 12 nm, 14 nm, 16 nm, 18 nm, or 20 nm after the manufacturing steps.

The manufacturing steps of membrane forming, joining, and cutting can be performed using one or more devices, such as a membrane forming or fusing device. The devices can be made by three dimensional printing process, micromachined, or other machining techniques. In some instances, the devices may be modular. The shape of the devices may in some instances affect the dimension and/or shape of the channels. The devices may comprise a positive and/or a negative mold for membranes (e.g., the first membrane described above). The devise may be made of metal.

The devices may comprise a platform for the membrane. In some instances, the platform may comprise a mold (e.g., negative mold) for the cell housing device. In some instances, the platform may comprise a plate. The platform may further comprise cutouts, or holes into which the membranes may mold into. The cutouts may affect a diameter of the channels (or lumens) to be made for a cell housing device. The platform may in some instances be placed at a predetermined height to offset from a different surface. The different surface may be a surface a membrane is configured to be depressed towards using the devices described herein. This offset height can determine the depth of the channels in the membranes (e.g., first membrane).

The devices may comprise various tools. In some instances, the tool may comprise a tip or a plurality of tips for deforming and/or fusing membranes. The tool can deform the first membrane by depressing portions of the first membrane. The tool can comprise a substantially flat surface configured to be parallel to the first membrane and one or more protrusions on the surface that can deform or depress portions of the first membrane. In some instances, the tool may comprise a plurality of protrusions. Each plurality of protrusions may comprise a cylinder.

An apparatus for manufacturing a cell housing device may be configured to support a membrane (e.g., a first membrane described above). The platform may comprise holes within or below the support, a second membrane may be located. A tool comprising a plurality of protrusions may be configured to couple with the platform. In some instances, the tool may press down upon the support platform. Optionally, the protrusions of the tool may be configured to mate with the holes of the platform. In some instances, a first membrane may be located on top of the platform (e.g., above its holes). The tool may press down upon the first membrane and may form a deformed membrane by pressing portions of the membrane through the holes. In some instances, utilizing a right pressure and/or temperature described herein, the deformed membrane may be fused together with a second membrane.

A chamber of a forming machine that holds various devices (e.g., platforms, and tools discussed above) and membranes for manufacturing a cell housing device. The chamber may be sealed. The chamber may be configured to hold the platform and/or tool. The chamber may provide a predetermined or desired temperature necessary for a membrane fusion to take place. The forming machine may have a sealed chamber with a gas inlet and/or vents. The forming machine may be configured to hold the membranes. For example, the forming machine may comprise a platform. A flat first membrane can be placed within the sealed chamber of the forming machine. Sequentially, or simultaneously as the chamber is heated to a predetermined temperature, a nitrogen gas or other gas may be introduced into the sealed chamber through a gas inlet while the vents are closed to reach a predetermined pressure. Using a tool the membrane may be deformed and a deformed first membrane may be produced. In some instances, vents can be opened after the deforming step is completed to vent the sealed chamber.

As described above, a tool may be used to deform the first membrane. The tool may comprise a single tip, or a plurality of tips. In some instances, a tip in the shape of the channel may be used to deform the membrane at a location the tip contacts the membrane. The tip may be cylindrical, conical, or tapered cylindrical in shape or other shapes. The tip may have a contact area at a free end. The contact area of the tip can contact a membrane. The area of the tip may be equal to or smaller than about 0.5 mm$^2$, 0.6 mm$^2$, 0.8 mm$^2$, 1.0 mm$^2$, 1.2 mm$^2$, 1.4 mm$^2$, 1.6 mm$^2$, 1.8 mm$^2$, 2.0 mm$^2$, 2.2 mm$^2$, 2.4 mm$^2$, 2.6 mm$^2$, 2.8 mm$^2$, 3.0 mm$^2$, 4.0 mm$^2$, or 5.0 mm$^2$. The area of the tip may be equal to or larger than about 0.2 mm$^2$, 0.3 mm$^2$, 0.4 mm$^2$, 0.5 mm$^2$, 0.6 mm$^2$, 0.7 mm$^2$, 0.8 mm$^2$, 0.9 mm$^2$, 1.0 mm$^2$, 1.2 mm$^2$, 1.4 mm$^2$, 1.6 mm$^2$, 1.8 mm$^2$, 2.0 mm$^2$, 2.2 mm$^2$, 2.4 mm$^2$, 2.6 mm$^2$, 2.8 mm$^2$, 3.0 mm$^2$, 4.0 mm$^2$, or 5.0 mm$^2$. The vertical distance that the tip travels after the initial contact with the membrane may help determine the height of the channel. The vertical distance that the tip travels after the initial contact with the membrane may be adjusted to achieve about a predetermined height of the channel.

Figure 8:
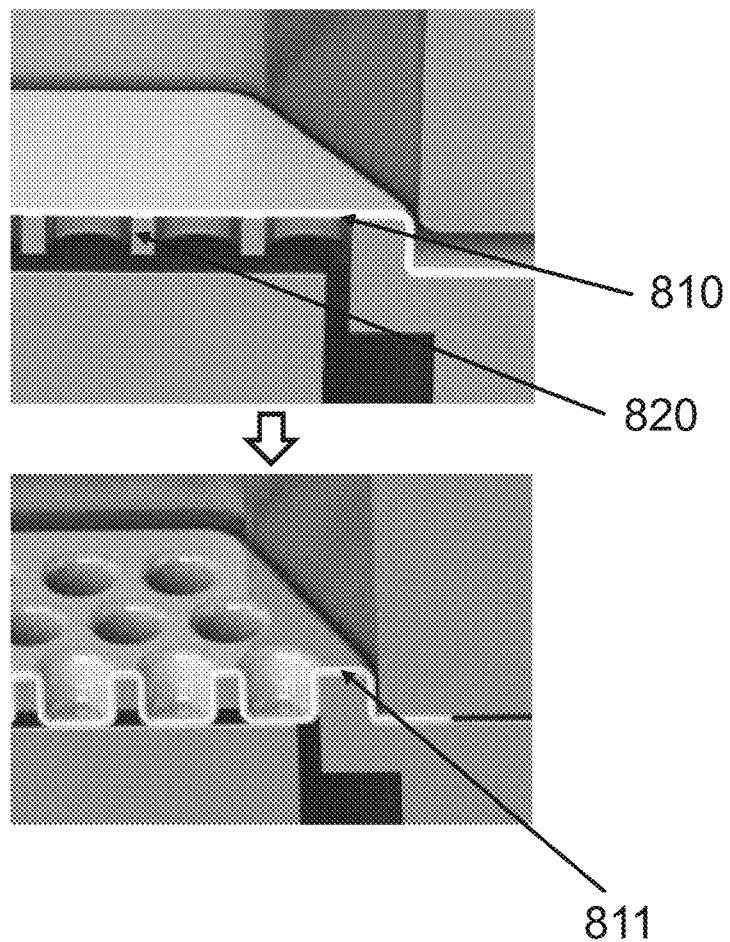
FIG. 8 illustrates a deformation of a membrane from a flat configuration to a formed configuration with channels, in accordance with some embodiments.

The first membrane can be deformed into the shape of the channel array. The first membrane can be deformed by thermoforming. The first membrane can be deformed by inflation-based thermoforming. Deforming the first membrane may comprise depressing portions the first membrane with a tool. In one example, the first membrane can be placed into the sealed chamber of the forming machine with a mold to form the channel array. The first membrane can be a flat sheet prior to the deforming step. The forming machine with the first membrane can heated to a critical predetermined temperature for deformation. Sequentially and/or concurrently, gas may be introduced into the sealed chamber through a gas inlet while the vents are closed to reach a critical predetermined pressure and produced a deformed first membrane. In some instances, the pressure can be provided by pumped in nitrogen gas. The critical pressure can be applied as a positive pressure or a negative pressure. The vents can be opened after the deforming step is completed to vent the sealed chamber. FIG. 8 shows a close up of the deformation of a membrane from a flat configuration to a formed configuration with channels. A flat first membrane 810 is placed atop a mold 820 within a sealed chamber. After the chamber is heated to a predetermined temperature and a predetermined pressure is applied to the membrane, the first membrane 811 deforms around the mold to form the channels. In some embodiments, the thermoforming enables the creation of a specific internal geometry, with a set height and aspect ratio to enable and improve engraftment and vascularization.

After the deformation of the first membrane, a second membrane can be fused to the first membrane to form the cell housing device. The second membrane may be substantially flat. The second membrane may be placed on one side of the deformed first membrane. The two membranes can be heated to a critical temperature for fusion. When a predetermined temperature and/or pressure for fusion have been reached, the two membranes can be compressed and/or fused together. The compression of the two membranes can occur at select locations across the first membrane. The compression can be facilitated by a mold or plate with features in the shape and spacing of the channel array. The heating can be performed in an oven. Alternatively, the heating can be performed by a tool with a heating element. The fused first and second membranes can form fusion at interfaces and form a compartment. The compartment may be interconnected, resulting in a device comprising as a single continuous open space having a volume. The compartment may be enclosed between the base and top surface of the device and may house cells. FIG. 9 shows fusing of a formed first membrane 1211 and a flat second membrane 1220 and the resulting device 1250 with fused first and second membranes.

Figure 10:
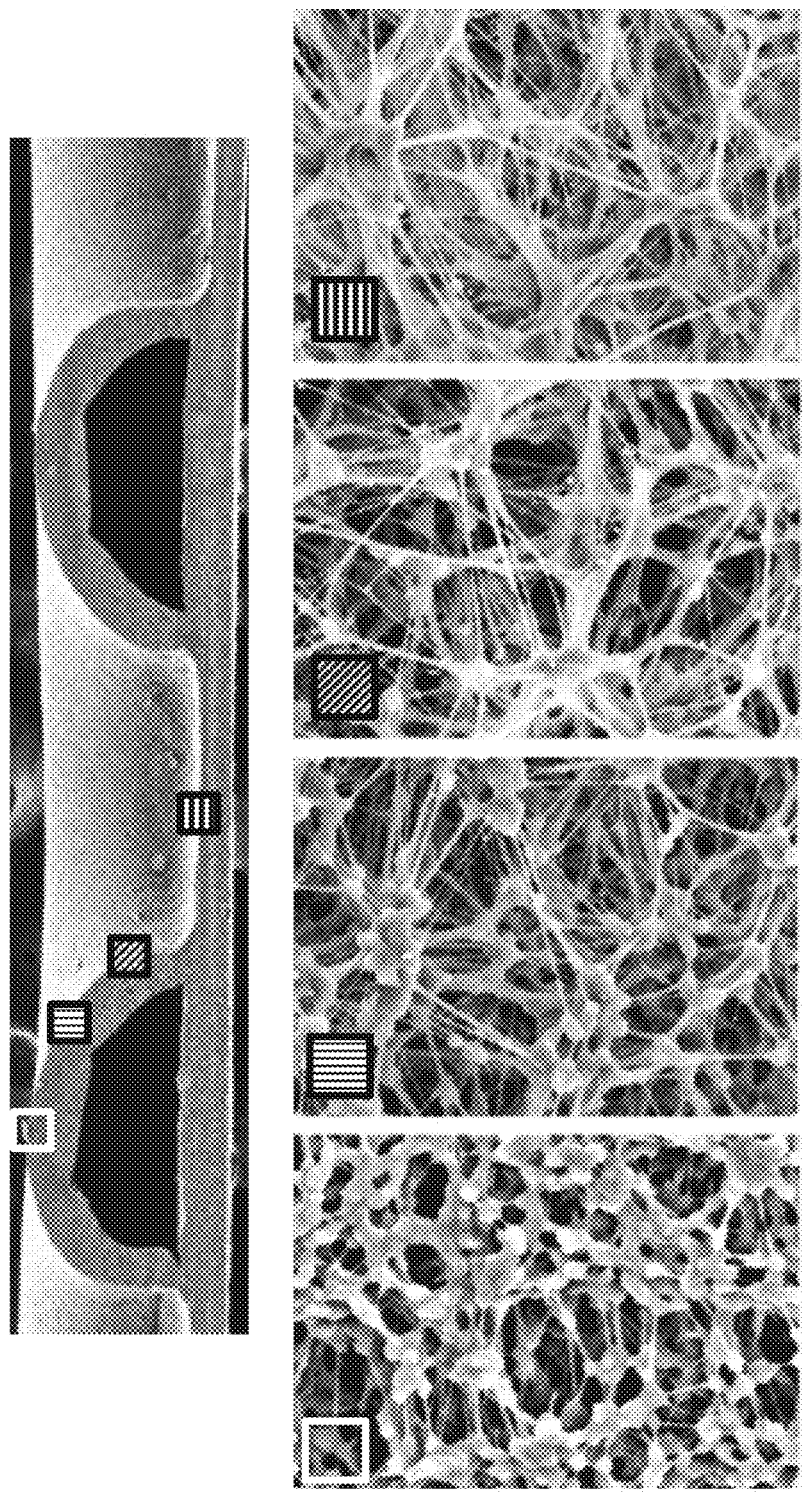
FIG. 10 shows a scanning electron micrograph of a cross section of a cell housing device and scanning electron micrographs at a higher magnification along various part of the cell housing device, in accordance with some embodiments.

The structure of the first and second membranes may be changed by the manufacturing process step. FIG. 10 shows a cross section of a cell housing device along various parts of the cell housing device, where the ultrastructure of the PVDF membrane changes from primarily nodes to primarily elongated fibrils where the material is deformed or fused. The first membrane or second membrane may comprise a plurality of nodes interconnected by a plurality of fibrils. During the deformation or fusion step, some of the node structures may change to elongated fibrils. The level of heat or level of pressure that the membrane is exposed to can affect the number of node structure. Generally in regions of the membrane that were not deformed or fused, e.g. top surface or top of channel, more nodes and less fibrils may be observed. Generally in regions of the membrane that underwent deformation or fusion, e.g. at the bottom of the channel or mid channel, more fibrils may be observed than in membranes that underwent less deformation or fusion. Generally in regions of the membrane that underwent deformation or fusion, e.g. at the bottom of the channel or mid channel, less nodes may be observed than in membranes that underwent less deformation or fusion. The nodes may be a depot of material that may be stretched into fibrils under heating and/or pressure in deformation or fusion steps. When there are no materials to transition from nodes to fibrils in structure, the membrane may have a breach in the deformation or fusion step. It is important that the deforming and fusion are performed without causing breach of the membranes. The number of node and fibril structure and the change in the number of node and fibril structure may be specific to the material of the membrane.

Figure 11:
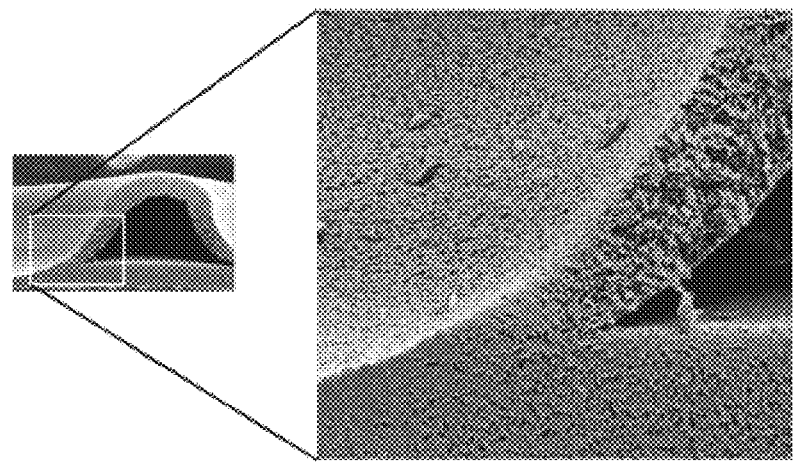
FIG. 11 shows scanning electron micrographs at a low magnification and a high magnification of a cross section of a cell housing device at the interface of fused first and second membranes, in accordance with some embodiments.
Figure 38:
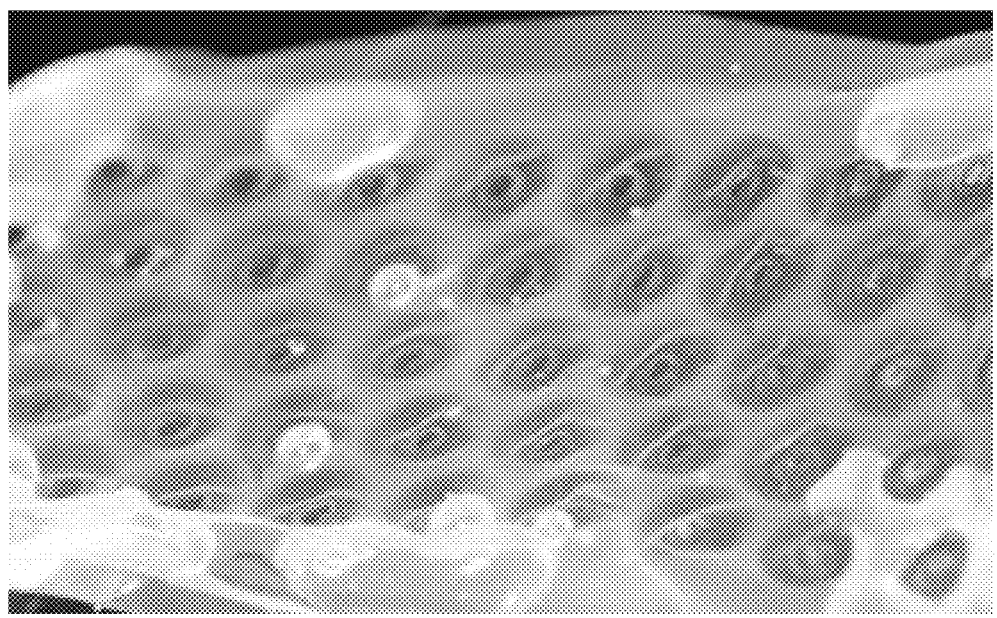
FIG. 38 shows an ePTFE cell housing device after a hydrophilic coating treatment in water, in accordance with some embodiments.

The first and second membrane can fuse without additional adhesives. The first and second membranes can self-seal without adhesives at critical temperature for fusion. The fusion between the first and second membrane can provide high seal integrity. The seam between the fused first and second membranes can be difficult to visualize, and the fused portion of the first and second membranes may appear as one continuous membrane by scanning electron microscopy as shown in FIG. 11. The high seal integrity may allow for the cell housing device to be filled at a higher pressure. Optionally, an adhesive can be placed in between the first and the second membrane before fusion. In some instances, the adhesive can be pressure and/or temperature sensitive. FIG. 38 shows a tool for sealing the perimeter of the device. FIG. 39 shows a scanning electron micrograph of the perimeter edge of a device that was sealed at 345° C. for 0.5 seconds, where the seam between the membranes is difficult to identify at the ultrastructural level.

The range of critical pressures and critical temperatures may be distinct for the material used as a membrane. For example for ePTFE, there may be a desired temperature that is necessary for a membrane to retain a deformed shape. In some instances, the desired temperature may be a temperature at which a material becomes sintered. In some instances, the range of critical pressures and/or critical temperatures may be distinct for each manufacturing step. For the deformation step, the critical pressure may be less than 10 psi, 20 psi, 30 psi, 40 psi, 50 psi, 60 psi, 70 psi, 80 psi, 90 psi, 100 psi, 110 psi, 120 psi, 130 psi, 140 psi, 150 psi, 160 psi, 170 psi, 180 psi, 190 psi, or 200 psi. For the deformation step, the critical temperature may be less than 100° C., 110° C., 120° C., 130° C., 140° C., 150° C., 160° C., 170° C., 180° C., 190° C., or 200° C. For the deformation step, the critical temperature may be less than 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., or 430° C. For the fusing step, the critical temperature may be less than 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 380° C., 390° C., 400° C., 410° C., 420° C., or 430° C. For the fusing step, the critical pressure may be less than 10 psi, 20 psi, 30 psi, 40 psi, 50 psi, 60 psi, 70 psi, 80 psi, 90 psi, 100 psi, 110 psi, 120 psi, 130 psi, 140 psi, 150 psi, 160 psi, 170 psi, 180 psi, 190 psi, or 200 psi. The combination of critical pressures and critical temperatures may need to be customized for each manufacturing step and material used. There may be critical pressure and/or critical temperature range for each material where the material can deform without secondary re-arrangement of the crystalline regions of the polymer. At the critical pressure and critical temperature range, the nodes in the thermoelastic material may stretch to more fibrillar structures to accommodate a new deformed or fused shape. However, outside of critical pressure and critical temperature ranges, the material may become crystalline and breach during the deformation or fusion.

Figure 15:
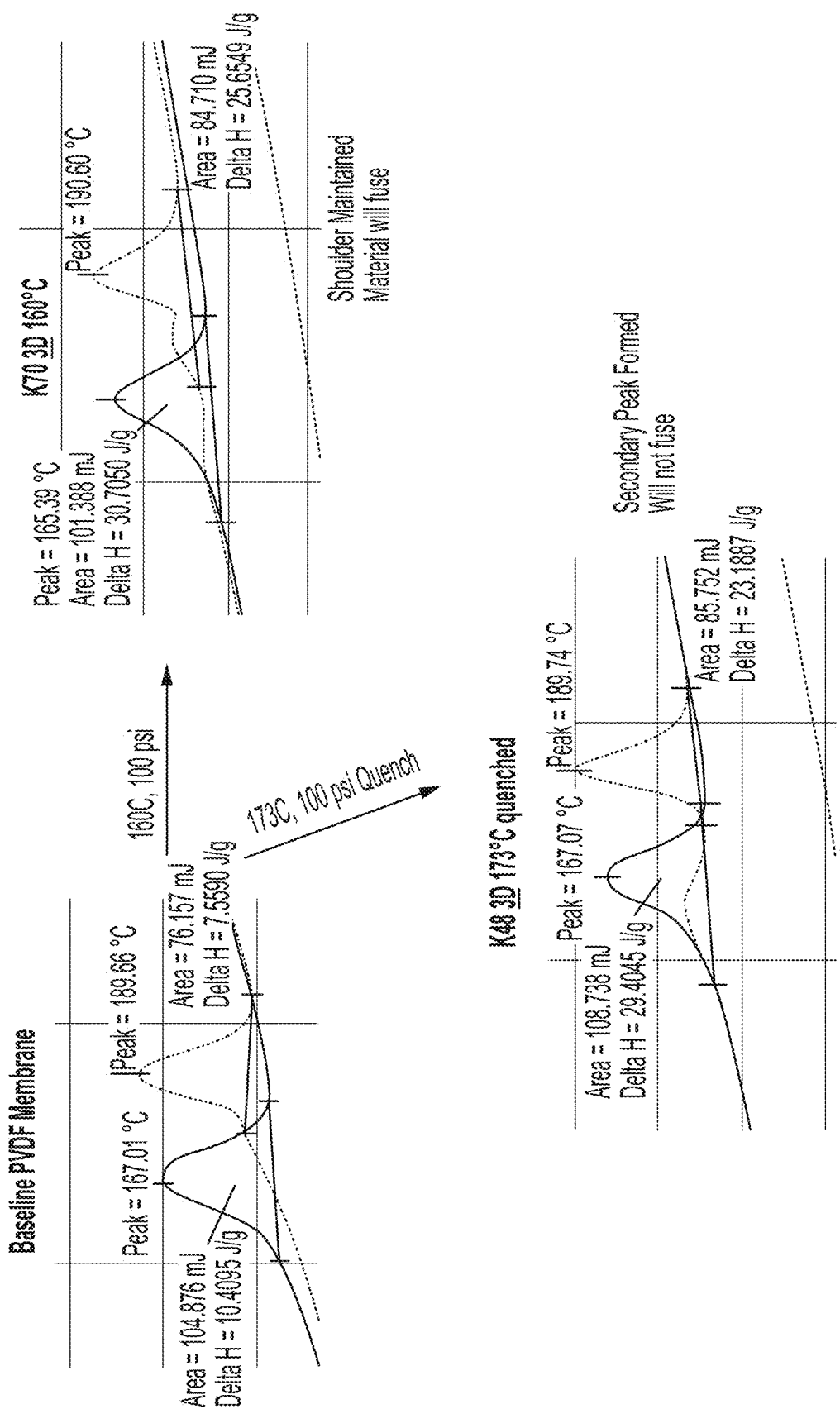
FIG. 15 shows the heat flow measurements of PVDF membranes before processing, after processing at 173° C. and 100 psi with rapid cooling, and, after processing at 160° C. and 100 psi, in accordance with some embodiments.

The membranes can have a breach if deformed or fused outside of the critical temperature and pressure ranges for deformation or fusion. The choice of temperature and pressures outside of the critical temperature and pressure ranges for deformation may result in a first membrane that may not fuse or fuse poorly to the second membrane in the fusion step. This breach in the first membrane may not be evident until the fusion step. When outside of the critical temperature or pressure ranges, the material of the membrane may increase in degree of crystallinity. The material for the first membrane with increased degree of crystallinity within may fuse poorly or not fuse to the material for the second membrane. The relative degree of crystallinity can be measured using by differential scanning calorimetry (DSC) to calculate the enthalpy of transition of the material. A secondary peak in the DSC heat flow measurement of a membrane may indicate a re-arrangement of the crystalline structure of the membrane and may indicate that the membrane may not readily fuse with another membrane. This re-arrangement may occur without increases in relative crystallinity. The re-arrangement may also occur without decreases in relative crystallinity. The arrangement of the crystalline regions of the membrane is an important factor in fusion, and the potential re-arrangement of the crystalline structure may not allow chain entanglement of the crystalline regions to another membrane during fusion. FIG. 15 shows another example of DSC heat flow measurement of a membrane deformed at 100 psi and 160° C. that maintained shoulder peak in comparison to the baseline PVDF membrane indicating that did not significantly change in its crystalline structure and will fuse to a second membrane. The heat flow measurement of membrane deformed at 100 psi and 173° C. with quenched cooling had a distinct secondary peak in the first melting endotherm, which indicated that this membraned formed a secondary crystalline region and will fail fusion to another membrane.

Figure 42:
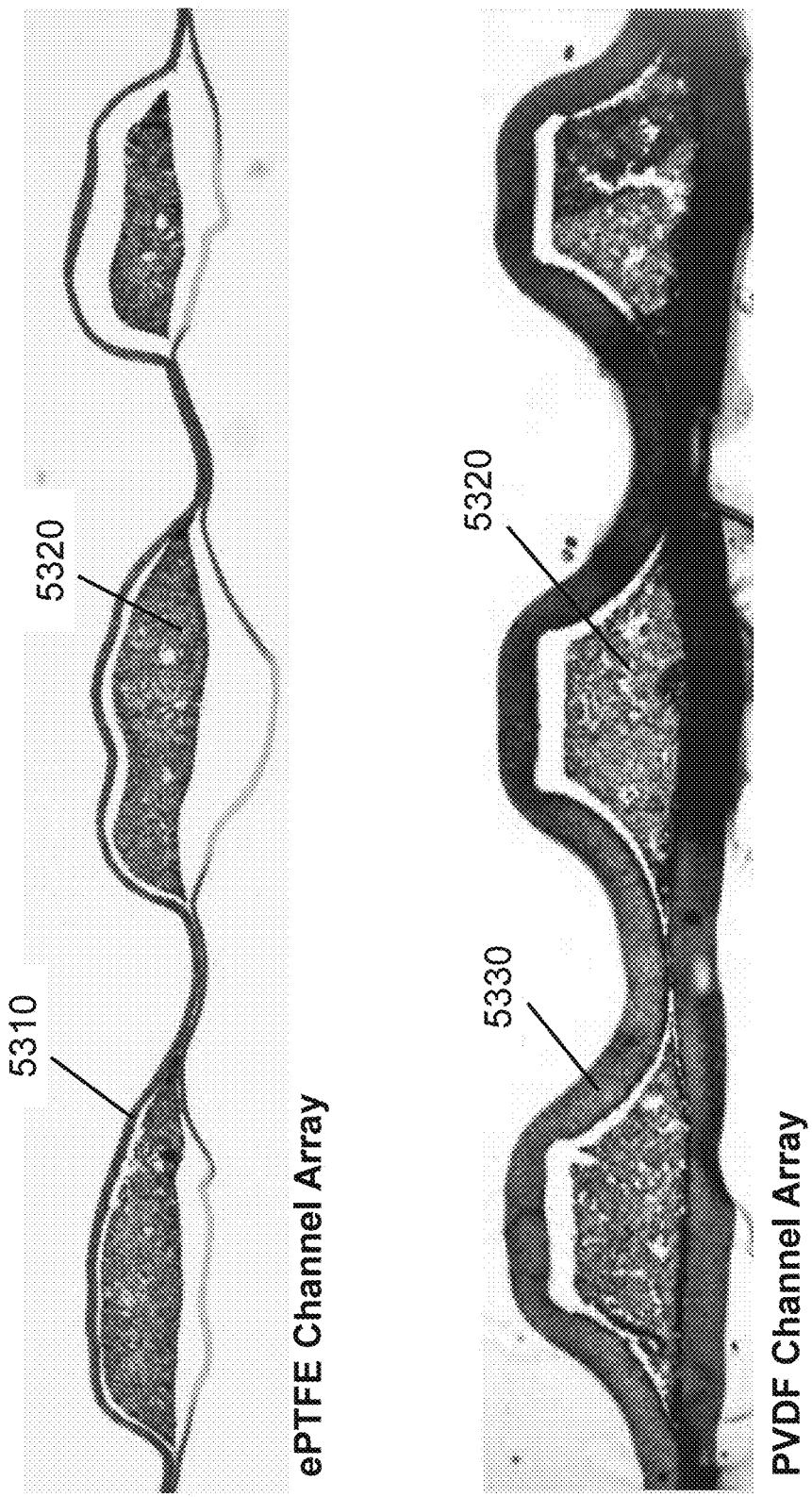
FIG. 42 shows H&E stained histological sections with complete filling of the continuous interior spaces of ePTFE and PVDF cell housing devices with cells, in accordance with some embodiments.

In some instances, a tip may be used to deform the first membrane. The tip may travel a predetermined vertical distance after the initial contact with the membrane to achieve about a predetermined height of the channel. In some instances, a tip may be used to fuse two membranes at a location the tip contacts the membranes wherein the first membrane has been previously deformed. Fusing may be performed with the tip, wherein the tip presses the first and second membrane in contact with each other for a predetermined time. In some instances, a tip may be used to deform the first membrane and fuse the first membrane to the second membrane in a single process or step. In some instances, the first and second membranes are vertically offset at a predetermined height. This vertical offset may determine the channel height. Deforming and fusing may be performed with the tip in one step, wherein the tip contacts a first membrane, moves vertically toward a second membrane offset from the first membrane, and presses first and second membrane in contact with each other for a predetermined time. In some instances, a single tip may be used on the membrane. FIG. 42 shows a schematic of fusion process by spot welding of two membranes with a 2 mm$^2$ tip. In other instances, a plurality of tips may be used on the membrane, e.g. concurrently.

In some instances, the tip may be moved laterally (x-y direction) and vertically (z direction) while the membrane or membranes are stationary. In some instances, the tip may only move vertically while a stage holding the membrane or membranes are moved laterally. In some instances, the tip may travel a predetermined lateral distance relative to the membrane surface and then travel a predetermined vertical distance down into the membrane and back up to a neutral vertical position, which may its previous vertical position. This cycle may repeat until a predetermined number of channels are deformed and/or fused on the membrane or membranes. In some instances, the stage holding the membrane may travel laterally to position at a predetermined location under a tip, and the tip may travel a predetermined vertical distance down into the membrane and back up to a neutral vertical position. This cycle may repeat until a predetermined number of channels are deformed and/or fused on the membrane or membranes. The movements of the tip and/or the stage holding the membrane may be programmed and automated. The tip may travel laterally about 100 μm, 200 μm, 300 μm, 400 μm, 500 μm, 600 μm, 700 μm, 800 μm, 900 μm, or 1000 μm in x- and/or y-direction in between cycles. The tip may travel vertically about 100 μm, 200 μm, 300 μm, 400 μm, 500 μm, 600 μm, 700 μm, 800 μm, 900 μm, or 1000 μm after contacting a membrane.

In manufacturing of the cell housing device using a tip, there may be critical time, temperature, and pressure ranges for deforming and/or fusion of the membranes. The time that the tip is in contact with the membrane may be referred to as tip contact time. In some instances, the tip contact time may be about 0.1 second, 0.2 second, 0.3 second, 0.4 second, 0.5 second, 0.6 second, 0.7 second, 0.8 second, 0.9 second, or 1 second. The tip contact time may be about 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 25 seconds, or 30 seconds. The tip may be heated to a temperature above the critical temperature for deformation and/or fusion. The tip may be heated to a temperature at about the critical temperature for deformation and/or fusion, substantially as described above. The tip may be heated about 0° C., 1° C., 2° C., 3° C., 4° C., 5° C., 6° C., 7° C., 8° C., 9° C., 10° C., 15° C., 20° C. above the critical temperatures. The tip may apply pressures of less than 10 psi, 20 psi, 30 psi, 40 psi, 50 psi, 60 psi, 70 psi, 80 psi, 90 psi, 100 psi, 110 psi, 120 psi, 130 psi, 140 psi, 150 psi, 160 psi, 170 psi, 180 psi, 190 psi, or 200 psi to the membrane for deformation and/or fusion.

Figure 37:
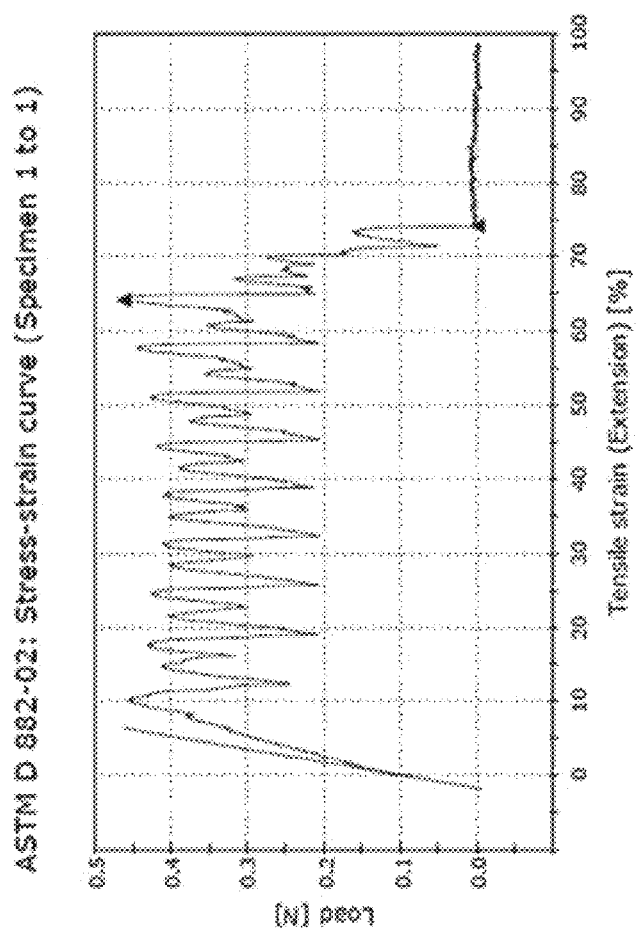
FIG. 37 shows a stress-strain curve of an exemplary peel test, in accordance with some embodiments.

In some instances, the first membrane may be sintered or unsintered prior to fusion. In some instances, the second membrane may be sintered or unsintered prior to fusion. In one example, the first membrane may be sintered and the second membrane may be unsintered prior to fusion. The membranes may be sintered at various temperatures and for various times. The sintered membrane may have a lower melting temperature than unsintered membrane of the same type. In one example, first membrane may be sintered at 370° C. for 7 minutes. FIG. 37 shows DSC measurements of ePTFE membranes sintered at 370° C. for 7 minutes and unsintered at 300° C., where the sintered membrane had a lower melting temperature of 320-325° C. as compared to 340-350° C. for unsintered ePTFE membrane. Optionally, whether or not membranes are sintered may be important for fusion of a first membrane to a second membrane. In some instances, a membrane being sintered may help the membrane become deformed and maintain the deformed shape. Optionally, a sintered membrane being fused to an unsintered membrane may provide desired characteristics, such as tight seals, device integrity, and/or shape.

The edges of the fused first and second membranes can be trimmed to remove the excess membrane on the perimeter of the cell housing device. In some instances, the trimming can be performed by punching. An alignment frame may be is used to mount and align the cell housing device and perimeter punch is used to cut the excess perimeter of the cell housing device.

Figure 20:
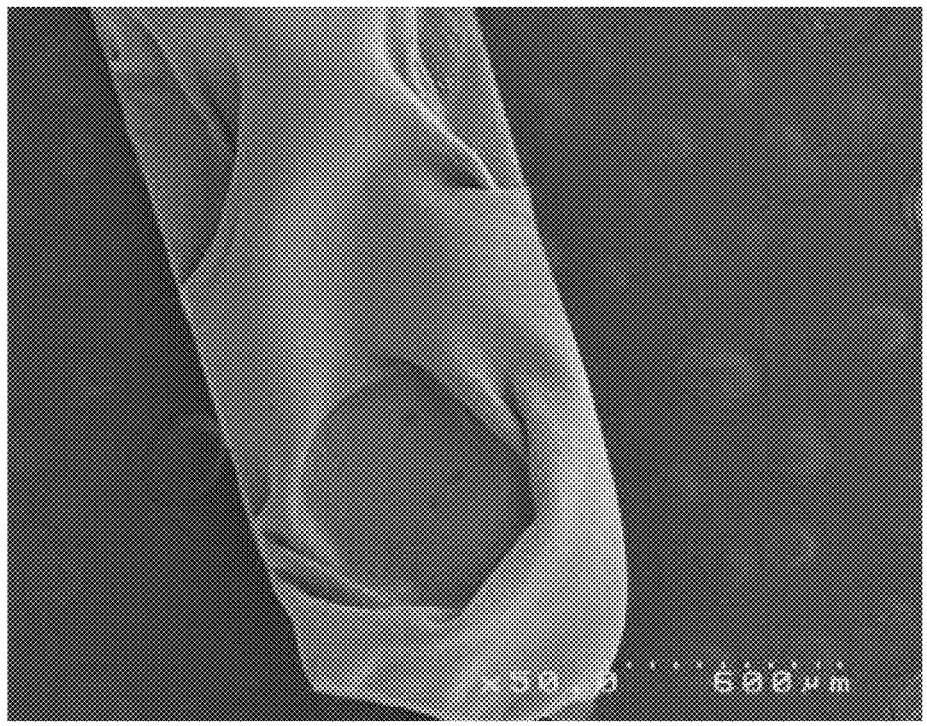
FIG. 20 shows scanning electron micrographs of an ePTFE cell housing device after deformation step performed at 360° C. and 6 psi and fusion step performed at 370° C. for 5 minutes, in accordance with some embodiments.
Figure 21:
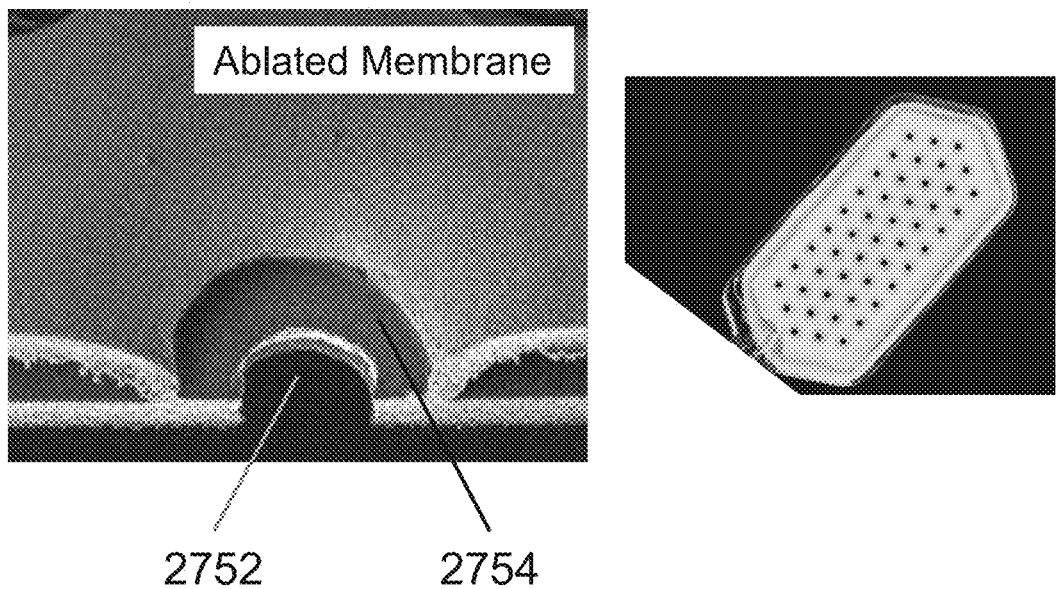
FIG. 21 shows a scanning electron micrograph and an image of a cell housing device with a lumen of a fused portion of cut by laser ablation, in accordance with some embodiments.
Figure 22:
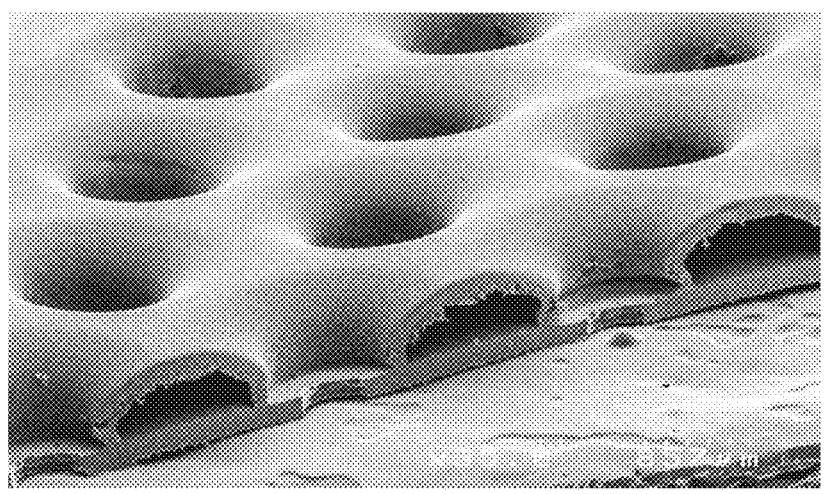
FIG. 22 shows a scanning electron micrograph of a cross section of a cell housing device after manufacturing, in accordance with some embodiments.

Per FIG. 20, the fused portion between the first and second membrane can be cut to form the lumen of the channels. The fused portions of the first membrane and the second membrane may be removed via laser ablation, thereby forming channels traversing through the device. FIG. 21 shows a scanning electron micrograph and an image of a cell housing device with a lumen 2752 of a fused portion 2754 of cut by laser ablation with a framed cell housing device. FIG. 22 shows a scanning electron micrograph of a cross section of a cell housing device after manufacturing steps including cutting through the channels to form the lumens. The cutting can be performed by laser etching or laser ablation. The removed part can be a portion of the area of the fused portion as to not compromise the seal of between the first and second membranes. The removed part can be about 0, 10, 20, 30, 40, 50, 60, 70, 80, 90, or 99% of the area of the fused portion.

Figure 23:
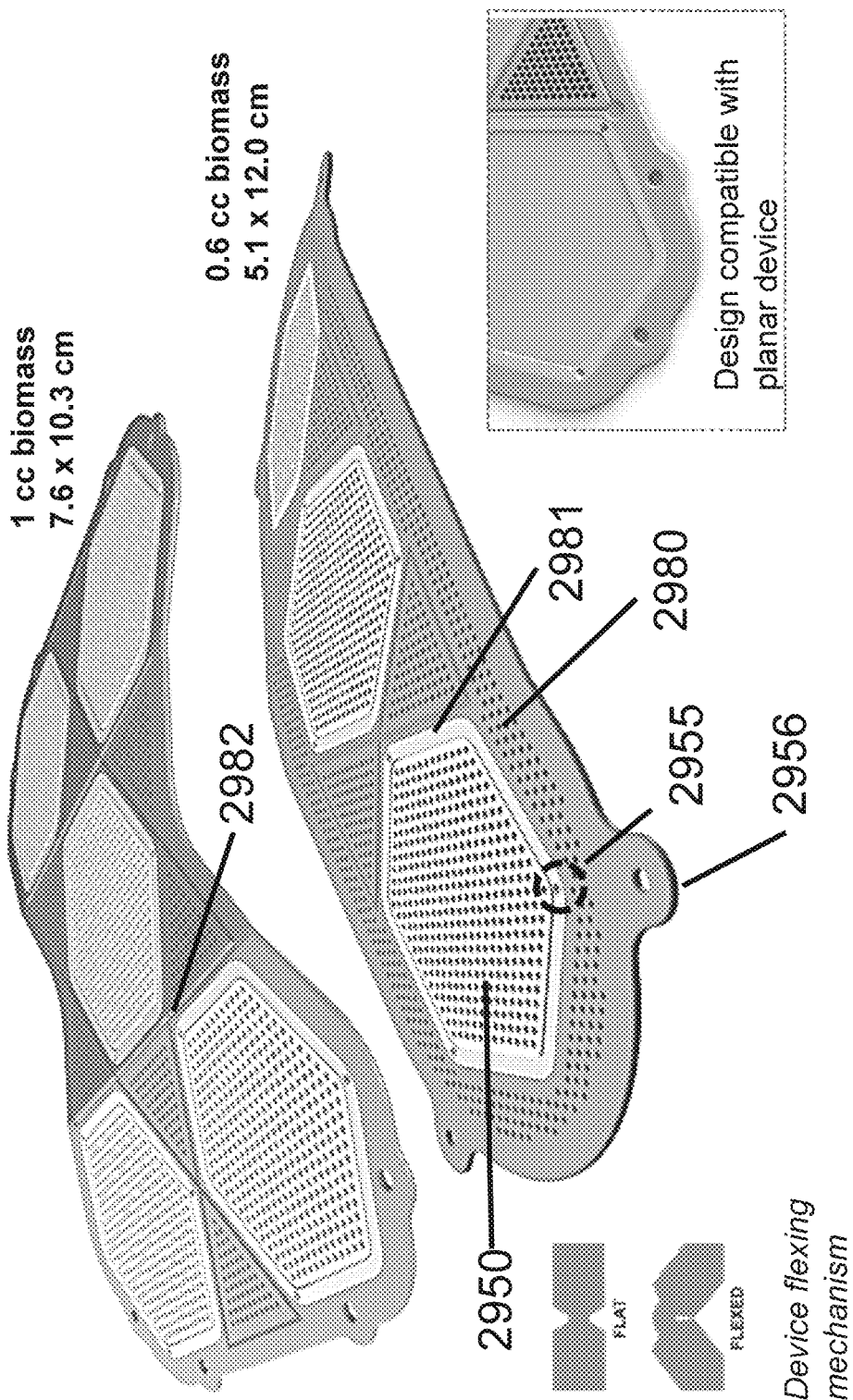
FIG. 23 illustrates designs of macrodevices fitted with hexagonal channel array devices and with flexing mechanisms, in accordance with some embodiments.

The assembled cell housing device can be provided as a part of a modular system, also referred to herein as a macrodevice. FIG. 23 illustrates one or more cell housing devices 2950, each that can be filled inside with a matrix comprising cells that can be assembled onto a frame 2980 to form the macrodevice. Multiple channel array devices, or cell housing devices with matrix, can be placed onto frames in various configurations. Each device may have a fill port 2955 for filling the inside of the device with a matrix. The fill port is designed to be small to reduce the likelihood for breach of the device seal. The fill port may be used to fill cells within the device. In some instances, the frames may comprise flexible backing materials or a structural support.

Optionally, a channel array device can be mounted to a subframe 2981 in addition to a frame. The frame may provide a flexible support for the channel array devices. The frame may prevent unwanted folding of the devices. The frame can have one or more flexing mechanisms that prevent buckling of sensitive device regions. The flexing mechanism 2982 can have notches that allow for bending of the frame at the notches. The flexing mechanism allows the assembly to flex along the tissue at the location of the assembly implantation. The frame can have a handling tab 2956. The handling tabs may be used for surgical handling and/or implantation of the assembled device. The frame can have holes to allow for transport.

The frame may have a flexing mechanism to prevent buckling of the cell housing devices mounted onto the frame. The flexing mechanism comprises small notches or cutaways while leaving a small portion of the frame intact. In some instances, the notches may be on top and bottom surfaces of the frame at about the same location while leaving a small portion of the frame intact in between the two notches. In other instances, the notches may be on one of the surfaces of the frame at while leaving a small portion of the frame intact. The notches may be various shapes, including generally conical, cylindrical, pyramidal, rectangular, or other shapes that remove a portion of the frame. The notches allow for the frame to bend at various angles, which can range from 0° to 90° in any given direction.

The macrodevice may have several configurations and dimensions depending on its application. In some instances, the macrodevice may have a width of at least 3 cm, 4 cm, 5 cm, 6 cm, or 7 cm. In some instances, the macrodevice may have a length of at least 5 cm, 6 cm, 7 cm, 8 cm, 9 cm, 10 cm, 11 cm, 12 cm, 13 cm, 14 cm, or 15 cm.

Figure 24:
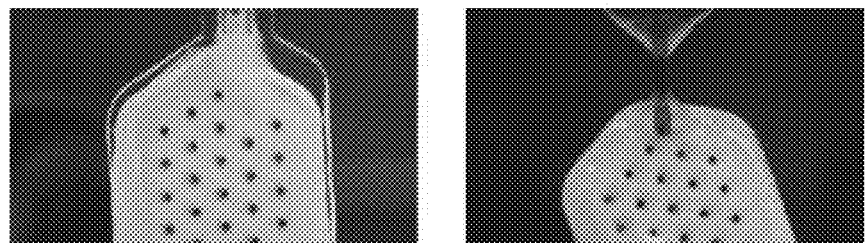
FIG. 24 shows filling of a cell housing device with a mixture containing cells in a configuration in which the device is mounted to a mechanical frame for support (Left), and in a configuration that uses an external filling tube and a frameless design (Right), in accordance with some embodiments.
Figure 25:
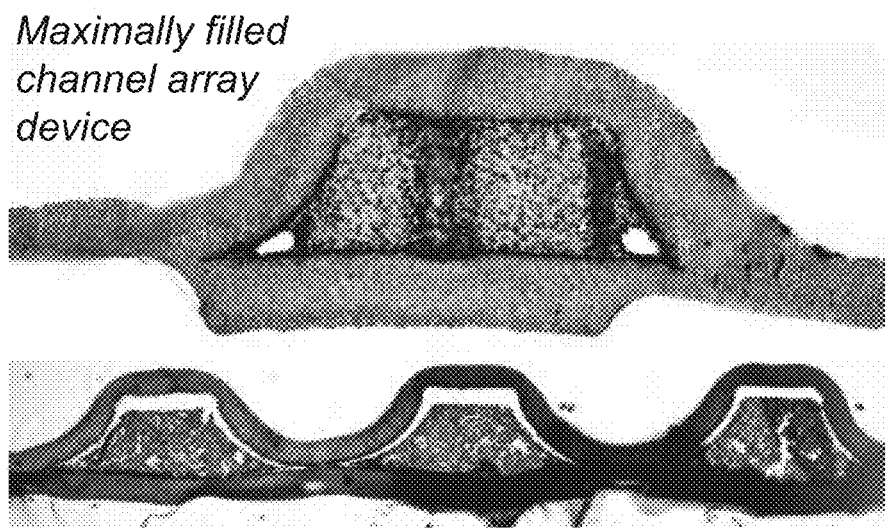
FIG. 25 shows hematoxylin and eosin (H&E) stained histological sections of a cell housing device filled with matrix with cells, in accordance with some embodiments.

The cell housing device can be filled with a matrix. In some instances, the cell housing device can be filled by pressure. In other instances, the cell housing device can be filled by centrifugation. FIG. 24 shows filling of a framed (left) and an unframed (right) PVDF cell housing device with a mixture containing cells. In some instances, a fill tube may be connected to the cell housing device to fill a frameless device. In other instances, in a framed cell housing device, the frame may allow for a fluid path from a fill hub to connect to a fill port on the device. Once the device is filled, the device may be separated from the fill tube or the fill hub and sealed. The frame also may be sealed. The device and/or the frame may be sealed with glue or a UV curable glue. The matrix can comprise cells or expression systems that produce biological products. The matrix can further comprise a cell culture medium. The matrix can further comprise a porous biocompatible material. The risk for seal breach can be reduced by leaving only a small area in the cell housing device unsealed for filling. The small area can be sealed after filling the cell housing device with the matrix. FIG. 25 shows a cell housing device filled with matrix with cells as visualized by hematoxylin and eosin (H&E) stained histological sections. In some instances, the following process may be utilized to fill a cell housing device (e.g., with cells). First, cells may be suspended in a medium. Second, the cells may be administered into a fill port under pressure. Third, the fill port may be removed. Finally, the fill port opening may be sealed (e.g., with UV cured glue).

The assembled channel array device or its components can be treated on their surfaces. The surfaces can be treated with materials to encourage vascularization. The coating may be VEGF, or other pro-angiogenic factors or substances. The outer surface can be treated with materials that impart anti-fouling properties. The surface of the device can be treated reduce the potential for fibrosis or formation of connective tissue around the device. The material of the device can be chosen to reduce the potential for fibrosis. The surface of the device can be treated to create physical features, or treated chemically to reduce fibrosis. The surface can be treated with hydrophilic coating. The hydrophilic coating may comprise a polymer, polyethelene glycol, polyvinyl alcohol, polydopanine, oact. FIG. 41 shows an example of a protocol for forming a hydrophilic coating on the surface of the membranes. The hydrophilic coating may impart hydrophilic properties to a hydrophobic surface prior to coating treatment. Improving hydrophilicity of the membrane surface may improve transport of hydrophilic molecules through the membrane, between the interior and exterior environments of the device. FIG. 38 shows an ePTFE cell housing device after a hydrophilic coating treatment in water, where air bubbles indicate the capability of water to fill inside the device and displace the air from inside the device.

The membranes of the cell housing device can comprise one or more porous materials. The membrane may comprise PTFE, ePTFE, PVDF, PCL, PE/PES, PP, PS, PMMA, PLGA, PLLA, or other thermoelastic materials. The material for the membrane may be synthesized by various methods. The synthesis method of the porous material may comprise expanding, solvent-casting, immersion precipitation and phase separation, electrospinning, methods that yield isoreticular network, methods that yield trabecular network, or other methods. The membrane may be a porous material that allows for transport through the material of materials with a molecular weight less than about 3000 kDa, 2000 kDa, 1000 kDa, 500 kDa, 400 kDa, 300 kDa, 200 kDa, 100 kDa, 50 kDa, 40 kDa, 30 kDa, 20 kDa, 10 kDa, 6 kDa, 5 kDa, 4 kDa, 3 kDa, 2 kDa, 1 kDa after the manufacturing process. The membranes may have an average pore size of about 5 nm, 10 nm, 15 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1700 nm, 2000 nm, or 2500 nm.

The dimensions of the channel array can be controlled by parameters in the manufacturing steps. The mold or plate can be used to deform the first membrane to a predetermined channel array design. The temperature during the deformation step can be used to change the depth of the channels. The pressure during deformation step can be used to change the depth of the channels. The combination of the temperature and pressure during the deformation step can be used to change the depth of the channels. The temperature and pressure during deformation may be specific to the material of the first membrane. The change in channel dimension can affect the three-dimensional shape of the interconnected pockets within the cell housing device. These manufacturing parameters can be used to adjust the configurations and dimensions of the cell housing for the channel array device. These parameters can be used to vary the SA:V ratio of the cell housing. The SA:V ratio of the cell housing may improve vascularization in and around the device.

Figure 28:
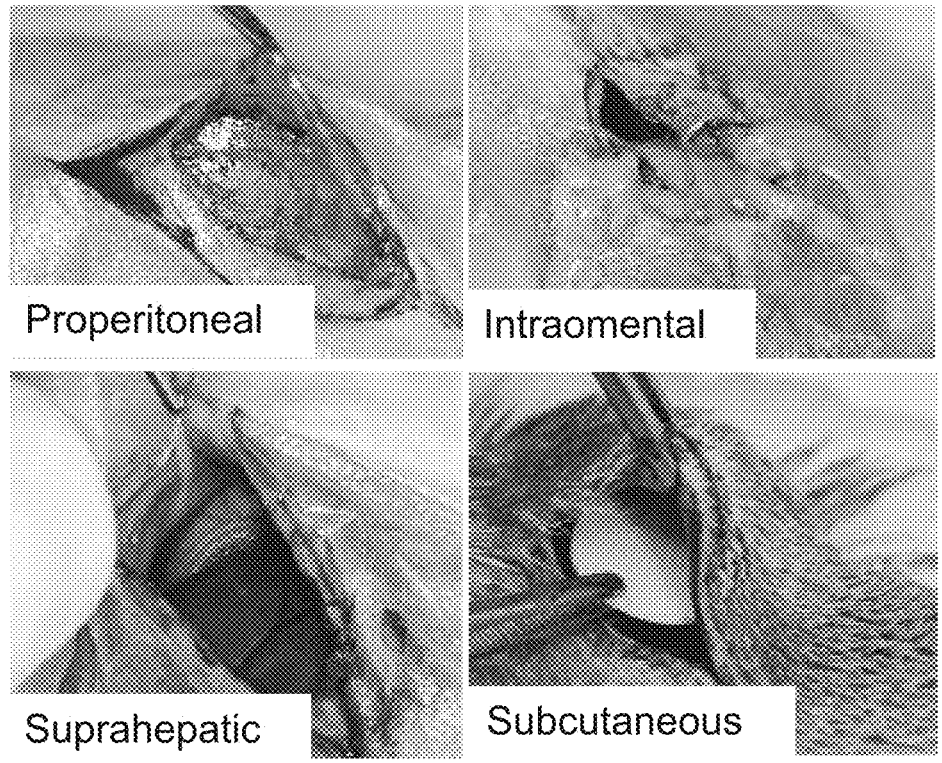
FIG. 28 shows properitoneal, intraomental, suprahepatic, and subcutaneous implantation of the cell housing device in rats, in accordance with some embodiments.

The device can be implanted in a subject in vivo at various sites. In some instances, the device on a frame can be implanted in a subject. In one example, the device can be placed by properitoneal or retrorectus implantation. In other example, the device can be placed by intra-omental implantation. In another example, the device can be placed by subcutaneous implantation. In another example, the device can be placed by suprahepatic implantation. FIG. 28 shows properitoneal, intraomental, suprahepatic, and subcutaneous implantation of the cell housing device in rats.

The device can be fixed in vivo at the implantation site. In one example, the device can be fixed in using a tissue adhesive. The tissue adhesive can be fibrin, cyanoacrylate, polyethylene glycol, albumin-based adhesive, or polymer-based adhesive. In another example, the device can be fixed using platelet-rich plasma.

Figure 29:
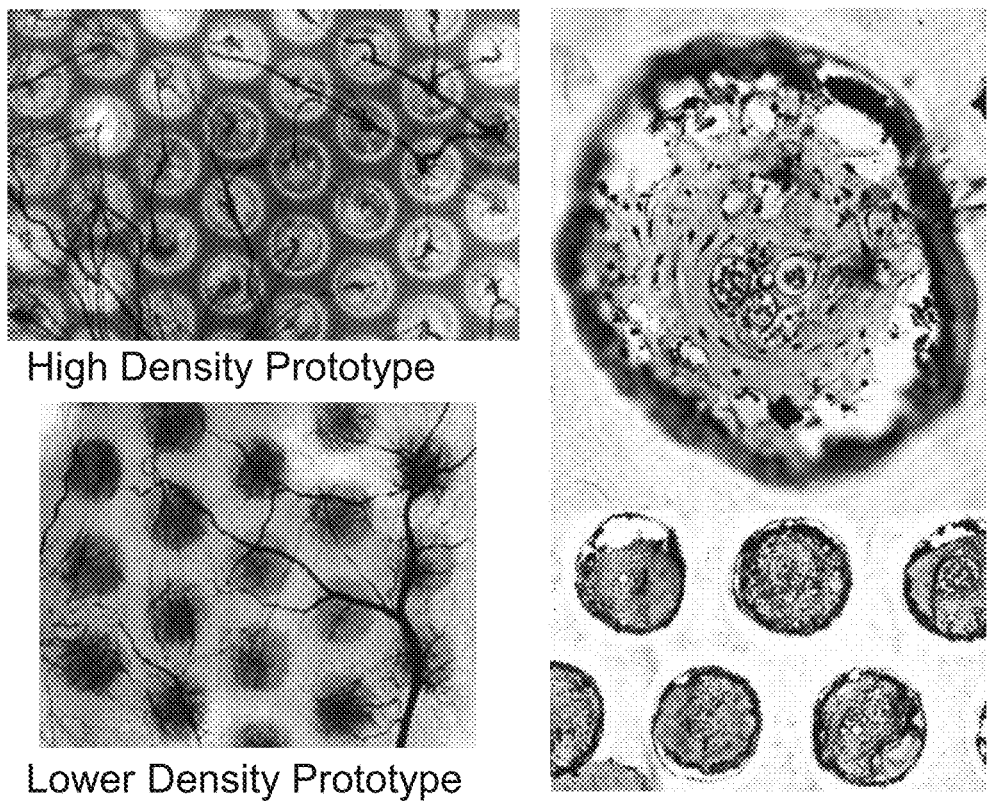
FIG. 29 shows the vascularization around the cell housing devices after in vivo implantation in rats and an H&E stained histological sections of the vasculature in the channels, in accordance with some embodiments.
Figure 30:
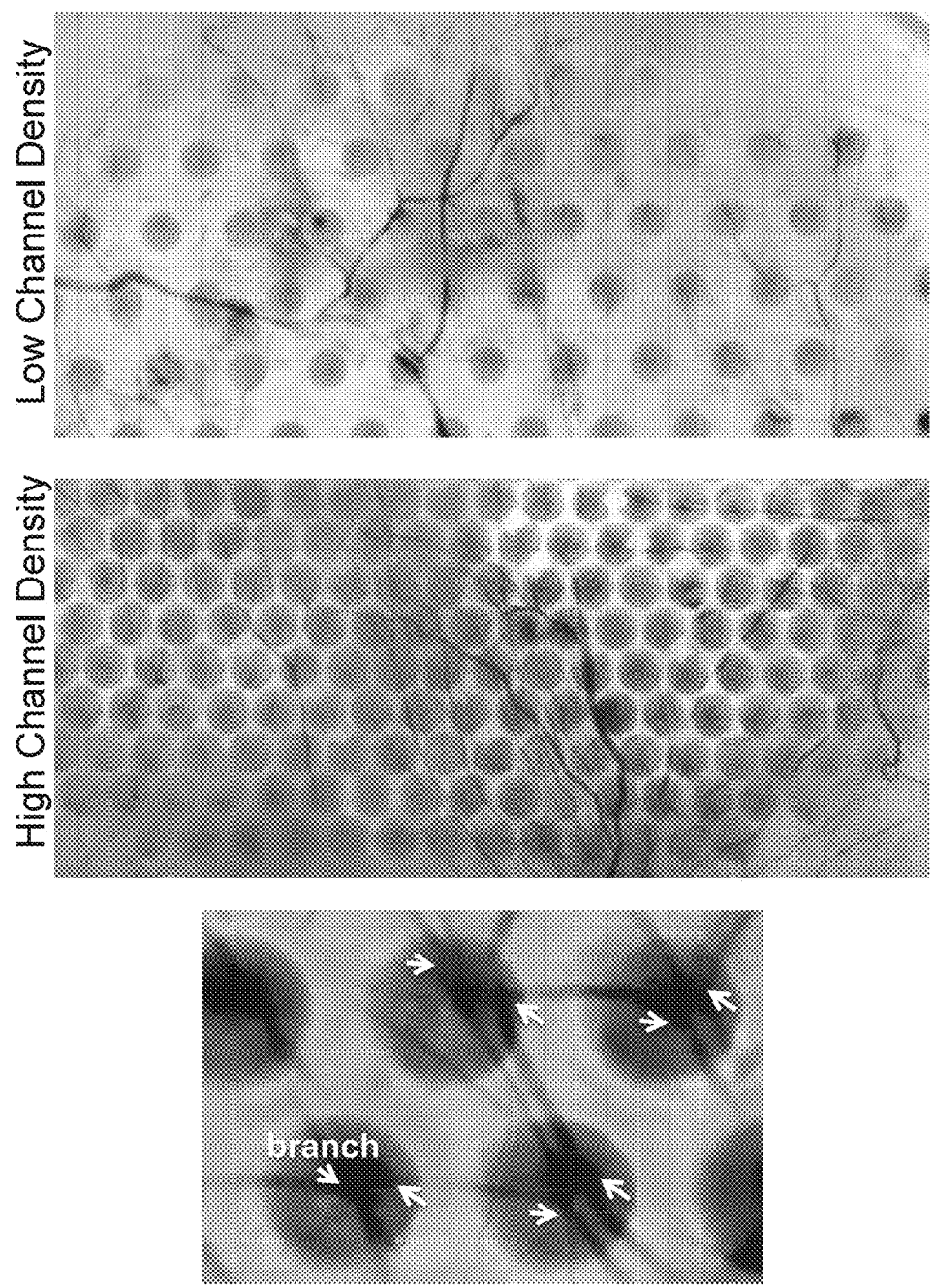
FIG. 30 shows the vascularization around the cell housing devices with a low channel density and a high channel density after in vivo implantation, in accordance with some embodiments.
Figure 31:
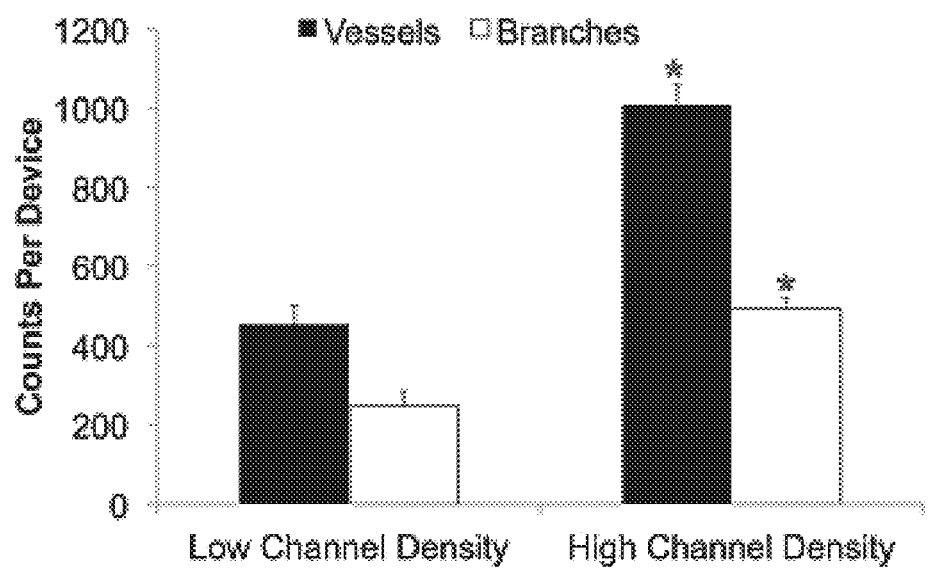
FIG. 31 shows the number of vessels and vessel branches per device observed in cell housing devices with a low channel density and a high channel density after in vivo implantation, in accordance with some embodiments.

After in vivo implantation, vessels may form around the device and through the channels in the device. FIGS. 31 and 32 show vasculature around the cell housing device and through the channels at 20 days and 90 days after implantation in a pre-peritoneal site in a rat. FIG. 29 shows the vascularization around the cell housing devices after in vivo implantation in rats and H&E stained histological sections of the vasculature in the channels. FIG. 30 shows the vascularization around the cell housing devices with a low channel density and a high channel density after in vivo implantation. The vessels may have smooth muscles cells, which are generally found in arteries. The vessels may have arterial features. FIG. 30 and FIG. 31 show that the density of the channels in the channel array device may affect the level of vascularization. Higher density of channels may increase the level of vascularization. Lower density of channel may decrease the level of vascularization. The diameter of the channels in the channel array device may affect the level of vascularization and branching of the vessels.

The cell housing device can be designed to achieve various functional goals. One of the goals of the cell housing device may be to provide at least one year of cell viability for the cells in the device after in vivo implantation. In some embodiments, the device is designed for at least one year of cell viability may have at least $4 \times 10^8$ cells. The device may be retrieved or explanted from the in vivo implantation site in a subject to assess the post-implantation cell viability and other functional assessments. The cell housing device may be designed to improve the mass transport within the device and through the membranes of the device. The cell housing device may be coated and/or implanted at sites to improve proximity to a host vascular supply. The cell housing device may be designed to stabilize the host-device interface to allow flexibility in the device without folding over on itself. The cell housing device may be designed to moderate tissue integration to provide stability to the device without comprising the integrity of the device. The cell housing device may be designed to use materials and coating that provide favorable non-specific biomaterial reactions.

Ultrathin Devices

While cell housing devices comprising channels have been primarily described herein, the cell housing devices do not necessarily need to comprise channels. For example, another approach to meet the various functional goals of the cell housing device can in some instances be met using an ultrathin cell housing device, also referred to herein as an ultrathin device. Accordingly, various parameters, properties, or descriptions (e.g., coating, materials, etc) described to a given embodiment of a cell housing device (e.g., one comprising channels) can be equally applicable to another embodiment of the cell housing device (e.g., ultrathin device).

Figure 57:
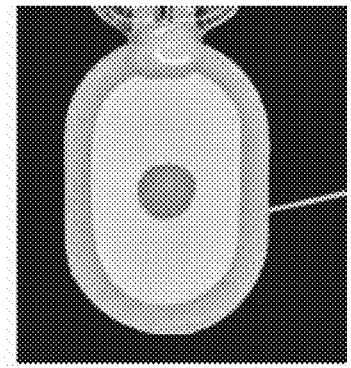
FIG. 57 shows an example of the PEEK frame holding a cell housing device with a fused dot in the center of the device, in accordance with some embodiments.
Figure 58:
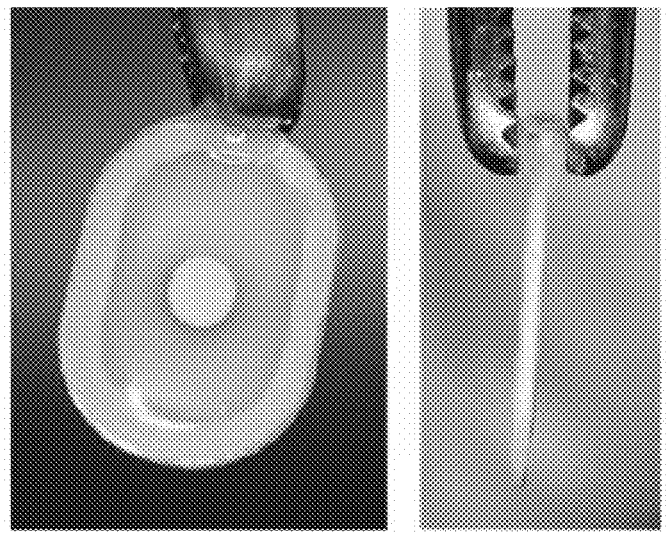
FIG. 58 shows images of a single frame module with a single cell housing device with a centrally fused dot that has been maximally filled on a frame, in accordance with some embodiments.

The ultrathin device may have a thin total cross-sectional thickness. Alternatively or in addition, the ultrathin device may have thin membranes. The membranes of the ultrathin device may be biocompatible polymers or biomaterials, such as ePTFE, PVDF, PEEK, PS, PES, PAN/PVC, Nylon, Polyurethanes, polycarbonate, polyacrylonitrile, glass fiber, polycaprolactone, hydrogel, polyesters, polyanhydrides, or cellulose. The membranes may also be made from permanent, non-degradable materials, or alternatively, biodegradable materials with controlled degradation profiles. The dimensions of the ultrathin device may provide a high SA:V ratio. The high SA:V ratio can enhance the transport of molecules in and out of the device, such as transport of nutrients and oxygens into the device for the indwelling cells in the device and insulin or other secreted products out of the device. The modeled insulin diffusion out of such an ultrathin device that is loaded with insulin-producing cells may be 0.4-10 ng/cm$^2$/10 min. The ultrathin device may not have channels running through the thickness of the device as with the channel array devices. FIGS. 57 and 58 show a schematic of an ultrathin device with at a cross-sectional thickness of 250 µm and filled with cells (black circles) and a macrodevice with three ultrathin devices.

The ultrathin device may have a total cross-sectional thickness that is about 250 µm. In some embodiments, the total cross-sectional thickness of the ultrathin device may be less than 5000 µm, 4000 µm, 3000 µm, 2000 µm, 1000 µm, 900 µm, 800 µm, 700 µm, 600 µm, 500 µm, 400 µm, 300 µm, 200 µm, 100 µm, or 50 µm. In some embodiments, the total cross-sectional thickness of the ultrathin device may be at least 1000 µm, 900 µm, 800 µm, 700 µm, 600 µm, 500 µm, 400 µm, 300 µm, 200 µm, 100 µm, 50 µm, or 10 µm.

The ultrathin device may have membranes with a thickness ranging from 2 µm to 25 µm. In some embodiments, the membranes of the ultrathin device are less than 100 µm, 90 µm, 80 µm, 70 µm, 60 µm, 50 µm, 40 µm, 30 µm, 20 µm, 10 µm, 5 µm, or 1 µm.

The ultrathin device may be designed to have a SA:V ratio appropriate for the transport of nutrients and desired products through the device. In some instances, the SA:V ratio may be equal to greater than 80 cm$^{-1}$. In other instances, the SA:V ratio may be equal to, or greater than about 20 cm$^{-1}$, 40 cm$^{-1}$, 60 cm$^{-1}$, 80 cm$^{-1}$, 100 cm$^{-1}$, 120 cm$^{-1}$, 150 cm$^{-1}$, or any value therebetween. The maximum oxygen diffusion distance of the device may be less than 50 µm, 100 µm, 150 µm, 200 µm, 250 µm, 300 µm, 350 µm, 400 µm, 450 µm, or 500 µm.

The properties of the membrane of the ultrathin device may be selected to enhance its function. One such property may be flux selectivity of the membrane. Various membrane properties, including microstructure, tortuosity, pore size, porosity, and/or thickness, may contribute to the flux selectivity. The flux selectivity may affect molecules that can pass through the membrane. As the microstructure affects the flux selectivity of the membrane, the processing of the membrane can affect its microstructure and its flux selectivity.

The properties of the membrane of the ultrathin device may be selected to improve its capability for immunoprotection. For instance, a membrane with a high flux selectivity may prevent a high amount of antibodies and complement proteins from moving across the membrane. The membrane with a high flux selectivity can also reduce diffusion of nutrients through the membrane to the interior of the cell housing device. A membrane with a medium flux selectivity may have a good flux properties for cell survival, reduced antigen release from dying cells, and some level of preventing antibodies from moving across the membrane. A membrane with a low flux selectivity may allow for a high flux to promote nutrient exchange through the membrane and may be able to restrict transport of cells across the membrane and not transport of molecules smaller than a cell. Also, membranes with medium or low flux selectivity may allow for potential exchange of antibodies and may have lower mechanical properties than membranes with higher flux selectivity.

Figure 47:
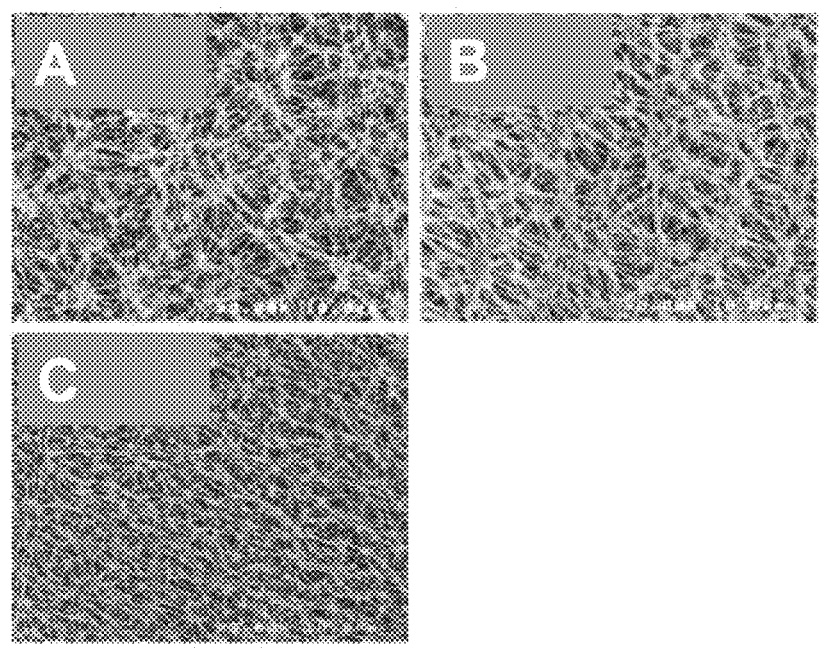
FIG. 47 shows scanning electron micrographs of different ePTFE membranes that can be used for ultrathin devices, in accordance with some embodiments.

Various types of membranes can be used for ultrathin devices. FIG. 47 shows scanning electron micrographs of ePTFE membranes of different porosity thickness that can be used for the ultrathin device. Table 1 shows various membrane properties including their flux, thickness, diffusion selectivity, and insulin flux. The diffusion selectivity is as defined as the ratio of antibody flux to insult flux, where the lower ratio indicates a more selective flux as insulin is a much smaller molecule than antibodies. The C membrane has a lower diffusion selectivity than the A and B membranes and is more selective in allowing the transports of larger molecules, such as antibodies, across its membrane.

TABLE 1

Membranes for ultrathin device

| Membrane | Flux type | Thickness [μm] | Diffusion selectivity *Lower value is more selective | Insulin flux [mol/m$^2$*s] |
|---|---|---|---|---|
| A | High | 5 | 1.8% | $1.3 \times 10^{-6}$ |
| B | High | 15 | 1.6% | $9.5 \times 10^{-7}$ |
| C | Permselective | 20 | ≤0.5% | $7.1 \times 10^{-7}$ |

Figure 48:
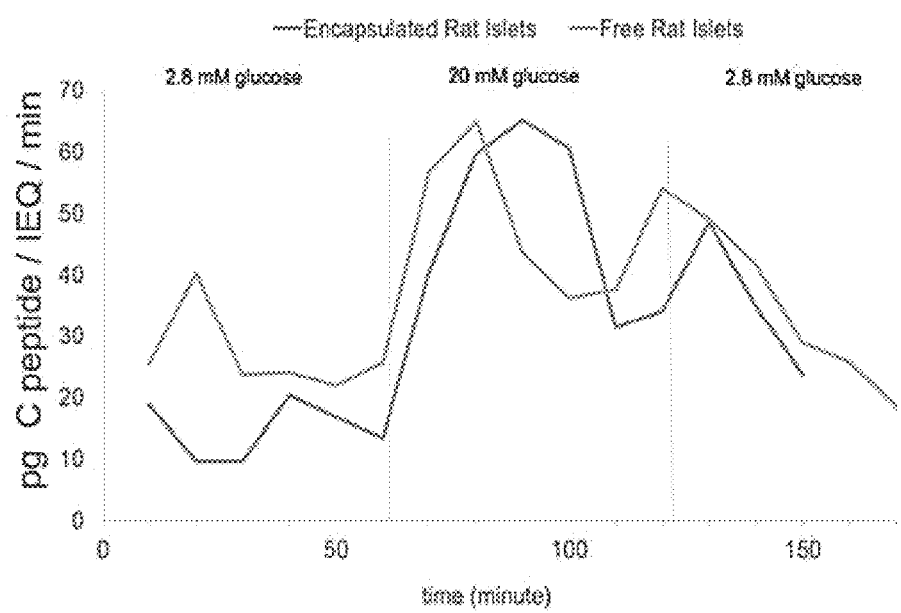
FIG. 48 shows flux of C-peptide in an implanted high flux ultrathin devices with a permselective membrane and filled with rat islet cells in response to a 20 mM glucose stimulus, in accordance with some embodiments.

As shown in FIG. 48, high flux ultrathin devices comprising a permselective membrane and filled with rat islet cells were able to produce and secrete insulin in response to a 20 mM glucose stimulus, as measured by the flux of C-peptide to outside of the ultrathin device. C-peptide, also known as the connecting peptide, is a polypeptide is cleaved from a proinsulin to form an insulin molecule. The level of C-peptides provides a level of insulin produced and secreted as the C-peptide is present in an equimolar amount to the insulin. Islets harvested from Sprague-Dawley rats were used to assess insulin transport kinetics after encapsulation within an ultrathin device. The ultrathin devices filled with encapsulated rat islet cells showed a delay of about 5-10 minutes in the release of insulin from the ultrathin device as compared to ultrathin devices filled with free rat islets measured as a dynamic GSIS (glucose stimulated insulin secretion) over time. The encapsulated islet cells are able to respond to the glucose stimulus and produce and release insulin. The encapsulation does not hinder the capability of the encapsulated cells to receive the glucose stimulus and respond to the glucose stimulus by producing and secreting insulin. The ultrathin devices filed with islet cells have diffusion kinetics that allow the resolution of biphasic insulin secretion and shut-off in response to the glucose concentration in its environment. GSIS occurs as a cell secretes insulin under exposure to glucose. The quantity of insulin secreted may be proportional to a level of glucose exposure. During GSIS, insulin secretion may decrease, stop, start, and increase, according to the level of glucose exposure. Some aspects further comprise releasing insulin from a cell in the cell housing device in an amount sufficient for a reduction of blood glucose level in the subject. In some aspects, releasing insulin stops when the blood glucose level in the subject is reduced to a normal level. In some aspects, releasing insulin re-starts when the cell in the cell housing device is re-exposed to a high blood glucose level in the subject.

Figure 49:
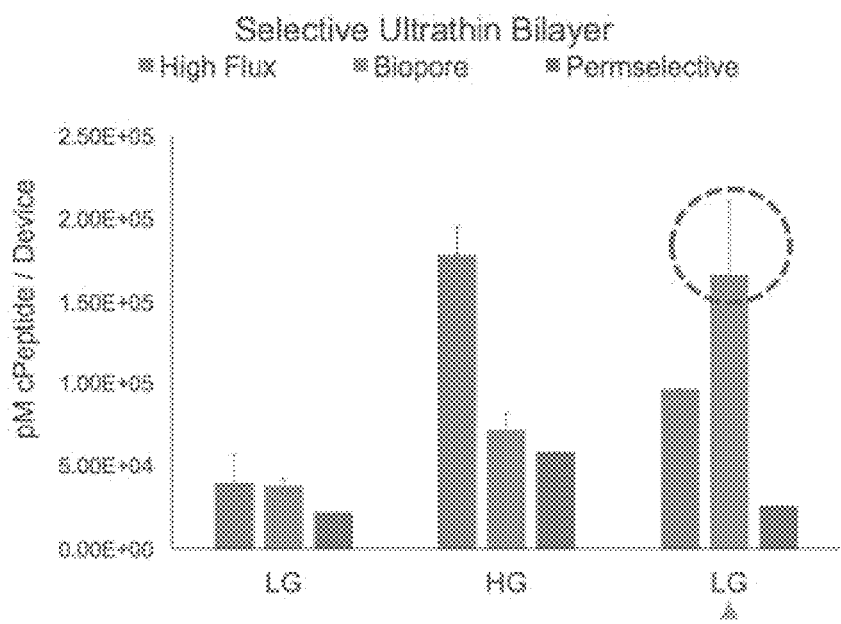
FIG. 49 shows the static C-peptide release in ultrathin devices with high flux membranes, or permselective membranes and filled with encapsulated islet cells before (LG or low glucose), during (HG), and after (LG) a high glucose stimulus, in accordance with some embodiments.

The choice of membrane can impact the flux kinetics of the insulin from the ultrathin devices and the responsivity of the ultrathin device to the glucose stimulus. FIG. 49 shows the static C-peptide release ultrathin devices comprising high flux membranes, or permselective membranes filled with encapsulated islet cells before (LG or low glucose), during (HG), and after (LG) a high glucose stimulus. The encapsulated islet cells in all three types of ultrathin membrane responded to the glucose stimulus. The ultrathin device with high flux membranes resulted in about $1.7 \times 10^5$ pM C-peptide per device under HG conditions while the ultrathin devices with permselective membranes resulted in about $5 \times 10^4$ pM C-peptide per device under HG conditions. For the ultrathin devices there was a delay in the release of the insulin in response to the HG condition. The delay in insulin release may be due to the retention of the insulin within the ultrathin device and may indicate that some membranes may be sticky to insulin. FIG. 50 shows the dynamic GSIS of ultrathin devices with AS-1 membranes. As AS-1 is a high flux membrane, this results in a high-flux ultrathin device that responds the high glucose stimulus of 20 mM by producing and secreting insulin and turns off the insulin production and secretion with the removal of the high glucose stimulus.

The ultrathin devices and cell housing devices can be prepared by a number of processes. These processes can include membrane fabrication, membrane coating, device assembly, and aseptic cell filling. The membranes can be fabricated and processed to achieve targeted properties. The targeted properties may include transport flux properties, mechanical properties, porosity, pore size, thickness, microstructure, or tortuosity. The fabrication process may include membrane stretching or sintering. The membrane can be further processed with a coating process to impart various desired properties. As described above, these coatings may include hydrophilic polymers, VEGF, or other molecules to encourage vascularization or protein transport. Then, the membranes can be fabricated and assembled into the devices. The ultrathin devices can be assembled using robotic assembly that can be automatic or semi-automatic assembly. The frame for the devices can be fabricated. Optionally, one or more ultrathin devices can be assembled onto the frames as macrodevices. The ultrathin devices can be filled aseptically with cells. The aseptic cell filling may be by a pressure fill process, centrifugation, gravity fill, open fill, or any combination thereof.

Figure 51:
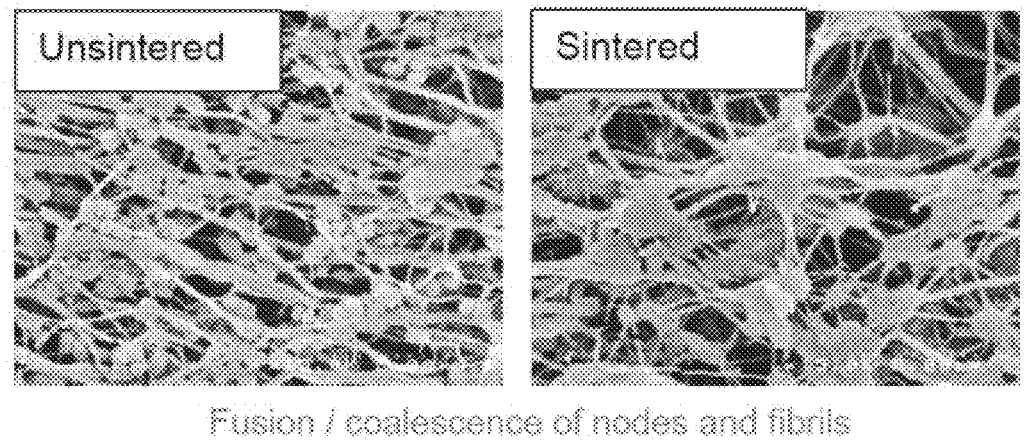
FIG. 51 shows scanning electron micrographs of unsintered and sintered membranes and change in the microstructure of the membrane, where there is fusion and coalescence of the nodes and fibrils of the membrane, in accordance with some embodiments.

The membranes may be sintered before fabrication into cell housing devices. The sintering process of the membrane may be used to alter the porosity and flux properties of the membrane. The sintering may increase the porosity of the membrane while maintaining its pore structure. The sintering can improve the mechanical stability and insulin flux of the membrane. FIG. 51 shows scanning electron micrographs of unsintered and sintered membranes and shows the change in the microstructure of the membranes, where there is fusion and coalescence of the nodes and fibrils of the membrane with sintering.

The sintering process can be very consistent with a low inter-lot variation. Table 2 shows the melting point temperatures of sintered membranes that range from about 326° C. to 333° C. and that is different from the melting point temperature of the unsintered membrane of about 345° C. as measured by DSC. The sintering process resulted in an inter-lot variation of 0.76%, indicating a consistency with the sintering process. Sintering of membranes can be used to alter the porosity of the membranes, which in turn can be used to tune the porosity and the flux properties of the cell housing device. The consistency in the sintering process may provide an attractive option to affect the membrane porosity and properties in high volume manufacturing of cell housing devices.

TABLE 2

Melting temperature of sintered membranes as measured by DSC

| Membrane | $T_m$ [° C.] |
| --- | --- |
| AU reference (unsintered) | 345.1 |
| AS Run 1 | 326.35 |
| AS Run 2 | 329.3 |
| AS Run 3 | 329.15 |
| AS Run 4 | 333.24 |
| AS Run 5 | 330.76 |

In some embodiments, the cell housing device assembled on to a frame may be fabricated with unsintered membranes and then brought through post-thermal curing to reduce porosity on the frame. This manufacturing method of assembly with unsintered membrane and post-thermal curing may reduce steps, time, and/or cost in the overall manufacturing process.

In some embodiments, the cell housing device may comprise at least one sintered membrane and at least one unsintered membrane. Such asymmetric sintering of the membranes of the cell housing device may provide a device with a controlled geometry. The use of different types of membranes in one cell housing device may induce curvatures in the device due to their different mechanical properties, where the first membrane may be more flexible or ductile than the second membrane. In some embodiments, the different types of membranes in one device may be a sintered membrane and an unsintered membrane.

Figure 52:
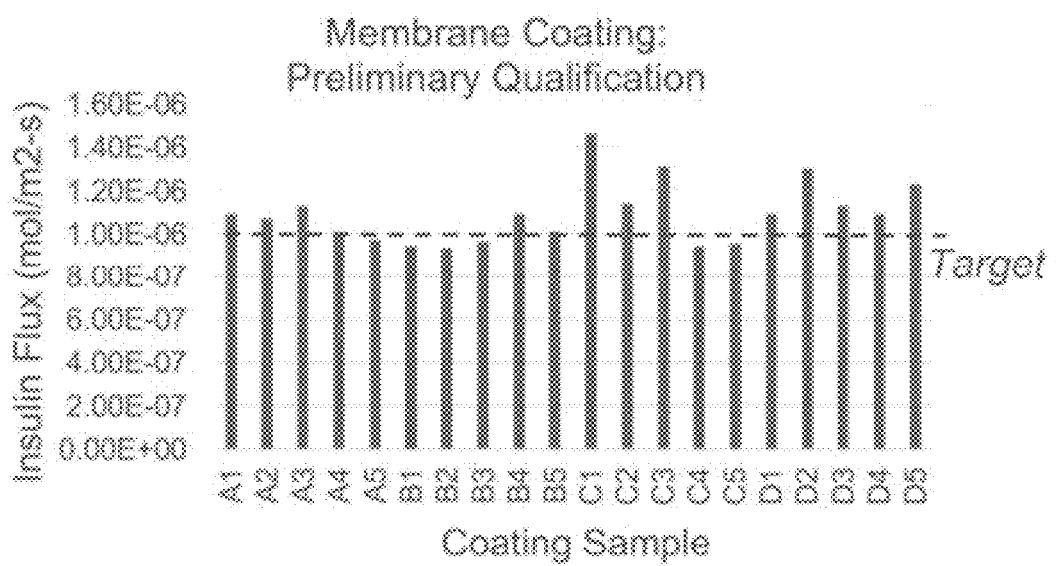
FIG. 52 shows a comparison of hydrophilic coating processes that resulted in membranes near the targeted insulin flux of $1 \times 10^{-6}$ mol/m$^2$/s, in accordance with some embodiments.

Coating of the membranes provides another approach to tune the flux properties of the cell housing device. The membrane may be coated with a hydrophilic coating before fabrication into cell housing devices. The hydrophilic coating may allow wetting of the membrane, allow for the ultrafiltration that can be used to load cells into the device, enable diffusion, and provide a biocompatible, neutral charge surface. FIG. 52 shows a comparison hydrophilic coating process that resulted in membranes near the targeted insulin flux of $1\times10^{-6}$ mol/m$^2$/s. The hydrophilic coating process resulted in an intra-lot variation of about 9% and inter-lot variation of about 8%.

In some embodiments, a hydrophobic membrane can be coating with a hydrophilic coating. The hydrophilic coating can be biocompatible and can improve the diffusion of insulin and other molecules. In some embodiments, an uncoated hydrophobic membrane may not allow for diffusion of insulin and other molecules. In some embodiments, the nanothin coating process may provide the appropriate level of permeability and insulin diffusion for the membrane and the cell housing device. In some embodiments, the semi-permeability of the membrane is configured to protect the cell from an immune attack. In some embodiments, the semi-permeability of the membrane is configured to protect the cell from an immune attack in the absence of an immune suppression therapy.

Because of the hydrophobic nature of ePTFE materials, a hydrophilic polymer can be polymerized around the ePTFE microstructure to enable membrane wetting and to lower the hydraulic resistance. This can facilitate ultrafiltration during the cell loading process and enable lower pressures to be used to introduce cells into the device. It can also create a neutral hydrophilic surface to minimize adsorption or attachment of host proteins and cells.

The framed and sintered membranes may be placed into 100% ethanol for 5 minutes followed by soaking in 30% ethanol for approximately 5 minutes. The membranes can be then soaked for approximately 5 minutes at room temperature in the coating solution comprised of 9 g APS, 27 mL of HPA and 18 mL of TEGDA in 30% ethanol. The polymerization reaction can be conducted at 70° C. ramping from room temperature at a rate of 3° C./min, controlled with Lab View software. The framed coated membranes can be removed from the coating solution and transferred to boiling 100% ethanol to remove unreacted monomers and then soaked in several changes of excess distilled water. Finally, the coated membranes are dried in a chamber with a continuous nitrogen stream.

Figure 53:
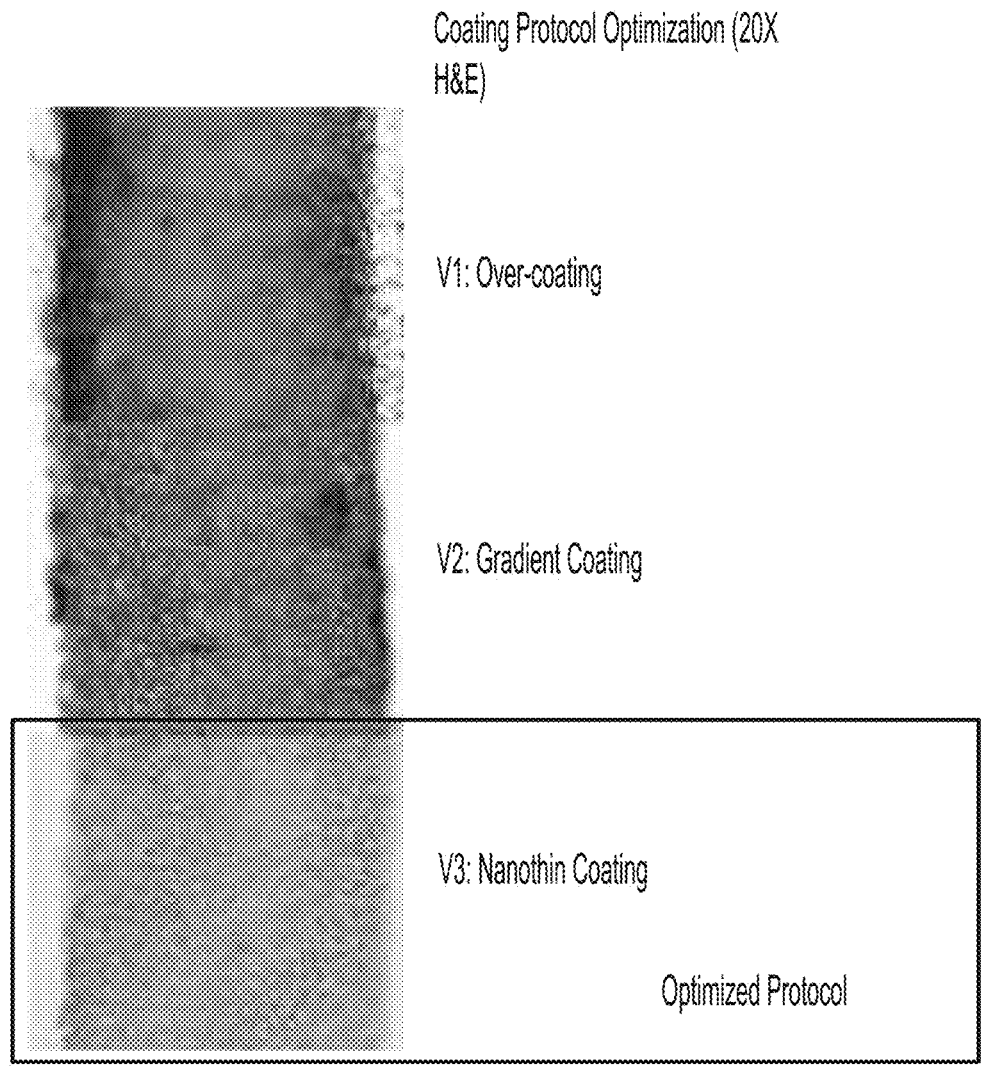
FIG. 53 shows membranes coated by three different coating processes V1, V2, and V3 that have been stained with H&E dye as an indication of the membrane hydrophilicity, in accordance with some embodiments.
Figure 54:
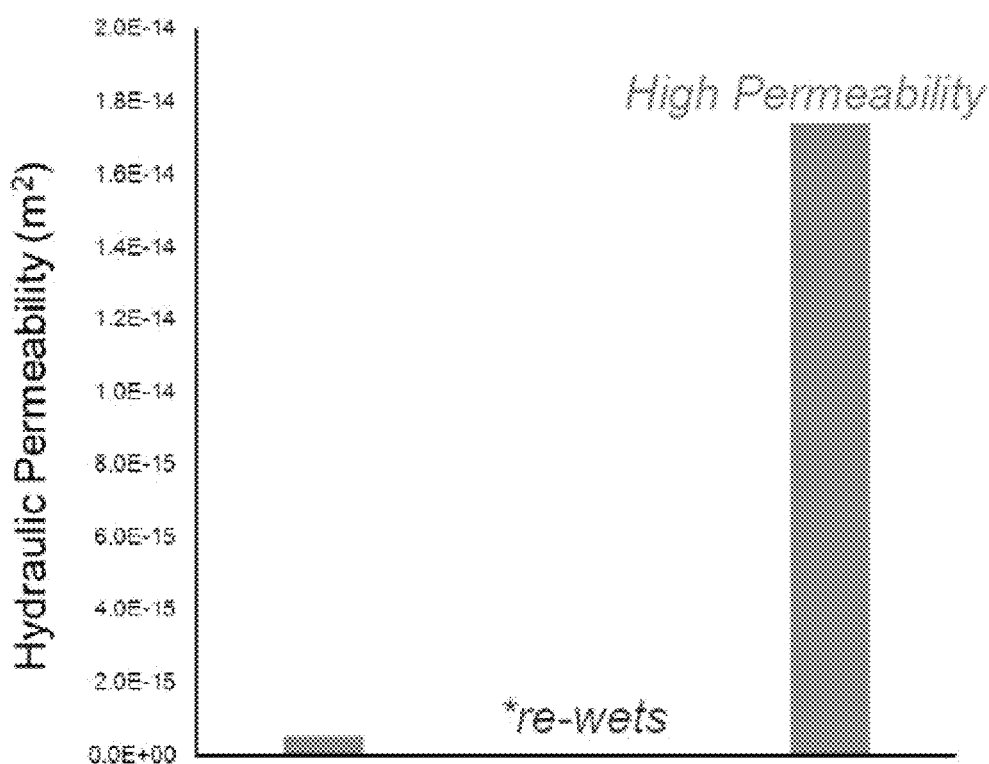
FIG. 54 shows the hydraulic permeability of a membrane, a membrane with the V1 coating process, and a membrane with the V3 coating process, in accordance with some embodiments.

FIG. 53 shows membranes coated by three different coating processes V1, V2, and V3 that have been stained with H&E dye as an indication of the membrane hydrophilicity. The membrane undergoing the V1 coating process appeared heavily dyed pink and appeared to be overcoated. The membrane undergoing the V2 coating process had variable levels of H&E dye staining that is stronger near its edges than the center and appeared to have a gradient coating. The membrane undergoing the V3 coating process had been coated by a nanothin coating process and appeared to be evenly coated throughout its cross sectional thickness. FIG. 54 shows the hydraulic permeability of a membrane, a membrane undergoing the V1 coating process, and a membrane undergoing the V3 coating process, where the V3-coated membrane showed a high permeability of about $1.8\times10^{-14}$ m$^2$ while the membrane and V1-coated membrane had a lower hydraulic permeability of less than $1\times10^{-15}$ m$^2$.

In some embodiments, the coated membranes in the ultrathin devices may have a hydraulic permeability of at least $1\times10^{-16}$ m$^2$, $1\times10^{-15}$ m$^2$, $1\times10^{-14}$ m$^2$, or $1\times10^{-13}$ m$^2$. In some embodiments, the first membrane and the second membrane of the ultrathin devices may have the same hydraulic permeability. In some embodiments, the first membrane and the second membrane of the ultrathin devices may have different hydraulic permeabilities. In some embodiments, different coating process may be used on first and the second membranes to achieve different hydraulic permeabilities. In some embodiments, the semi-permeability of the first membrane, the second membrane, or both is configured to protect the cell from an immune attack. In some embodiments, the semi-permeability of the first membrane, the second membrane, or both is configured to protect the cell from an immune attack in the absence of an immune suppression therapy The coating process may be designed and scaled up to coating multiple membranes or multiple cell housing devices at once. In some embodiments, the coating process may be scaled up to coat 40 human cell housing devices at once. FIG. 55 shows a set up to scale up the coating process along with a dry and a wet coated membrane. The high light transmission observed with the transillumination of the wet, coated membranes demonstrate the wettability of the coated membrane and serve as an indication of hydrophilic property and permeability of the coated membrane.

Figure 56:
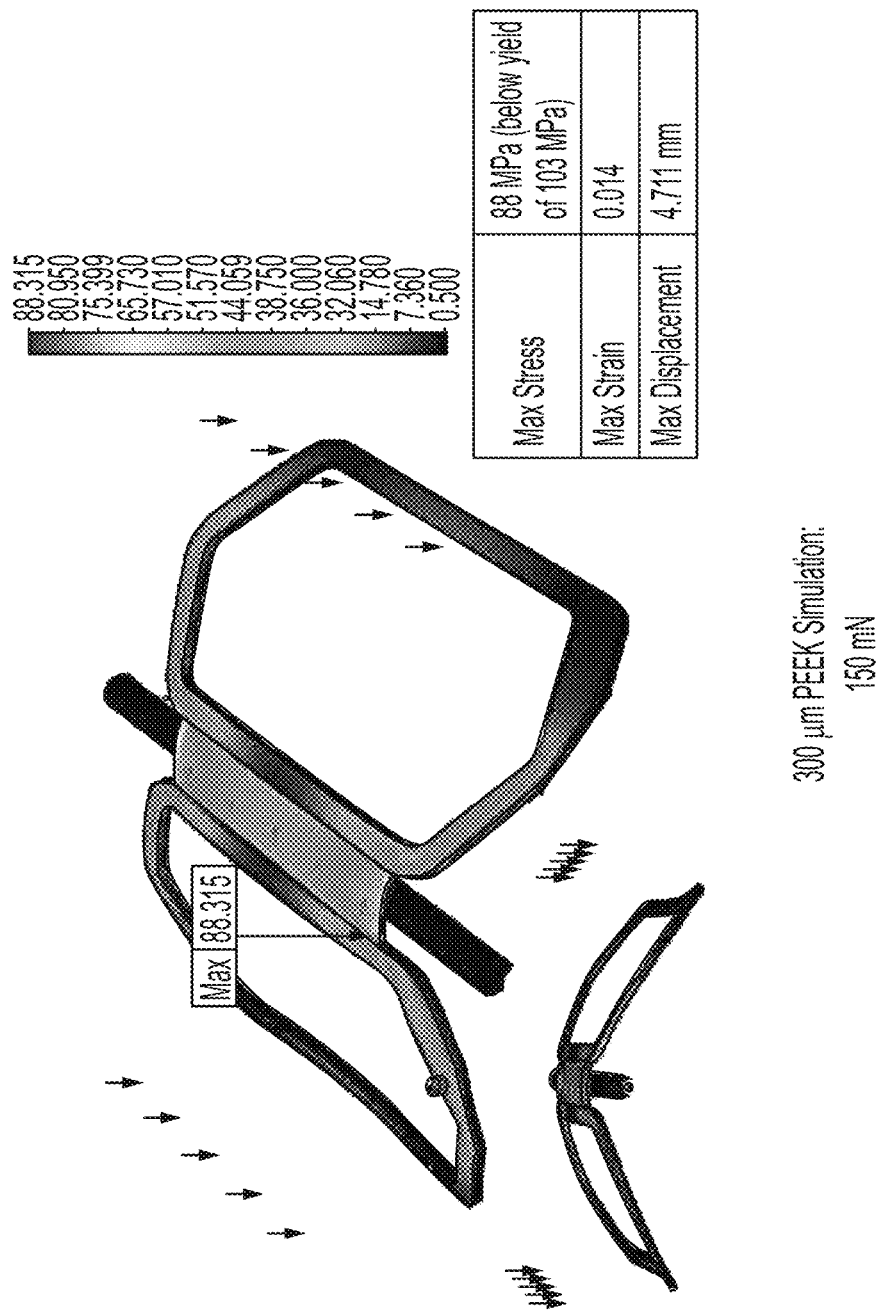
FIG. 56 shows a simulation of the mechanical properties of a 300 μm thick PEEK frame for two cell housing devices under a force of 150 mN, in accordance with some embodiments.

The frame for cell housing device may comprise various materials. In some embodiments, the frame may be a biocompatible material. As described above, the frame may hold one cell housing device or multiple cell housing devices. The frame may have similar mechanical properties as the host biological tissues surrounding the device after in vivo implantation. One measure of the mechanical property of a material is its Young's modulus. FIG. 56 shows the Young's modulus of various biological and synthetic materials and ranges of targeted Young's modulus for the candidate membrane, candidate frame material, and for the entire device (composite Young's modulus). The target Young's modulus for membranes may range from $10^6$ to $10^9$ Pa. The target Young's modulus for frame materials may range from $10^8$ to $10^9$ Pa. The target Young's modulus for device composite, also referred to as macrodevice or device with a frame, may range from $10^7$ to $10^9$ Pa, in between the ranges for the device alone and the frame alone. In some embodiments, the membrane may have a Young's modulus of at least $10^5$ Pa, $10^6$ Pa, $10^7$ Pa, $10^8$ Pa, or $10^9$ Pa. In some embodiments, the frame may have a Young's modulus of at least $10^7$ Pa, $10^8$ Pa, or $10^9$ Pa. In some embodiments, the device composite may have a Young's modulus of at least $10^7$ Pa, $10^8$ Pa, or $10^9$ Pa.

In some embodiments, the frame may comprise polyether ether ketone (PEEK). FIG. 57 shows the a simulation of the mechanical properties of a 300 μm thick PEEK frame for two cell housing devices under a force of 150 mN. The simulation shows that the PEEK frame would have a maximum stress of about 88 MPa, which is below the yield stress of about 103 MPa, maximum strain of about 0.014, and a maximum displacement of about 4.711 mm.

Figure 59:
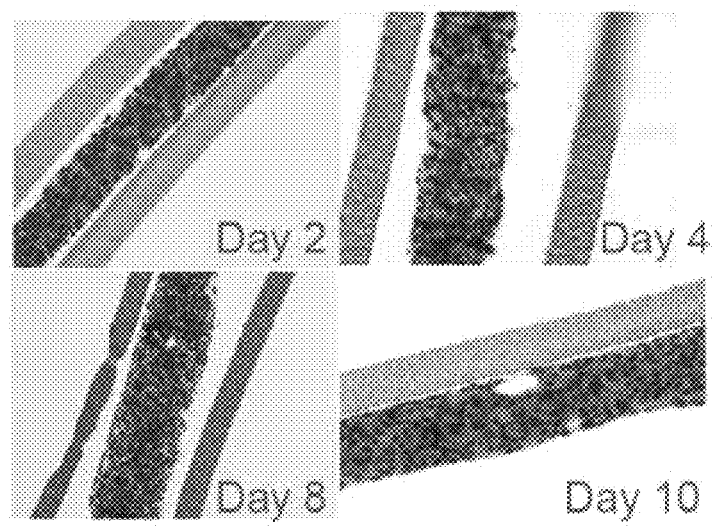
FIG. 59 shows H&E stained histological sections at day 2, 4, 8, and 10 in maximally filled cell housing devices stored under standard conditions of 20% oxygen and 37° C. with high cell viability over the 10 days of storage, in accordance with some embodiments.

FIG. 58 shows an example of the PEEK frame holding a cell housing device with a fused dot in the center of the device. The frame may be micromachined or machined using a method appropriate to achieve its targeted dimension. FIG. 59 shows a single frame module, comprising a single cell housing device with a centrally fused dot on a frame that has been maximally filled. The filled device with the centrally fused dot on the frame shows limited lateral expansion of the membrane.

Figure 89A:
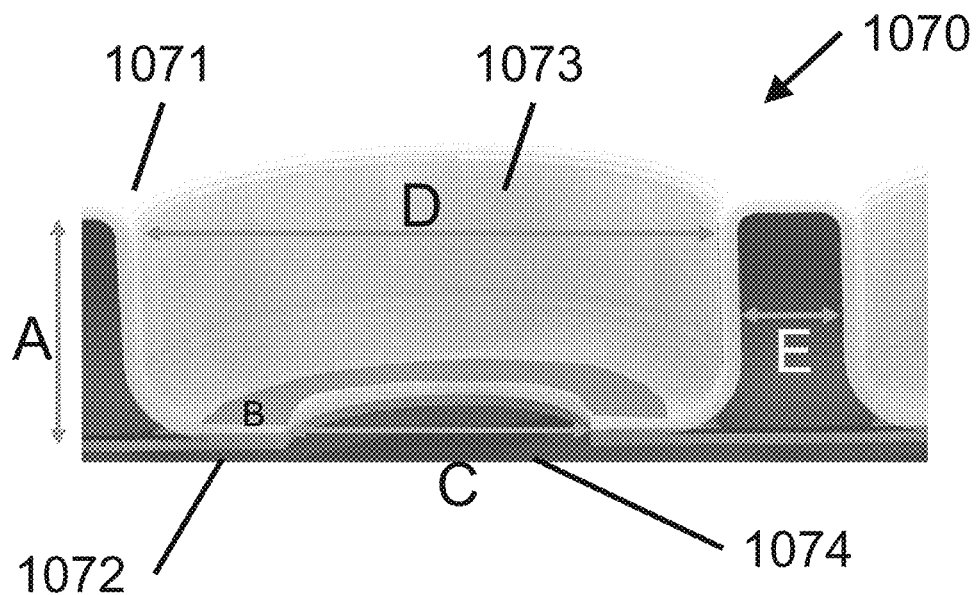
FIG. 89A shows an image of exemplary geometric parameters of a channel array device, in accordance with some embodiments.

FIGS. 89A and B show various configurations of the macrodevices with multiple devices held by a macrodevice frame. In one design, the macrodevice frame can be flexible and hold multiple devices. In some embodiments, the macrodevice frame can be a flexible, integrating frame for holding multiple devices and have with a porous structure surrounding individual cell housing devices.

Figure 60:
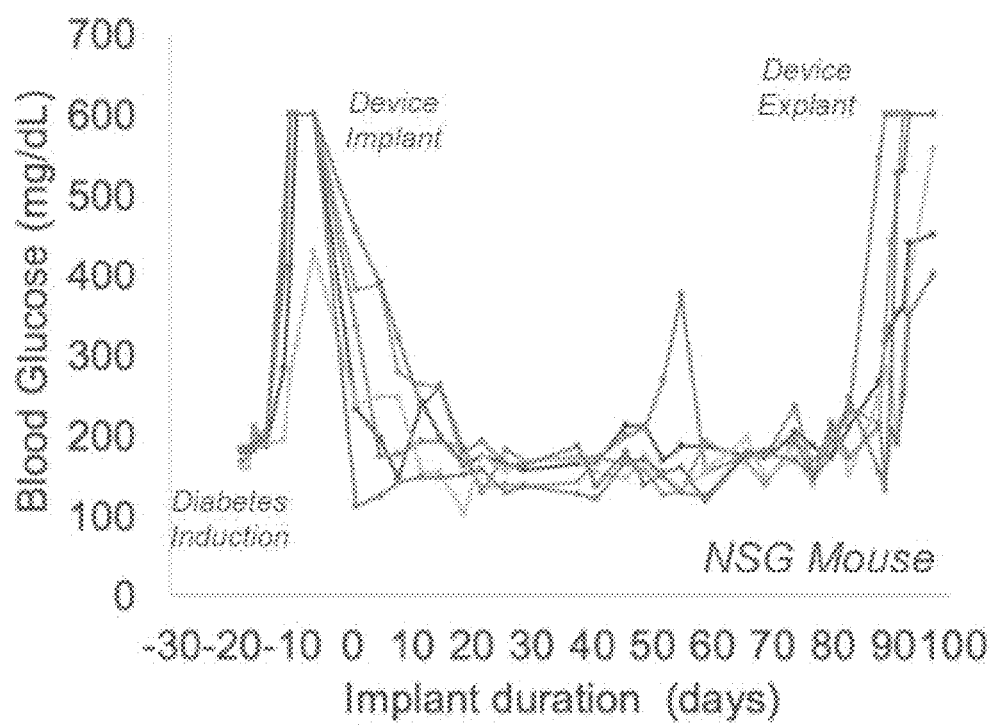
FIG. 60 shows the blood glucose levels over 90 day implantation of ultrathin cell housing devices with AS-1 membrane and filled with SC-islet cells in a NOD scid gamma (NSG) mouse model, an immunodeficient mouse model, in accordance with some embodiments.

The cell housing devices may be maximally filled with cells as shown in FIG. 59. FIG. 60 shows at least 10 days of cell viability in the maximally filled cell housing devices and stored under standard conditions of 20% oxygen and 37° C. as evidenced by the presence of cells in the H&E stained histological sections. The cell housing devices filled with cells may be stored under various conditions to extend the viability of cells within the cell housing device before implantation. The cell housing devices filled with cells may be stored under various temperatures, at 4° C., 23° C., or 37° C. In some embodiments, the cell housing devices filled with cells may be stored at temperatures of at least 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In some embodiments, the cell housing devices filled with cells may be stored at hypoxic, normoxic, or hyperoxic conditions.

The two membranes of the cell housing devices may be fused along its surface into discrete dots. There may be various configurations of the fused dot shape, diameter or distances, and density (e.g. center to center spacing) of the device. The dots may be circular, rectangular, triangular, linear, or other shapes. The dots may have various cross-sectional distances or diameter. In some embodiments, the dot diameter may be at least 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.5 mm, or 5.0 mm.

The device may have one fused dot or multiple fused dots. The dots may be spaced regularly. The dots may be spaced apart regularly into a matrix array. The dots may be spaced irregularly or randomly. In some embodiments, the dots may be spaced apart, center to center, by at least 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, or 10.0 mm. In some embodiments, the dots may be placed on top of each other and overlap.

The total surface area of the dots may cover a portion of the surface area of the membranes of the cell housing device. The surface area of the membranes of the cell housing device that is covered by the dots may be a portion that does not interfere with its ability to maintain cell viability, cell function, and release of molecules from the interior of the device. In some embodiments, less than 30%, 25%, 20%, 15%, 10%, 9%, 8%, 7%, 6%, 5%, 4%, 3%, 2%, or 1% of the surface area of the membranes may be covered by the dots.

The dots may provide an adhesive restraint for the membranes of the devices from bending away from each other. The dot density and diameters can be selected to restrict the deformation, bending, or expansion of the membranes of the devices away from each other during filling of the device. The dot diameter and density can impact the allowable filling volume by creating a series of counters. Devices with a shorter dot pitch may have a higher dot density than devices with a longer dot pitch for a device of the same dimensions. For the devices have the same dot diameters and the device dimensions, a device with shorter dot pitch can have smaller internal volume available for filling than a device with a longer dot pitch.

The dimensions of the dots may be adjusted to control the volume within the cell housing device and the SA:V ratio. In some embodiments, the surface area of the dots may be increased to decrease the volume within the cell housing device. In turn, the increased surface area of the channels may provide a higher SA:V ratio for the cell housing device. In some embodiments, the surface area of the dots may be decreased to increase the volume within the cell housing device. The decrease in the surface area of the dots may provide an lower SA:V ratio for the cell housing device.

The dots may be created in various patterns. The dots may be created in a pattern that maintains the capability of filling devices uniformly and throughout the entire device. The dot pattern can be designed to tune the volume and/or amount of cells that can be loaded into the device. The dot pattern can be designed to restrain the membranes of the device from expanding or bending during filling of the device with cells. In some embodiments, the device may have one dot. In some embodiments, the device may have multiple dots. In some embodiments, the device may have at least 1, 2, 3, 4, 5, 6, 7, 8, 9, 10, 11, 12, 13, 14, 15 16, 17, 18, 19, 20, 21, 22, 23, 24, 25, 26, 27, 28, 29, or 30 dots.

The thickness of the device during filling can be further controlled by applying external restraint to the outer surfaces of the device. The external restraint can be placed on the outside surfaces of the membranes of the cell housing devices and cover a large portion or the entire surface of the membranes. The external restraint may physically limit the deformation of the membranes of the devices away from each other during filling. The external restraints can be porous to help expel the air that is displaced from the interior of the device as the device is filled. The external restraint can be further tunable by using a spacer with a target distance in between the porous restraints. The spacer may correspond to the overall thickness of the device before filling.

The dots may be created by various processes to fuse the membranes in discrete dots. The dots may be created by the fusion process using the spot welding process described herein. The dots may be created by placement of an adhesive onto desired locations for the dots on a first membrane and subsequently bringing the first membrane in contact with a second membrane. The adhesive dots can be built up in multiple layers. In some embodiments, the adhesive dots are built up in two layers. In some embodiments, the adhesive may be placed onto the membraned in an automated or a semi-automated process. In some embodiments, an automated dispenser may be programmed to dispense a specified volume or weight of an adhesive at a specified location. In some embodiments, the dispenser may be provided with the information regarding the dimension of the membrane and the dot pattern to guide the dispensing of the adhesive onto the membrane. The dots may be created by a combination of the adhesive placement and spot welding process.

Many adhesives may be suitable for creating fused dots. The adhesives may be cyanoacrylates, urethane acrylates, UV-cured epoxies, thermally cured epoxies, or 2-part epoxies wherein one element may be embedded within the membrane (monomer), and the other may be applied in solution around it (crosslinker). Alternatively or in combination, solvents may be used to partially solubilize the membrane junction to create a bond.

The properties of the adhesive and pattern of adhesive placement can be used to tune the dot diameter and density and the thickness of the device during filling. The adhesive properties may impact the rate of adhesive incursion into the membrane. The first application may establish the effective diameter of the dots. The incursion rate can be a function of the viscosity of the adhesive. Depending on the chemistry of the adhesive, the incursion rate may be impacted by the charge and degree of hydrophilization of the membrane. The coating, membrane, and adhesive properties together can shape the density of the dot pattern. Alternatively or in addition, the dot pattern can be controlled by a pico-pulse adhesive dispenser that regulates these parameters by time, and the dispensing by the dispenser can be a nonlinear dispensing.

In some embodiments, the adhesive has a viscosity of about 200 cP to 450 cP. In some embodiments, the adhesive has a viscosity of at least 10 cP, 20 cP, 30 cP, 40 cP, 50 cP, 60 cP, 70 cP, 80 cP, 90 cP, 100 cP, 200 cP, 300 cP, 400 cP, 500 cP, 600 cP, 700 cP, 800 cP, 900 cP, or 1000 cP.

The cell housing devices can be scaled to various sizes while maintaining various parameters constant. The device can be scaled to provide equivalent microenvironment, for example, in a device for mouse implantation as in a device for human implantation. Various parameters that are important to the function of the device can be maintained to be constant. These parameters can be diffusion distance of a molecule of interest, such as insulin, or SA:V ratio. As size of the device can affect the mechanical properties, the device may be designed to maintain the flexibility of the device without folding over at the target implant site. The scaled up device can be designed to be compatible with filling of the device at a higher throughput as the filling process is also scaled up. The scaled device design may incorporate an updated fluid path to improve the final seal of the device after filling. The scaled device design may incorporate an integrated macrodevice frame for multiple devices in place of the basic flexible macrodevice frame as shown in FIGS. 74A and B.

Provided herein, is an ePTFE cell housing device, comprising a first membrane and a second membrane opposite and attached to the first membrane. The first membrane may comprise a first surface and a second surface. The first surface may comprise a plurality of channels and an opposing second face having a surface area. The first membrane and the second membrane may form an enclosed compartment providing a volume for housing a cell within the ePTFE device.

The exemplary PVDF channel array device may attenuate under UV light.

Although an exemplary frameless ePTFE channel array device may enable ePTFE transcription, in some circumstances, the device may distort in vivo. The exemplary frameless ePTFE channel array devices employ a stabilizing frame, as well as straight and angled filling tubes, respectively. The angled filling tube may provide improved fluid flow. Further the angled filling tube may increase the dead space within the fill tube attached to the membrane. Finally, the angled filling tube may reduce the necessity for laser vision during manufacturing. As seen, the angled filling tube is askew from a symmetrical bisecting plane of the membrane, whereas the straight filling tube is co-planar or parallel to the symmetrical bisecting plane of the membrane.

Further provided herein is a method of manufacturing a cell housing device. The method may comprise providing a first membrane, forming a plurality of channels within the first membrane, and fusing a second membrane to the first membrane. The first membrane may comprise a first face and a second face. The second face may oppose the first face. The plurality of channels may be formed within the first face of the first membrane. The second membrane may be fused to the second face of the first membrane. The fusing of the second face of the first membrane and the second membrane may form a compartment. The compartment may be configured for housing a cell between the second face of the first membrane and the second membrane.

Figure 86A:
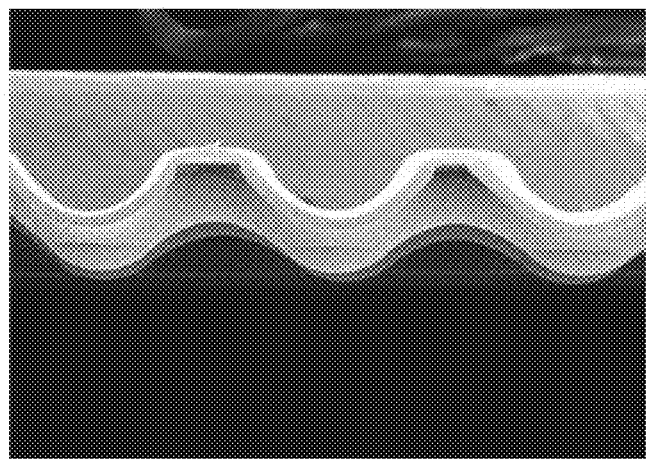
FIG. 86A shows an image of an exemplary positive mold for a channel array device, in accordance with some embodiments.
Figure 86B:
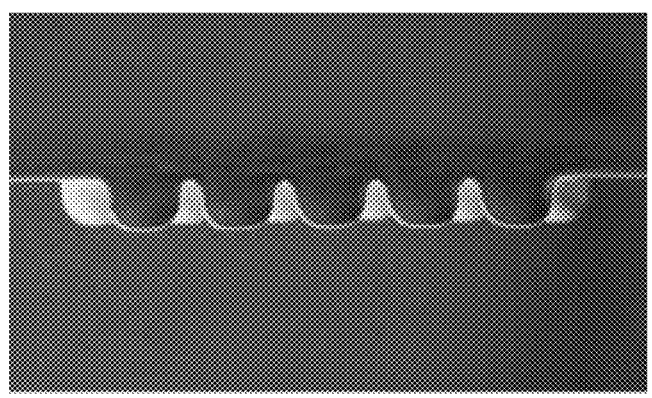
FIG. 86B shows an image of an exemplary negative mold for a channel array device, in accordance with some embodiments.

The forming of the plurality of channels within the first face of the first membrane is performed by a mold 1021 1022. The mold may comprise a positive mold 1021, as seen in FIG. 86A or a negative mold 1022, as seen in FIG. 86A. The positive mold 1021 may contact the second face of the first membrane whereas the negative mold 1022 may contact the first face of the membrane. The use of a negative mold 1022 may improve the 3D thermoforming of the membrane to produce membranes with a more optimal thickness and porosity.

The upper portion of the exemplary channel array device may enable the insertion of cells into the device via an external filling tube. The lower portion of the exemplary channel array device comprises the membrane. The external filling tube as shown may comprise an angled filling tube, wherein the filling tube is askew from a symmetrical bisecting plane of the membrane. The upper portion of the exemplary channel array device may further act as a mechanical frame for support. The exemplary channel array device may have an internal volume of about 24 μl, a channel quality of about 50, a footprint of about 1×0.5 cm, a channel of 1 mm, and a channel-to-channel (C-C) distance of about 1 mm. As seen per FIG. 87, the exemplary channel array device comprises a frame. The insertion tube 1040 may be manually attached over the frame. The exemplary channel array device shown in FIG. 87 may comprise a rodent channel array device.

A pocket frame may enable incorporation of the fluid path within the channel array device. Further, the pocket frame is easier to manufacture, without requiring the manual addition of an insertion tube. A plurality of such channel array devices may be formed at once. The plurality of co-formed channel array devices may be easily filled, separated, and sealed to allow for autonomous and/or machine operated manufacturing. The pocket frame within the channel array device may be formed by Selective Laser Sintering (SLS), injection molding, solvent casting, machining, or any combination thereof. Such a process may allow for a sufficiently high control over the geometry and resolution of the pocket frame.

Additionally, the pocket frame may be configured to impart torsional resistance, bending resistance, or both for the channel array device through its hoop strength. Such resistance may be provided by the pocket frame having a variable thickness, width, cross sectional shape, or any combination thereof. Further, the pocket frame sealed between the first and second membranes can be configured to be air tight to prevent contamination.

Figure 106A:
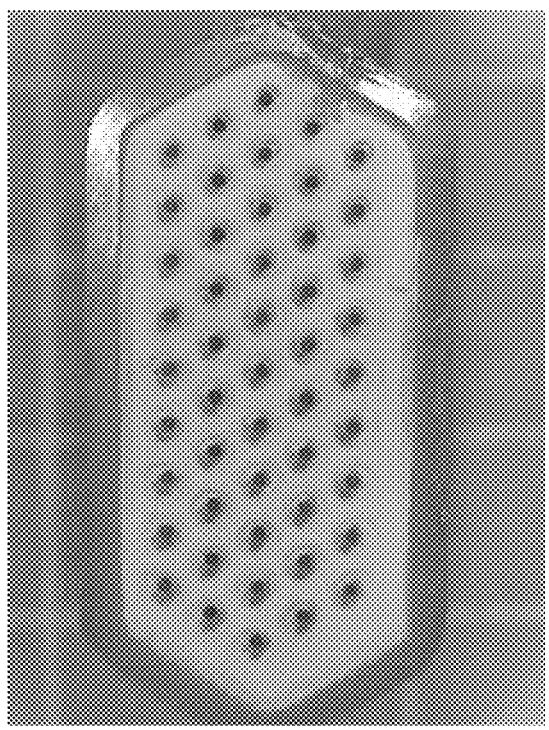
Figure 106B:
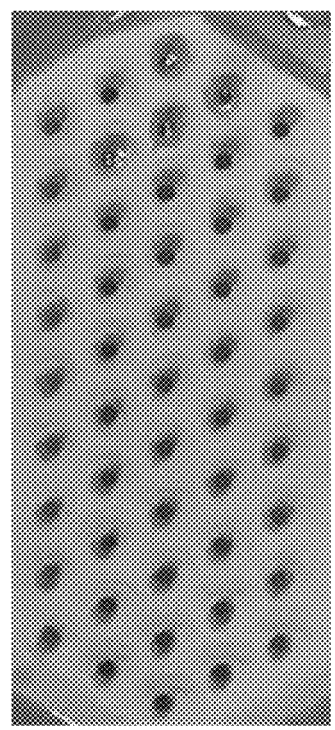

Finally, per FIGS. 106a and 106b, respectively, the pocket frame 1051 within the channel array device 1050 allows for a greater and more uniform mass flow than a channel array device 1050 with fill port.

Per FIGS. 107A-B, the geometrical design parameters of the channel array device 1070 are optimized for increased effectiveness. The geometry of the channels in the channel array device 1070 may be defined by a cell chamber height (A), a fusion area (B), an opening diameter (C), channel diameter (D), and a channel spacing (E).

The cell chamber height (A) may be measured as a maximum normal distance between an interior surface of the first membrane 1071 and an interior surface of the second membrane 1072. The cell chamber height (A) may be measured as an average of the maximum normal distances between an interior surface of the first membrane 1071 and an interior surface of the second membrane 1072 for all the channels 1073 in the channel array device 1070. In some embodiments, the cell chamber height (A) is at least about 300 µm. Per Table 3 below, the cell chamber height (A) may be optimized to alter the diffusive flux, foreign body response, vascularization, atraumatic cell loading and, and volume/footprint of the device.

The fusion area (B) may be measured as a total surface area where the first membrane 1071 and the second membrane 1072 are fused. The fusion area (B) may alternatively be measured or correlated as the surface area of the upper surface of the first membrane 1071 that is generally parallel to the second membrane 1072. Per Table 3 below, the fusion area (B) may be optimized to alter the seal integrity, foreign body response, and vascularization of the device.

In some embodiments, the device 1070 further comprises an opening 1074 through the first membrane 1071 and the second membrane 1072 within the channel 1073. The opening 1074 may have an opening diameter (C). The opening diameter (C) may be measured as an average, a maximum, or a minimum inner diameter of the opening 1074. The opening diameter (C) may be measured as an average, a maximum, or a minimum opening diameter (C) of the plurality of openings 1074 within the plurality of channels 1073 within the device 1070. In some embodiments, the opening 1074 has a concentricity with respect to the channel 1073 of at most 25% the channel diameter (D). Per Table 3 below, the opening diameter (C) may be optimized to alter the seal integrity, foreign body response, and vascularization of the device.

In some embodiments, the channel diameter (D) is measured as the maximum, minimum, or average inner diameter of the channel 1073. In some embodiments, the channel diameter (D) is measured as the maximum, minimum, or average normal inner diameter of the channel 1073. In some embodiments, the channel diameter (D) is measured at a narrowest point in the channel. In some embodiments, the channel has an average diameter of about 400 µm to about 3,000 µm. Per Table 3 below, the channel diameter (D) may be optimized to alter the diffusive flux, foreign body response, vascularization, atraumatic cell loading and, and volume/footprint of the device.

The channel spacing (E) may be measured as the maximum, minimum, or average distance between the inner surfaces of two adjacent channels 1073. The channel spacing (E) may be measured as the maximum, minimum, or average normal distance between the inner surfaces of two adjacent channels 1073. The channel spacing (E) may be measured as an average of the maximum, minimum, or average distances between the inner surfaces of two adjacent channels 1073, for each of the plurality of channels 1073. In some embodiments, a center of each channel is separated from the center of another channel by a distance of about 75 µm to about 500 µm. Per Table 3 below, the channel spacing (E) may be optimized to alter the diffusive flux, atraumatic cell loading, and volume/footprint of the device.

Figure 89B:
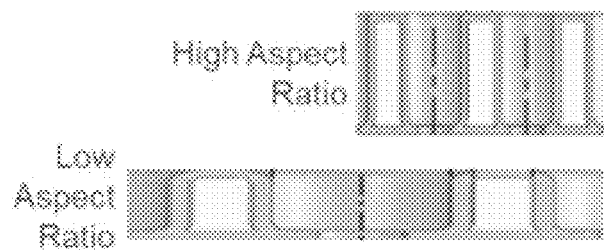
FIG. 89B shows an illustration of an exemplary channel assay device with a high aspect ratio (top) and a low aspect ratio (bottom), in accordance with some embodiments.
Figure 89C:
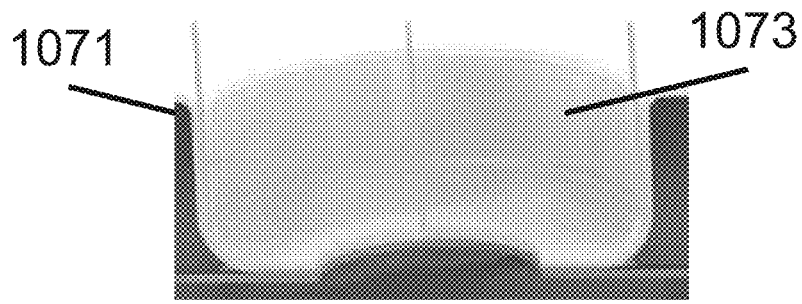
FIG. 89C shows an illustration of the cylindrical design parameters exemplary channel assay device, in accordance with some embodiments.

The channels 1073 may be further characterized per FIG. 89B by their aspect ratio. The aspect ratio may be calculated as a ratio between the cell chamber height (A) and the channel diameter (D). The aspect ratio may be at least about 0.5.

TABLE 3

Channel Design Parameter and Effects

| Design Parameter | Seal Integrity | Diffusive Flux (SA:V) | Foreign Body Response | Vascularization | Atraumatic Cell Loading | Volume Footprint |
|---|---|---|---|---|---|---|
| Cell Chamber Height (A) |  | X | X | X | X | X |
| Fusion Area "Shelf" (B) | X |  | X | X |  |  |
| Laser Hole Diameter (C) | X |  | X | X |  |  |
| Channel Diameter (D) |  | X | X |  |  | X |
| Channel Spacing (E) |  | X |  |  | X | X |

Per FIGS. 107C, the geometry of the channels can be designed and optimized for use. Uniform cylindricity, circularity, and perpendicularity of the channels 1073 with respect to the first surface of the first membrane 1073 enable optimal use and cell growth.

Figure 90A:
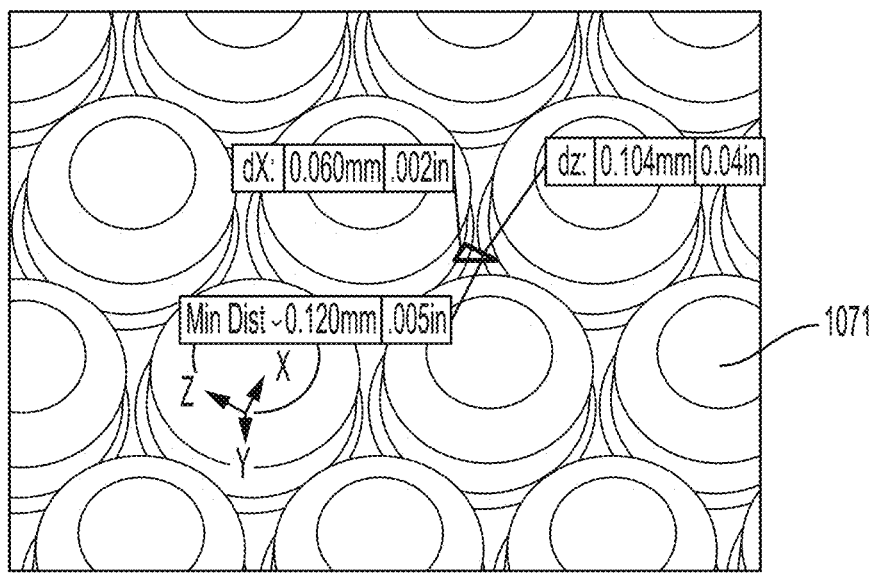
FIG. 90A shows an illustration of a high density channel array (150 μm spacing), in accordance with some embodiments.
Figure 90B:
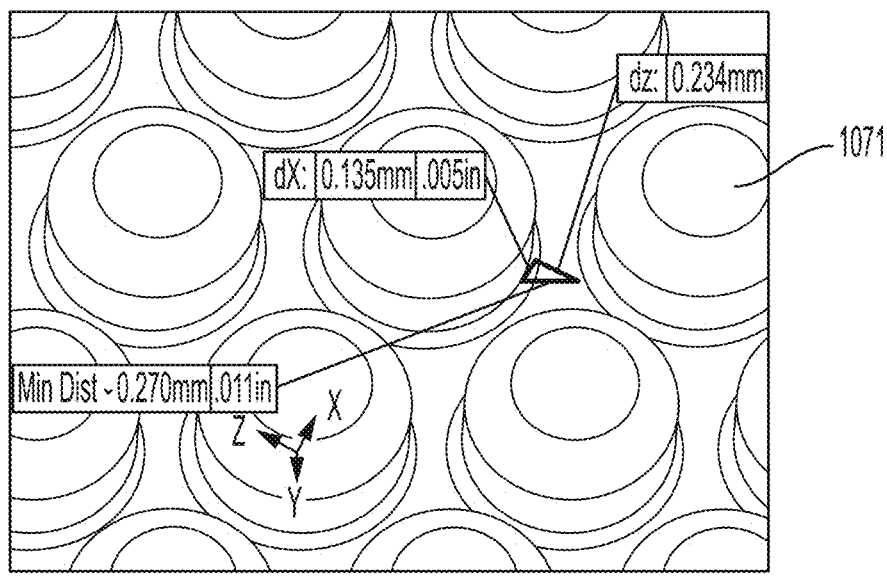
FIG. 90B shows an illustration of a low density channel array (270 μm spacing), in accordance with some embodiments.

FIGS. 108A-B, shows the inner face of an exemplary first membrane of a channel array, whereby the spacing and sizing of the channels enable an increased surface to volume ratio, as delineated in Table 4 below. FIG. 90A displays an exemplary channel array having a channel spacing of 150 µm, and FIG. 90B displays an exemplary channel array having a channel spacing of 270 µm.

In some embodiments, the channel array device 1070 has at least one of a length and a width of about 0.25 cm to about 3 cm. In some embodiments, each of the plurality of channels 1073 is generally perpendicular with respect to the first membrane. In some embodiments, the channels 1073 are arranged in a rectilinear array. In some embodiments, the channels 1073 are arranged in a polar array. In some embodiments, the device has a number of channels per area along a transverse plane is greater than about 50/cm2. In some embodiments, the device has a surface area to the volume ratio of at least about 40 cm−1. In some embodiments, the channel array device 1070 comprises a compartment between the first membrane and the second membrane. The compartment may comprise a single continuous open space. The compartment may have a volume of about 8 uL to about 600 uL.

In some embodiments, the method of producing a channel array further comprises laser ablating a portion of the first membrane and the second membrane within the plurality of channels. In some embodiments, the laser ablation removes the fused portions of the first membrane and the second membrane to form an opening.

Figure 91A:
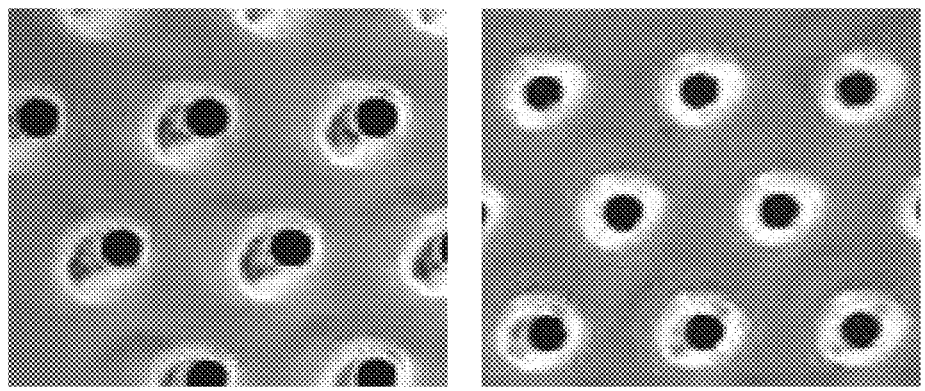
FIG. 91A shows a detailed image of an exemplary laser drilled channel array device, in accordance with some embodiments.

In some embodiments, the opening has a concentricity with respect to the channel of at most 25% the diameter of the channel. FIG. 91A (left) shows a detailed image of an exemplary laser drilled channel array devices, whereby the openings have an unacceptable concentricity with respect to the channel of greater than about 25%. FIG. 91A (right) shows a detailed image of an exemplary laser drilled channel array devices, whereby the openings have an acceptable concentricity with respect to the channel of less than about 25%. Per FIG. 91C increased concentricity improves the uniformity of the width of the fused area around each opening, which enables increased bonding strength and sealing. Additionally, increased concentricity increases the surface area to volume ratio and reduces the required size of the sealing area necessary for strength and integrity, whereby decreasing the seal surface area reduces the residual "shelf" that stimulates FBR and creates additional diffusion distance of centralized vessels.

Figure 91B:
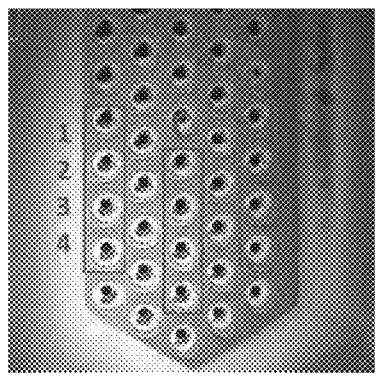
FIG. 91B shows an image of an exemplary laser drilled channel array device, in accordance with some embodiments.
Figure 91C:
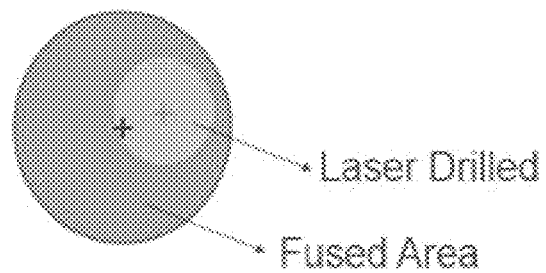
FIG. 91C shows a diagram for measuring the concentricity of an opening within a channel, in accordance with some embodiments.
Figure 92:
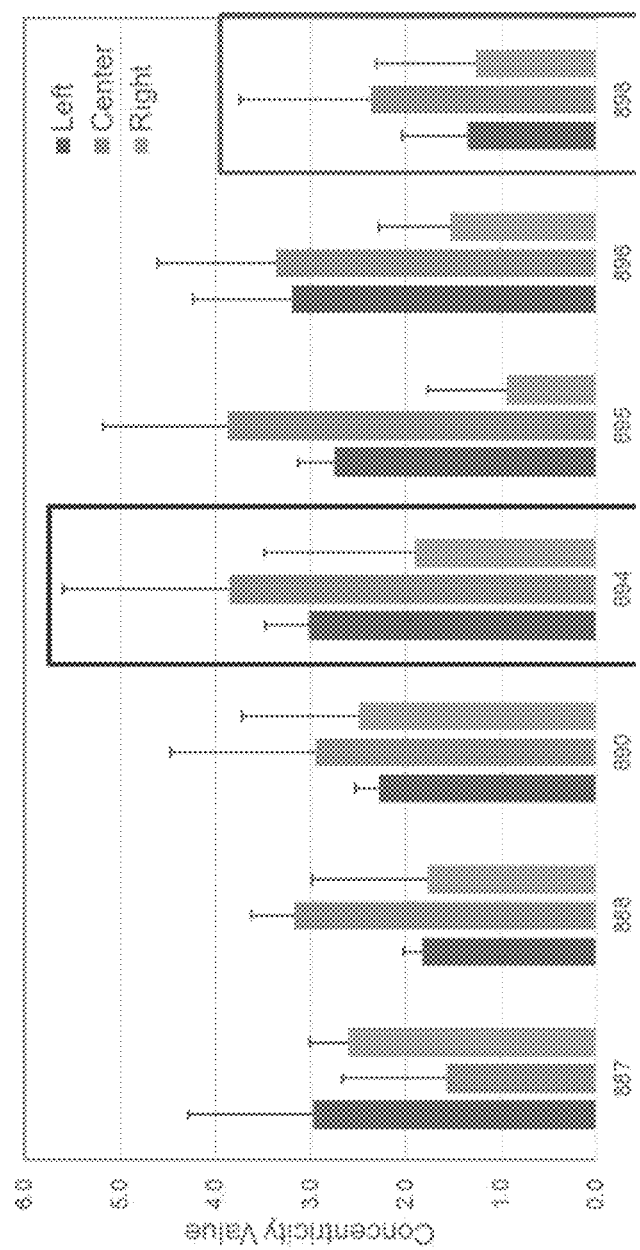
FIG. 92 shows a graph of measured concentricities of exemplary openings and channels

Alignment of the openings and channels from left to right across the exemplary array device per FIG. 91B is shown in FIG. 92, whereby a concentricity values of 0 correspond to perfect concentricity. For instance, laser ablating parameters associated with test 894 (center) formed an opening with a much higher concentricity value than the parameters associated with ablating parameters associated with test 898 (right).

Figure 93A:
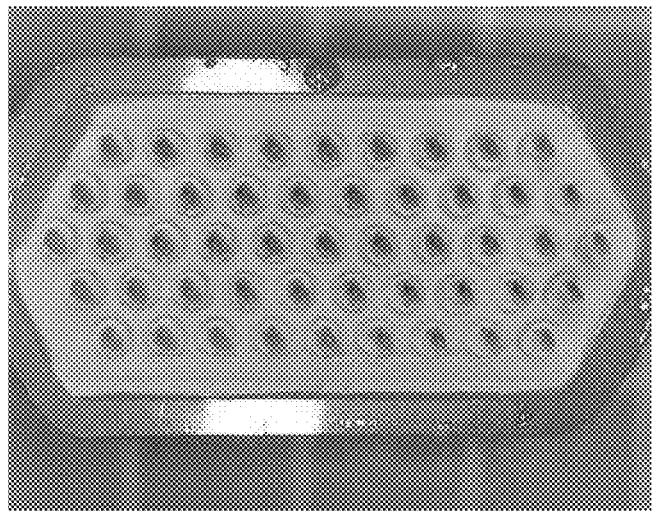
FIG. 93A shows an image of an exemplary laser drilled channel array device, in accordance with some embodiments.
Figure 93B:
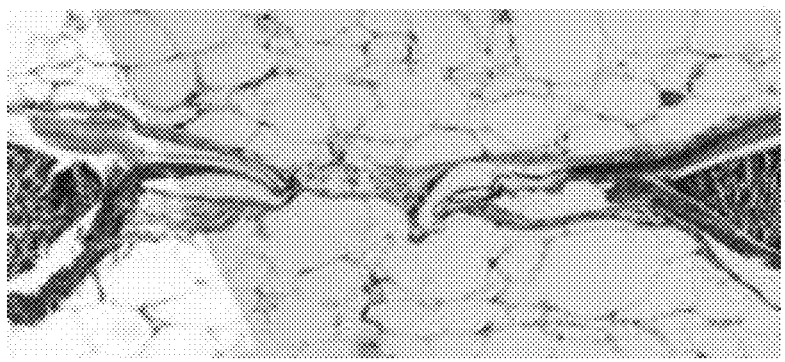
FIG. 93B shows an image of the seal interface of a channel array device, in accordance with some embodiments.
Figure 94A:
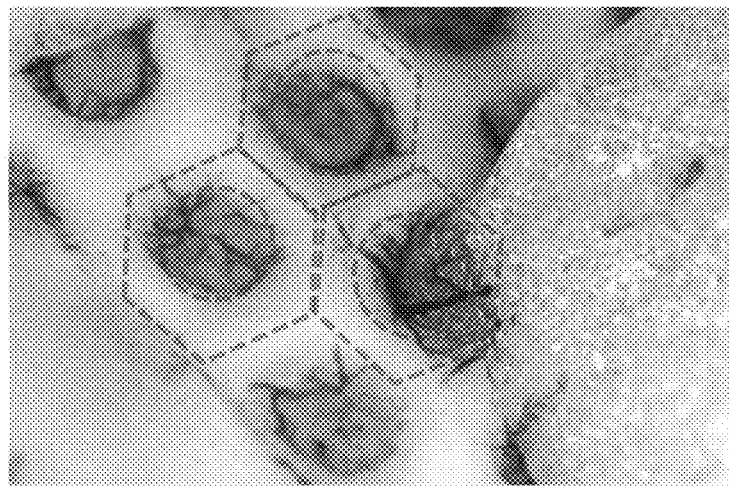
FIG. 94A shows a high image of the vascularization around an implanted channel array device, in accordance with some embodiments.
Figure 94B:
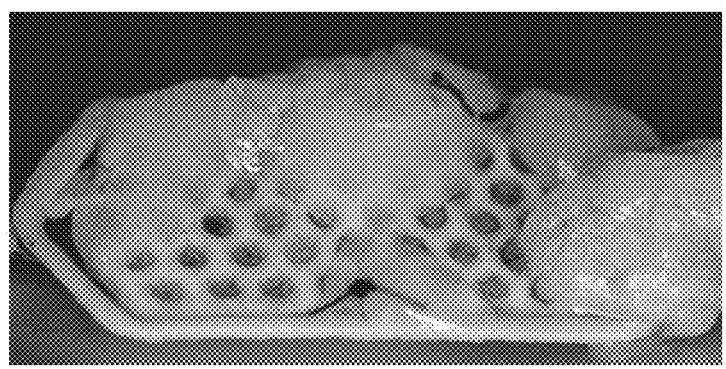
FIG. 94B shows a low magnification image of the vascularization around an implanted channel array device, in accordance with some embodiments.
Figure 95:
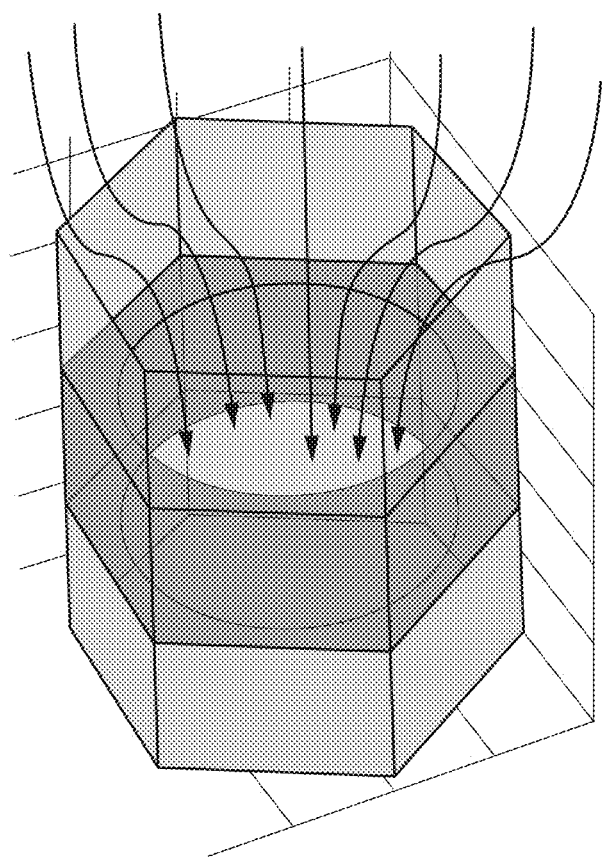
FIG. 95 shows a diagram of blood vessel host integration, in accordance with some embodiments.

FIG. 93A shows an image of an exemplary laser drilled channel array device. FIG. 93B shows an image of the seal interface of a channel array device. FIG. 94A-B show a high and low magnification images of the vascularization around an implanted channel array device. FIG. 95 shows a diagram of blood vessel host integration, in accordance with some embodiments. In some embodiments, at least one of the first membrane and the second membrane are configured to enable vascularization of the cell within the device. In some embodiments, at least one of the first membrane and the second membrane are configured to enable vascularization of the cell within the device in absence of an immune suppression therapy.

Figure 96A:
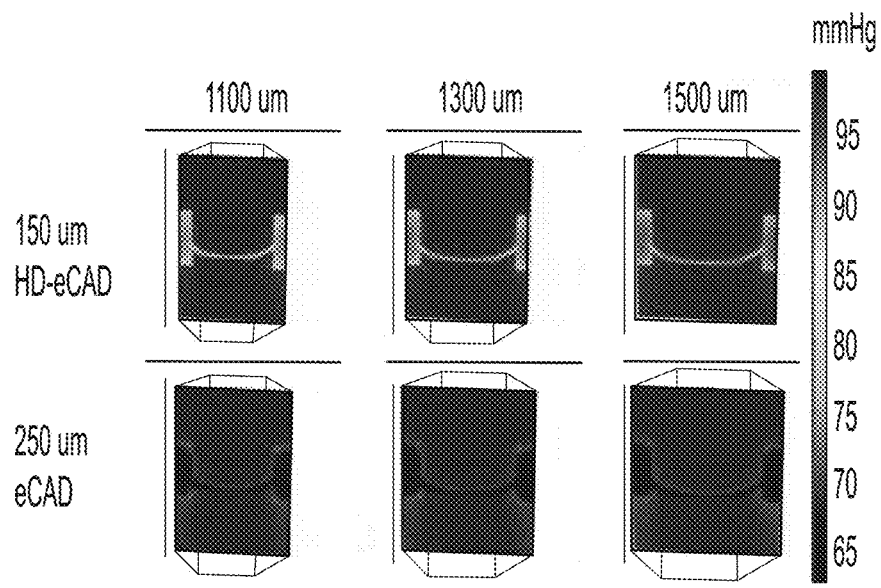
FIG. 96A shows the equilibrium $O_2$ tension distributions within exemplary channel array devices, in accordance with some embodiments.
Figure 96B:
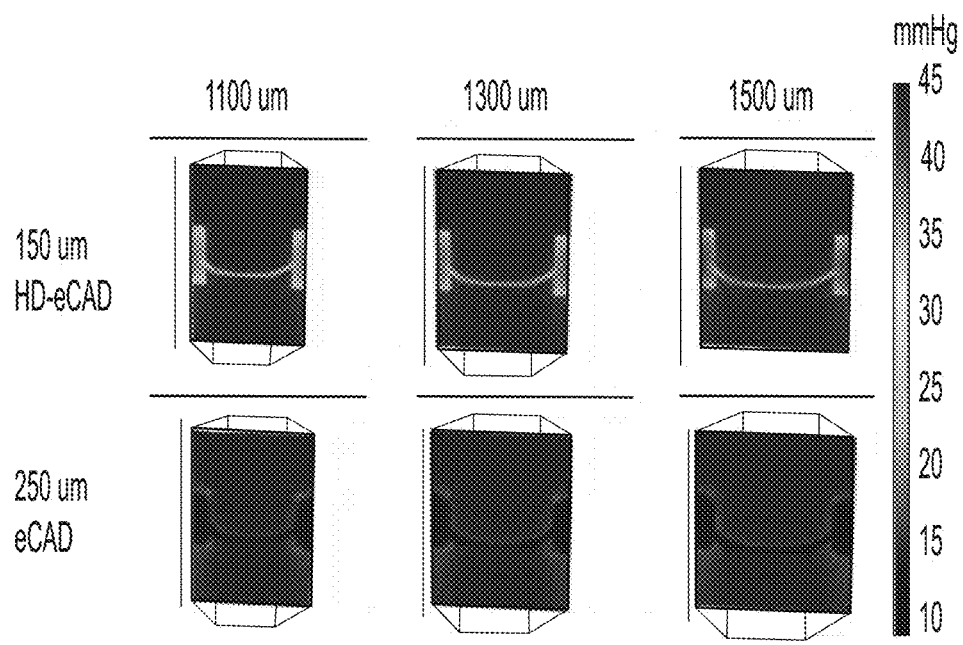
FIG. 96B shows the equilibrium $O_2$ tension distributions within exemplary channel array devices, in accordance with some embodiments.

The equilibrium $O_2$ tension distribution with venous capillary of exemplary channels at a pressure of 100 mmHg is shown in FIG. 96A at channel diameters of 1,100 µm, 1,300 µm, and 1,500 µm, and at channel edge to edge distances of 150 µm and 250 µm. Additionally, the equilibrium $O_2$ tension distribution with venous capillary of exemplary channels at a pressure of 45 mmHg is shown in FIG. 96A at channel diameters of 1,100 µm, 1,300 µm, and 1,500 µm, and at channel edge to edge distances of 150 µm and 250 µm.

Figure 98:
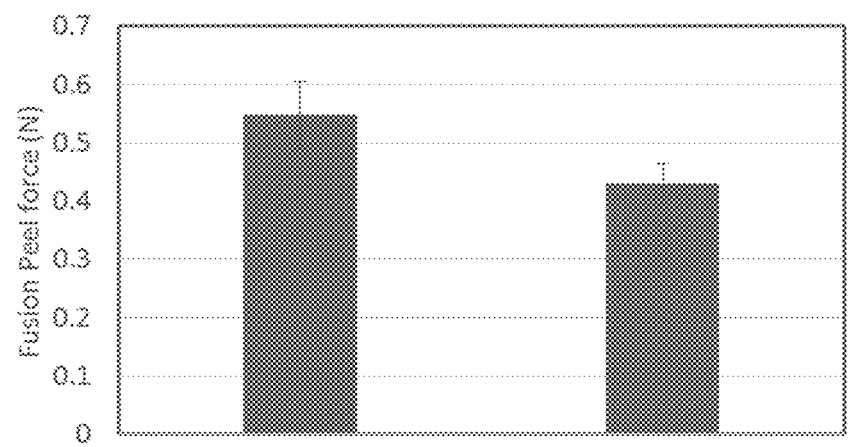
FIG. 98 shows a graph measuring the fusion peel force of exemplary membranes, in accordance with some embodiments.

In some embodiments, molding the plurality of channels with a mold comprises thermoforming the plurality of channels. FIGS. 115A-B show top perspective and cross-sectioned images, respectively, of exemplary unsintered membrane thermoformed at 360° C. for 7 minutes at a negative pressure of 3 psi. As seen, the thermoforming processes yields molded channels free of cracks or structural collapse. Such a thermoforming process enables sharp bends and large cell chamber heights 1150 of about 558 µm, which increase the surface area to volume ratio and provide sufficient room for housing the cells. Although, thermoforming of the exemplary membrane cause no blow outs, per FIG. 98, alternative membranes and processes may enable greater fusion strengths due to reduced sintering and greater malleability. Such methods and membranes may be further able to produce greater cell chamber heights 1150.

Figure 99A:
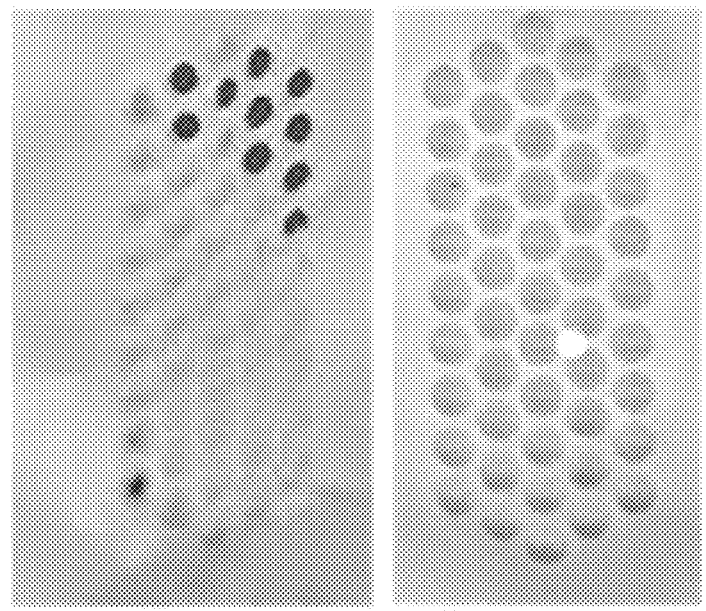
FIG. 99A shows an image of exemplary blown-out and fully formed membrane channels, in accordance with some embodiments.
Figure 100:
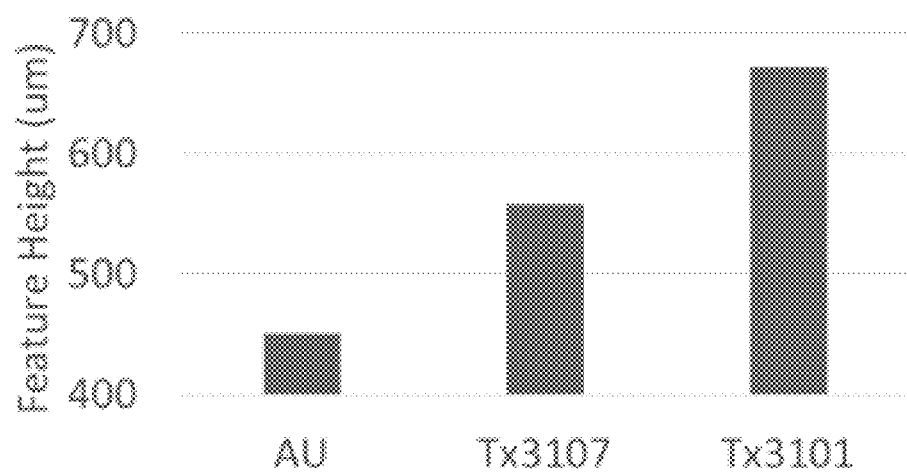

FIG. 99A shows arrays of channels with blowouts (left) and without blowouts (right). As seen above, thermoforming the exemplary membrane at 3.5 psi and 370° C. for 7 minutes yielded the channels, shown per 118B, with the greatest cell chamber height. Per FIG. 100 and Table 6 below, the membrane of 118B enables a superior cell chamber height of about 672 µm and a cell volume of about 27 ul.

TABLE 6

Membrane types and associated parameters

| Membrane Type | Feature Height (µm) | Fill volume (µL) | Theoretical Cell Dose |
|---|---|---|---|
| A | 450 | ~16 | 1.34E+07 |
| B | 558 | ~21 | 1.77E+07 |
| C | 672 | ~27 | 2.27E+07 |

Figure 101:
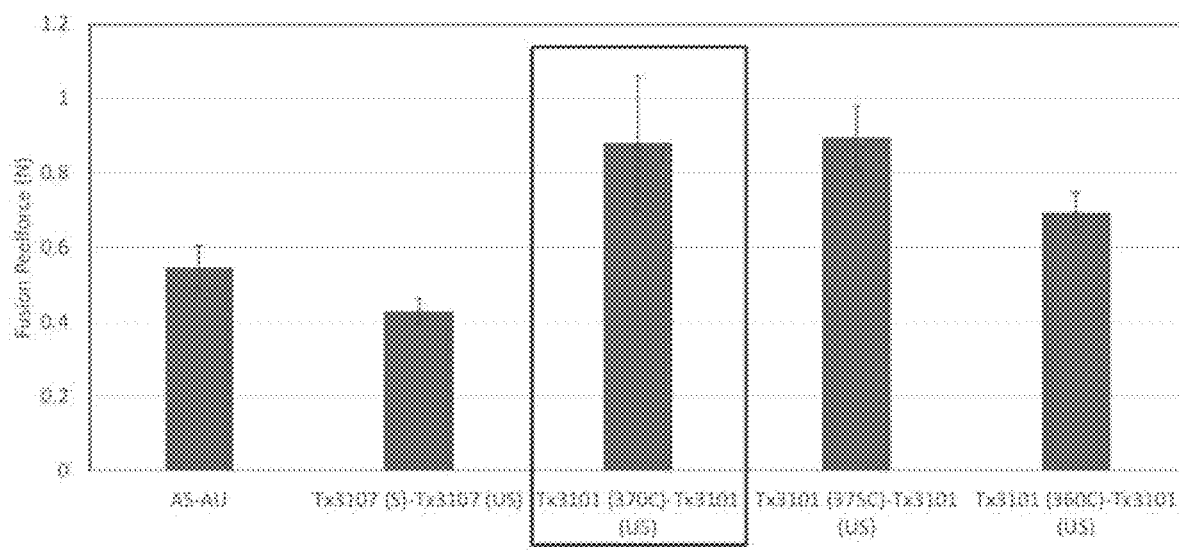
Figure 103:
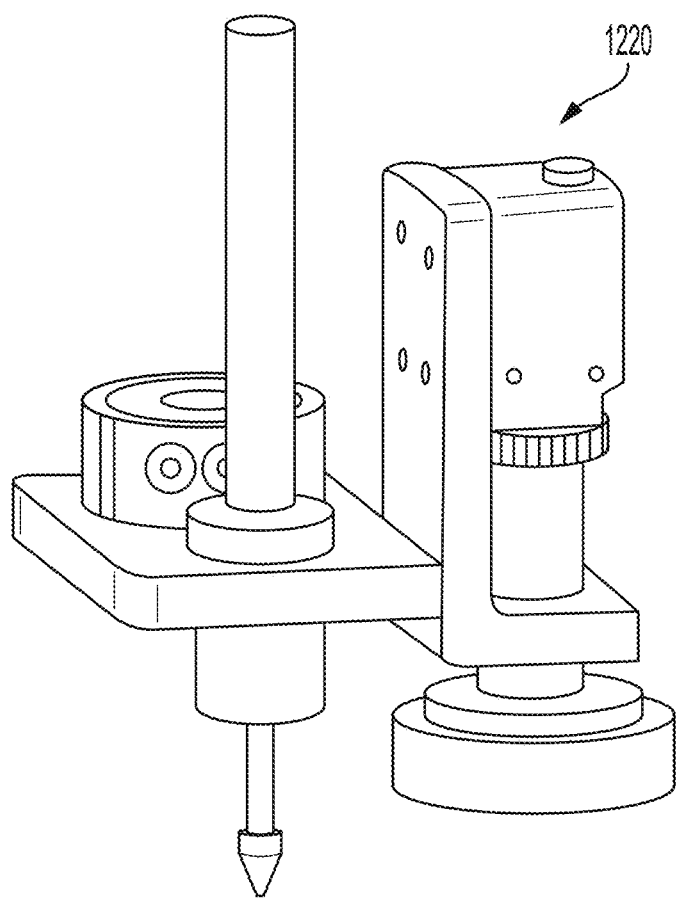

Additionally, per FIG. 101 thermoforming at a temperature of about 370° C. enables increased fusion peel resistance force of a membrane whose channels were formed with the fusion tool of FIG. 103A at a temperature of 474° C., a fusion time of 0.05 seconds, and a Z offset of 2.625 mm.

Figure 99B:
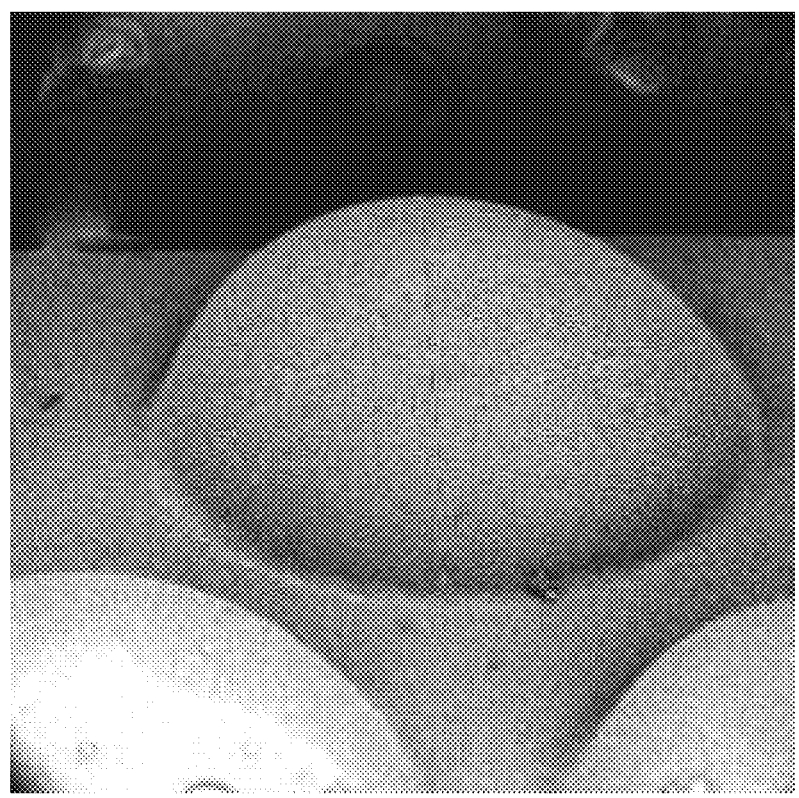
Figure 102A:
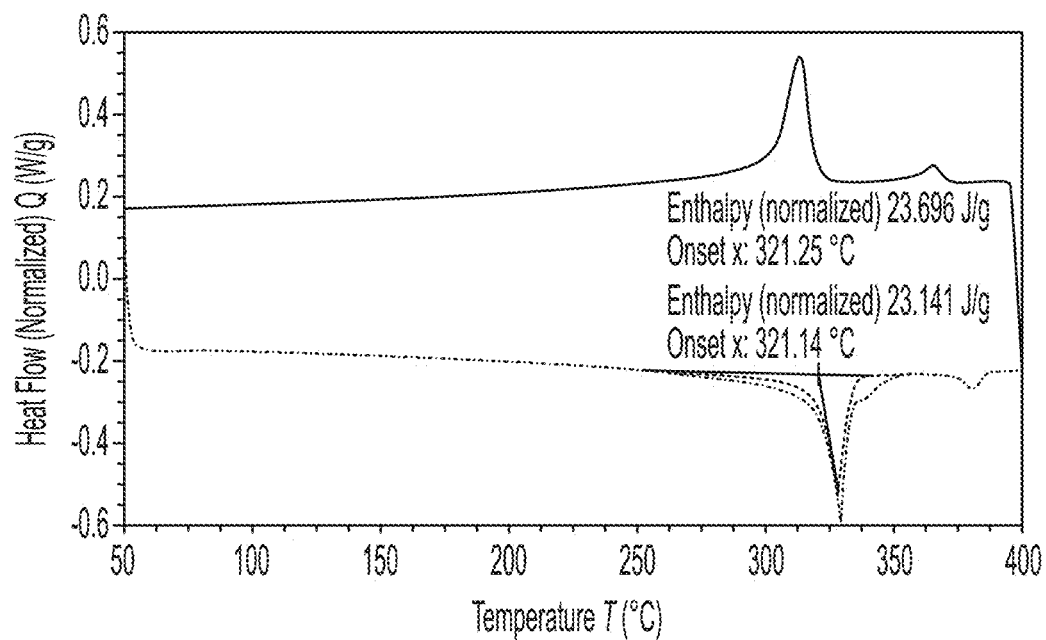
Figure 102B:
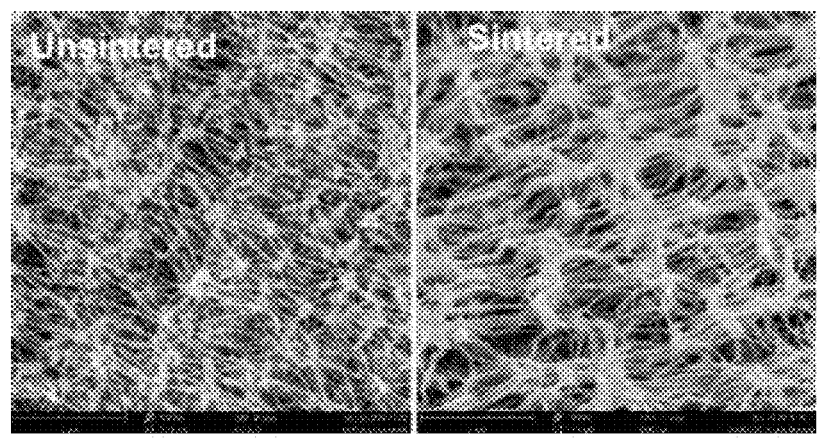

Further, FIG. 102A shows a differential scanning calorimetry graph for the exemplary membrane of FIG. 99B, with a normalized enthalpy at 23.696 J/g and onset x of 321.25° C., and with a normalized enthalpy at 23.141 J/g and onset x of 321.14° C. Further, FIG. 102B shows an electron micrograph of the membrane with sintering of the membrane (right) and no sintering of the membrane (left). Sintering of the membrane may increase the stability of the cell device.

FIGS. 122A and 122B show an illustration and an image of an exemplary thermal fusion tool. The thermal fusion tool may comprise a positional based fusion tool configurable to impart a set number of fusion strikes, each strike for a set fusion time. In some embodiments, the set fusion time is less than about 1 second. In some embodiments, the fusion tool 1220 strikes the first membrane at each of the one or more points for 1 to 6 times. In some embodiments, the fusion tool 1220 strikes the first membrane at each of the one or more points for at most about 16 times. Further the temperature of the fusion head can be adjusted to alter the properties of the channels and fusions formed thereby. In some embodiments, the set fusion temperature is about 250° C. to about 600° C. In some embodiments, the fusion tool 1220 has a striking contact area of at least about 0.07 mm$^2$. In some embodiments, the fusion tool 1220 contacts the side of the first membrane opposite the thermoformed face.

In some embodiments, the channels are formed by placing the first membrane and the second membrane in a frame 1221 and striking one or more points on the first membrane with the fusion tool 1220. In some embodiments, the frame encompasses at least a portion of the outer edges of the first membrane and the second membrane. The first membrane and the second membrane may be generally parallel during the fusion. The first membrane and the second membrane may be generally aligned, whereby the entirety or majority of the second membrane is covered by the first membrane. The first membrane and the second membrane may be separated by a gap distance. In some embodiments, the gap distance is about 300 μm to about 1,200 μm.

In some embodiments, striking the first membrane pierces the first membrane, the second membrane, or both and fuses a portion of the first membrane to the second membrane. In some embodiments, at least one of the first membrane and the second membrane is substantially flat. In some embodiments, at least one of the first membrane and the second membrane comprises an unsintered flat sheet.

Figure 104:
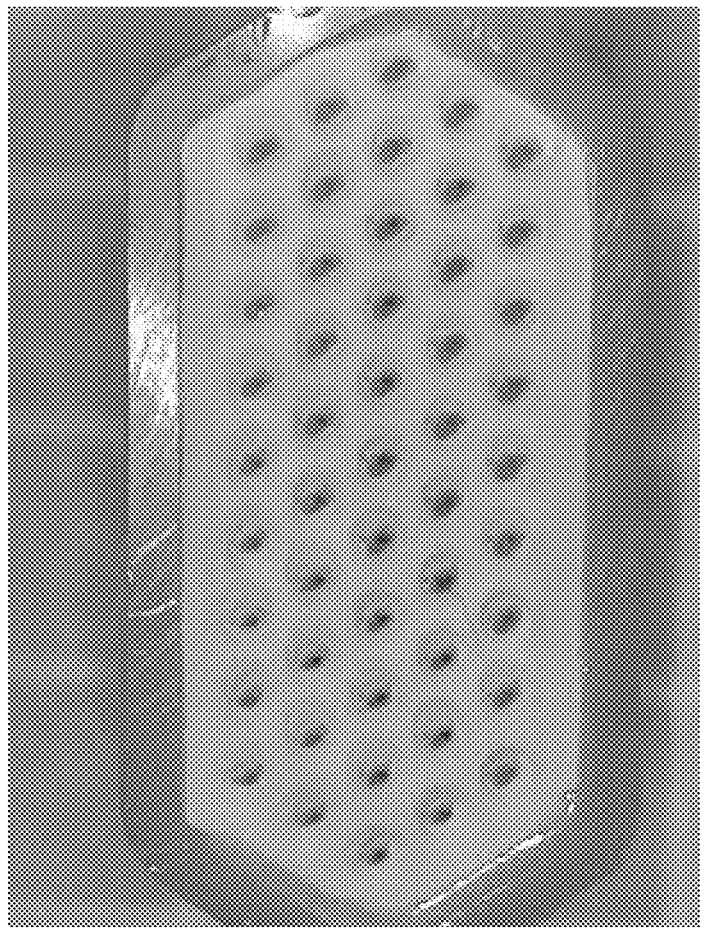
Figure 105A:
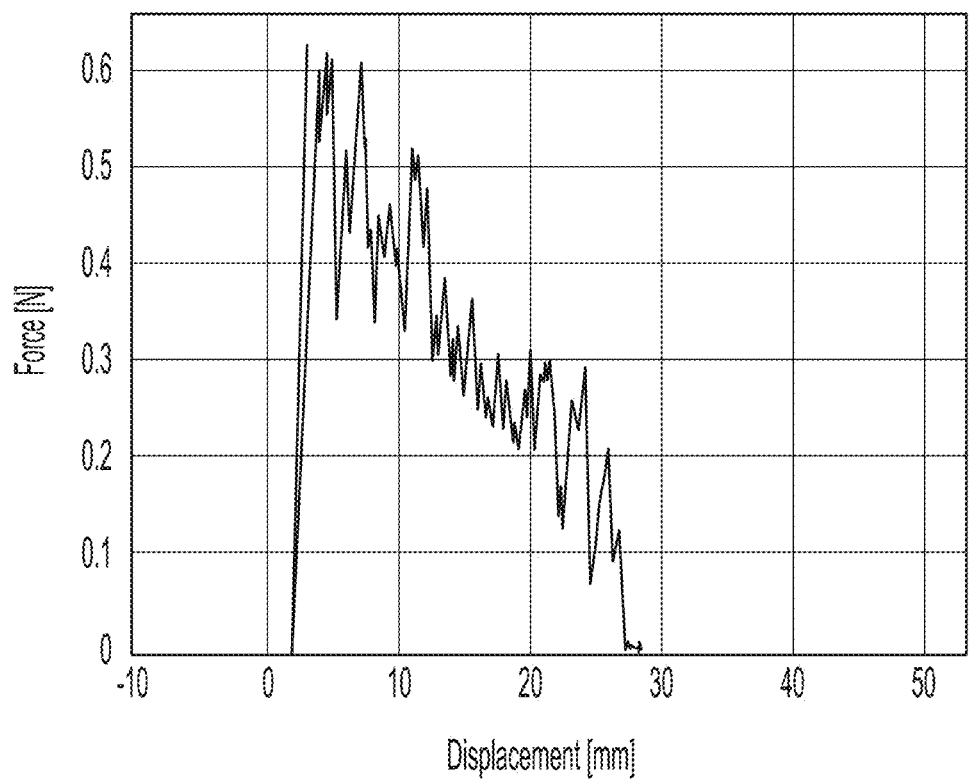
Figure 105B:
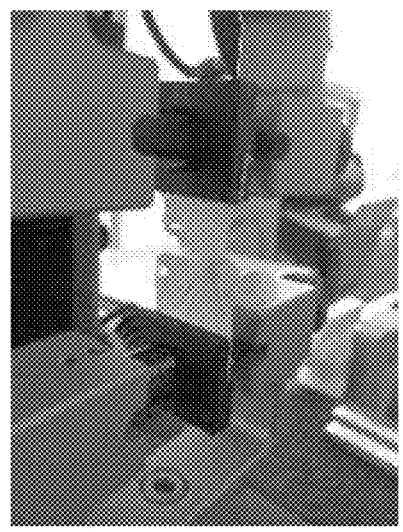

Optimization of the fusion striking parameters may be required to prevent inconsistencies such as those shown in FIG. 104 whereas some areas the fusion is misaligned and inconsistent. Tensile peel strength test results per FIG. 105B, measured by the exemplary apparatus shown in FIG. 105B, implies that the fusion strength is inversely proportional to the quantity of un-parallelism.

Figure 97A:
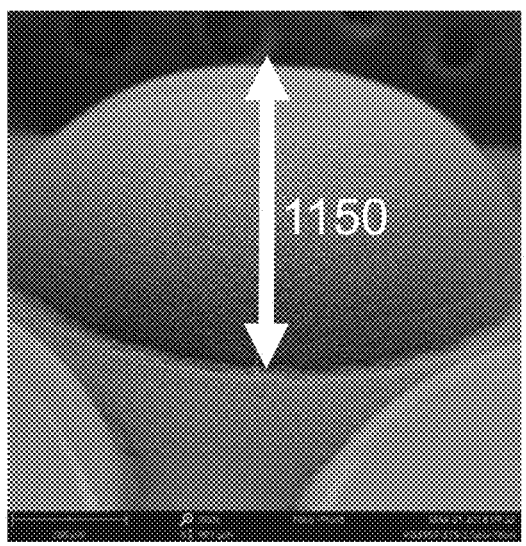
FIG. 97A shows an image of a thermoformed channel of an exemplary channel array device, in accordance with some embodiments.
Figure 97B:
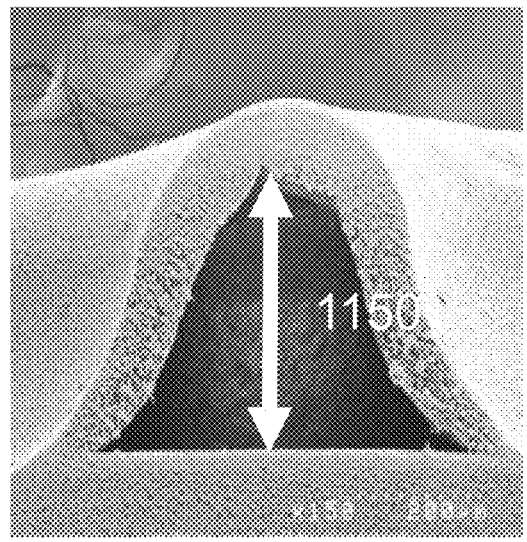
FIG. 97B shows an image of the internal chamber height of a single channel of a channel array device, in accordance with some embodiments.

Although laser drilling openings in the post-fusion device, per FIGS. 125A-B, may improve the concentricity of the openings, misalignment of such a laser drilling tool may impart additional inconsistencies. While such errors can be fixed with adhesive, per FIG. 97B, incorporation of a load cell within the fusion probe and the use of robotic manufacturing and guidance equipment improve the manufacturing method to enable less rework time, scrap and leaks. Incorporation of a load cell enables accurate calibration of fusion forces independent of tooling geometry. Development of robot enabled fusion parameters for optimized improves processing speeds and reduces thermal shrinking impacts. A vision guidance system improves concentricity of fusion with respect to thermoformed channel.

Figure 107:
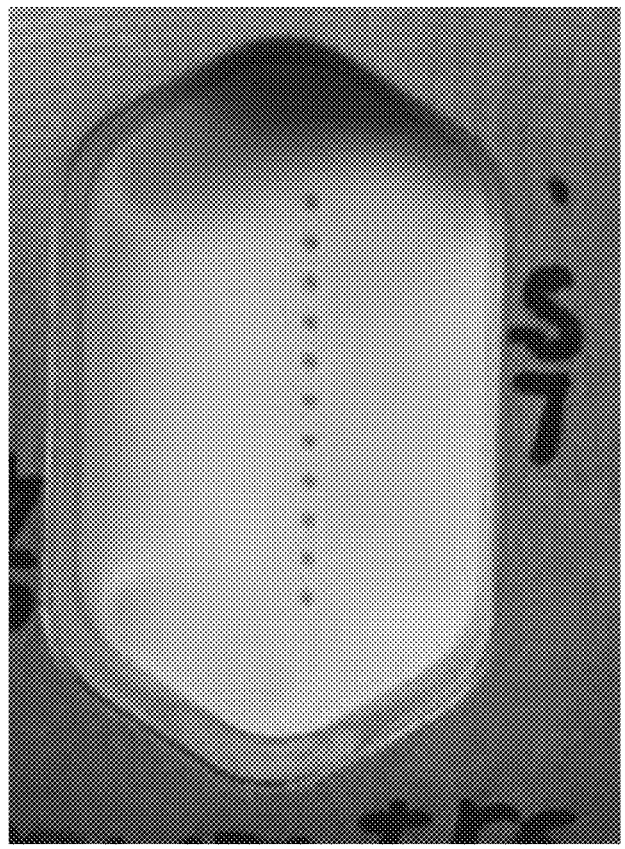

An alternative exemplary load-sensitive thermal fusion tool may comprise a tip, a load cell, and a frame configured to hold the membrane. The thermal fusion tool may comprise a positional based fusion tool configurable to impart a set fusion force over a set fusion time, for a set number of fusion strikes. The load cell enables the fusion tool to fuse each point at the same force. An exemplary array device comprising a single row of channels formed by the thermal fusion tool is shown in FIG. 107.

Per FIG. 108 the shortest fusion time of about 0.05 seconds formed the strongest peel force fusion between the membranes (0.45 N). As the peel force is indicative of fusion strength, the low fusion time may increase the stability and longevity of the device. A full device formed by the thermal fusion tool at a fusion temperature of 800° F. with one strike per location and a fusion force of about 6 pounds is shown in FIG. 109. The round uniform shape of the channels, as well as the peel force stress-strain curve of the device in FIG. 110 indicate confirm the high fusion strength of about 0.45 N.

Exemplary the channel array devices with channels made with 2, 4, 6, and 8 fusion strikes in FIG. 111. Per FIG. 112, although 8 fusion strikes produced the strongest fusion, four fusion strikes produced the strongest fusion while leaving the channels intact.

FIG. 113 shows a bar graph of the fusion strength/peel force (N) versus the fusion force of exemplary channel array devices with a first deformed membrane and a second flat membrane at a fusion temperature of 800° F., a fusion time of 0.05 seconds, with one fusion strike. Although a fusion strike force of 6 and 12 pounds yielded devices with higher peel forces of about 0.4N and about 0.36N respectfully, no observable relationship between the two variables was determined. Higher fusion strike forces may be less ideal due to the associated deterioration the fusion tool tip and the membrane frame. This correlation is confirmed per FIGS. 138A-B which show that the exemplary array channel devices comprising membranes formed with a fusion force of 8 pounds exhibited membrane tearing, wrinkling, and oblong or double channels. As such fusion forces of below 8 pounds for the exemplary membrane are more idea.

FIG. 115 shows that a device whose channels are formed 4 fusion strikes with a fusion force of 6 pounds are stronger device (0.65N) than device whose channels are formed 4 fusion strikes with a fusion force of 3 pounds (0.47N), wherein both devices are formed at a fusion temperature of 800° F. and a fusion time of 0.05 seconds. Further, FIG. 116 displays that devices formed at a fusion temperature of 800° F. and a fusion time of 0.05 seconds with four strikes with a six pound force (~0.65), and two strikes with an eight pound force (~0.7N) yielded stronger devices than exemplary devices formed with 1 or 2 strikes with a six pound force (~0.47N).

FIG. 117A shows an image of an exemplary array device with a 3×3 array of channels that are formed concurrently, whereby each channel of a plurality of channels is struck once before one channel is struck a second time. Per FIG. 117A concurrent striking forms an exemplary device with a greater peel strength (0.9N) than a device fused by sequential striking (0.75 N) each channel twice before striking another channel.

A comparison of the peel force of the exemplary fused membranes is shown in FIG. 118 and Table 7 below, whereas membrane A is formed by load cell fusion tool striking 2 times with a force of 8 pounds, whereas membrane B is formed by load cell fusion tool striking 4 times with a force of 6 pounds, and whereas membrane C is formed by the non-load enabled cell fusion tool.

TABLE 7

Comparison of Fused Membrane Peel Forces

| Membrane | Fusion strikes | Fusion force (lb) | Highest average peel force (N) |
|---|---|---|---|
| A | 1 | 12 | ~0.4N (Single row) |
| B | 2 | 8 | ~0.4-0.7N (Single row) |
| C | 4 | 6 | ~0.65N (Single row) |

Membranes A and C are shown in FIG. 119, whereas membrane A displays a consist uniform fusion. For membrane A, no significant difference in measured fusion strength was found over the range of fusion forces applied. For membrane B, fusion forces of less than 8 pounds yielded the strongest membranes with less tearing, wrinkling and drag. And for membrane C the highest fusion strength was measured at 6 pounds. Membranes A and C are further compared in FIG. 121, whereas membrane C clearly displays a more consistent and higher peel force.

FIG. 120 shows low and high resolution microscopy images of exemplary membrane portions fused at a temperature of 800° F., for a fusion time of 0.05 seconds, with a fusion force of 6 pounds and for four fusion strikes. These images display that the exemplary membrane has a fusion strength of about 1.38 N, which is equal to the full strength of the unfused membrane.

FIG. 121 shows a detailed image of a fused channel of a membrane having a seal size of about 170+/−8 µm. FIG. 122A displays the high concentricity of the laser ablated and fusion areas. Finally, FIG. 148 shows the fusion force/peel forces (N) of exemplary pre-laser channel array devices made using non-load cell enabled (generation 1) and load cell enabled (generation 2) fusion tools, whereas the exemplary membrane formed with the load cell enabled fusion tool from a membrane displays a significantly high (1.52N) peel force.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "generally perpendicular" refers to a relationship between two or more surfaces that are within 1 degree, 2 degrees, 3 degrees, 4, degrees, 5 degrees, 6 degrees, 7 degrees, 8 degrees, 9 degrees, 10 degrees or increments therein of perpendicular.

As used herein, the term "generally parallel" refers to a relationship between two or more surfaces that are within 1 degree, 2 degrees, 3 degrees, 4, degrees, 5 degrees, 6 degrees, 7 degrees, 8 degrees, 9 degrees, 10 degrees or increments therein of parallel.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The disclosure is further limited by the following non-limiting examples.

Example 1

Hexagonal Channel Array Devices for Evaluation in Small Animals

This example describes configuration of hexagonal channel array devices for evaluation in small animals. FIG. 6 shows renderings of hexagonal channel array devices of varying sizes. The channel array device designed for testing in rats has an elongated hexagonal shape and is 1.9 cm×0.8 cm in dimension. The rat device has 93 channels, a SA:V ratio of 82 $cm^{-1}$, a safe volume of 97%, and can hold a volume of 43 µl. The channel array device designed for testing in mice has a hexagonal shape and is 0.64 cm×0.55 cm in dimension. The mouse device has 19 channels, a SA:V ratio of 82 $cm^{-1}$, a safe volume of 95%, and can hold a volume of 10 µl. The mid device is 1.4 cm×0.55 cm, has 49 channels, a SA:V ratio of 83 $cm^{-1}$, a safe volume of 96%, and can hold a volume of 24 µl. The devices can be scaled in size while keeping the SA:V ratio constant.

Example 2

Ultrastructural Analysis of PVDF Membrane After Deformation Step

Figure 12:
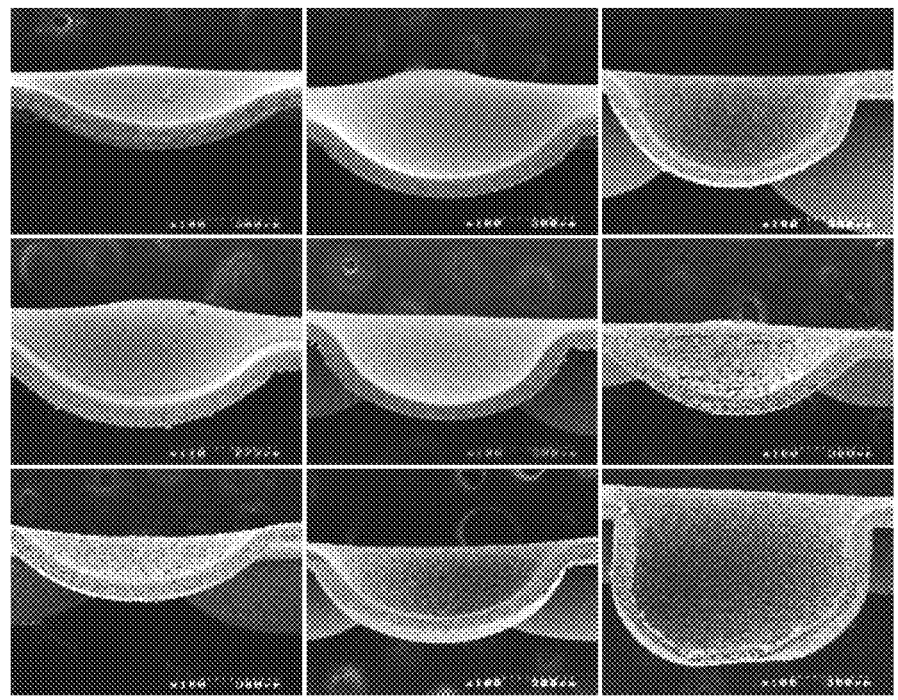
FIG. 12 shows scanning electron micrographs of cross section of polyvinylidene fluoride (PVDF) membranes after undergoing deformation step at various temperatures and pressures, in accordance with some embodiments.
Figure 16:
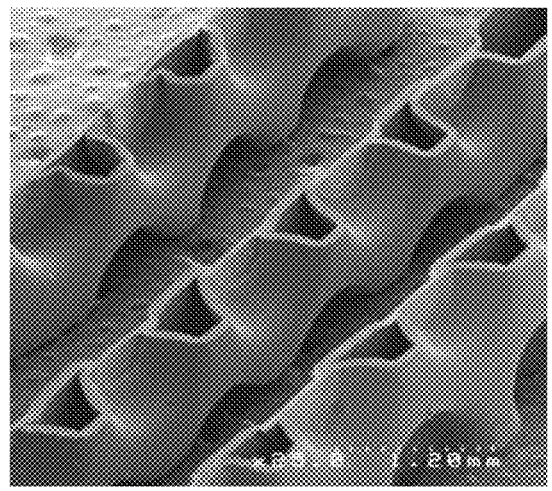
FIG. 16 shows scanning electron micrographs of cross section of cell housing devices where deforming step was performed at different pressure and temperature conditions, in accordance with some embodiments.
Figure 17:
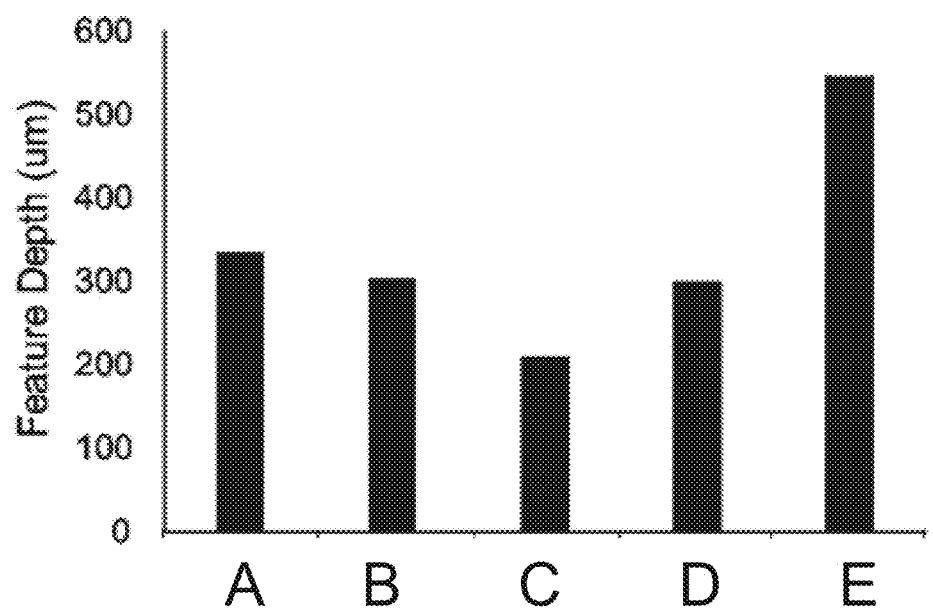
FIG. 17 shows the measured channel depths in cell housing devices where deforming step was performed at different pressure and temperature conditions, in accordance with some embodiments.

This example describes the ultrastructural analysis of PVDF membrane after deformation step. PVDF membranes underwent the deformation step under a combination of pressures and temperatures. The combinations were 65 psi and 135° C., 65 psi and 150° C., 65 psi and 165° C., 100 psi and 135° C., 100 psi and 150° C., 100 psi and 165° C., 140 psi and 135° C., 140 psi and 150° C., and 140 psi and 165° C. FIG. 12 and FIG. 16 show scanning electron micrographs of cross section of the PVDF membranes after undergoing deformation step. FIG. 17 shows measured channel depths or feature depths (µm) for the cell housing devices where deforming step was performed at different pressure and temperature conditions. The PVDF membranes had different channel depths depending on the temperature and pressure conditions, with the higher temperature of 165° C. generally yielding deeper channels. The dimension of the channels can be controlled by the temperature and pressure conditions. The control of the channel dimensions is important as it dictates the SA:V ratio of the cell housing device.

Example 3

Analysis of PVDF Cell Housing Device After Fusion Step

Figure 13:
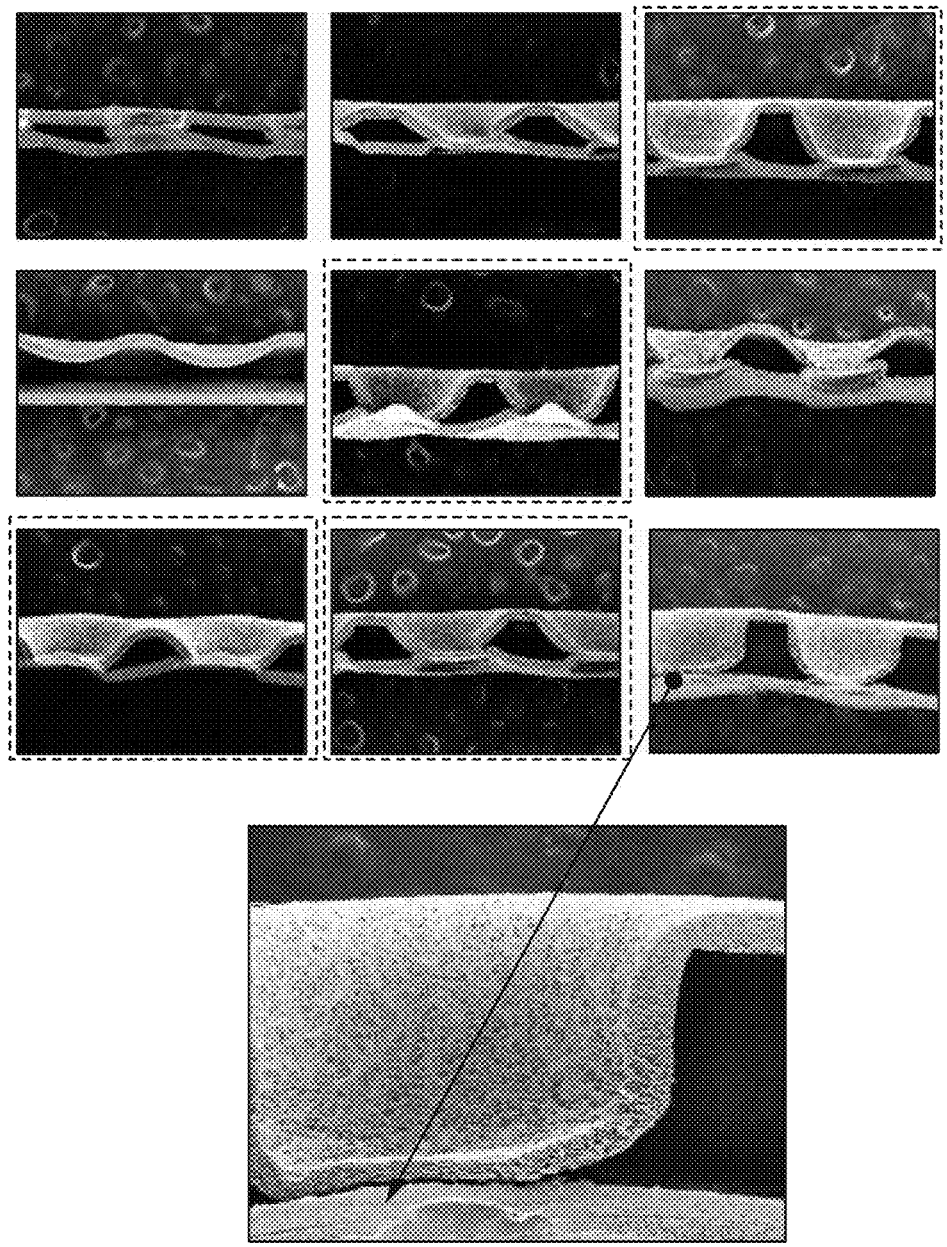
FIG. 13 shows scanning electron micrographs of cross section of cell housing devices after undergoing fusion step at various temperatures and pressures, in accordance with some embodiments.

This example describes the analysis of PVDF cell housing device after fusion step. First PVDF membranes underwent the deformation step under 65 psi and 135° C., 65 psi and 150° C., 65 psi and 165° C., 100 psi and 135° C., 100 psi and 150° C., 100 psi and 165° C., 140 psi and 135° C., 140 psi and 150° C., or 140 psi and 165° C. Then, the deformed membranes were fused to a second PVDF membrane at 225° C. FIG. 13 shows scanning electron micrographs of cross section of the PVDF cell housing devices after undergoing fusion step. The first membranes that were deformed at 65 psi and 165° C., 100 psi and 150° C., 140 psi and 135° C., and 140 psi and 150° C. fused to the second membranes. The first membranes that were deformed outside of those temperature and pressure parameters had poor fusion where the seams between the first and second membranes are clearly visible in the scanning electron micrograph.

Figure 19:
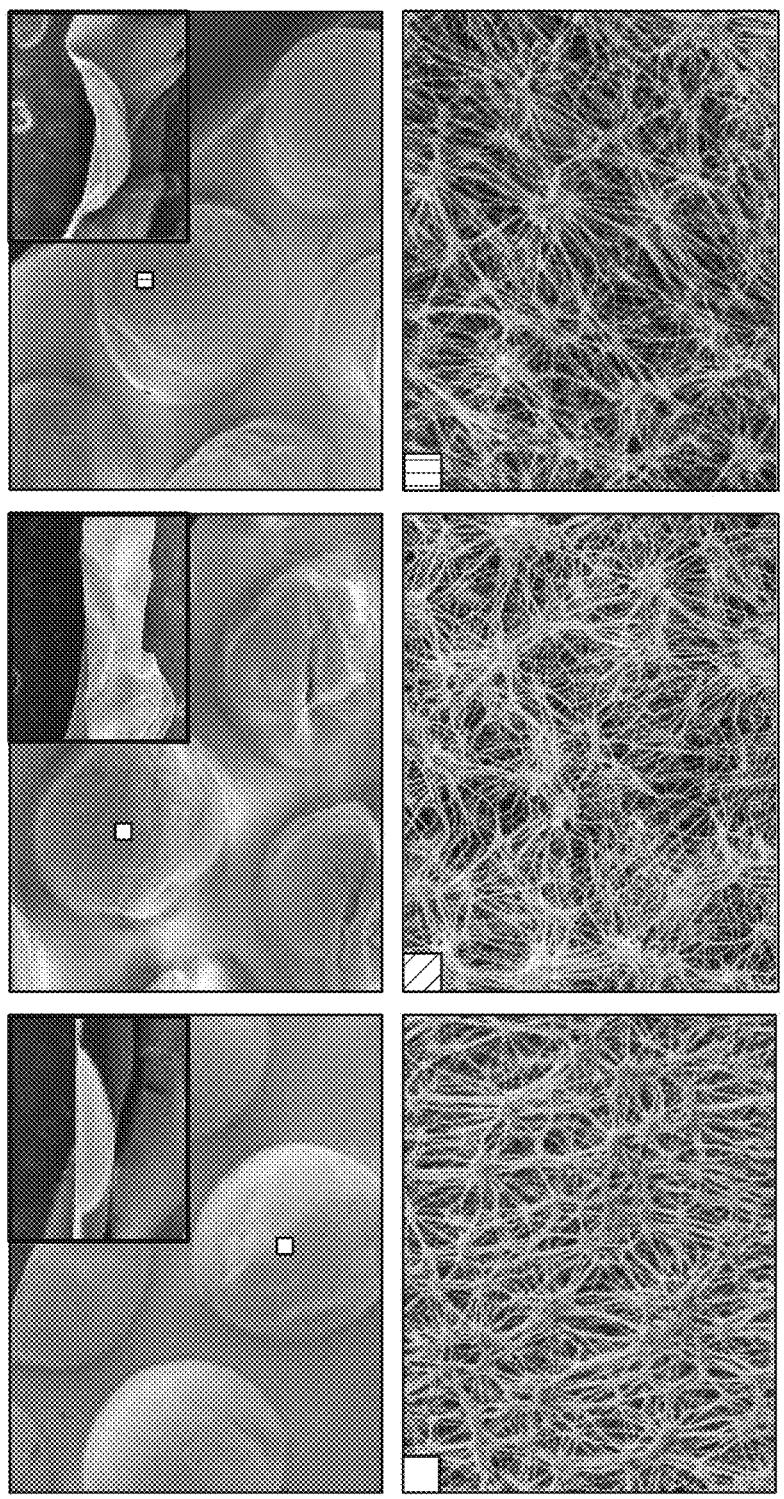
FIG. 19 shows scanning electron micrographs at a low magnification and a high magnification of first membrane of expanded polytetrafluoroethylene (ePTFE) after deformation step performed at various temperatures and pressures, in accordance with some embodiments.

FIG. 19 shows scanning electron micrographs of cross section of cell housing device with poor fusion, where deforming step was performed at various pressures and temperatures. The heat flow measurement of the membrane deformed at 165° C. and 140 psi by DSC showed a secondary peak at about 175° C., which indicate crystalline re-arrangement of this deformed membrane. The heat flow measurement of the membrane deformed at 150° C. and 100 psi and fused successfully to the second membrane did not show a secondary peak.

Example 4

DSC Analysis of Fused and Unfused Conditions

This example describes the DSC analysis of fused and unfused conditions. First PVDF membranes underwent the deformation step under 100 psi and 160° C. or 100 psi and 173° C. followed by quenching. FIG. 20 shows that heat flow measurement of membrane deformed at 100 psi and 160° C. had a small shoulder peak and was similar to the baseline PVDF membrane, indicating that this membrane conserved crystalline arrangement and will fuse to a second membrane. The heat flow measurement of membrane deformed at 100 psi and 173° C. had a secondary peak, which indicated that this membraned formed crystalline region and will not fuse to a second membrane.

Example 5

Surface Profile of Cell Housing Device

This example describes the surface profile of the cell housing device. FIG. 18 shows surface inferometry of the cell housing device, which had smooth surface with consistent geometry in its channel array. The active regions had smooth, porous surfaces while the fused regions had flat surfaces.

Example 6

Ultrastructural Analysis of ePTFE After Deformation and Fusion Steps

This example describes the ultrastructural analysis of ePTFE membrane after deformation and fusion steps. The ePTFE membranes underwent the deformation step at 30 psi and 340° C., 4 psi and 360° C., or 6 psi and 360° C. FIG. 19 shows scanning electron micrographs of the ePTFE membranes after undergoing deformation step. The ePTFE membranes were able to form channels. Generally as temperature increased, more deformation and fewer nodes were observed. FIG. 20 shows fused ePTFE membranes that underwent deformation step at 6 psi and 360° C. and fusion step at 370° C. for 5 minutes. The ePTFE membrane requires different temperature and pressure ranges for deformation and fusion steps as compared to PVDF membrane. The manufacturing steps described here may be applied to membranes of different materials to successfully form cell housing device.

Example 7

In Vivo Implantation of Cell Housing Device in Rats

This example describes in vivo implantation of cell housing device in rats. These devices had similar channel diameters of about 350 μm but had different channel spacings. The low density device had a channel spacing of about 500 μm between the channels while the high density device had a channel spacing of about 200 μm. The cell housing devices with high channel density and low channel density were implanted in vivo in normal rats in various locations by properitoneal, intraomental, suprahepatic, and subcutaneous implantations as shown in FIG. 28. FIG. 29 shows vascularization around the cell housing devices after properitoneal implantation. Microvessels were observed in each of the channels in the device. The H&E histology of the vasculature indicated presence of smooth muscle cells, which are found in arteries. FIG. 37 shows the more vascularization and more branching of the vessels that were observed in the high channel density device as compared to the low channel density device. FIG. 32 shows the count per device of vessels and branches for the low channel density and high channel density devices. The high channel density device had about 1000 vessels per device as compared to about 500 vessels per device for the low channel density device. The high channel density device also had significantly more branches at about 500 branches per device as compared to about 300 branches per device for the low channel density device. Higher channel density devices resulted in more vascularization around the device. The benefit of increased vascularization as seen in higher channel devices may need to be balanced with the integrity of the device as more channels are added to the device. The channel density can affect the level of vascularization around the cell housing device.

Figure 43:
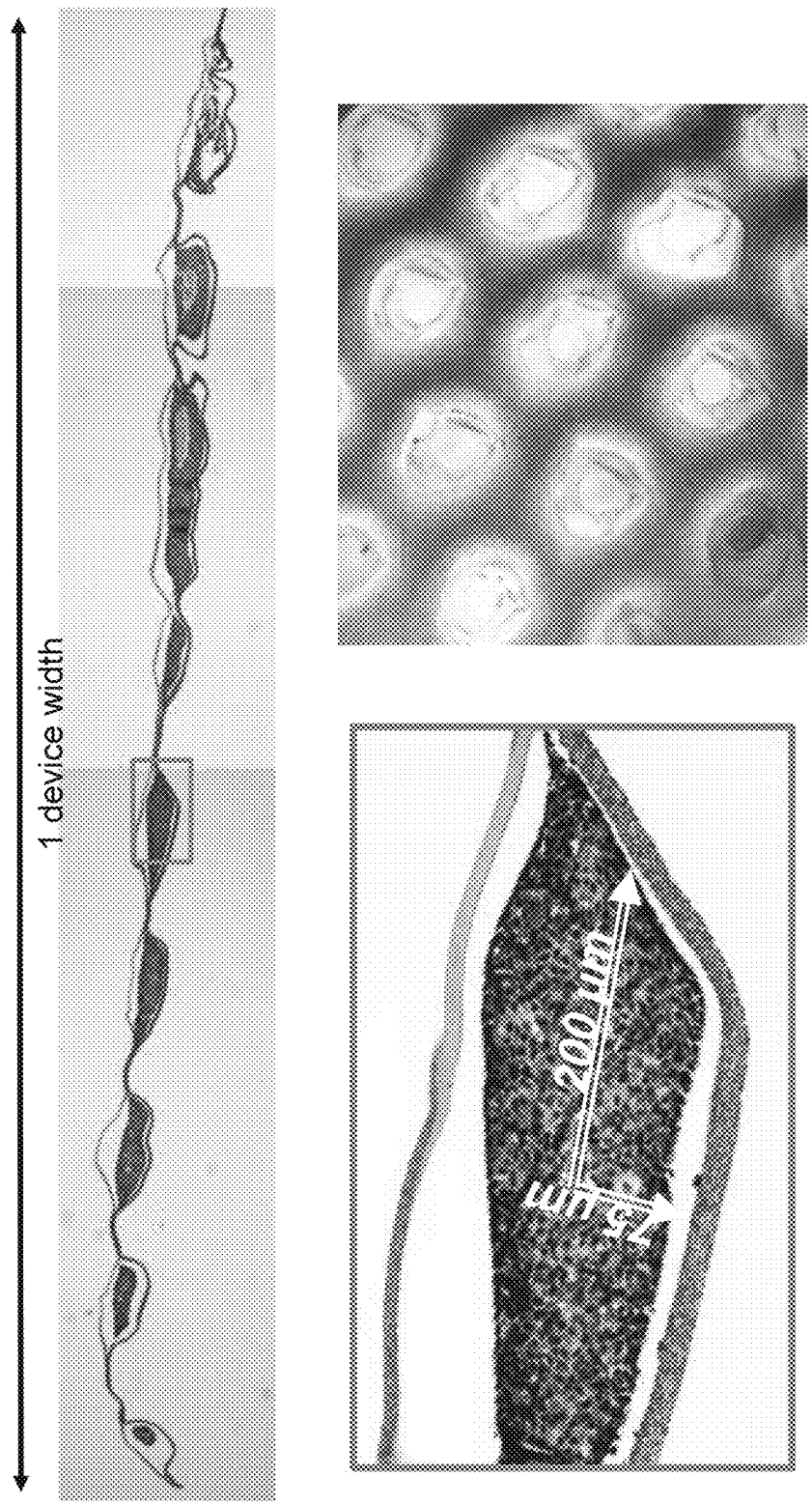
FIG. 43 shows images of an ePTFE cell housing device filled to maximum capacity with cells, in accordance with some embodiments.

The cell housing devices were filled with cells in preparation for in vivo implantation. FIG. 42 shows H&E stained histological sections with complete filling of the continuous interior spaces of various cell housing devices with cells. A device made with 20 μm thick ePTFE membranes 5310 (top) was filled with cells 5320 throughout its single continuous interior space. This device may have a modeled insulin diffusion rate of about 11 ng/cm$^2$ per 10 minutes. Shown on the bottom, a device made with 125 μm thick PVDF membranes 5330 was filled with cells 5320 throughout its single continuous interior space. This device may have a modeled insulin diffusion rate of about 6 ng/cm$^2$ per 10 minutes. FIG. 43 shows images of an ePTFE cell housing device that was filled to maximum capacity with cells. On the top panel, the H&E stained histological section shows the single continuous interior space of the device filled with cells throughout the entire device. On bottom left, a close up image shows a microtissue containing cells within one pockets of interior space with a height of about 150 μm and width of about 400 μm. A 5× magnification light micrograph of the ePTFE cell housing device is shown on the bottom right, demonstrating the continuous filling of its interior space in the manufactured cell housing device with channels. This demonstrates the capability to fill the entire interior space of the cell housing device with cells.

Figure 26:
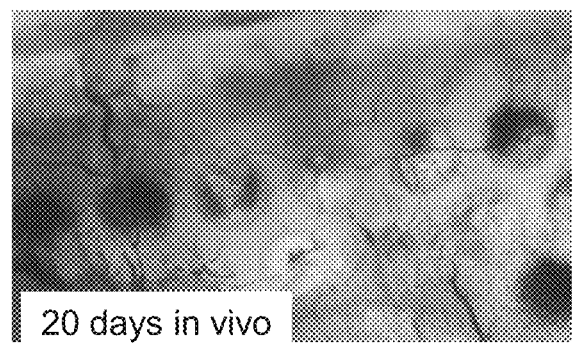
FIG. 26 shows the vasculature around the cell housing device after 20 day implantations in a rat, in accordance with some embodiments.
Figure 27:
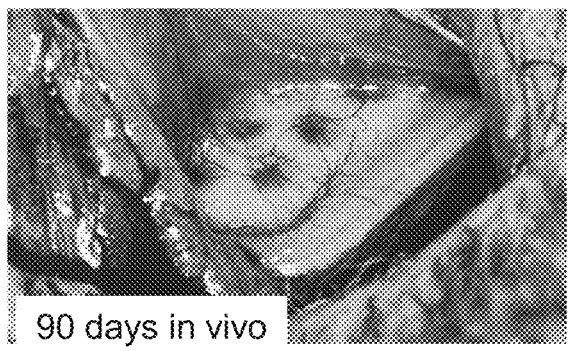
FIG. 27 shows the vasculature around the cell housing device after 90 days implantations in a rat, in accordance with some embodiments.

The cell housing devices were implanted in vivo in rats for an extended period of time, and the cells within the cell housing device survived the extended in vivo implantation. FIG. 26 and FIG. 27 show vasculature around the cell housing device and through the channels at 20 days (FIG.

Figure 44:
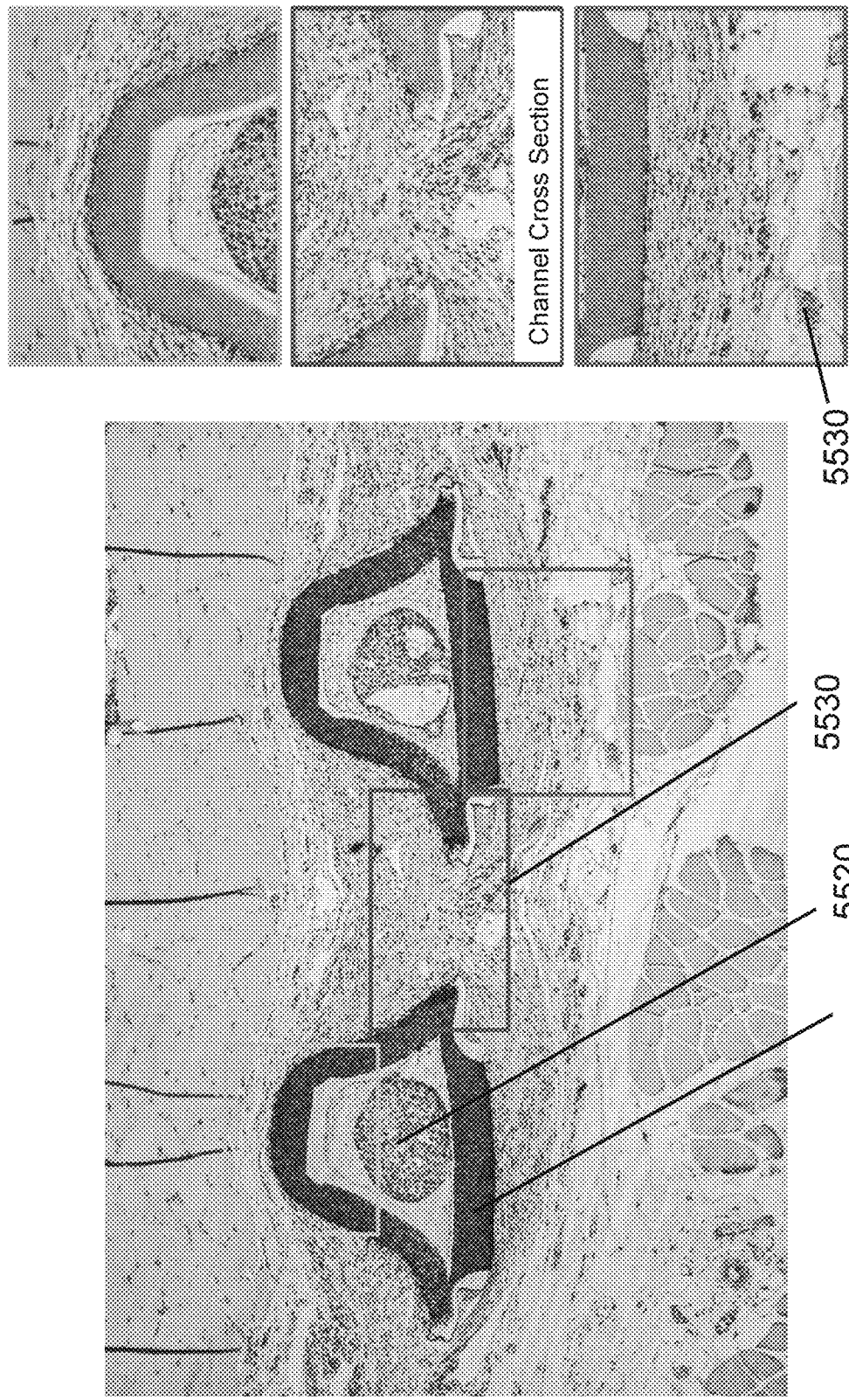
FIG. 44 shows H&E stained histological sections of a PVDF cell housing device with cells after 90 days in vivo implantation at pre-peritoneal site in a rat, in accordance with some embodiments.
Figure 45:
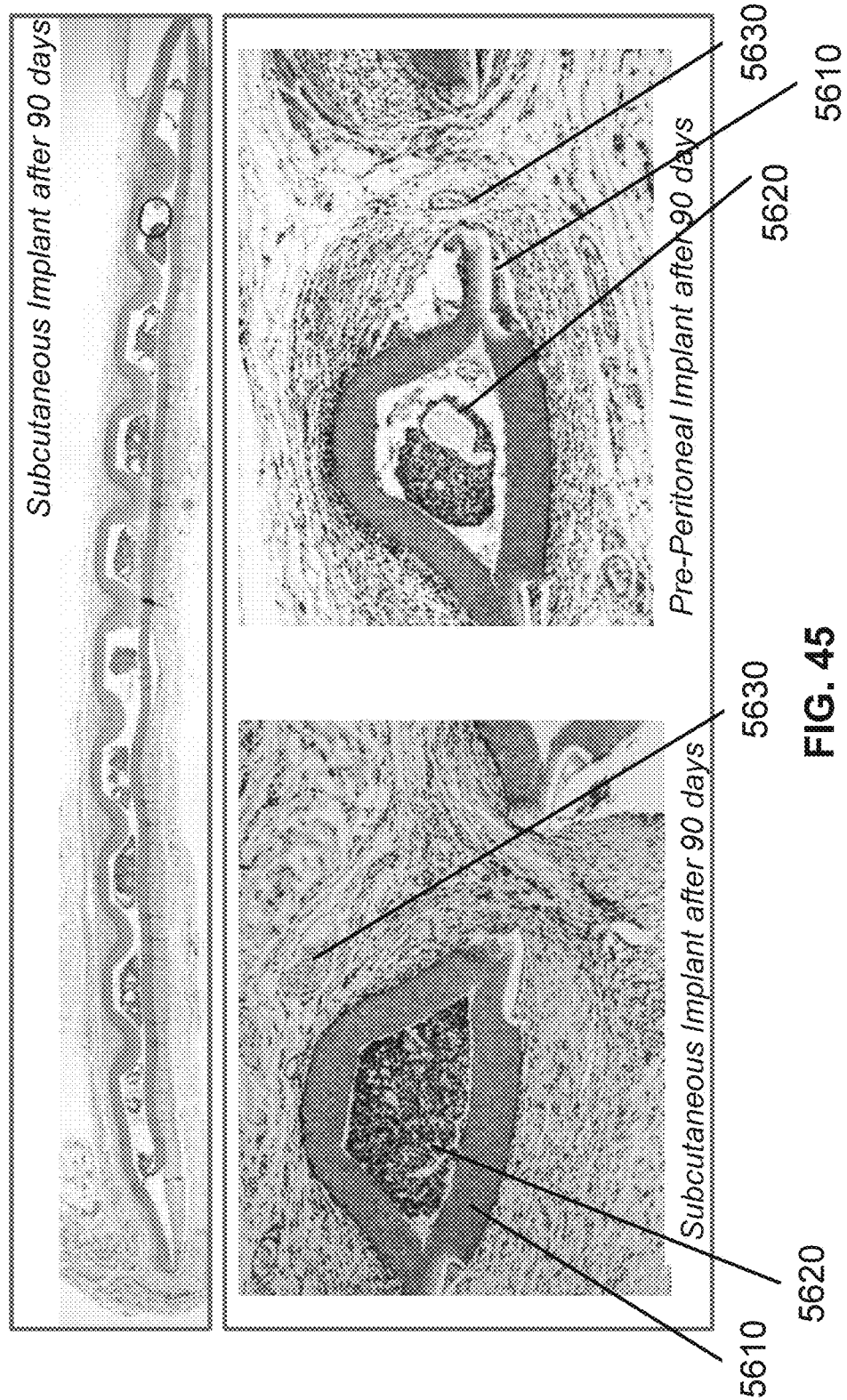
FIG. 45 shows H&E stained histological sections of a PVDF cell housing device filled with SC islet cells after 90 day implantation in subcutaneous and pre-peritoneal sites in rats, in accordance with some embodiments.
Figure 46:
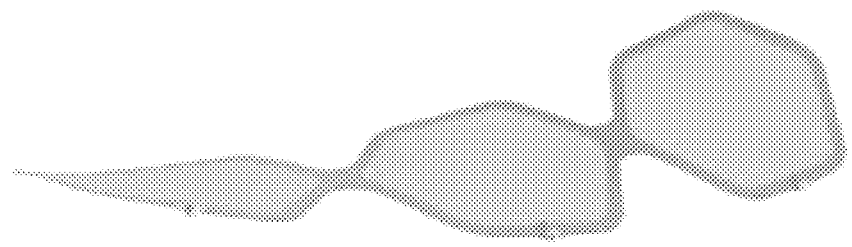
FIG. 46 shows an example of a macrodevice comprising three ultrathin devices, in accordance with some embodiments.

26) and 90 days (FIG. 27) after implantation in a pre-peritoneal site in a nude rat. FIG. 44 shows H&E stained histological sections of a PVDF cell housing device 5510 with cells 5520 after 90 days in vivo implantation at pre-peritoneal site in a rat. The SC islet cells 5520 within devices 5510 implanted in pre-peritoneal sites had high cell content at 90 days along with visible vascularization 5530 around the device and through the channels. The host tissue formed new tissue around the device and through the channels of the device. FIG. 45 shows H&E stained histological sections of a PVDF cell housing device 5610 filled with SC islet cells 5620 after 90 day implantation in subcutaneous and pre-peritoneal sites in nude rats capable of foreign body response. The SC islet cells 5620 within devices 5610 implanted in both subcutaneous and pre-peritoneal sites had high cell content at 90 days, indicating that the SC islet cells survived for 90 days in the device at both implantation sites. Vascularization 5630 was observed around the device and through the channels of devices implanted at both subcutaneous and pre-peritoneal sites. Some of the vascularization appeared to have arteriole-like features and defined vascular walls that were multiple cell layers thick. The outer surface of the devices appeared to integrate into the host tissue at both implant sites, with a higher density of fibrosis around the device in subcutaneous sites but no apparent impact on survival of cells within the device (top and bottom left). The host tissues were also present through the channels of the devices, providing support for vascular tissue and further mechanical stability for the device. This demonstrates the capability to implant a cell housing device with cells in multiple implantation sites, maintain a high cell viability of the cells within the device for an extended period of time, and have vascularization and new tissues form around and through the device.

Example 8

Cluster Size Impacting Design

This example describes how cluster size can impact design. Cluster size refers to the size of cell aggregates loaded into the device.

Example 9

Deformation Condition of ePTFE Membrane

This example shows results of deformation condition on ePTFE membranes. FIG. 41 shows ePTFE cell housing devices formed by thermal deformation at 360° C. and 6 psi (as-formed; top), and subsequently hard cast with resin for cross sectional imaging (bottom). As-formed ePTFE membranes did not appear to hold their channel shapes and have more fibril structures than nodes. The ePTFE membrane that was hard cast with resin appeared to hold their channel shape after deformation step.

Example 10

T-Peel Test of Two Flat ePTFE Membranes

This example describes a T-peel test of sintered and unsintered ePTFE membranes to test the bond strength of fused ePTFE membranes. FIG. 43 shows the load at break (N) by ASTM T-peel test—according to ASTM D882-08 standards for thin film tensile testing of two flat ePTFE membranes fused at different temperatures for different lengths of time (1, 5, 15 seconds). The ePTFE membranes were either sintered (AS) at 370° C. for 7 minutes or unsintered (AU) prior to fusion. The sintered ePTFE membranes had a melting temperature of about 320° C.-325° C. and unsintered ePTFE membrane had a melting temperature of about 340° C.-350° C. as measured by DSC. Two flat ePTFE membranes were fused together at various temperatures ranging from 302° C.-427° C. for 1, 5, or 15 seconds. After undergoing the ASTM T-peel test, the load at break or failure (N) were recorded. Generally, fusion between sintered-sintered membranes (AS/AS) had the lowest loads at failure, ranging from near 0 N to about 0.3 N, as compared to unsintered-unsintered membranes (AU/AU), ranging from near 0 N to about 1 N, or unsintered-sintered membranes (AU/AS), and ranging from about 0.2 N to 0.7 N. Generally, fusion of AU/AU membranes had higher load at failure. Generally, the load at failure increased with increasing fusion temperature. Generally, having at least one unsintered membrane resulted in higher load at failure.

Example 11

T-Peel Test of ePTFE Devices

This example describes a T-peel test of ePTFE devices. FIG. 38 shows a tool used for ASTM T-peel test according to ASTM D882-08 standards for thin film tensile testing. The tool was used to test fused cell housing ePTFE devices and shows a tested device at failure. The graph shows the stress-strain curve of an ePTFE device, with the first membrane sintered and deformed and the second membrane flat and unsintered, that were fused at 474° C. for 0.05 seconds. The ePTFE device had a failure strain of greater than 60% and achieved about 0.4 N of load, which was about 78% of the load of fused flat membranes with more fused areas. This stress-strain curve demonstrated that the fused sites are fused and remained fused even at high tensile strains.

Example 12

Burst Pressure of ePTFE Devices

This example describes measuring the burst pressure of a cell housing device. To test the strength of the seal of the device, the device was filled with water at 1 psi per 10 seconds, and the pressure at failure, or burst pressure, was measured. FIG. 39 shows an ePTFE cell housing device without a frame that is filled for burst pressure testing and a graph of filling pressure (psi) at failure for an ePTFE cell housing device (eCAD) prototype. For a PVDF prototype, the burst pressure at failure was about 10 psi. For an ePTFE prototype, the burst pressure at failure was about 11 psi. This burst pressure is far higher than maximum loading pressure of about 2 psi that the device may be exposed to under typical filling conditions.

Example 13

Cell Housing Device Prototypes

Figure 14:
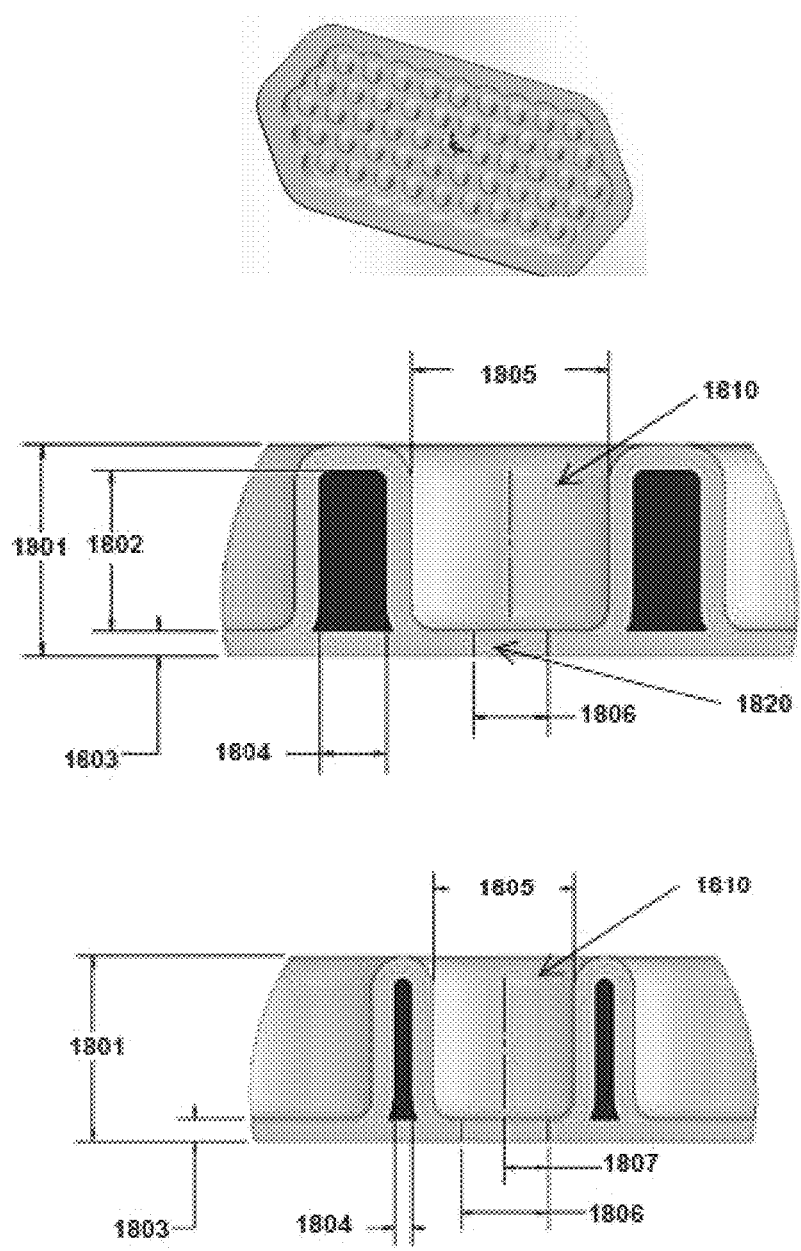
FIG. 14 shows a rendering of a cell housing device with scalloped perimeter and variations of channel dimensions to achieve various SA:V ratio, in accordance with some embodiments.

This example describes prototypes of cell housing devices. FIG. 14 shows a rendering of a cell housing device with scalloped perimeter and variations of channel dimensions to achieve various SA:V ratio. Per FIG. 14, the cell housing device may be characterized by an overall height 1801, an inner height 1802, a membrane thickness 1803, an interior spacing 1804, an inner diameter 1805, a through hole inner diameter 1806, and a through hole spacing 1807.

In some embodiments, the overall height 1801 is about 400 μm to about 1,600 μm. In some embodiments, the overall height 1801 is at least about 400 μm. In some embodiments, the overall height 1801 is at most about 1,600 μm. In some embodiments, the overall height 1801 is about 400 μm to about 600 μm, about 400 μm to about 850 μm, about 400 μm to about 1,000 μm, about 400 μm to about 1,200 μm, about 400 μm to about 1,400 μm, about 400 μm to about 1,600 μm, about 600 μm to about 850 μm, about 600 μm to about 1,000 μm, about 600 μm to about 1,200 μm, about 600 μm to about 1,400 μm, about 600 μm to about 1,600 μm, about 850 μm to about 1,000 μm, about 850 μm to about 1,200 μm, about 850 μm to about 1,400 μm, about 850 μm to about 1,600 μm, about 1,000 μm to about 1,200 μm, about 1,000 μm to about 1,400 μm, about 1,000 μm to about 1,600 μm, about 1,200 μm to about 1,400 μm, about 1,200 μm to about 1,600 μm, or about 1,400 μm to about 1,600 μm. In some embodiments, the overall height 1801 is about 400 μm, about 600 μm, about 850 μm, about 1,000 μm, about 1,200 μm, about 1,400 μm, or about 1,600 μm. In some embodiments, the inner height 1802 is about 300 μm to about 1,200 μm. In some embodiments, the inner height 1802 is at least about 300 μm. In some embodiments, the inner height 1802 is at most about 1,200 μm. In some embodiments, the inner height 1802 is about 300 μm to about 400 μm, about 300 μm to about 650 μm, about 300 μm to about 800 μm, about 300 μm to about 1,000 μm, about 300 μm to about 1,200 μm, about 400 μm to about 650 μm, about 400 μm to about 800 μm, about 400 μm to about 1,000 μm, about 400 μm to about 1,200 μm, about 650 μm to about 800 μm, about 650 μm to about 1,000 μm, about 650 μm to about 1,200 μm, about 800 μm to about 1,000 μm, about 800 μm to about 1,200 μm, or about 1,000 μm to about 1,200 μm. In some embodiments, the inner height 1802 is about 300 μm, about 400 μm, about 650 μm, about 800 μm, about 1,000 μm, or about 1,200 μm.

In some embodiments, the membrane thickness 1803 is about 50 μm to about 250 μm. In some embodiments, the membrane thickness 1803 is at least about 50 μm. In some embodiments, the membrane thickness 1803 is at most about 250 μm. In some embodiments, the membrane thickness 1803 is about 50 μm to about 75 μm, about 50 μm to about 100 μm, about 50 μm to about 125 μm, about 50 μm to about 150 μm, about 50 μm to about 175 μm, about 50 μm to about 200 μm, about 75 μm to about 100 μm, about 75 μm to about 125 μm, about 75 μm to about 150 μm, about 75 μm to about 175 μm, about 75 μm to about 200 μm, about 100 μm to about 125 μm, about 100 μm to about 150 μm, about 100 μm to about 175 μm, about 100 μm to about 200 μm, about 125 μm to about 150 μm, about 125 μm to about 175 μm, about 125 μm to about 200 μm, about 150 μm to about 175 μm, about 150 μm to about 200 μm, or about 175 μm to about 200 μm. In some embodiments, the membrane thickness 1803 is about 50 μm, about 75 μm, about 100 μm, about 125 μm, about 150 μm, about 175 μm, about 200 μm, or about 250 μm.

In some embodiments, the interior spacing 1804 is about 40 μm to about 500 μm. In some embodiments, the interior spacing 1804 is at least about 40 μm. In some embodiments, the interior spacing 1804 is at most about 500 μm. In some embodiments, the interior spacing 1804 is about 40 μm to about 60 μm, about 40 μm to about 80 μm, about 40 μm to about 100 μm, about 40 μm to about 150 μm, about 40 μm to about 200 μm, about 40 μm to about 270 μm, about 40 μm to about 350 μm, about 40 μm to about 400 μm, about 40 μm to about 500 μm, about 60 μm to about 80 μm, about 60 μm to about 100 μm, about 60 μm to about 150 μm, about 60 μm to about 200 μm, about 60 μm to about 270 μm, about 60 μm to about 350 μm, about 60 μm to about 400 μm, about 60 μm to about 500 μm, about 80 μm to about 100 μm, about 80 μm to about 150 μm, about 80 μm to about 200 μm, about 80 μm to about 270 μm, about 80 μm to about 350 μm, about 80 μm to about 400 μm, about 80 μm to about 500 μm, about 100 μm to about 150 μm, about 100 μm to about 200 μm, about 100 μm to about 270 μm, about 100 μm to about 350 μm, about 100 μm to about 400 μm, about 100 μm to about 500 μm, about 150 μm to about 200 μm, about 150 μm to about 270 μm, about 150 μm to about 350 μm, about 150 μm to about 400 μm, about 150 μm to about 500 μm, about 200 μm to about 270 μm, about 200 μm to about 350 μm, about 200 μm to about 400 μm, about 200 μm to about 500 μm, about 270 μm to about 350 μm, about 270 μm to about 400 μm, about 270 μm to about 500 μm, about 350 μm to about 400 μm, about 350 μm to about 500 μm, or about 400 μm to about 500 μm. In some embodiments, the interior spacing 1804 is about 40 μm, about 60 μm, about 80 μm, about 100 μm, about 150 μm, about 200 μm, about 270 μm, about 350 μm, about 400 μm, or about 500 μm.

In some embodiments, the interior diameter 1805 is about 300 μm to about 1,600 μm. In some embodiments, the interior diameter 1805 is at least about 300 μm. In some embodiments, the interior diameter 1805 is at most about 1,600 μm. In some embodiments, the interior diameter 1805 is about 300 μm to about 500 μm, about 300 μm to about 700 μm, about 300 μm to about 900 μm, about 300 μm to about 1,100 μm, about 300 μm to about 1,300 μm, about 300 μm to about 1,600 μm, about 500 μm to about 700 μm, about 500 μm to about 900 μm, about 500 μm to about 1,100 μm, about 500 μm to about 1,300 μm, about 500 μm to about 1,600 μm, about 700 μm to about 900 μm, about 700 μm to about 1,100 μm, about 700 μm to about 1,300 μm, about 700 μm to about 1,600 μm, about 900 μm to about 1,100 μm, about 900 μm to about 1,300 μm, about 900 μm to about 1,600 μm, about 1,100 μm to about 1,300 μm, about 1,100 μm to about 1,600 μm, or about 1,300 μm to about 1,600 μm. In some embodiments, the interior diameter 1805 is about 300 μm, about 500 μm, about 700 μm, about 900 μm, about 1,100 μm, about 1,300 μm, or about 1,600 μm.

In some embodiments, the through hole inner diameter 1806 is about 100 μm to about 600 μm. In some embodiments, the through hole inner diameter 1806 is at least about 100 μm. In some embodiments, the through hole inner diameter 1806 is at most about 600 μm. In some embodiments, the through hole inner diameter 1806 is about 100 μm to about 200 μm, about 100 μm to about 300 μm, about 100 μm to about 400 μm, about 100 μm to about 500 μm, about 100 μm to about 600 μm, about 200 μm to about 300 μm, about 200 μm to about 400 μm, about 200 μm to about 500 μm, about 200 μm to about 600 μm, about 300 μm to about 400 μm, about 300 μm to about 500 μm, about 300 μm to about 600 μm, about 400 μm to about 500 μm, about 400 μm to about 600 μm, or about 500 μm to about 600 μm. In some embodiments, the through hole inner diameter 1806 is about 100 μm, about 200 μm, about 300 μm, about 400 μm, about 500 μm, or about 600 μm.

In some embodiments, the through hole spacing 1807 is about 100 μm to about 400 μm. In some embodiments, the through hole spacing 1807 is at least about 100 μm. In some embodiments, the through hole spacing 1807 is at most about 400 μm. In some embodiments, the through hole spacing 1807 is about 100 μm to about 200 μm, about 100 μm to about 300 μm, about 100 μm to about 400 μm, about 200 µm to about 300 µm, about 200 µm to about 400 µm, or about 300 µm to about 400 µm. In some embodiments, the through hole spacing 1807 is about 100 µm, about 200 µm, about 300 µm, or about 400 µm.

In one example, the device may have channel 1810 with an inner diameter 1805 of 800 µm and an inner height 1802 of 650 µm and a through hole 1820 with a through hole inner diameter 1806 of 300 µm. This device may have an overall height 1801 of 850 µm with a 100 µm membrane thickness 1803 and an interior spacing 1804 of 270 µm between the channels 1810. This device may have a SA:V ratio of 77 cm$^{-1}$. In another example, the device may have channel 1810 with an inner diameter 1805 of 650 µm and an inner height 1802 of 650 µm and a through hole 1820 with a through hole inner diameter of 400 µm. This device may have an overall height 1801 of 850 µm with a 100 µm membrane thickness 1803 and an interior spacing 1804 of 80 µm between the channels 1810. This device may have a SA:V ratio of 138 cm$^{-1}$. The channel 1810 dimension and spacing may be adjusted to achieve different SA:V ratios. The device may have a through hole spacing 1807 of about 200 µm.

Example 14

Human Device Prototype

Figure 40:
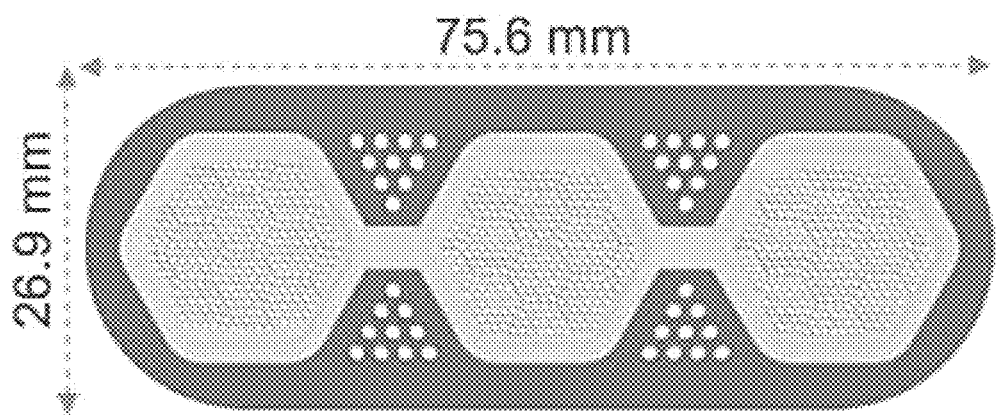
FIG. 40 shows a prototype of three cell housing devices assembled onto a frame for human use, in accordance with some embodiments.

This example describes a prototype of the cell housing devices assembled onto a frame for human use. FIG. 40 shows a prototype of three cell housing devices assembled onto a frame for human use. The cell housing devices may be hexagonal in shape. The frame may have a dimension of about 26.9 mm×75.6 mm and maybe oval in shape with perforation in the spaces between the cell housing devices. The cell housing devices may be about 850 µm thick with a 20 cm$^2$ footprint. The assembled device may hold about 400 million cells with a cell mass volume of about 350 µL. These cells may be capable of producing insulin.

Example 15

Surface Modification of Membrane

This example describes the process of modifying the membrane surface. A membrane may be treated to impart hydrophilic properties on a membrane with a hydrophobic surface. The surface of the membrane may be modified by crosslinking a polymer with hydrophilic properties. The polymer may also be biocompatible and form a biocompatible coating on the membrane. In one example, hydroxypropyl acrylate (HPA) may be crosslinked with tetra(ethylene glycol) diacrylate (TEGDA) on to the membrane in a heat-initiated polymerization process with ammonium persulphate (APS) initiator. FIG. 41 shows an example of a protocol for forming a hydrophilic coating on the surface of the membranes. An ePTFE device was soaked 100% ethanol and then in 30% ethanol for 3 minutes. The device was soaked in 3% HPA, 2% TEGDA, 1% APS in 30% ethanol for 5 minutes and heated from room temperature to 80° C. Then, the device was boiled in 100% ethanol for 5 minutes, soaked in Milli-Q water or ultrapure water for 30 minutes, and dried. FIG. 38 shows an ePTFE cell housing device after a hydrophilic coating treatment soaking in water. FIG. 41 shows electron micrographs of an ePTFE device after the surface modification.

Example 16

Dot Diameter and Density of the Device

This example describes the dot diameter and density (e.g. center to center spacing) of the devices. The adhesive dots were built up in 2 layers. The devices were manually flipped to create the pattern of adhesive dots that act to restrict the thickness of the device during cell filling. A pattern of 37 dots, each dot about 1.25 mm in diameter with a center-to-center spacing of 3.3 mm, was deposited in 2 successive layers. First, the pattern was developed against the membrane by applying adhesive in 0.05 second applications and curing each dot individually for 1 second. A smaller second layer was applied on top of the first pattern with 0.03 second dispensing times, and was left uncured. The perimeter adhesive was then placed as described herein, and the membrane was placed on top of the uncured adhesive with machine vision. After 1 second of incursion time, the entire assembly was cured by first curing the perimeter, and then sweeping the internal area to cure the dot pattern for 28 and 112 seconds, respectively. The completed device was then manually removed from the assembly platform and placed into a secondary container for post-assembly thermal curing at 37° C. for 2 hours.

Example 17

Parameters of Dot Diameters and Filling of the Device

Figure 2:
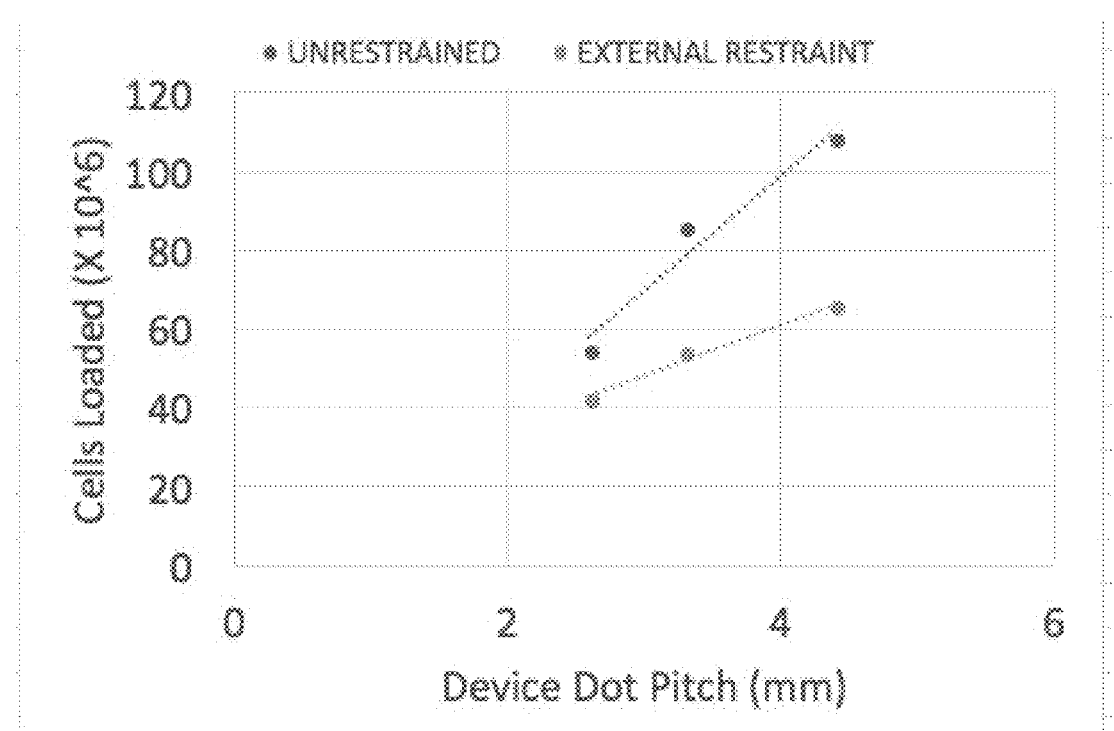
FIG. 2 shows the amount of cells that loaded into the devices vary with the dot pitch and presence of restraints, in accordance with some embodiments.

This example describes the filling volume of the devices with various configurations of dots. The dot diameter and density (e.g. center to center spacing) can impact the allowable filling volume by creating a series of columns. The devices were prepared as described in Example 16 with various configurations of dots. The devices were prepared with a pattern of dots, each dot about 1.25 mm in diameter and a dot pitch of 2.6 mm, 3.3 mm, or 4.4 mm, where the center of one dot was placed apart from the center of its adjacent dot by the dot pitch distance. Devices with a shorter dot pitch may have a higher dot density than devices with a longer dot pitch for a device of the same dimensions. For the devices have the same dot diameters and the device dimensions, a device with shorter dot pitch can have smaller internal volume available for filling than a device with a longer dot pitch. Then, the devices were loaded with a cell suspension while unrestrained on the outside of the device or with external restraints. The external restraints may prevent the membranes of the device from expanding outwardly away from each other. FIG. 2 shows the amount of cells that were loaded into the devices vary with the dot pitch and presence of restraints. A small amount of cells were loaded as the dot pitch decreased. The cell amount decreased from 108×10$^6$ cells in devices with a dot pitch of 4.4 mm and loaded without a restraint to a cell amount of 42×10$^6$ cells in devices with a dot pitch of 2.6 mm and loaded with external restraint. For the devices with the same dot pitch, a larger amount of cells that were loaded into the devices decreased when loaded with an external restraint.

Example 18

Adhesive Dots on Cell Housing Device

In creating dots on the cell housing devices, the device can be manually flipped to create the pattern of adhesive dots that act to restrict the thickness of the device during cell filling. For example, a pattern of 37 dots, each dot about 1.25 mm in diameter with a center-to-center spacing of 3.3 mm, was deposited in 2 successive layers. First, the pattern was developed against the membrane by applying adhesive in 0.05 second applications and curing each dot individually for 1 second. A smaller second layer was applied on top of the first pattern with 0.03 second dispensing times, and was left uncured. The perimeter adhesive was then placed onto the membrane, and the membrane was placed on top of the uncured adhesive with machine vision. After 1 second of incursion time, the entire assembly was cured by first curing the perimeter, and then sweeping the internal area to cure the dot pattern for 28 and 112 seconds, respectively. The completed device was then manually removed from the assembly platform and placed into a secondary container for post-assembly thermal curing at 37° C. for 2 hours.

Example 19

In Vivo Implantation of Ultrathin Device

This example described the implantation of ultrathin cell housing devices into a NOD scid gamma (NSG) mouse model, an immunodeficient mouse model. Diabetes was induced in the NGS mice, where the blood glucose levels of the mice rose to over 400 mg/dL as shown in FIG. 61. After the diabetes induction, ultrathin devices were implanted in the epididymal fat pad of the mice. FIG. 61A shows an example of the implanted ultrathin device. These implanted ultrathin devices comprised high flux ePTFE membranes with hydrophilic coating and 8 million SC islet cells. After the implantation of the ultrathin devices, the blood glucose levels in all test mice decreased to about 100 mg/dL and close to the levels before the diabetes induction for 90 days until the removal or explant of the ultrathin devices as shown in FIG. 61. The explanted ultrathin devices were analyzed by histology. FIGS. 62B and C show a high density of cells throughout the device, including the core of the device after 90 days of implantation in a NSG mouse model. The ultrathin device filled with islet cells can be implanted into in a diabetic subject and reduce and normalize the blood glucose level in the subject over a prolonged period of time.

Example 20

In Vivo Implantation of AS-1 Ultrathin Device

Figure 62:
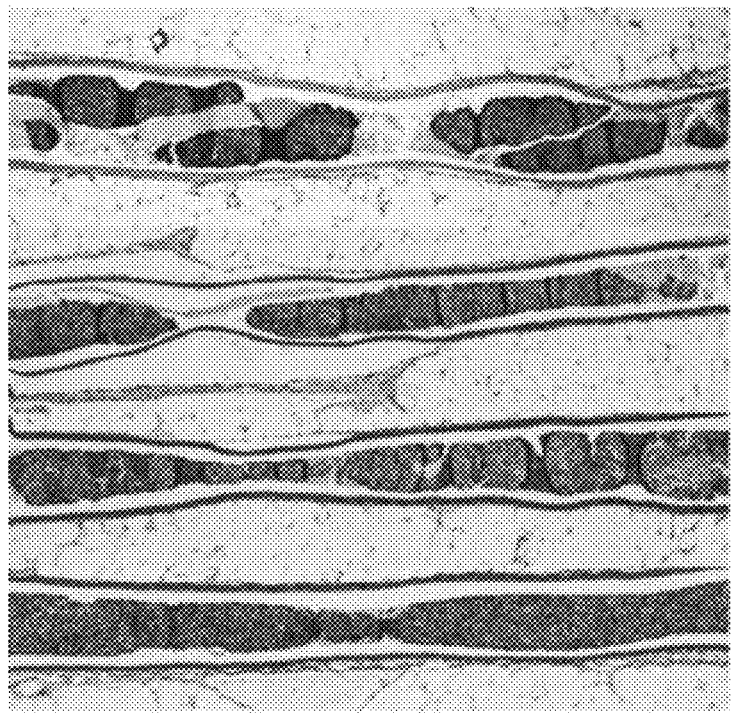
FIG. 62 shows low magnification images of histological sections of cell-filled ultrathin devices with AS-1 membranes and filled with SEM-01 cells after 30 days of in vivo implantation in a mouse model, in accordance with some embodiments.
Figure 63:
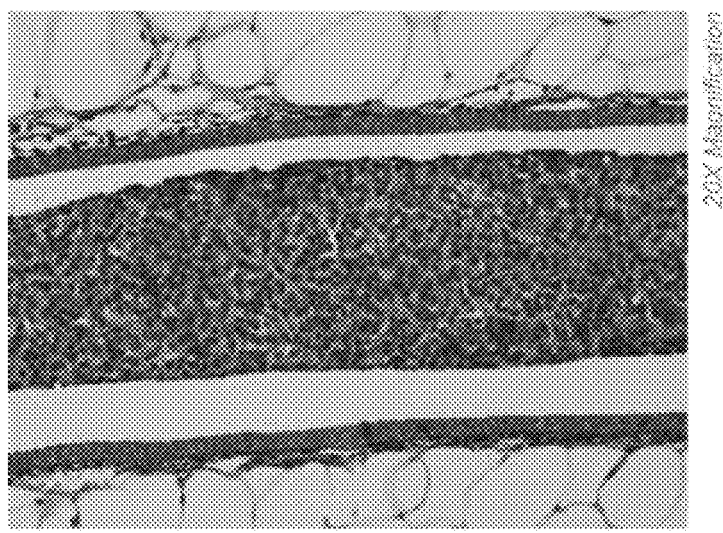
FIG. 63 shows a high magnification image of the histological sections of cell-filled ultrathin devices with AS-1 membranes and filled with SEM-01 cells after 30 days of in vivo implantation in a mouse model, in accordance with some embodiments.

This example describes the condition of cells within the ultrathin devices after 30 day and 3 months in vivo implantation in a mouse model. FIG. 62 shows low magnification images of histological sections of cell-filled ultrathin devices after 30 days of in vivo implantation in a mouse model. The ultrathin devices were made with AS-1 membranes and filled with SC-Islet cells designated SEM-01. FIG. 63 shows a high magnification image of the histological sections. The cells were well distributed and viable throughout the device after 30 days in vivo.

Example 21

In Vivo Implantation of Endocrine Cells in Ultrathin Device

Figure 64:
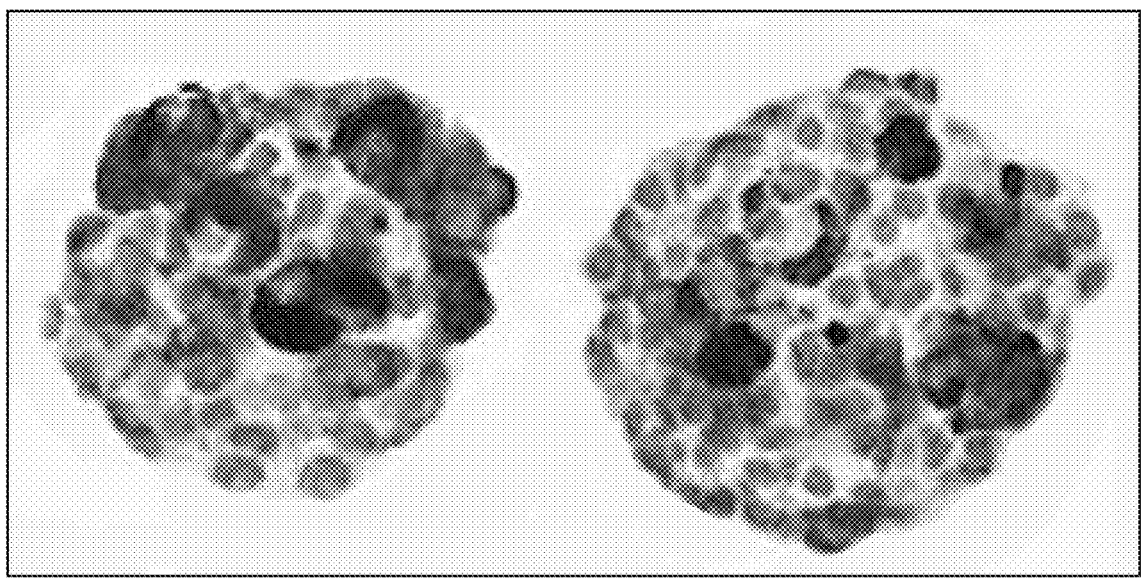
FIG. 64 shows microaggregates of endocrine cells before encapsulation and filling into a cell housing device, in accordance with some embodiments.
Figure 65:
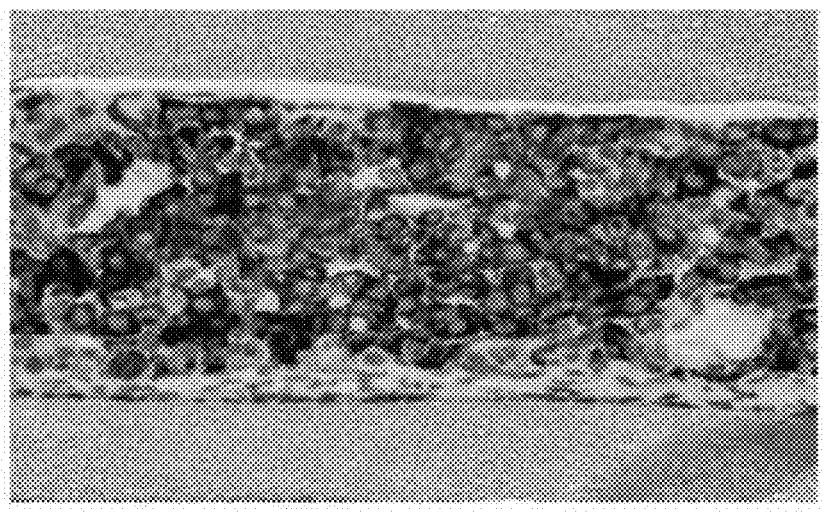
FIG. 65 shows a stained histological image of an ultrathin device filled with microaggregates of endocrine cells after 3 months of implantation in a mouse, in accordance with some embodiments.

This example describes the cell phenotype of endocrine cells in the ultrathin devices after 3 months in vivo implantation in a mouse model. FIG. 64 shows microaggregates of endocrine cells before encapsulation and filling into a cell housing device. FIG. 65 shows a stained histological image of an ultrathin device filled with microaggregates of endocrine cells after 3 months of in vivo implantation in a mouse. The blue stain indicates the nucleus, orange-brown stain indicated the presence of C-peptide, and the pink stain indicates the presence of glucagon. The orange-brown and pink stain in the microaggregates in FIG. 64 indicates the presence of active endocrine cells secreting C-peptide and glucagon. The orange-brown and pink stain in the microaggregates in FIG. 65 indicates that the endocrine cells in the ultrathin device remain viable and active and maintain their endocrine phenotype, secreting C-peptide and glucagon, during the 3 months of in vivo implantation.

Example 22

Intraperitoneal Glucose Tolerance Test with Ultrathin Device

Figure 66:
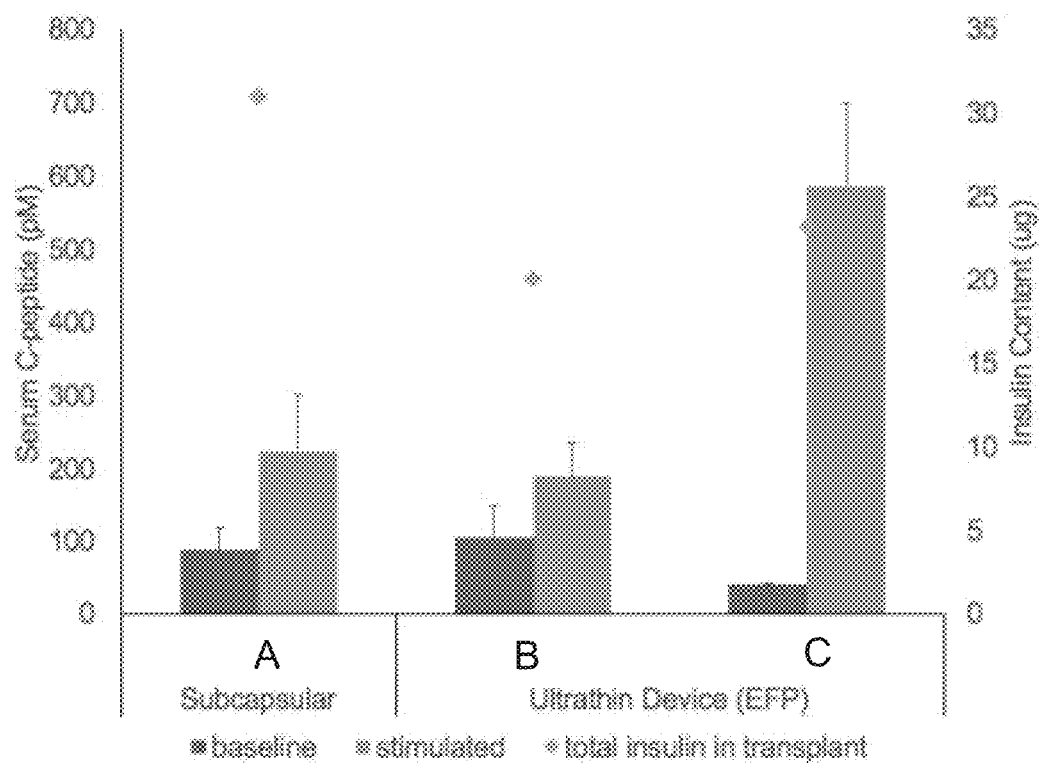
FIG. 66 shows the levels of serum C-peptide and total insulin content in mice implanted with endocrine cells or endocrine cell-filled ultrathin devices, in accordance with some embodiments.

This example describes an intraperitoneal glucose tolerance test with various configurations of the ultrathin device. FIG. 66 shows the levels of serum C-peptide and total insulin content in mice implanted with endocrine cells or endocrine cell-filled ultrathin devices. The test groups were D601mcRA2 endocrine cells implanted subcapsularly (group A), ultrathin devices with AS-1 membrane and filled with D601 cells (group B), and ultrathin devices with type A ePTFE membranes and filled with D601 cells (group C). The cells or devices were implanted in mice and underwent for intraperitoneal glucose tolerance test. The serum C-peptide levels were measured at baseline (blue) and with a 30 minute glucose stimulus (orange) along with the total insulin content in the transplant. All groups showed an increase of serum C-peptide level with the glucose stimulation, indicating insulin production with the glucose stimulation. The group A had serum C-peptide levels about 100 pM at baseline and about 250 pM with the glucose stimulus and had a total insulin content of about 700 µg. The group B had serum C-peptide levels about 100 pM at baseline and about 200 pM with the glucose stimulus and had a total insulin content of about 500 µg. The group C had serum C-peptide levels about 50 pM at baseline and about 600 pM with the glucose stimulus and had a total insulin content of about 550 µg. This example shows the evidence of glucose control with the increases in insulin production as measured by increased serum C-peptide levels.

Example 23

Host-Ultrathin Device Interaction in a Nude Mouse Model

Figure 67:
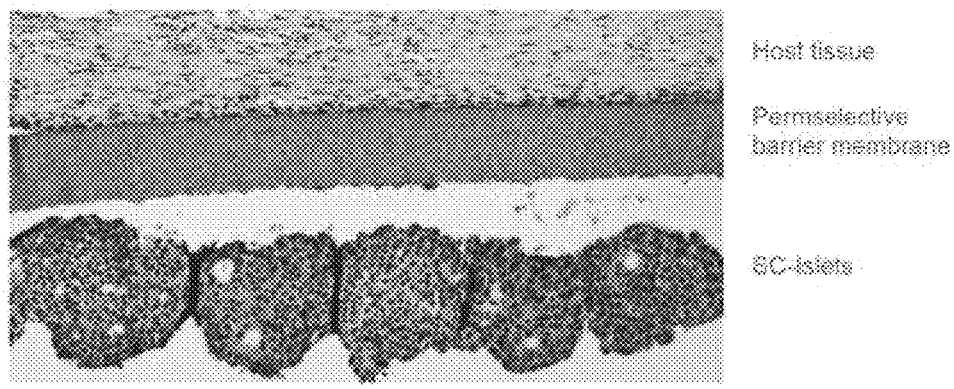
FIG. 67 shows an H&E stained image of an explant of an ultrathin device comprising coated permselective membranes filled with SC-islet cells after 3 months in a nude rat at a pre-peritoneal site, in accordance with some embodiments.

This example describes the host-ultrathin device interaction after device implantation in a nude mouse model. FIG. 67 shows a H&E stained image of an explant of an ultrathin device comprising coated permselective membranes filled with SC-islet cells after 3 months in a nude rat at a pre-peritoneal site. The image shows mitigation of foreign body response (FBR) in the ultrathin device with the permselective membrane that has a hydrophilic coating by the lack of macrophages and macrophage fusions, and angiogenesis. The image also shows the separation of the host tissue from interior of the ultrathin device and a concentration of viable cells within the device.

Example 24

Figure 68:
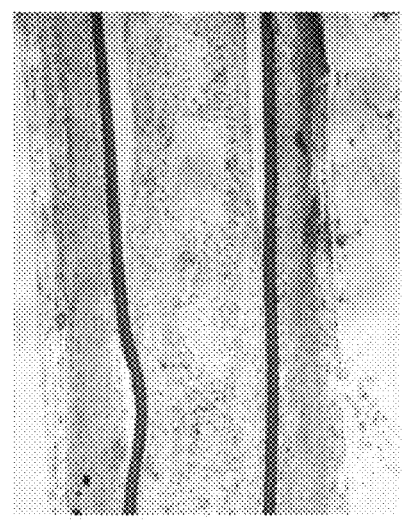
FIG. 68 shows an H&E stained image of an ultrathin device filled with 16 million SC-islet cells after a 12 week implantation at a pre-peritoneal site in a nude mouse model, in accordance with some embodiments.
Figure 69:
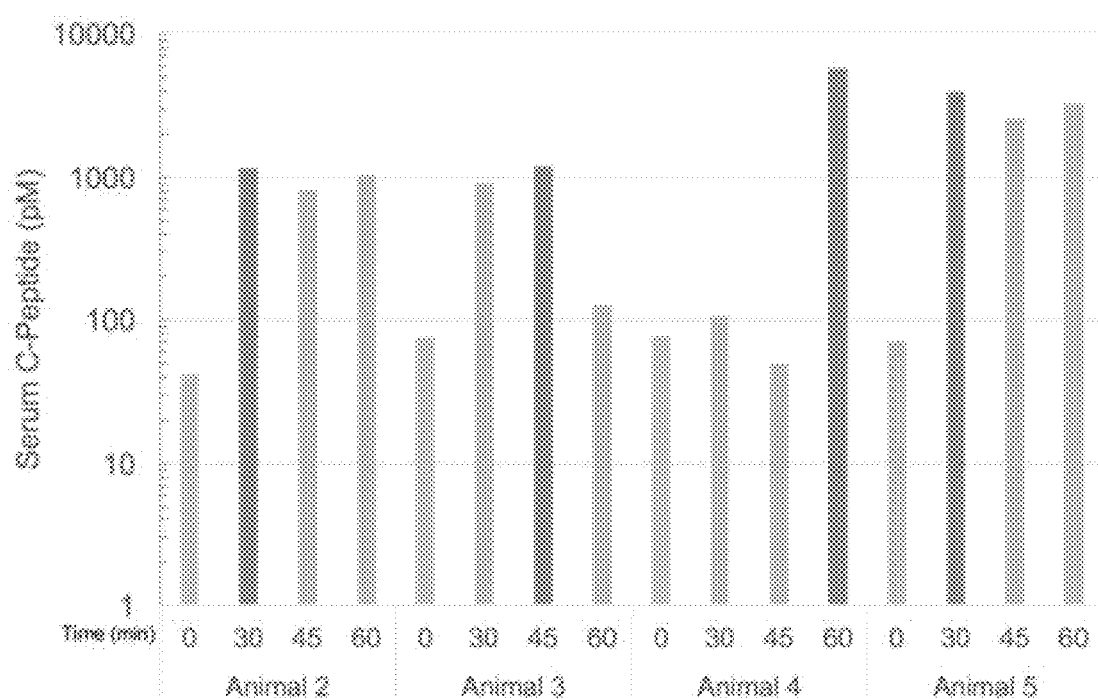
FIG. 69 shows the serum C-peptide levels over a course of 60 minutes in 4 different mice implanted with the ultrathin device filled with the SC-islet cells, in accordance with some embodiments.

Cell Viability and Phenotype in Implanted Devices Filled with SC-Islet Cells This example describes the maintenance of cell viability and phenotype after a 12 week implantation of ultrathin devices filled with SC-islet cells in a nude mouse model. FIG. 68 shows a H&E stained image of an ultrathin device filled with 16 million SC-islet cells after a 12 week implantation at a pre-peritoneal site in a nude mouse model. The image shows a high level of cell viability in the device core after 12 weeks in vivo. FIG. 69 shows that after administration of glucose to the peritoneal cavity, the serum C-peptide levels over a course of 60 minutes in 4 different mice implanted with the ultrathin device filled with the SC-islet cells. The serum C-peptide increased in the four mice from about 30-100 pM at 0 minutes to about or over 1000 pM over time. This indicates that the SC-islet cells in the ultrathin devices implanted in the mice are active and have maintained their capability to produce insulin.

Example 25

Figure 70A:
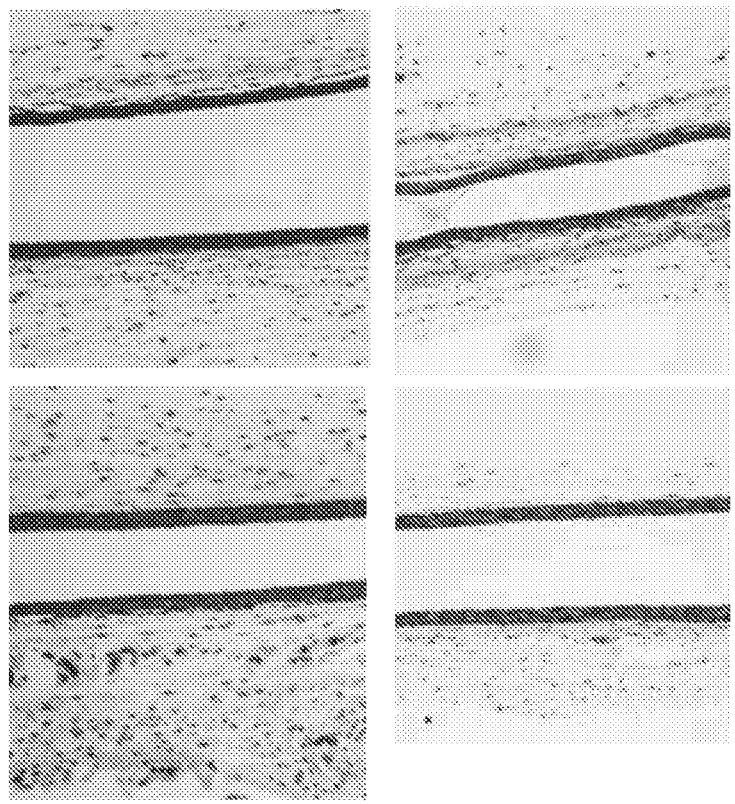
FIG. 70A and FIG. 70B show H&E stained images of empty ultrathin devices with AS-1 membranes implanted in an immunocompetent Black 6 mouse model that did not elicit a foreign body response (FBR), in accordance with some embodiments.
Figure 70B:

Biocompatibility of Ultrathin Devices Implanted in an Immunocompetent Mouse Model This example describes the biocompatibility of ultrathin devices with AS-1 membranes implanted in an immunocompetent Black 6 mouse model. Empty mouse-sized ultrathin devices with coated AS-1 membranes were placed subcutaneously in Black 6 mouse to assess the baseline host reaction against the materials for the ultrathin devices. After 1 month, the devices were assessed for maintenance of the device integrity from the host tissue and cells and for foreign body response (FBR). FIGS. 70A and 84B show a lack of cells inside the devices and a lack of FBR. FBR has been described as peaking within the first month (Beets, 1998). The images indicate that the integrity of the device was maintained while in vivo and the device materials and coating are biocompatible and do not elicit a FBR.

Example 26

Implantation of Ultrathin Devices in a Diabetic NSG Mouse Model

Figure 71:
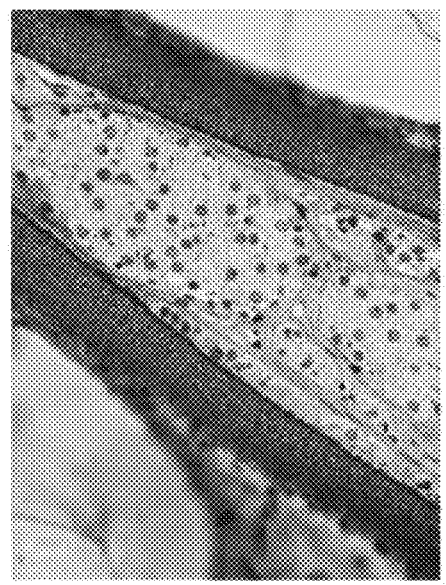
FIG. 71 shows an H&E stained image of the ultrathin device with viable, intact rat islet cells after 90 days in vivo, in accordance with some embodiments.
Figure 72:
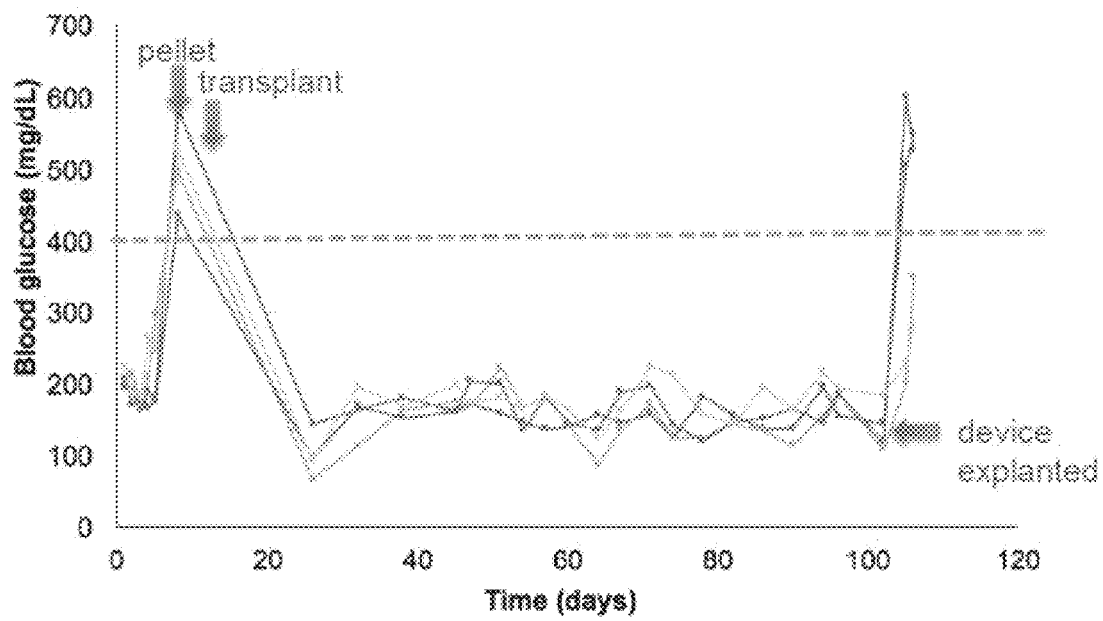
FIG. 72 shows the blood glucose levels before, during, and after 90 days of ultrathin device implantation in a diabetic mouse model, in accordance with some embodiments.

This example describes implantation of ultrathin devices with AS-1 membranes and encapsulated rat islet cells in a diabetic NSG mouse model. Ultrathin devices with AS-1 membranes and filled with 400 IEQ rat islet cells were implanted into diabetic NSG mice for 90 days. FIG. 71 shows a H&E stained image of the ultrathin device with viable, intact rat islet cells after 90 days in vivo. FIG. 72 shows the blood glucose levels before and over 90 days of ultrathin device implantation. After the induction of the diabetes, the animals were administered an insulin pellet to control glycemia for the initial 10-20 days of the experiment. After the implantation of the ultrathin device (labeled as "transplant"), the blood glucose levels decreased from over 400 mg/dL to between about 100 mg/dL to about 300 mg/dL over the 90 days of implantation. The blood glucose level increased after the device was explanted from the mice. This indicates an implanted ultrathin device can provide a prolonged glucose control.

Example 27

Cell Filling of Ultrathin Device

Figure 87:
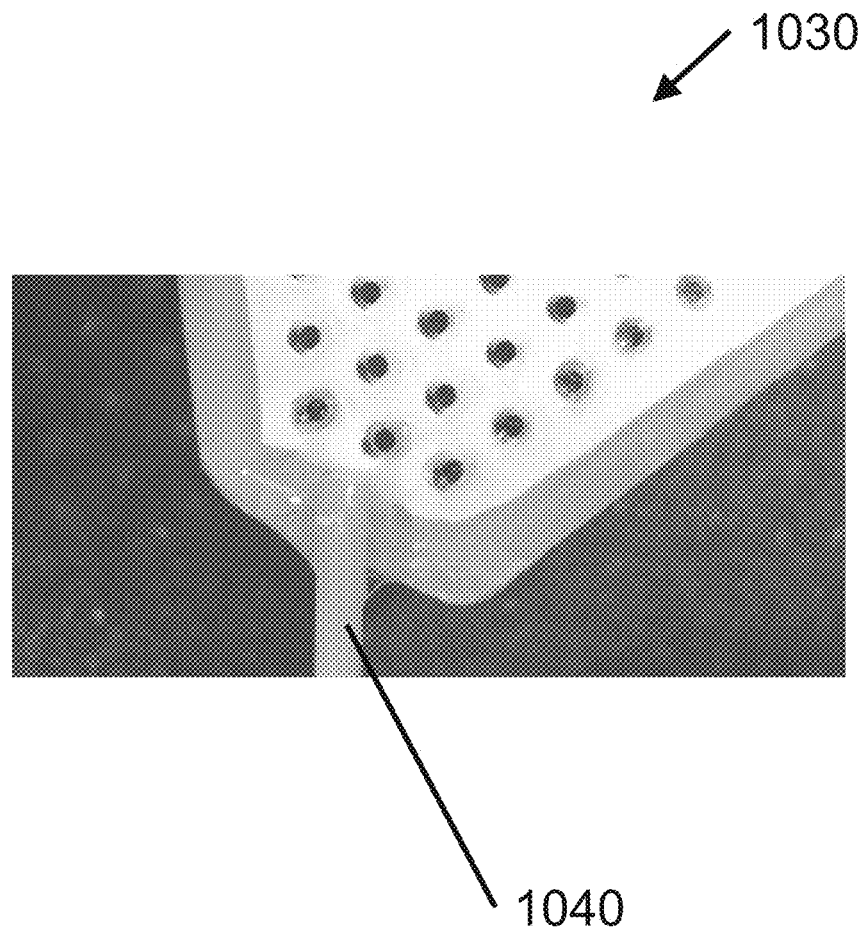
FIG. 87 shows an image of an exemplary a rodent channel array device with a manual fill tube inserted over the frame, in accordance with some embodiments.
Figure 88A:
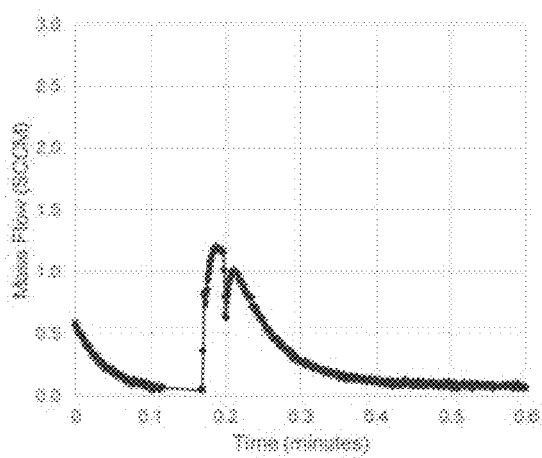
FIG. 88A shows a the mass flow of a channel array device with a fill port, in accordance with some embodiments.
Figure 88B:
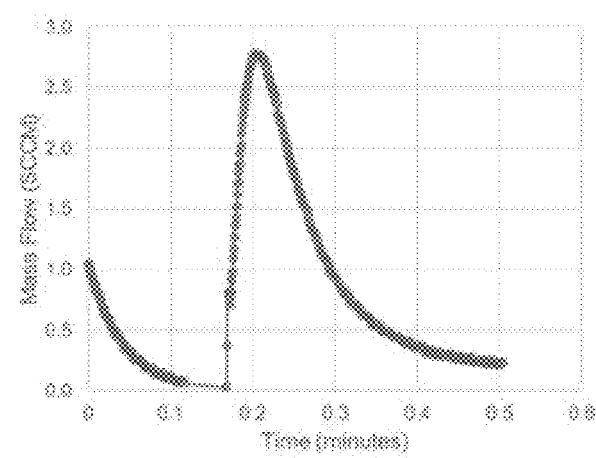
FIG. 88B shows a the mass flow of a channel array device with an integrated fluid path, in accordance with some embodiments.

FIGS. 87 and 88 show the various configurations of the ultrathin devices. The ultrathin devices designed for implantation in a mouse model can be filled with 8 million cells and have a fused dot in the center of the device. The ultrathin devices designed for human implantation can have no fused dot or an array of dots and be filled with 133 million cells.

Example 28

Mass Flow of Ultrathin Devices with Dots

FIG. 75A shows an ultrathin device for human implantation with an array of spot welds that provide an adhesive restraint for the two membranes of the device from bending away from each other as the device is filled. FIG. 75B shows a set up with porous metal platens to provide external restraint for the ultrathin devices to reduce the two membranes of the device from bending away from each other as the device is filled. The external porous restraint may be used in filling any cell housing devices, including ultrathin devices and ultrathin devices with spot welds. FIG. 77 shows the mass flow rate measured from filling of ultrathin devices for human implantation with 3.3 mm dot pitch with or without external porous restraint. The mass flows measured in $cm^3/min$ or standard cubic centimeter per minute (sccm) were similar with or without external porous restraint, reaching peaks of about 7.5 or 8 sccm at about 10 seconds and decreasing over time. The mass flow was slightly higher without external porous restraint after reaching the initial peak. FIG. 78 shows an H&E stained image of the cells distribution throughout the entire ultrathin device with adhesive restraint, similar to the device shown in FIG. 75A. This demonstrates the capability of filling devices with adhesive restraint uniformly throughout the entire device.

Example 29

Cell Filling of Ultrathin Devices with No Dots or with Dots

This example describes cell filling of ultrathin devices with no dots or with dots. FIGS. 79A and B show the two configurations of hexagonal ultrathin devices with no dots (A) and with 3.3 mm dot array matrix (B) throughout the device. FIG. 80 shows the amount of cells that can fill a single ultrathin device with no dots, as in FIG. 79A, and with 3.3 mm dot array matrix, as in FIG. 79B. The device with no dots could be filled with about 120 million cells, and the device with 3.3 mm dot matrix could be filled with about 80 million cells. This demonstrates that the dot array matrices can be used to tune the cell loading and restrain the membranes of the device from expanding or bending during filling of the device with cells.

Example 30

Cell Filling of Ultrathin Devices with Restraints

Figure 81A:
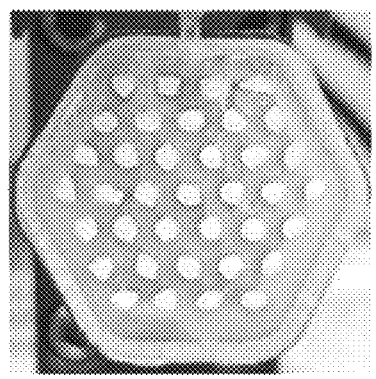
FIG. 81A and FIG. 81B show the two configurations of hexagonal ultrathin devices with 3.3 mm dot array matrix that were filled without any restraint (FIG. 81A) and filled with porous platens spaced apart at with a 400 μm spacer (FIG. 81B), in accordance with some embodiments.
Figure 81B:
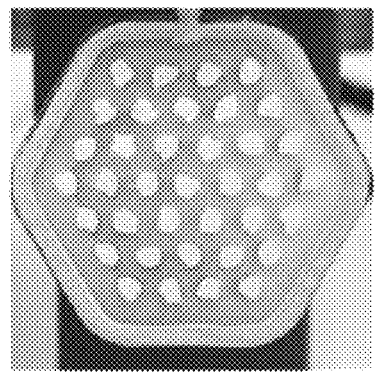
Figure 82:
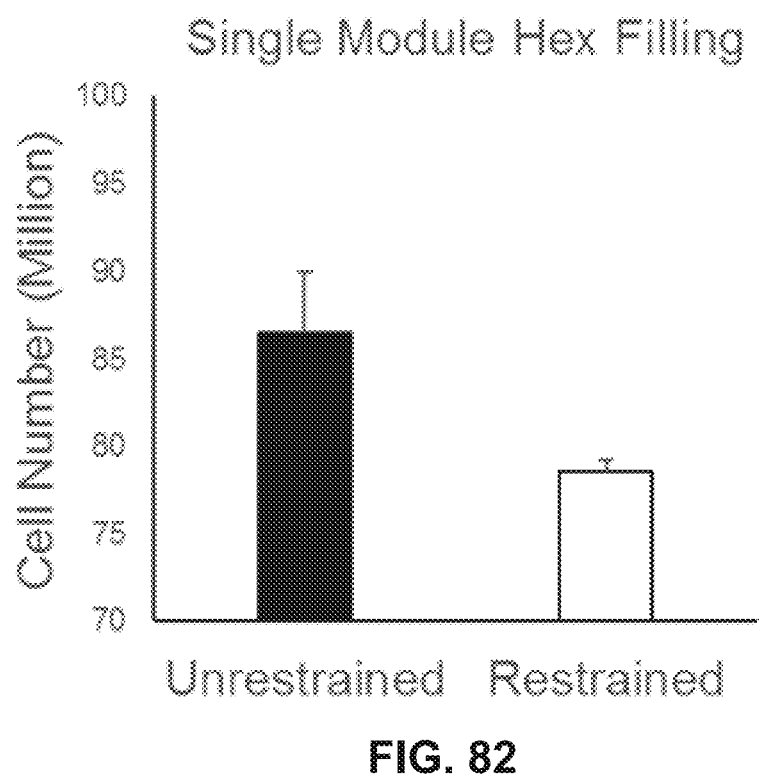
FIG. 82 shows the amount of cells that can fill a single ultrathin device without any restraint, as in FIG. 81A, and with porous restraints, as in FIG. 81B, in accordance with some embodiments.

This example describes cell filling of ultrathin devices with or without porous restraints. FIGS. 81A and B show the two configurations of hexagonal ultrathin devices with 3.3 mm dot array matrix that were filled without any restraint (A) and filled with porous platens spaced apart at with a 400

μm spacer (B). FIG. 82 shows the amount of cells that can fill a single ultrathin device without any restraint, as in FIG. 81A, and with porous restraints, as in FIG. 81B. The device without any restraint could be filled with about 87 million cells, and the device with porous restraints could be filled with about 80 million cells. This demonstrates that the porous restraints can reduce membrane expansion and bending during filling of the device. The restraint can be further tunable by using a spacer with a target distance in between the porous restraints.

Example 31

In Vivo Implantation in a Mini-Pig Model

Figure 83A:
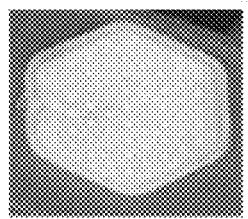
FIG. 83A shows an example of an ultrathin device with a 2.6 mm dot pitch in a human single module design implanted into the mini-pigs, in accordance with some embodiments.
Figure 83B:
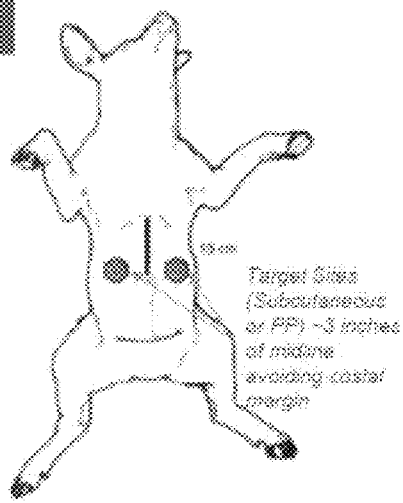
FIG. 83B shows the target pre-peritoneal or subcutaneous implantation sites in a mini-pig at about 3 inches away from the midline and avoiding the costal margin, in accordance with some embodiments.
Figure 83C:
FIG. 83C shows subcutaneous dissection with electrocautery to prepare for implantation of the device, in accordance with some embodiments.
Figure 83D:
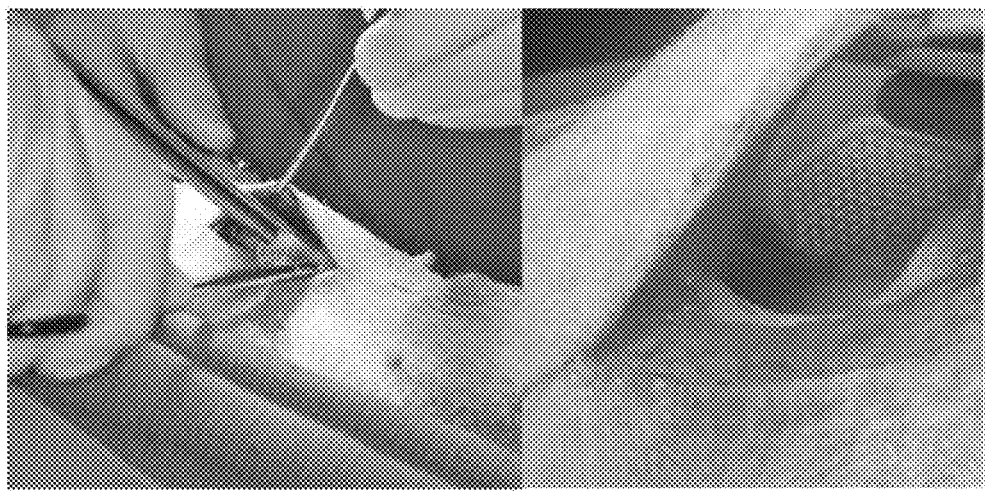
FIG. 83D shows pre-peritoneal dissection with a lighted retractor to prepare for implantation of the device, in accordance with some embodiments.

This example describes a mini-pig implantation study of human-sized ultrathin devices. Ten mini-pigs were implanted with an empty ultrathin device, or an ultrathin device filled with SC-islet cells (SEM-01) or pig islet cells at pre-peritoneal or subcutaneous sites. FIG. 83A shows an example of an ultrathin device with a 2.6 mm dot pitch in a human single module design implanted into the mini-pigs. FIG. 83B shows the target pre-peritoneal or subcutaneous implantation sites in a mini-pig at about 3 inches away from the midline and avoiding the costal margin. FIG. 83C shows subcutaneous dissection with Bovie electrocautery to prepare for implantation of the device. FIG. 83D shows pre-peritoneal dissection with a lighted retractor to prepare for implantation of the device. The dissection of the implant site can be tailored for different implantation approaches. FIG. 84A shows examples of subcutaneous placement of the ultrathin devices. FIG. 84B shows examples of pre-peritoneal placement of the ultrathin devices. FIG. 85 shows examples of mini-pigs 2 weeks after the subcutaneous (SQ) and pre-peritoneal (PP) implantation of ultrathin devices. The images show no gross evidence of inflammation around the implantation sites, and animals did not exhibit signs of distress or pain.

What is claimed is:

1. A cell housing device, comprising:
   a first membrane having a first surface, and a second surface opposing the first surface;
   a second membrane opposite and attached to the second surface of the first membrane, wherein the first membrane and the second membrane form an enclosed compartment configured to house a cell population, wherein the enclosed compartment includes a plurality of continuous interconnected compartments formed between the first membrane and the second membrane, and wherein at least one of the first membrane and the second membrane is sintered; and
   a frame extending at least partially along an outer edge of the first membrane and the second membrane.

2. The device of claim 1, wherein at least a portion of the device has a thickness between about 10 μm and about 500 μm.

3. The device of claim 1, further comprising a plurality of interconnected channels formed between the first membrane and the second membrane.

4. The device of claim 3, wherein the plurality of channels are arranged in a rectilinear array or a polar array.

5. The device of claim 3, wherein a center of each of the plurality of channels is separated from the center of an adjacent channel by a distance of about 75 μm to about 2.5 mm.

6. The device of claim 3, wherein each of the plurality of channels has a height to diameter ratio of at least about 0.2.

7. The device of claim 3, wherein the device has a number of channels per area along a transverse plane that is greater than about 50/cm$^2$.

8. The device of claim 1, wherein the first membrane and/or the second membrane comprise polyvinylidene fluoride (PVDF), polytetrafluoroethylene (PTFE), expanded polytetrafluoroethylene (ePTFE), polycaprolactone (PCL), polyethylene (PE), polyethersulfone (PES), polypropylene (PP), polystyrene (PS), poly(methyl methacrylate) (PMMA), poly(lactic-co-glycolic acid) (PLGA), poly(l-lactic acid) (PLLA), and/or any combination thereof.

9. The device of claim 1, wherein the frame is configured to receive the first and second membranes.

10. The device of claim 9, wherein the frame is configured to receive a plurality of first membranes and a plurality of second membranes.

11. The device of claim 1, wherein the frame comprises a flexing mechanism configured to prevent buckling of the cell housing device.

12. The device of claim 1, further comprising the cell population.

13. The device of claim 12, wherein the cell population is capable of glucose-stimulated insulin secretion (GSIS).

14. The device of claim 1, further comprising a coating on the first membrane and/or the second membrane, wherein the coating comprises a hydrophilic polymer.

15. The device of claim 1, wherein the device has an insulin diffusion coefficient of about $2\times10^{-6}$ cm$^2$/s to about $1\times10^{-5}$ cm$^2$/s.

16. The device of claim 1, wherein the device has a maximum oxygen diffusion distance of less than about 150 μm.

17. The device of claim 1, wherein at least one of the first membrane and the second membrane is semi-permeable.

18. The device of claim 1, wherein at least one of the first membrane and the second membrane is configured to enable vascularization of a cell within the device in absence of an immune suppression therapy.

19. The device of claim 3, wherein the plurality of channels are generally perpendicular with respect to the first membrane.

20. The device of claim 1, wherein the compartment has a surface area to volume ratio of at least about 40 cm$^{-1}$.

21. The device of claim 8, wherein the first membrane and/or the second membrane comprise expanded polytetrafluoroethylene (ePTFE).

22. The device of claim 1, wherein the first membrane and/or the second membrane comprise an average pore size in the range of 5 nm to 2500 nm.

23. The device of claim 1, wherein the sintered membrane is sintered in a semi-permeable portion of the sintered membrane.

24. A cell housing device, comprising:
   a first membrane having a first surface and a second surface opposing the first surface;
   a second membrane opposite and attached to the second surface of the first membrane wherein the first membrane and the second membrane form an enclosed compartment configured to house a cell population, wherein the enclosed compartment includes a plurality of continuous interconnected compartments between the first membrane and the second membrane, and wherein at least one of the first membrane and the second membrane is sintered; and
   a frame extending at least partially along an outer edge of the first membrane and the second membrane, wherein a thickness of a portion of the device including the first membrane and the second membrane has a thickness between or equal to 50 μm and 500 μm and wherein a length of the device is between or equal to 4.0 cm and 6.0 cm.

25. The device of claim 1, wherein both the first membrane and the second membrane are sintered.

26. The device of claim 1, wherein the first membrane and the second membrane are bonded directly to each other.

27. The device of claim 2, wherein the portion of the device includes the first membrane and the second membrane.

28. The device of claim 1, wherein a length of the device is between or equal to 4.0 cm and 6.0 cm.

29. The device of claim 1, further comprising a plurality of channels formed in at least one selected from the first membrane and the second membrane, wherein the plurality of channels extend at least partially in a thickness direction of the device.

30. The device of claim 29, further comprising a plurality of through holes formed in at least a portion of the channels, wherein the plurality of through holes extend through the first membrane and the second membrane.

* * * * *